United States Patent
Bonini et al.

(10) Patent No.: US 11,597,755 B2
(45) Date of Patent: Mar. 7, 2023

(54) TCR AND PEPTIDES

(71) Applicants: Ospedale San Raffaele S.r.l., Milan (IT); Fondazione Centro San Raffaele, Milan (IT)

(72) Inventors: Maria Chiara Bonini, Milan (IT); Eliana Ruggiero, Milan (IT); Zulma Irene Magnani, Milan (IT); Luca Aldo Edoardo Vago, Milan (IT); Attilio Bondanza, Milan (IT); Fabio Ciceri, Milan (IT)

(73) Assignees: Ospedale San Raffaele S.r.l., Milan (IT); Fondazione Centro San Raffaele, Milan (IT)

( * ) Notice: Subject to any disclaimer, the term of this patent is extended or adjusted under 35 U.S.C. 154(b) by 100 days.

(21) Appl. No.: 16/605,561

(22) PCT Filed: Apr. 24, 2018

(86) PCT No.: PCT/EP2018/060477
§ 371 (c)(1),
(2) Date: Oct. 16, 2019

(87) PCT Pub. No.: WO2018/197492
PCT Pub. Date: Nov. 1, 2018

(65) Prior Publication Data
US 2020/0123220 A1    Apr. 23, 2020

Related U.S. Application Data

(60) Provisional application No. 62/489,226, filed on Apr. 24, 2017.

(51) Int. Cl.
| | | |
|---|---|---|
| *C07K 14/725* | (2006.01) | |
| *A61P 35/00* | (2006.01) | |
| *A61K 35/17* | (2015.01) | |
| *C07K 14/47* | (2006.01) | |
| *C12N 5/0783* | (2010.01) | |
| *A61K 38/00* | (2006.01) | |

(52) U.S. Cl.
CPC .......... *C07K 14/7051* (2013.01); *A61K 35/17* (2013.01); *A61P 35/00* (2018.01); *C07K 14/4748* (2013.01); *C12N 5/0636* (2013.01); *A61K 38/00* (2013.01); *C07K 2319/30* (2013.01); *C07K 2319/55* (2013.01)

(58) Field of Classification Search
CPC ............ C07K 14/7051; C07K 14/4748; A61P 35/00; A61K 35/17; C12N 5/0636
See application file for complete search history.

(56) References Cited

U.S. PATENT DOCUMENTS

2004/0126362 A1    7/2004   Gaiger et al.
2014/0212888 A1    7/2014   Watanabe et al.

FOREIGN PATENT DOCUMENTS

| WO | WO-99/41397 A1 | 8/1999 |
| WO | WO-01/79518 A2 | 10/2001 |
| WO | WO-2005/056595 A2 | 6/2005 |
| WO | WO-2016/022400 A1 | 2/2016 |
| WO | WO-2016/161273 A1 | 10/2016 |

OTHER PUBLICATIONS

"Two bright new faces in gene therapy", Nat. Biotechnol., 14(5):556 (May 1996).
Altschul et al., Basic Local Alignment Search Tool, J. Mol. Biol., 215:403-10 (1990).
Ausubel et al., Current Protocols in Molecular Biology, and periodic supplements, ch 9, 13, and 16, John Wiley & Sons (1995).
Ausubel et al., Short Protocols in Molecular Biology, 4th edition, Ch. 18 (1999).
Ausubel et al., Short Protocols in Molecular Biology, 4th edition, pp7-58 to 7-60 (1999).
Bolotin et al., MiXCR: software for comprehensive adaptive immunity profiling, Nat. Methods, 12(5):380-1 (May 2015).
Bonini et al., HSV-TK gene transfer into donor lymphocytes for control of allogeneic graft-versus-leukemia, Science, 276(5319):1719-24 (Jun. 1997).
Brochet et al., IMGT/V-QUEST: the highly customized and integrated system for IG and TR standardized V-J and V-D-J sequence analysis, Nucleic Acids Res., 36(Web Server Issue): W503-8 (Jul. 2008).
Chlewicki et al., High-affinity, peptide-specific T cell receptors can be generated by mutations in CDR1, CDR2 or CDR3, J. Mol. Biol., 346(1):223-39 (Feb. 2005).
Ciceri et al., Infusion of suicide-gene-engineered donor lymphocytes after family haploidentical haemopoietic stem-cell transplantation for leukaemia (the TK007 trial): a non-randomised phase I-II study, Lancet Oncol., 10(5):489-500 (May 2009).
Coffin et al., Retroviruses, Cold Spring Harbour Laboratory Press, pp. 758-763 (1997).
Devereux et al., A comprehensive set of sequence analysis programs for the VAX, Nucleic Acids Research, 12(1):387-95 (1984).
Di Stasi et al., Review of the Results of WT1 Peptide Vaccination Strategies for Myelodysplastic Syndromes and Acute Myeloid Leukemia from Nine Different Studies, Front Immunol., 6:36 (Feb. 2015).
Doubrovina et al., Mapping of novel peptides of WT-1 and presenting HLA alleles that induce epitope-specific HLA-restricted T cells with cytotoxic activity against WT-1 (+) leukemias, Blood, 120(8):1633-46 (Aug. 2012).
Gait (ed.), Oligonucleotide Synthesis: A Practical Approach, Oxford, England: IRL Press Limited (1984).

(Continued)

*Primary Examiner* — Amy E Juedes
*Assistant Examiner* — Peter Johansen
(74) *Attorney, Agent, or Firm* — Marshall, Gerstein & Borun LLP

(57) ABSTRACT

TCR AND PEPTIDES A T-cell receptor (TCR), which binds to a Wilms tumour 1 protein (WT1) peptide when presented by a major histocompatibility complex (MHC).

41 Claims, 48 Drawing Sheets

Specification includes a Sequence Listing.

(56) References Cited

OTHER PUBLICATIONS

Gessler et al., Homozygous deletion in Wilms tumours of a zinc-finger gene identified by chromosome jumping, Nature, 343(6260)774-8 (Feb. 1990).
Giudicelli et al., IMGT/V-QUEST: IMGT standardized analysis of the immunoglobulin (IG) and T cell receptor (TR) nucleotide sequences, Cold Spring Harbor Protocols, 2011(6):695-715 (2011).
International Application No. PCT/EP2018/060477, International Preliminary Report on Patentability, dated Oct. 29, 2019.
International Application No. PCT/EP2018/060477, International Search Report and Written Opinion, dated Aug. 29, 2018.
Jaigirdar et al., A High-avidity WT1-reactive T-Cell Receptor Mediates Recognition of Peptide and Processed Antigen but not Naturally Occurring WT1-positive Tumor Cells, J. Immunother., 39(3):105-16 (Apr. 2016).
Kapp et al., CD8+ T-cell responses to tumor-associated antigens correlate with superior relapse-free survival after allo-SCT, Bone Marrow Transplant, 43(5):399-410 (Mar. 2009).
Kwakkenbos et al., Generation of stable monoclonal antibody-producing B cell receptor-positive human memory B cells by genetic programming, Nat. Med., 16(1):123-8 (Jan. 2010).
Lewis et al., Human immunodeficiency virus infection of cells arrested in the cell cycle, EMBO J., 11(8):3053-8 (Aug. 1992).
Lilley et al., Methods in Enzymology: DNA Structures Part A: Synthesis and Physical Analysis of DNA, Academic Press (1992).
Lombardo et al., Gene editing in human stem cells using zinc finger nucleases and integrase-defective lentiviral vector delivery, Nat. Biotechnol., 25(11):1298-306 (Nov. 2007).
Lévy et al., Lentiviral vectors displaying modified measles virus gp overcome pre-existing immunity in in vivo-like transduction of human T and B cells, Mol. Ther., 20(9):1699-712 (Sep. 2012).
Okamoto et al., Improved expression and reactivity of transduced tumor-specific TCRs in human lymphocytes by specific silencing of endogenous TCR, Cancer Res., 69(23):9003-11 (Dec. 2009).
Oliveira et al., Tracking genetically engineered lymphocytes long-term reveals the dynamics of T cell immunological memory, Science Trans. Med., 7(317):317ra198 (Dec. 2015).
Poljak, Structure, Production and structure of diabodies, Structure, 2(12):1121-3 (1994).
Provasi et al., Editing T cell specificity towards leukemia by zinc finger nucleases and lentiviral gene transfer, Nat. Med., 18(5):807-15 (May 2012).
Roe et al., DNA Isolation and Sequencing: Essential Techniques, Chichester, West Sussex: John Wiley & Sons (1996).
Ruggiero et al., High-resolution analysis of the human T-cell receptor repertoire, Nat. Commun., 6:8081 (Sep. 2015).
Sambrook et al., Molecular Cloning: a Laboratory Manual, Cold Harbor Laboratory, 2nd edition (1989).
Schmitt et al., Generation of higher affinity T cell receptors by antigen-driven differentiation of progenitor T cells in vitro, Nat. Biotechnol., 35(12):1188-1195 (Dec. 2017).
Smith et al., Changing the peptide specificity of a human T-cell receptor by directed evolution, Nat. Commun., 5:5223 (Nov. 2014).
Sommermeyer et al., Minimal amino acid exchange in human TCR constant regions fosters improved function of TCR gene-modified T cells, J. Immunol., 184(11):6223-31 (Jun. 2010).
Tatusova et al., Blast 2 Sequences, a new tool for comparing protein and nucleotide sequences, FEMS Microbiol. Lett., 174(2):247-50 (1999).
Tatusova et al., Erratum to "Blast 2 Sequences, a new tool for comparing protein and nucleotide sequences", FEMS Microbiol. Lett., 177:187-8 (1999).
Tyler et al., WT1-specific T-cell responses in high-risk multiple myeloma patients undergoing allogeneic T cell-depleted hematopoietic stem cell transplantation and donor lymphocyte infusions, Blood, 121(2):308-17 (Jan. 2013).
Yang et al., A tumor suppressor and oncogene: the WT1 story, Leukemia, 21(5):868-76 (May 2007).
Smithgall et al., Identification of a novel WT1 HLA A*0201-restricted CTL epitope using whole gene in vitro priming, Blood (ASH Annual Meeting Abstracts), Nov. 16, 2001, vol. 98, 11 abstract 121a.
Celis et al., Identification of potential CTL epitopes of tumor-assocated antigen MAGE-1 for five common HLA-A alleles, Molecular Immunology, vol. 31, Dec. 8, 1994, pp. 1423 to 1430.
Dao et al., An immunogenic WT1-derived peptide that induces T cell response in the context of HLA-A*02:01 and HLA-A*24:02 molecules, Oncoimmunology, 6(2):e1252895 (Dec. 2016).
Rezvani et al., T-cell responses directed against multiple HLA-A*0201-restricted epitopes derived from Wilms' tumor 1 protein in patients with leukemia and healthy donors: identification, quantification, and characterization, Clin. Cancer Res., 11(24 Pt. 1):8799-807 (Dec. 2005).
Written Opinion and Search Report from Singapore Application No. 11201909864T dated Feb. 24, 2021.
Coico et al., Biology of the T Lymphocyte, Chapter 8, pp. 101-112, "Biology of the T Lymphocyte" in: Immunology: A Short Course, Fifth Edition, Hoboken, New Jersey: John Wiley & Sons, Inc. (2003).

| Donor | Peptide | Sequence |
|---|---|---|
| HD1 | 40 | AAQWAPVLDFAPPGA |
| | 41 | APVLDFAPPGASAYG |
| HD2 | 54 | QCLSAFTVHFSGQFT |
| | 77 | EDPMGQQGSLGEQQY |
| | 90 | SQLECMTWNQMNLGA |
| HD3 | 40 | AAQWAPVLDFAPPGA |
| | 41 | APVLDFAPPGASAYG |
| | Specific Nonamer | VLDFAPPGA |
| HD4 | 17 | TCVPEPASQHTLRSG |
| | 18 | EPASQHTLRSGPGCL |
| | 99 | HSTGYESDNHTTPIL |
| | 100 | YESDNHTTPILCGAQ |
| HD5 | 101 | NHTTPILCGAQYRIH |
| HD6 | Specific Nonamer | VLDFAPPGA |
| HD7 | 40 | AAQWAPVLDFAPPGA |
| | 41 | APVLDFAPPGASAYG |
| | 91 | CMTWNQMNLGATLKG |
| | 92 | NQMNLGATLKGVAAG |
| HD8 | 24 | DPGGIWAKLGAAEAS |
| HD9 | 101 | NHTTPILCGAQYRIH |
| | 125 | KRHQRRHTGVKPFQC |
| | 137 | PSCQKKFARSDELVR |
| HD10 | Specific Nonamer | VLDFAPPGA |

WT1-specific T cells+
AML HLA-B35*02 blasts

WT1-specific T cells+
AML unrelated blasts

E:T=10:1

Dominant clonotypes:

<u>α-chain</u>
**TRAV30*01-TRAJ20*01**
CDR3: CGTAWINDYKLSF

<u>β-chain</u>
**TRBV12-4*01- TRBD2*01 -TRBJ1-5*01**
CDR3: CASRKTGGYSNQPQHF

Dominant clonotypes:

α-chain
TRAV8-4*01-TRAJ22*01
CDR3: CAVRLSGSARQLTF

TRAV38-2/DV8*01-TRAJ47*01
CDR3: CAYRSLKYGNKLVF

β-chain
TRBV11-2*01- TRBD2*02-TRBJ2-7*01
CDR3: CASSLLGDEQYF

TRBV7-2- TRBD1*01- TRBJ2-7*01
CDR3: CASSLVALQGAGEQYF

Dominant clonotypes:

α-chain
TRAV12-1*01-TRAJ23*01
CDR3: CVVNLLSNQGGKLIF

β-chain
TRBV4-3*01- TRBD2- TRBJ1-4*01
CDR3: CASSQDYLVSNEKLFF

Dominant clonotypes:

<u>α-chain (peptide 17)</u>
TRAV17*01-TRAJ29*01
CDR3: CATDAYSGNTPLVF
<u>α-chain (peptide 99-100)</u>
TRAV21*01-TRAJ23*01
CDR3: CAVRAEIYNQGGKLIF <u>β-chain (peptide 17)</u>
TRBV6-1*01- TRBD1*01-TRBJ1-1*01
CDR3: CASRAAGLDTEAFF
<u>β-chain (peptide 99-100)</u>
TRBV6-6*01- TRBD1/TRBD2- TRBJ2-7*01
CDR3: CASTQTPYEQYF
TRBV12-3*01- TRBD2*02- TRBJ1-2*01
CDR3: CASSTVGGEDYGYTF Dominant clonotypes:

α-chain
TRAV13-1*02-TRAJ28*01
CDR3: CAASMAGAGSYQLTF

β-chain
TRBV10-3*01- TRBD1*01-TRBJ2-7*01
CDR3: CAISVGQGALYEQYF

TRBV9*01- TRBD1*01- TRBJ1-2*01
CDR3: CASSVARDRRNYGYTF

Dominant clonotypes:

α-chain
TRAV29/DV5*01-TRA31*01
CDR3: CAANNARLMF

TRAV29/DV5*01-TRAJ49*01
CDR3: CAASATGNQFYF

β-chain
TRBV12-3*01 - TRBD1*01 -TRBJ2-1*01
CDR3: CASSDTRAREQFF

TRBV5-1*01 - TRBD1*01 -TRBJ2-2*01
CDR3: CASSPGQHGELFF

FIG. 6G

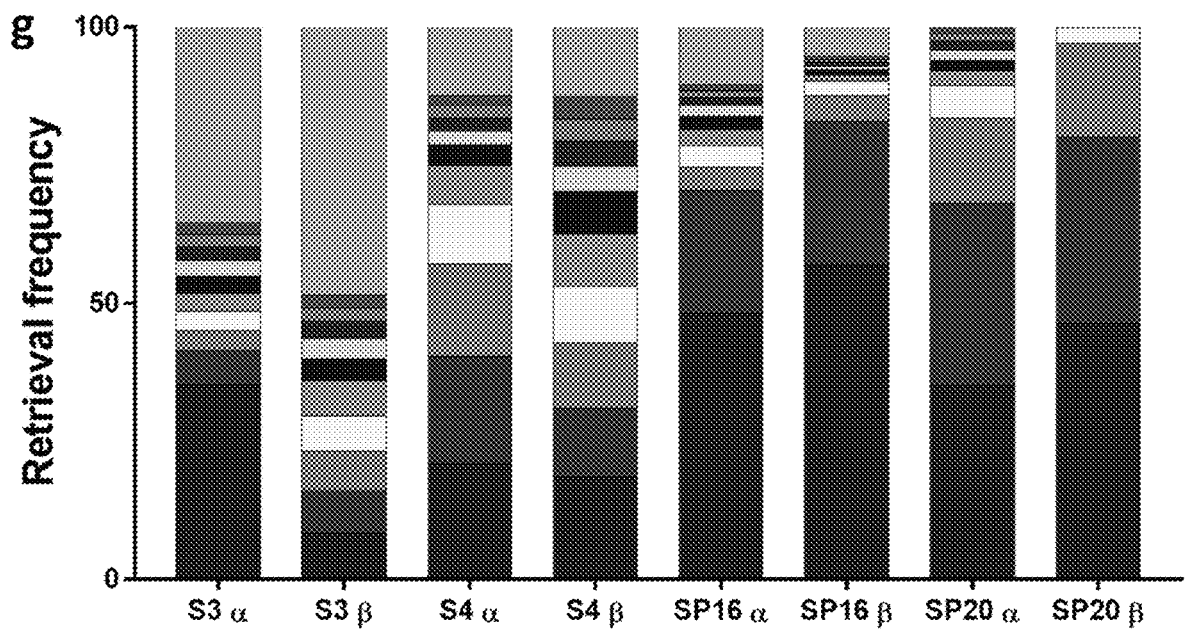

Dominant clonotypes:
α-chain (overlapping portion of peptide 40 and 41 )
TRAV5*01-TRAJ34*01
CDR3: CAERLNTDKLIF

TRAV17*01 -TRAJ12*01
CDR3: CATDGDSSYKLIF

α-chain (overlapping portion of peptide 91 and 92)
TRAV22*01-TRAJ24*02
CDR3: CAVEATDSWGKLQF

TRAV13-1*02 -TRAJ50*01
CDR3: CAVRTSYDKVIF

β-chain (overlapping portion of peptide 40 and 41)
TRBV20-1*01 - TRBD1*01- TRBJ1-3*01
CDR3: CSARDSVSGNTIYF

TRBV20-1*01 - TRBD1*01- TRBJ1-2*01
CDR3: CSARDVLTGDYGYTF

β-chain (overlapping portion of peptide 91 and 92)
TRBV29-1*01 - TRBD2*02 - TRBJ2-1*01
CDR3: CSVGGSGSYNEQFF

TRBV12-4*01 - TRBD2- TRBJ2-5*01
CDR3: CASSLGLSISQETQYF

Dominant clonotypes:

α-chain
TRAV41*01-TRAJ47*01
CDR3: CAVTVGNKLVF

β-chain
TRBV6-1*01- TRBD1*01-TRBJ2-1*01
CDR3: CASRGWREQFF

Dominant clonotypes:

α-chain (peptide 101)
TRAV41*01-TRAJ34*01
CDR3: CAARSYNTDKLIF
α-chain (peptide 125)
TRAV29/DV5*01-TRAJ31*01
CDR3: CAASYNNARLMF
α-chain (peptide 137)
TRAV29/DV5*01-TRAJ31*01
CDR3: CAASYNNARLMF β-chain (peptide 101)
TRBV5-8*01- TRBD1*01-TRBJ2-5*01
CDR3: CASSWGYQETQYF
β-chain (peptide 125)
TRBV18*01- TRBD1*01- TRBJ1-2*01
CDR3: CASSPTGGEYYGYTF
β-chain (peptide 137)
TRBV6-5*01- TRBD1*01- TRBJ1-6*01
CDR3: CASSSYPLRTGRYNSYNSPLHF Dominant clonotypes:

α-chain
TRAV29/DV5*01-TRAJ30*01
CDR3: CAASGGRDDKIIF

β-chain
TRBV6-5*01- TRBD1*01- TRBJ2-3*01
CDR3: CASSYSRTESTDTQYF

SEQUENCE LISTING

```
<160> NUMBER OF SEQ ID NOS: 299

<210> SEQ ID NO 1
<211> LENGTH: 5
<212> TYPE: PRT
<213> ORGANISM: Artificial Sequence
<220> FEATURE:
<223> OTHER INFORMATION: TCR (T-cell receptor) amino acid sequence,
      Donor HD1

<400> SEQUENCE: 1

Lys Ala Leu Tyr Ser
1               5

<210> SEQ ID NO 2
<211> LENGTH: 7
<212> TYPE: PRT
<213> ORGANISM: Artificial Sequence
<220> FEATURE:
<223> OTHER INFORMATION: TCR amino acid sequence, Donor HD1

<400> SEQUENCE: 2

Leu Leu Lys Gly Gly Glu Gln
1               5

<210> SEQ ID NO 3
<211> LENGTH: 13
<212> TYPE: PRT
<213> ORGANISM: Artificial Sequence
<220> FEATURE:
<223> OTHER INFORMATION: TCR amino acid sequence, Donor HD1

<400> SEQUENCE: 3

Cys Gly Thr Ala Trp Ile Asn Asp Tyr Lys Leu Ser Phe
1               5                   10
```

```
<210> SEQ ID NO 4
<211> LENGTH: 132
<212> TYPE: PRT
<213> ORGANISM: Artificial Sequence
<220> FEATURE:
<223> OTHER INFORMATION: TCR amino acid sequence, Donor HD1

<400> SEQUENCE: 4
```

Met Glu Thr Leu Leu Lys Val Leu Ser Gly Thr Leu Leu Trp Gln Leu
1               5                   10                  15

Thr Trp Val Arg Ser Gln Gln Pro Val Gln Ser Pro Gln Ala Val Ile
            20                  25                  30

Leu Arg Glu Gly Glu Asp Ala Val Ile Asn Cys Ser Ser Ser Lys Ala
        35                  40                  45

Leu Tyr Ser Val His Trp Tyr Arg Gln Lys His Gly Glu Ala Pro Val
    50                  55                  60

Phe Leu Met Ile Leu Leu Lys Gly Gly Glu Gln Lys Gly His Glu Lys
65                  70                  75                  80

Ile Ser Ala Ser Phe Asn Glu Lys Lys Gln Gln Ser Ser Leu Tyr Leu
                85                  90                  95

Thr Ala Ser Gln Leu Ser Tyr Ser Gly Thr Tyr Phe Cys Gly Thr Ala
            100                 105                 110

Trp Ile Asn Asp Tyr Lys Leu Ser Phe Gly Ala Gly Thr Thr Val Thr
        115                 120                 125

Val Arg Ala Asn
    130

```
<210> SEQ ID NO 5
<211> LENGTH: 272
<212> TYPE: PRT
<213> ORGANISM: Artificial Sequence
<220> FEATURE:
<223> OTHER INFORMATION: TCR amino acid sequence, Donor HD1

<400> SEQUENCE: 5
```

Met Glu Thr Leu Leu Lys Val Leu Ser Gly Thr Leu Leu Trp Gln Leu
1               5                   10                  15

Thr Trp Val Arg Ser Gln Gln Pro Val Gln Ser Pro Gln Ala Val Ile
            20                  25                  30

Leu Arg Glu Gly Glu Asp Ala Val Ile Asn Cys Ser Ser Ser Lys Ala
        35                  40                  45

Leu Tyr Ser Val His Trp Tyr Arg Gln Lys His Gly Glu Ala Pro Val
    50                  55                  60

Phe Leu Met Ile Leu Leu Lys Gly Gly Glu Gln Lys Gly His Glu Lys
65                  70                  75                  80

Ile Ser Ala Ser Phe Asn Glu Lys Lys Gln Gln Ser Ser Leu Tyr Leu
                85                  90                  95

Thr Ala Ser Gln Leu Ser Tyr Ser Gly Thr Tyr Phe Cys Gly Thr Ala
            100                 105                 110

Trp Ile Asn Asp Tyr Lys Leu Ser Phe Gly Ala Gly Thr Thr Val Thr
        115                 120                 125

Val Arg Ala Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

```
Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 6
<211> LENGTH: 5
<212> TYPE: PRT
<213> ORGANISM: Artificial Sequence
<220> FEATURE:
<223> OTHER INFORMATION: TCR amino acid sequence, Donor HD1

<400> SEQUENCE: 6

Ser Gly His Asp Tyr
1               5

<210> SEQ ID NO 7
<211> LENGTH: 6
<212> TYPE: PRT
<213> ORGANISM: Artificial Sequence
<220> FEATURE:
<223> OTHER INFORMATION: TCR amino acid sequence, Donor HD1

<400> SEQUENCE: 7

Phe Asn Asn Asn Val Pro
1               5

<210> SEQ ID NO 8
<211> LENGTH: 16
<212> TYPE: PRT
<213> ORGANISM: Artificial Sequence
<220> FEATURE:
<223> OTHER INFORMATION: TCR amino acid sequence, Donor HD1

<400> SEQUENCE: 8

Cys Ala Ser Arg Lys Thr Gly Gly Tyr Ser Asn Gln Pro Gln His Phe
1               5                   10                  15

<210> SEQ ID NO 9
<211> LENGTH: 136
<212> TYPE: PRT
<213> ORGANISM: Artificial Sequence
<220> FEATURE:
<223> OTHER INFORMATION: TCR amino acid sequence, Donor HD1

<400> SEQUENCE: 9

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60
```

-continued

```
Leu Ile Tyr Phe Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
                100                 105                 110

Ser Arg Lys Thr Gly Gly Tyr Ser Asn Gln Pro Gln His Phe Gly Asp
                115                 120                 125

Gly Thr Arg Leu Ser Ile Leu Glu
            130                 135

<210> SEQ ID NO 10
<211> LENGTH: 312
<212> TYPE: PRT
<213> ORGANISM: Artificial Sequence
<220> FEATURE:
<223> OTHER INFORMATION: TCR amino acid sequence, Donor HD1

<400> SEQUENCE: 10

Met Gly Ser Trp Thr Leu Cys Cys Val Ser Leu Cys Ile Leu Val Ala
  1               5                  10                  15

Lys His Thr Asp Ala Gly Val Ile Gln Ser Pro Arg His Glu Val Thr
                 20                  25                  30

Glu Met Gly Gln Glu Val Thr Leu Arg Cys Lys Pro Ile Ser Gly His
             35                  40                  45

Asp Tyr Leu Phe Trp Tyr Arg Gln Thr Met Met Arg Gly Leu Glu Leu
         50                  55                  60

Leu Ile Tyr Phe Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
                100                 105                 110

Ser Arg Lys Thr Gly Gly Tyr Ser Asn Gln Pro Gln His Phe Gly Asp
                115                 120                 125

Gly Thr Arg Leu Ser Ile Leu Glu Asp Leu Asn Lys Val Phe Pro Pro
            130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
                180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
        210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
                260                 265                 270

Tyr Gln Gln Gly Val Leu Ser Ala Thr Ile Leu Tyr Glu Ile Leu Leu
            275                 280                 285
```

```
Gly Lys Ala Thr Leu Tyr Ala Val Leu Val Ser Ala Leu Val Leu Met
            290                 295                 300

Ala Met Val Lys Arg Lys Asp Phe
305                 310

<210> SEQ ID NO 11
<211> LENGTH: 314
<212> TYPE: PRT
<213> ORGANISM: Artificial Sequence
<220> FEATURE:
<223> OTHER INFORMATION: TCR amino acid sequence, Donor HD1

<400> SEQUENCE: 11

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Lys Thr Gly Gly Tyr Ser Asn Gln Pro Gln His Phe Gly Asp
        115                 120                 125

Gly Thr Arg Leu Ser Ile Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 12
<211> LENGTH: 6
```

<212> TYPE: PRT
<213> ORGANISM: Artificial Sequence
<220> FEATURE:
<223> OTHER INFORMATION: TCR amino acid sequence, Donor HD2

<400> SEQUENCE: 12

Ser Ser Val Pro Pro Tyr
1               5

<210> SEQ ID NO 13
<211> LENGTH: 8
<212> TYPE: PRT
<213> ORGANISM: Artificial Sequence
<220> FEATURE:
<223> OTHER INFORMATION: TCR amino acid sequence, Donor HD2

<400> SEQUENCE: 13

Tyr Thr Ser Ala Ala Thr Leu Val
1               5

<210> SEQ ID NO 14
<211> LENGTH: 14
<212> TYPE: PRT
<213> ORGANISM: Artificial Sequence
<220> FEATURE:
<223> OTHER INFORMATION: TCR amino acid sequence, Donor HD2

<400> SEQUENCE: 14

Cys Ala Val Arg Leu Ser Gly Ser Ala Arg Gln Leu Thr Phe
1               5                   10

<210> SEQ ID NO 15
<211> LENGTH: 134
<212> TYPE: PRT
<213> ORGANISM: Artificial Sequence
<220> FEATURE:
<223> OTHER INFORMATION: TCR amino acid sequence, Donor HD2

<400> SEQUENCE: 15

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

Leu Leu Leu Lys Tyr Thr Ser Ala Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Arg Leu Ser Gly Ser Ala Arg Gln Leu Thr Phe Gly Ser Gly Thr Gln
        115                 120                 125

Leu Thr Val Leu Pro Asp
            130

<210> SEQ ID NO 16
<211> LENGTH: 274
<212> TYPE: PRT
<213> ORGANISM: Artificial Sequence
<220> FEATURE:

<223> OTHER INFORMATION: TCR amino acid sequence, Donor HD2

<400> SEQUENCE: 16

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

Leu Leu Leu Lys Tyr Thr Ser Ala Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Arg Leu Ser Gly Ser Ala Arg Gln Leu Thr Phe Gly Ser Gly Thr Gln
        115                 120                 125

Leu Thr Val Leu Pro Asp Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 17
<211> LENGTH: 7
<212> TYPE: PRT
<213> ORGANISM: Artificial Sequence
<220> FEATURE:
<223> OTHER INFORMATION: TCR amino acid sequence, Donor HD2

<400> SEQUENCE: 17

Thr Ser Glu Ser Asp Tyr Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: TCR amino acid sequence, Donor HD2

```
<400> SEQUENCE: 18

Gln Glu Ala Tyr Lys Gln Gln Asn
1               5

<210> SEQ ID NO 19
<211> LENGTH: 14
<212> TYPE: PRT
<213> ORGANISM: Artificial Sequence
<220> FEATURE:
<223> OTHER INFORMATION: TCR amino acid sequence, Donor HD2

<400> SEQUENCE: 19

Cys Ala Tyr Arg Ser Leu Lys Tyr Gly Asn Lys Leu Val Phe
1               5                   10

<210> SEQ ID NO 20
<211> LENGTH: 136
<212> TYPE: PRT
<213> ORGANISM: Artificial Sequence
<220> FEATURE:
<223> OTHER INFORMATION: TCR amino acid sequence, Donor HD2

<400> SEQUENCE: 20

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Ser Leu Lys Tyr Gly Asn Lys Leu Val Phe Gly Ala Gly
        115                 120                 125

Thr Ile Leu Arg Val Lys Ser Tyr
    130                 135

<210> SEQ ID NO 21
<211> LENGTH: 276
<212> TYPE: PRT
<213> ORGANISM: Artificial Sequence
<220> FEATURE:
<223> OTHER INFORMATION: TCR amino acid sequence, Donor HD2

<400> SEQUENCE: 21

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60
```

-continued

```
Met Ile Leu Val Ile Arg Gln Glu Ala Tyr Lys Gln Gln Asn Ala Thr
 65                  70                  75                  80

Glu Asn Arg Phe Ser Val Asn Phe Gln Lys Ala Ala Lys Ser Phe Ser
                 85                  90                  95

Leu Lys Ile Ser Asp Ser Gln Leu Gly Asp Ala Ala Met Tyr Phe Cys
            100                 105                 110

Ala Tyr Arg Ser Leu Lys Tyr Gly Asn Lys Leu Val Phe Gly Ala Gly
        115                 120                 125

Thr Ile Leu Arg Val Lys Ser Tyr Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 22
<211> LENGTH: 5
<212> TYPE: PRT
<213> ORGANISM: Artificial Sequence
<220> FEATURE:
<223> OTHER INFORMATION: TCR amino acid sequence, Donor HD2

<400> SEQUENCE: 22

Ser Gly His Ala Thr
1               5

<210> SEQ ID NO 23
<211> LENGTH: 6
<212> TYPE: PRT
<213> ORGANISM: Artificial Sequence
<220> FEATURE:
<223> OTHER INFORMATION: TCR amino acid sequence, Donor HD2

<400> SEQUENCE: 23

Phe Gln Asn Asn Gly Val
1               5

<210> SEQ ID NO 24
<211> LENGTH: 12
<212> TYPE: PRT
<213> ORGANISM: Artificial Sequence
<220> FEATURE:
<223> OTHER INFORMATION: TCR amino acid sequence, Donor HD2
```

<400> SEQUENCE: 24

Cys Ala Ser Ser Leu Leu Gly Asp Glu Gln Tyr Phe
1               5                   10

<210> SEQ ID NO 25
<211> LENGTH: 132
<212> TYPE: PRT
<213> ORGANISM: Artificial Sequence
<220> FEATURE:
<223> OTHER INFORMATION: TCR amino acid sequence, Donor HD2

<400> SEQUENCE: 25

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Leu Gly Asp Glu Gln Tyr Phe Gly Pro Gly Thr Arg Leu
        115                 120                 125

Thr Val Thr Glu
    130

<210> SEQ ID NO 26
<211> LENGTH: 308
<212> TYPE: PRT
<213> ORGANISM: Artificial Sequence
<220> FEATURE:
<223> OTHER INFORMATION: TCR amino acid sequence, Donor HD2

<400> SEQUENCE: 26

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Leu Gly Asp Glu Gln Tyr Phe Gly Pro Gly Thr Arg Leu
        115                 120                 125

Thr Val Thr Glu Asp Leu Asn Lys Val Phe Pro Pro Glu Val Ala Val
    130                 135                 140

```
Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 27
<211> LENGTH: 310
<212> TYPE: PRT
<213> ORGANISM: Artificial Sequence
<220> FEATURE:
<223> OTHER INFORMATION: TCR amino acid sequence, Donor HD2

<400> SEQUENCE: 27

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Leu Gly Asp Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190
```

```
Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
                275                 280                 285

Leu Tyr Ala Val Leu Val Ser Ala Leu Val Leu Met Ala Met Val Lys
        290                 295                 300

Arg Lys Asp Ser Arg Gly
305             310

<210> SEQ ID NO 28
<211> LENGTH: 5
<212> TYPE: PRT
<213> ORGANISM: Artificial Sequence
<220> FEATURE:
<223> OTHER INFORMATION: TCR amino acid sequence, Donor HD2

<400> SEQUENCE: 28

Ser Gly His Thr Ala
1               5

<210> SEQ ID NO 29
<211> LENGTH: 6
<212> TYPE: PRT
<213> ORGANISM: Artificial Sequence
<220> FEATURE:
<223> OTHER INFORMATION: TCR amino acid sequence, Donor HD2

<400> SEQUENCE: 29

Phe Gln Gly Asn Ser Ala
1               5

<210> SEQ ID NO 30
<211> LENGTH: 16
<212> TYPE: PRT
<213> ORGANISM: Artificial Sequence
<220> FEATURE:
<223> OTHER INFORMATION: TCR amino acid sequence, Donor HD2

<400> SEQUENCE: 30

Cys Ala Ser Ser Leu Val Ala Leu Gln Gly Ala Gly Glu Gln Tyr Phe
1               5                   10                  15

<210> SEQ ID NO 31
<211> LENGTH: 136
<212> TYPE: PRT
<213> ORGANISM: Artificial Sequence
<220> FEATURE:
<223> OTHER INFORMATION: TCR amino acid sequence, Donor HD2

<400> SEQUENCE: 31

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30
```

Glu Lys Gly Lys Asp Val Glu Leu Arg Cys Asp Pro Ile Ser Gly His
            35                  40                  45

Thr Ala Leu Tyr Trp Tyr Arg Gln Ser Leu Gly Gln Gly Leu Glu Phe
 50                  55                  60

Leu Ile Tyr Phe Gln Gly Asn Ser Ala Pro Asp Lys Ser Gly Leu Pro
 65                  70                  75                  80

Ser Asp Arg Phe Ser Ala Glu Arg Thr Gly Gly Ser Val Ser Thr Leu
            85                  90                  95

Thr Ile Gln Arg Thr Gln Gln Glu Asp Ser Ala Val Tyr Leu Cys Ala
            100                 105                 110

Ser Ser Leu Val Ala Leu Gln Gly Ala Gly Glu Gln Tyr Phe Gly Pro
            115                 120                 125

Gly Thr Arg Leu Thr Val Thr Glu
            130                 135

<210> SEQ ID NO 32
<211> LENGTH: 312
<212> TYPE: PRT
<213> ORGANISM: Artificial Sequence
<220> FEATURE:
<223> OTHER INFORMATION: TCR amino acid sequence, Donor HD2

<400> SEQUENCE: 32

Met Gly Thr Arg Leu Leu Phe Trp Val Ala Phe Cys Leu Leu Gly Ala
 1               5                  10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
            35                  40                  45

Thr Ala Leu Tyr Trp Tyr Arg Gln Ser Leu Gly Gln Gly Leu Glu Phe
 50                  55                  60

Leu Ile Tyr Phe Gln Gly Asn Ser Ala Pro Asp Lys Ser Gly Leu Pro
 65                  70                  75                  80

Ser Asp Arg Phe Ser Ala Glu Arg Thr Gly Gly Ser Val Ser Thr Leu
            85                  90                  95

Thr Ile Gln Arg Thr Gln Gln Glu Asp Ser Ala Val Tyr Leu Cys Ala
            100                 105                 110

Ser Ser Leu Val Ala Leu Gln Gly Ala Gly Glu Gln Tyr Phe Gly Pro
            115                 120                 125

Gly Thr Arg Leu Thr Val Thr Glu Asp Leu Asn Lys Val Phe Pro Pro
            130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
            165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
            210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

```
Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Phe
305                 310

<210> SEQ ID NO 33
<211> LENGTH: 314
<212> TYPE: PRT
<213> ORGANISM: Artificial Sequence
<220> FEATURE:
<223> OTHER INFORMATION: TCR amino acid sequence, Donor HD2

<400> SEQUENCE: 33

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Val Ala Leu Gln Gly Ala Gly Glu Gln Tyr Phe Gly Pro
        115                 120                 125

Gly Thr Arg Leu Thr Val Thr Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300
```

```
Ala Met Val Lys Arg Lys Asp Ser Arg Gly
305                 310
```

<210> SEQ ID NO 34
<211> LENGTH: 6
<212> TYPE: PRT
<213> ORGANISM: Artificial Sequence
<220> FEATURE:
<223> OTHER INFORMATION: TCR amino acid sequence, Donor HD3

<400> SEQUENCE: 34

```
Asn Ser Ala Ser Gln Ser
1               5
```

<210> SEQ ID NO 35
<211> LENGTH: 6
<212> TYPE: PRT
<213> ORGANISM: Artificial Sequence
<220> FEATURE:
<223> OTHER INFORMATION: TCR amino acid sequence, Donor HD3

<400> SEQUENCE: 35

```
Val Tyr Ser Ser Gly Asn
1               5
```

<210> SEQ ID NO 36
<211> LENGTH: 15
<212> TYPE: PRT
<213> ORGANISM: Artificial Sequence
<220> FEATURE:
<223> OTHER INFORMATION: TCR amino acid sequence, Donor HD3

<400> SEQUENCE: 36

```
Cys Val Val Asn Leu Leu Ser Asn Gln Gly Gly Lys Leu Ile Phe
1               5                   10                  15
```

<210> SEQ ID NO 37
<211> LENGTH: 134
<212> TYPE: PRT
<213> ORGANISM: Artificial Sequence
<220> FEATURE:
<223> OTHER INFORMATION: TCR amino acid sequence, Donor HD3

<400> SEQUENCE: 37

```
Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
                20                  25                  30

Asn Val Pro Glu Gly Ala Thr Val Ala Phe Asn Cys Thr Tyr Ser Asn
            35                  40                  45

Ser Ala Ser Gln Ser Phe Phe Trp Tyr Arg Gln Asp Cys Arg Lys Glu
        50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Leu Leu Ser Asn Gln Gly Gly Lys Leu Ile Phe Gly Gln Gly Thr Glu
        115                 120                 125

Leu Ser Val Lys Pro Asn
        130
```

```
<210> SEQ ID NO 38
<211> LENGTH: 274
<212> TYPE: PRT
<213> ORGANISM: Artificial Sequence
<220> FEATURE:
<223> OTHER INFORMATION: TCR amino acid sequence, Donor HD3

<400> SEQUENCE: 38
```

Met Ile Ser Leu Arg Val Leu Val Ile Leu Trp Leu Gln Leu Ser
 1               5                  10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Leu Leu Ser Asn Gln Gly Gly Lys Leu Ile Phe Gly Gln Gly Thr Glu
        115                 120                 125

Leu Ser Val Lys Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

```
<210> SEQ ID NO 39
<211> LENGTH: 5
<212> TYPE: PRT
<213> ORGANISM: Artificial Sequence
<220> FEATURE:
<223> OTHER INFORMATION: TCR amino acid sequence, Donor HD3

<400> SEQUENCE: 39
```

Leu Gly His Asn Ala
 1               5

```
<210> SEQ ID NO 40
```

```
<211> LENGTH: 6
<212> TYPE: PRT
<213> ORGANISM: Artificial Sequence
<220> FEATURE:
<223> OTHER INFORMATION: TCR amino acid sequence, Donor HD3

<400> SEQUENCE: 40

Tyr Ser Leu Glu Glu Arg
1               5

<210> SEQ ID NO 41
<211> LENGTH: 16
<212> TYPE: PRT
<213> ORGANISM: Artificial Sequence
<220> FEATURE:
<223> OTHER INFORMATION: TCR amino acid sequence, Donor HD3

<400> SEQUENCE: 41

Cys Ala Ser Ser Gln Asp Tyr Leu Val Ser Asn Glu Lys Leu Phe Phe
1               5                   10                  15

<210> SEQ ID NO 42
<211> LENGTH: 138
<212> TYPE: PRT
<213> ORGANISM: Artificial Sequence
<220> FEATURE:
<223> OTHER INFORMATION: TCR amino acid sequence, Donor HD3

<400> SEQUENCE: 42

Met Gly Cys Arg Leu Leu Cys Cys Ala Val Leu Cys Leu Leu Gly Ala
1               5                   10                  15

Gly Glu Leu Val Pro Met Glu Thr Gly Val Thr Gln Thr Pro Arg His
            20                  25                  30

Leu Val Met Gly Met Thr Asn Lys Lys Ser Leu Lys Cys Glu Gln His
        35                  40                  45

Leu Gly His Asn Ala Met Tyr Trp Tyr Lys Gln Ser Ala Lys Lys Pro
    50                  55                  60

Leu Glu Leu Met Phe Val Tyr Ser Leu Glu Glu Arg Val Glu Asn Asn
65                  70                  75                  80

Ser Val Pro Ser Arg Phe Ser Pro Glu Cys Pro Asn Ser Ser His Leu
                85                  90                  95

Phe Leu His Leu His Thr Leu Gln Pro Glu Asp Ser Ala Leu Tyr Leu
            100                 105                 110

Cys Ala Ser Ser Gln Asp Tyr Leu Val Ser Asn Glu Lys Leu Phe Phe
        115                 120                 125

Gly Ser Gly Thr Gln Leu Ser Val Leu Glu
    130                 135

<210> SEQ ID NO 43
<211> LENGTH: 314
<212> TYPE: PRT
<213> ORGANISM: Artificial Sequence
<220> FEATURE:
<223> OTHER INFORMATION: TCR amino acid sequence, Donor HD3

<400> SEQUENCE: 43

Met Gly Cys Arg Leu Leu Cys Cys Ala Val Leu Cys Leu Leu Gly Ala
1               5                   10                  15

Gly Glu Leu Val Pro Met Glu Thr Gly Val Thr Gln Thr Pro Arg His
            20                  25                  30

Leu Val Met Gly Met Thr Asn Lys Lys Ser Leu Lys Cys Glu Gln His
        35                  40                  45
```

-continued

Leu Gly His Asn Ala Met Tyr Trp Tyr Lys Gln Ser Ala Lys Lys Pro
     50                  55                  60

Leu Glu Leu Met Phe Val Tyr Ser Leu Glu Glu Arg Val Glu Asn Asn
 65                  70                  75                  80

Ser Val Pro Ser Arg Phe Ser Pro Glu Cys Pro Asn Ser Ser His Leu
                 85                  90                  95

Phe Leu His Leu His Thr Leu Gln Pro Glu Asp Ser Ala Leu Tyr Leu
                100                 105                 110

Cys Ala Ser Ser Gln Asp Tyr Leu Val Ser Asn Glu Lys Leu Phe Phe
            115                 120                 125

Gly Ser Gly Thr Gln Leu Ser Val Leu Glu Asp Leu Asn Lys Val Phe
            130                 135                 140

Pro Pro Glu Val Ala Val Phe Glu Pro Ser Glu Ala Glu Ile Ser His
145                 150                 155                 160

Thr Gln Lys Ala Thr Leu Val Cys Leu Ala Thr Gly Phe Phe Pro Asp
                165                 170                 175

His Val Glu Leu Ser Trp Trp Val Asn Gly Lys Glu Val His Ser Gly
                180                 185                 190

Val Ser Thr Asp Pro Gln Pro Leu Lys Glu Gln Pro Ala Leu Asn Asp
            195                 200                 205

Ser Arg Tyr Cys Leu Ser Ser Arg Leu Arg Val Ser Ala Thr Phe Trp
        210                 215                 220

Gln Asn Pro Arg Asn His Phe Arg Cys Gln Val Gln Phe Tyr Gly Leu
225                 230                 235                 240

Ser Glu Asn Asp Glu Trp Thr Gln Asp Arg Ala Lys Pro Val Thr Gln
                245                 250                 255

Ile Val Ser Ala Glu Ala Trp Gly Arg Ala Asp Cys Gly Phe Thr Ser
            260                 265                 270

Val Ser Tyr Gln Gln Gly Val Leu Ser Ala Thr Ile Leu Tyr Glu Ile
        275                 280                 285

Leu Leu Gly Lys Ala Thr Leu Tyr Ala Val Leu Val Ser Ala Leu Val
        290                 295                 300

Leu Met Ala Met Val Lys Arg Lys Asp Phe
305                 310

<210> SEQ ID NO 44
<211> LENGTH: 316
<212> TYPE: PRT
<213> ORGANISM: Artificial Sequence
<220> FEATURE:
<223> OTHER INFORMATION: TCR amino acid sequence, Donor HD3

<400> SEQUENCE: 44

Met Gly Cys Arg Leu Leu Cys Cys Ala Val Leu Cys Leu Leu Gly Ala
 1               5                  10                  15

Gly Glu Leu Val Pro Met Glu Thr Gly Val Thr Gln Thr Pro Arg His
                 20                  25                  30

Leu Val Met Gly Met Thr Asn Lys Lys Ser Leu Lys Cys Glu Gln His
             35                  40                  45

Leu Gly His Asn Ala Met Tyr Trp Tyr Lys Gln Ser Ala Lys Lys Pro
     50                  55                  60

Leu Glu Leu Met Phe Val Tyr Ser Leu Glu Glu Arg Val Glu Asn Asn
 65                  70                  75                  80

Ser Val Pro Ser Arg Phe Ser Pro Glu Cys Pro Asn Ser Ser His Leu
                 85                  90                  95

```
        Phe Leu His Leu His Thr Leu Gln Pro Glu Asp Ser Ala Leu Tyr Leu
                        100                 105                 110

Cys Ala Ser Ser Gln Asp Tyr Leu Val Ser Asn Glu Lys Leu Phe Phe
                        115                 120                 125

Gly Ser Gly Thr Gln Leu Ser Val Leu Glu Asp Leu Lys Asn Val Phe
                        130                 135                 140

Pro Pro Glu Val Ala Val Phe Glu Pro Ser Glu Ala Glu Ile Ser His
        145                 150                 155                 160

Thr Gln Lys Ala Thr Leu Val Cys Leu Ala Thr Gly Phe Tyr Pro Asp
                        165                 170                 175

His Val Glu Leu Ser Trp Trp Val Asn Gly Lys Glu Val His Ser Gly
                        180                 185                 190

Val Ser Thr Asp Pro Gln Pro Leu Lys Glu Gln Pro Ala Leu Asn Asp
                        195                 200                 205

Ser Arg Tyr Cys Leu Ser Ser Arg Leu Arg Val Ser Ala Thr Phe Trp
                        210                 215                 220

Gln Asn Pro Arg Asn His Phe Arg Cys Gln Val Gln Phe Tyr Gly Leu
        225                 230                 235                 240

Ser Glu Asn Asp Glu Trp Thr Gln Asp Arg Ala Lys Pro Val Thr Gln
                        245                 250                 255

Ile Val Ser Ala Glu Ala Trp Gly Arg Ala Asp Cys Gly Phe Thr Ser
                        260                 265                 270

Glu Ser Tyr Gln Gln Gly Val Leu Ser Ala Thr Ile Leu Tyr Glu Ile
                        275                 280                 285

Leu Leu Gly Lys Ala Thr Leu Tyr Ala Val Leu Val Ser Ala Leu Val
                        290                 295                 300

Leu Met Ala Met Val Lys Arg Lys Asp Ser Arg Gly
        305                 310                 315

<210> SEQ ID NO 45
<211> LENGTH: 5
<212> TYPE: PRT
<213> ORGANISM: Artificial Sequence
<220> FEATURE:
<223> OTHER INFORMATION: TCR amino acid sequence, Donor HD4

<400> SEQUENCE: 45

Thr Ser Ile Asn Asn
1               5

<210> SEQ ID NO 46
<211> LENGTH: 7
<212> TYPE: PRT
<213> ORGANISM: Artificial Sequence
<220> FEATURE:
<223> OTHER INFORMATION: TCR amino acid sequence, Donor HD4

<400> SEQUENCE: 46

Ile Arg Ser Asn Glu Arg Glu
1               5

<210> SEQ ID NO 47
<211> LENGTH: 14
<212> TYPE: PRT
<213> ORGANISM: Artificial Sequence
<220> FEATURE:
<223> OTHER INFORMATION: TCR amino acid sequence, Donor HD4
```

```
<400> SEQUENCE: 47

Cys Ala Thr Asp Ala Tyr Ser Gly Asn Thr Pro Leu Val Phe
1               5                   10

<210> SEQ ID NO 48
<211> LENGTH: 133
<212> TYPE: PRT
<213> ORGANISM: Artificial Sequence
<220> FEATURE:
<223> OTHER INFORMATION: TCR amino acid sequence, Donor HD4

<400> SEQUENCE: 48

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asp
            100                 105                 110

Ala Tyr Ser Gly Asn Thr Pro Leu Val Phe Gly Lys Gly Thr Arg Leu
        115                 120                 125

Ser Val Ile Ala Asn
    130

<210> SEQ ID NO 49
<211> LENGTH: 273
<212> TYPE: PRT
<213> ORGANISM: Artificial Sequence
<220> FEATURE:
<223> OTHER INFORMATION: TCR amino acid sequence, Donor HD4

<400> SEQUENCE: 49

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asp
            100                 105                 110

Ala Tyr Ser Gly Asn Thr Pro Leu Val Phe Gly Lys Gly Thr Arg Leu
        115                 120                 125

Ser Val Ile Ala Asn Ile Gln Asn Pro Asp Pro Ala Val Tyr Gln Leu
    130                 135                 140
```

```
Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser
```

```
<210> SEQ ID NO 50
<211> LENGTH: 6
<212> TYPE: PRT
<213> ORGANISM: Artificial Sequence
<220> FEATURE:
<223> OTHER INFORMATION: TCR amino acid sequence, Donor HD4

<400> SEQUENCE: 50

Asp Ser Ala Ile Tyr Asn
1               5

<210> SEQ ID NO 51
<211> LENGTH: 7
<212> TYPE: PRT
<213> ORGANISM: Artificial Sequence
<220> FEATURE:
<223> OTHER INFORMATION: TCR amino acid sequence, Donor HD4

<400> SEQUENCE: 51

Ile Gln Ser Ser Gln Arg Glu
1               5

<210> SEQ ID NO 52
<211> LENGTH: 16
<212> TYPE: PRT
<213> ORGANISM: Artificial Sequence
<220> FEATURE:
<223> OTHER INFORMATION: TCR amino acid sequence, Donor HD4

<400> SEQUENCE: 52

Cys Ala Val Arg Ala Glu Ile Tyr Asn Gln Gly Gly Lys Leu Ile Phe
1               5                   10                  15

<210> SEQ ID NO 53
<211> LENGTH: 135
<212> TYPE: PRT
<213> ORGANISM: Artificial Sequence
<220> FEATURE:
<223> OTHER INFORMATION: TCR amino acid sequence, Donor HD4

<400> SEQUENCE: 53

Met Glu Thr Leu Leu Gly Leu Leu Ile Leu Trp Leu Gln Leu Gln Trp
1               5                   10                  15
```

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
                100                 105                 110

Ala Glu Ile Tyr Asn Gln Gly Gly Lys Leu Ile Phe Gly Gln Gly Thr
                115                 120                 125

Glu Leu Ser Val Lys Pro Asn
            130                 135

<210> SEQ ID NO 54
<211> LENGTH: 275
<212> TYPE: PRT
<213> ORGANISM: Artificial Sequence
<220> FEATURE:
<223> OTHER INFORMATION: TCR amino acid sequence, Donor HD4

<400> SEQUENCE: 54

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
                100                 105                 110

Ala Glu Ile Tyr Asn Gln Gly Gly Lys Leu Ile Phe Gly Gln Gly Thr
                115                 120                 125

Glu Leu Ser Val Lys Pro Asn Ile Gln Asn Pro Asp Pro Ala Val Tyr
            130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
                180                 185                 190

Ser Asn Ser Ala Val Ala Trp Ser Asn Lys Ser Asp Phe Ala Cys Ala
                195                 200                 205

Asn Ala Phe Asn Asn Ser Ile Ile Pro Glu Asp Thr Phe Phe Pro Ser
            210                 215                 220

Pro Glu Ser Ser Cys Asp Val Lys Leu Val Glu Lys Ser Phe Glu Thr
225                 230                 235                 240

-continued

```
Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 55
<211> LENGTH: 5
<212> TYPE: PRT
<213> ORGANISM: Artificial Sequence
<220> FEATURE:
<223> OTHER INFORMATION: TCR amino acid sequence, Donor HD4

<400> SEQUENCE: 55

Met Asn His Asn Ser
1               5

<210> SEQ ID NO 56
<211> LENGTH: 6
<212> TYPE: PRT
<213> ORGANISM: Artificial Sequence
<220> FEATURE:
<223> OTHER INFORMATION: TCR amino acid sequence, Donor HD4

<400> SEQUENCE: 56

Ser Ala Ser Glu Gly Thr
1               5

<210> SEQ ID NO 57
<211> LENGTH: 14
<212> TYPE: PRT
<213> ORGANISM: Artificial Sequence
<220> FEATURE:
<223> OTHER INFORMATION: TCR amino acid sequence, Donor HD4

<400> SEQUENCE: 57

Cys Ala Ser Arg Ala Ala Gly Leu Asp Thr Glu Ala Phe Phe
1               5                   10

<210> SEQ ID NO 58
<211> LENGTH: 133
<212> TYPE: PRT
<213> ORGANISM: Artificial Sequence
<220> FEATURE:
<223> OTHER INFORMATION: TCR amino acid sequence, Donor HD4

<400> SEQUENCE: 58

Met Ser Ile Gly Leu Leu Cys Cys Val Ala Phe Ser Leu Leu Trp Ala
1               5                   10                  15

Ser Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Asn Ser Met Tyr Trp Tyr Arg Gln Asp Pro Gly Met Gly Leu Arg Leu
    50                  55                  60

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
            100                 105                 110
```

Arg Ala Ala Gly Leu Asp Thr Glu Ala Phe Phe Gly Gln Gly Thr Arg
            115                 120                 125

Leu Thr Val Val Glu
    130

<210> SEQ ID NO 59
<211> LENGTH: 309
<212> TYPE: PRT
<213> ORGANISM: Artificial Sequence
<220> FEATURE:
<223> OTHER INFORMATION: TCR amino acid sequence, Donor HD4

<400> SEQUENCE: 59

Met Ser Ile Gly Leu Leu Cys Cys Val Ala Phe Ser Leu Leu Trp Ala
1               5                   10                  15

Ser Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Asn Ser Met Tyr Trp Tyr Arg Gln Asp Pro Gly Met Gly Leu Arg Leu
    50                  55                  60

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
            100                 105                 110

Arg Ala Ala Gly Leu Asp Thr Glu Ala Phe Phe Gly Gln Gly Thr Arg
            115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 60
<211> LENGTH: 311

```
<212> TYPE: PRT
<213> ORGANISM: Artificial Sequence
<220> FEATURE:
<223> OTHER INFORMATION: TCR amino acid sequence, Donor HD4

<400> SEQUENCE: 60
```

| | | | | | | | | | | | | | | |
|---|---|---|---|---|---|---|---|---|---|---|---|---|---|---|
| Met | Ser | Ile | Gly | Leu | Leu | Cys | Cys | Val | Ala | Phe | Ser | Leu | Leu | Trp | Ala |
| 1 | | | | 5 | | | | | 10 | | | | | 15 | |

Ser Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Asn Ser Met Tyr Trp Tyr Arg Gln Asp Pro Gly Met Gly Leu Arg Leu
    50                  55                  60

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
            100                 105                 110

Arg Ala Ala Gly Leu Asp Thr Glu Ala Phe Phe Gly Gln Gly Thr Arg
        115                 120                 125

Leu Thr Val Val Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

```
<210> SEQ ID NO 61
<211> LENGTH: 5
<212> TYPE: PRT
<213> ORGANISM: Artificial Sequence
<220> FEATURE:
<223> OTHER INFORMATION: TCR amino acid sequence, Donor HD4

<400> SEQUENCE: 61
```

Met Asn His Asn Tyr
1               5

<210> SEQ ID NO 62
<211> LENGTH: 6
<212> TYPE: PRT
<213> ORGANISM: Artificial Sequence
<220> FEATURE:
<223> OTHER INFORMATION: TCR amino acid sequence, Donor HD4

<400> SEQUENCE: 62

Ser Val Gly Ala Gly Ile
1               5

<210> SEQ ID NO 63
<211> LENGTH: 12
<212> TYPE: PRT
<213> ORGANISM: Artificial Sequence
<220> FEATURE:
<223> OTHER INFORMATION: TCR amino acid sequence, Donor HD4

<400> SEQUENCE: 63

Cys Ala Ser Thr Gln Thr Pro Tyr Glu Gln Tyr Phe
1               5                  10

<210> SEQ ID NO 64
<211> LENGTH: 131
<212> TYPE: PRT
<213> ORGANISM: Artificial Sequence
<220> FEATURE:
<223> OTHER INFORMATION: TCR amino acid sequence, Donor HD4

<400> SEQUENCE: 64

Met Ser Ile Ser Leu Leu Cys Cys Ala Ala Phe Pro Leu Leu Trp Ala
1               5                   10                  15

Gly Pro Val Asn Ala Gly Val Thr Gln Thr Pro Lys Phe Arg Ile Leu
            20                  25                  30

Lys Ile Gly Gln Ser Met Thr Leu Gln Cys Thr Gln Asp Met Asn His
        35                  40                  45

Asn Tyr Met Tyr Trp Tyr Arg Gln Asp Pro Gly Met Gly Leu Lys Leu
    50                  55                  60

Ile Tyr Tyr Ser Val Gly Ala Gly Ile Thr Asp Lys Gly Glu Val Pro
65                  70                  75                  80

Asn Gly Tyr Asn Val Ser Arg Ser Thr Thr Glu Asp Phe Pro Leu Arg
                85                  90                  95

Leu Glu Leu Ala Ala Pro Ser Gln Thr Ser Val Tyr Phe Cys Ala Ser
            100                 105                 110

Thr Gln Thr Pro Tyr Glu Gln Tyr Phe Gly Pro Gly Thr Arg Leu Thr
        115                 120                 125

Val Thr Glu
    130

<210> SEQ ID NO 65
<211> LENGTH: 307
<212> TYPE: PRT
<213> ORGANISM: Artificial Sequence
<220> FEATURE:
<223> OTHER INFORMATION: TCR amino acid sequence, Donor HD4

<400> SEQUENCE: 65

Met Ser Ile Ser Leu Leu Cys Cys Ala Ala Phe Pro Leu Leu Trp Ala
1               5                   10                  15

Gly Pro Val Asn Ala Gly Val Thr Gln Thr Pro Lys Phe Arg Ile Leu
            20                  25                  30

-continued

```
Lys Ile Gly Gln Ser Met Thr Leu Gln Cys Thr Gln Asp Met Asn His
            35                  40                  45

Asn Tyr Met Tyr Trp Tyr Arg Gln Asp Pro Gly Met Gly Leu Lys Leu
    50                  55                  60

Ile Tyr Tyr Ser Val Gly Ala Gly Ile Thr Asp Lys Gly Glu Val Pro
65                  70                  75                  80

Asn Gly Tyr Asn Val Ser Arg Ser Thr Glu Asp Phe Pro Leu Arg
                85                  90                  95

Leu Glu Leu Ala Ala Pro Ser Gln Thr Ser Val Tyr Phe Cys Ala Ser
                100                 105                 110

Thr Gln Thr Pro Tyr Glu Gln Tyr Phe Gly Pro Gly Thr Arg Leu Thr
            115                 120                 125

Val Thr Glu Asp Leu Asn Lys Val Phe Pro Pro Glu Val Ala Val Phe
            130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
            195                 200                 205

Arg Leu Arg Val Ser Ala Thr Phe Trp Gln Asn Pro Arg Asn His Phe
            210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
            275                 280                 285

Tyr Ala Val Leu Val Ser Ala Leu Val Leu Met Ala Met Val Lys Arg
            290                 295                 300

Lys Asp Phe
305

<210> SEQ ID NO 66
<211> LENGTH: 309
<212> TYPE: PRT
<213> ORGANISM: Artificial Sequence
<220> FEATURE:
<223> OTHER INFORMATION: TCR amino acid sequence, Donor HD4

<400> SEQUENCE: 66

Met Ser Ile Ser Leu Leu Cys Cys Ala Ala Phe Pro Leu Leu Trp Ala
1               5                   10                  15

Gly Pro Val Asn Ala Gly Val Thr Gln Thr Pro Lys Phe Arg Ile Leu
            20                  25                  30

Lys Ile Gly Gln Ser Met Thr Leu Gln Cys Thr Gln Asp Met Asn His
            35                  40                  45

Asn Tyr Met Tyr Trp Tyr Arg Gln Asp Pro Gly Met Gly Leu Lys Leu
    50                  55                  60

Ile Tyr Tyr Ser Val Gly Ala Gly Ile Thr Asp Lys Gly Glu Val Pro
65                  70                  75                  80
```

```
Asn Gly Tyr Asn Val Ser Arg Ser Thr Thr Glu Asp Phe Pro Leu Arg
                85                  90                  95

Leu Glu Leu Ala Ala Pro Ser Gln Thr Ser Val Tyr Phe Cys Ala Ser
            100                 105                 110

Thr Gln Thr Pro Tyr Glu Gln Tyr Phe Gly Pro Gly Thr Arg Leu Thr
        115                 120                 125

Val Thr Glu Asp Leu Lys Asn Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Ser Arg Gly
305

<210> SEQ ID NO 67
<211> LENGTH: 5
<212> TYPE: PRT
<213> ORGANISM: Artificial Sequence
<220> FEATURE:
<223> OTHER INFORMATION: TCR amino acid sequence, Donor HD4

<400> SEQUENCE: 67

Ser Gly His Asn Ser
1               5

<210> SEQ ID NO 68
<211> LENGTH: 6
<212> TYPE: PRT
<213> ORGANISM: Artificial Sequence
<220> FEATURE:
<223> OTHER INFORMATION: TCR amino acid sequence, Donor HD4

<400> SEQUENCE: 68

Phe Asn Asn Asn Val Pro
1               5

<210> SEQ ID NO 69
<211> LENGTH: 15
<212> TYPE: PRT
<213> ORGANISM: Artificial Sequence
<220> FEATURE:
<223> OTHER INFORMATION: TCR amino acid sequence, Donor HD4
```

<400> SEQUENCE: 69

Cys Ala Ser Ser Thr Val Gly Gly Glu Asp Tyr Gly Tyr Thr Phe
1               5                   10                  15

<210> SEQ ID NO 70
<211> LENGTH: 135
<212> TYPE: PRT
<213> ORGANISM: Artificial Sequence
<220> FEATURE:
<223> OTHER INFORMATION: TCR amino acid sequence, Donor HD4

<400> SEQUENCE: 70

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Thr Val Gly Gly Glu Asp Tyr Gly Tyr Thr Phe Gly Ser Gly
        115                 120                 125

Thr Arg Leu Thr Val Val Glu
    130                 135

<210> SEQ ID NO 71
<211> LENGTH: 311
<212> TYPE: PRT
<213> ORGANISM: Artificial Sequence
<220> FEATURE:
<223> OTHER INFORMATION: TCR amino acid sequence, Donor HD4

<400> SEQUENCE: 71

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Thr Val Gly Gly Glu Asp Tyr Gly Tyr Thr Phe Gly Ser Gly
        115                 120                 125

Thr Arg Leu Thr Val Val Glu Asp Leu Asn Lys Val Phe Pro Pro Glu
    130                 135                 140

```
Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
                260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
290                 295                 300

Met Val Lys Arg Lys Asp Phe
305                 310

<210> SEQ ID NO 72
<211> LENGTH: 313
<212> TYPE: PRT
<213> ORGANISM: Artificial Sequence
<220> FEATURE:
<223> OTHER INFORMATION: TCR amino acid sequence, Donor HD4

<400> SEQUENCE: 72

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
        50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Thr Val Gly Gly Glu Asp Tyr Gly Tyr Thr Phe Gly Ser Gly
        115                 120                 125

Thr Arg Leu Thr Val Val Glu Asp Leu Lys Asn Val Phe Pro Pro Glu
130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190
```

```
Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Ser Arg Gly
305                 310
```

```
<210> SEQ ID NO 73
<211> LENGTH: 6
<212> TYPE: PRT
<213> ORGANISM: Artificial Sequence
<220> FEATURE:
<223> OTHER INFORMATION: TCR amino acid sequence, Donor HD5

<400> SEQUENCE: 73

Asp Ser Ala Ser Asn Tyr
1               5

<210> SEQ ID NO 74
<211> LENGTH: 7
<212> TYPE: PRT
<213> ORGANISM: Artificial Sequence
<220> FEATURE:
<223> OTHER INFORMATION: TCR amino acid sequence, Donor HD5

<400> SEQUENCE: 74

Ile Arg Ser Asn Val Gly Glu
1               5

<210> SEQ ID NO 75
<211> LENGTH: 15
<212> TYPE: PRT
<213> ORGANISM: Artificial Sequence
<220> FEATURE:
<223> OTHER INFORMATION: TCR amino acid sequence, Donor HD5

<400> SEQUENCE: 75

Cys Ala Ala Ser Met Ala Gly Ala Gly Ser Tyr Gln Leu Thr Phe
1               5                   10                  15

<210> SEQ ID NO 76
<211> LENGTH: 134
<212> TYPE: PRT
<213> ORGANISM: Artificial Sequence
<220> FEATURE:
<223> OTHER INFORMATION: TCR amino acid sequence, Donor HD5

<400> SEQUENCE: 76

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30
```

```
Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
                100                 105                 110

Met Ala Gly Ala Gly Ser Tyr Gln Leu Thr Phe Gly Lys Gly Thr Lys
                115                 120                 125

Leu Ser Val Ile Pro Asn
                130
```

<210> SEQ ID NO 77
<211> LENGTH: 274
<212> TYPE: PRT
<213> ORGANISM: Artificial Sequence
<220> FEATURE:
<223> OTHER INFORMATION: TCR amino acid sequence, Donor HD5

<400> SEQUENCE: 77

```
Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
                100                 105                 110

Met Ala Gly Ala Gly Ser Tyr Gln Leu Thr Phe Gly Lys Gly Thr Lys
                115                 120                 125

Leu Ser Val Ile Pro Asn Ile Gln Asn Pro Asp Pro Ala Val Tyr Gln
                130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
                180                 185                 190

Asn Ser Ala Val Ala Trp Ser Asn Lys Ser Asp Phe Ala Cys Ala Asn
                195                 200                 205

Ala Phe Asn Asn Ser Ile Ile Pro Glu Asp Thr Phe Phe Pro Ser Pro
                210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255
```

```
Leu Leu Lys Val Ala Gly Phe Asn Leu Leu Met Thr Leu Arg Leu Trp
            260                 265                 270
Ser Ser
```

<210> SEQ ID NO 78
<211> LENGTH: 5
<212> TYPE: PRT
<213> ORGANISM: Artificial Sequence
<220> FEATURE:
<223> OTHER INFORMATION: TCR amino acid sequence, Donor HD5

<400> SEQUENCE: 78

```
Glu Asn His Arg Tyr
1               5
```

<210> SEQ ID NO 79
<211> LENGTH: 6
<212> TYPE: PRT
<213> ORGANISM: Artificial Sequence
<220> FEATURE:
<223> OTHER INFORMATION: TCR amino acid sequence, Donor HD5

<400> SEQUENCE: 79

```
Ser Tyr Gly Val Lys Asp
1               5
```

<210> SEQ ID NO 80
<211> LENGTH: 15
<212> TYPE: PRT
<213> ORGANISM: Artificial Sequence
<220> FEATURE:
<223> OTHER INFORMATION: TCR amino acid sequence, Donor HD5

<400> SEQUENCE: 80

```
Cys Ala Ile Ser Val Gly Gln Gly Ala Leu Tyr Glu Gln Tyr Phe
1               5                   10                  15
```

<210> SEQ ID NO 81
<211> LENGTH: 134
<212> TYPE: PRT
<213> ORGANISM: Artificial Sequence
<220> FEATURE:
<223> OTHER INFORMATION: TCR amino acid sequence, Donor HD5

<400> SEQUENCE: 81

```
Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30

Glu Thr Gly Thr Pro Val Thr Leu Arg Cys His Gln Thr Glu Asn His
        35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Val Gly Gln Gly Ala Leu Tyr Glu Gln Tyr Phe Gly Pro Gly Thr
        115                 120                 125
```

Arg Leu Thr Val Thr Glu
    130

<210> SEQ ID NO 82
<211> LENGTH: 310
<212> TYPE: PRT
<213> ORGANISM: Artificial Sequence
<220> FEATURE:
<223> OTHER INFORMATION: TCR amino acid sequence, Donor HD5

<400> SEQUENCE: 82

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30

Glu Thr Gly Thr Pro Val Thr Leu Arg Cys His Gln Thr Glu Asn His
        35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Val Gly Gln Gly Ala Leu Tyr Glu Gln Tyr Phe Gly Pro Gly Thr
        115                 120                 125

Arg Leu Thr Val Thr Glu Asp Leu Asn Lys Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 83
<211> LENGTH: 312
<212> TYPE: PRT
<213> ORGANISM: Artificial Sequence
<220> FEATURE:

<223> OTHER INFORMATION: TCR amino acid sequence, Donor HD5

<400> SEQUENCE: 83

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
                20                  25                  30

Glu Thr Gly Thr Pro Val Thr Leu Arg Cys His Gln Thr Glu Asn His
            35                  40                  45

Arg Tyr Met Tyr Trp Tyr Arg Gln Asp Pro Gly His Gly Leu Arg Leu
        50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Val Gly Gln Gly Ala Leu Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 84
<211> LENGTH: 5
<212> TYPE: PRT
<213> ORGANISM: Artificial Sequence
<220> FEATURE:
<223> OTHER INFORMATION: TCR amino acid sequence, Donor HD5

<400> SEQUENCE: 84

Ser Gly Asp Leu Ser
1               5

<210> SEQ ID NO 85

```
<211> LENGTH: 6
<212> TYPE: PRT
<213> ORGANISM: Artificial Sequence
<220> FEATURE:
<223> OTHER INFORMATION: TCR amino acid sequence, Donor HD5

<400> SEQUENCE: 85

Tyr Tyr Asn Gly Glu Glu
1               5

<210> SEQ ID NO 86
<211> LENGTH: 16
<212> TYPE: PRT
<213> ORGANISM: Artificial Sequence
<220> FEATURE:
<223> OTHER INFORMATION: TCR amino acid sequence, Donor HD5

<400> SEQUENCE: 86

Cys Ala Ser Ser Val Ala Arg Asp Arg Arg Asn Tyr Gly Tyr Thr Phe
1               5                  10                  15

<210> SEQ ID NO 87
<211> LENGTH: 135
<212> TYPE: PRT
<213> ORGANISM: Artificial Sequence
<220> FEATURE:
<223> OTHER INFORMATION: TCR amino acid sequence, Donor HD5

<400> SEQUENCE: 87

Met Gly Phe Arg Leu Leu Cys Cys Val Ala Phe Cys Leu Leu Gly Ala
1               5                  10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Ala Arg Asp Arg Arg Asn Tyr Gly Tyr Thr Phe Gly Ser Gly
        115                 120                 125

Thr Arg Leu Thr Val Val Glu
    130                 135

<210> SEQ ID NO 88
<211> LENGTH: 311
<212> TYPE: PRT
<213> ORGANISM: Artificial Sequence
<220> FEATURE:
<223> OTHER INFORMATION: TCR amino acid sequence, Donor HD5

<400> SEQUENCE: 88

Met Gly Phe Arg Leu Leu Cys Cys Val Ala Phe Cys Leu Leu Gly Ala
1               5                  10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45
```

Leu Ser Val Tyr Trp Tyr Gln Gln Ser Leu Asp Gln Gly Leu Gln Phe
            50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Ala Arg Asp Arg Arg Asn Tyr Gly Tyr Thr Phe Gly Ser Gly
            115                 120                 125

Thr Arg Leu Thr Val Val Glu Asp Leu Asn Lys Val Phe Pro Pro Glu
            130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
            165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Phe
305                 310

<210> SEQ ID NO 89
<211> LENGTH: 313
<212> TYPE: PRT
<213> ORGANISM: Artificial Sequence
<220> FEATURE:
<223> OTHER INFORMATION: TCR amino acid sequence, Donor HD5

<400> SEQUENCE: 89

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
            50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

```
Leu Ser Ser Leu Glu Leu Gly Asp Ser Ala Leu Tyr Phe Cys Ala Ser
            100                 105                 110

Ser Val Ala Arg Asp Arg Arg Asn Tyr Gly Tyr Thr Phe Gly Ser Gly
        115                 120                 125

Thr Arg Leu Thr Val Val Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser Arg Gly
305                 310

<210> SEQ ID NO 90
<211> LENGTH: 6
<212> TYPE: PRT
<213> ORGANISM: Artificial Sequence
<220> FEATURE:
<223> OTHER INFORMATION: TCR amino acid sequence, Donor HD6

<400> SEQUENCE: 90

Asn Ser Met Phe Asp Tyr
1               5

<210> SEQ ID NO 91
<211> LENGTH: 7
<212> TYPE: PRT
<213> ORGANISM: Artificial Sequence
<220> FEATURE:
<223> OTHER INFORMATION: TCR amino acid sequence, Donor HD6

<400> SEQUENCE: 91

Ile Ser Ser Ile Lys Asp Lys
1               5

<210> SEQ ID NO 92
<211> LENGTH: 10
<212> TYPE: PRT
<213> ORGANISM: Artificial Sequence
<220> FEATURE:
<223> OTHER INFORMATION: TCR amino acid sequence, Donor HD6
```

```
<400> SEQUENCE: 92

Cys Ala Ala Asn Asn Ala Arg Leu Met Phe
1               5                   10

<210> SEQ ID NO 93
<211> LENGTH: 136
<212> TYPE: PRT
<213> ORGANISM: Artificial Sequence
<220> FEATURE:
<223> OTHER INFORMATION: TCR amino acid sequence, Donor HD6

<400> SEQUENCE: 93

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Asn Asn Ala Arg Leu Met Phe Gly Asp Gly
        115                 120                 125

Thr Gln Leu Val Val Lys Pro Asn
    130                 135

<210> SEQ ID NO 94
<211> LENGTH: 276
<212> TYPE: PRT
<213> ORGANISM: Artificial Sequence
<220> FEATURE:
<223> OTHER INFORMATION: TCR amino acid sequence, Donor HD6

<400> SEQUENCE: 94

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Asn Asn Ala Arg Leu Met Phe Gly Asp Gly
        115                 120                 125

Thr Gln Leu Val Val Lys Pro Asn Ile Gln Asn Pro Asp Pro Ala Val
    130                 135                 140
```

Tyr Gln Leu Arg Asp Ser Lys Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 95
<211> LENGTH: 5
<212> TYPE: PRT
<213> ORGANISM: Artificial Sequence
<220> FEATURE:
<223> OTHER INFORMATION: TCR amino acid sequence, Donor HD6

<400> SEQUENCE: 95

Ser Gly His Asn Ser
1               5

<210> SEQ ID NO 96
<211> LENGTH: 6
<212> TYPE: PRT
<213> ORGANISM: Artificial Sequence
<220> FEATURE:
<223> OTHER INFORMATION: TCR amino acid sequence, Donor HD6

<400> SEQUENCE: 96

Phe Asn Asn Asn Val Pro
1               5

<210> SEQ ID NO 97
<211> LENGTH: 13
<212> TYPE: PRT
<213> ORGANISM: Artificial Sequence
<220> FEATURE:
<223> OTHER INFORMATION: TCR amino acid sequence, Donor HD6

<400> SEQUENCE: 97

Cys Ala Ser Ser Asp Thr Arg Ala Arg Glu Gln Phe Phe
1               5                   10

<210> SEQ ID NO 98
<211> LENGTH: 133
<212> TYPE: PRT
<213> ORGANISM: Artificial Sequence
<220> FEATURE:
<223> OTHER INFORMATION: TCR amino acid sequence, Donor HD6

<400> SEQUENCE: 98

Met Asp Ser Trp Thr Phe Cys Cys Val Ser Leu Cys Ile Leu Val Ala
1               5                   10                  15

```
Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
        50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Asp Thr Arg Ala Arg Glu Gln Phe Phe Gly Pro Gly Thr Arg
        115                 120                 125

Leu Thr Val Leu Glu
        130

<210> SEQ ID NO 99
<211> LENGTH: 309
<212> TYPE: PRT
<213> ORGANISM: Artificial Sequence
<220> FEATURE:
<223> OTHER INFORMATION: TCR amino acid sequence, Donor HD6

<400> SEQUENCE: 99

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
        50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Asp Thr Arg Ala Arg Glu Gln Phe Phe Gly Pro Gly Thr Arg
        115                 120                 125

Leu Thr Val Leu Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240
```

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 100
<211> LENGTH: 311
<212> TYPE: PRT
<213> ORGANISM: Artificial Sequence
<220> FEATURE:
<223> OTHER INFORMATION: TCR amino acid sequence, Donor HD6

<400> SEQUENCE: 100

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Asp Thr Arg Ala Arg Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

```
Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 101
<211> LENGTH: 6
<212> TYPE: PRT
<213> ORGANISM: Artificial Sequence
<220> FEATURE:
<223> OTHER INFORMATION: TCR amino acid sequence, Donor HD7

<400> SEQUENCE: 101

Asp Ser Ser Ser Thr Tyr
1               5

<210> SEQ ID NO 102
<211> LENGTH: 7
<212> TYPE: PRT
<213> ORGANISM: Artificial Sequence
<220> FEATURE:
<223> OTHER INFORMATION: TCR amino acid sequence, Donor HD7

<400> SEQUENCE: 102

Ile Phe Ser Asn Met Asp Met
1               5

<210> SEQ ID NO 103
<211> LENGTH: 12
<212> TYPE: PRT
<213> ORGANISM: Artificial Sequence
<220> FEATURE:
<223> OTHER INFORMATION: TCR amino acid sequence, Donor HD7

<400> SEQUENCE: 103

Cys Ala Glu Arg Leu Asn Thr Asp Lys Leu Ile Phe
1               5                   10

<210> SEQ ID NO 104
<211> LENGTH: 132
<212> TYPE: PRT
<213> ORGANISM: Artificial Sequence
<220> FEATURE:
<223> OTHER INFORMATION: TCR amino acid sequence, Donor HD7

<400> SEQUENCE: 104

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Arg Leu Asn Thr Asp Lys Leu Ile Phe Gly Thr Gly Thr Arg Leu Gln
        115                 120                 125
```

Val Phe Pro Asn
    130

<210> SEQ ID NO 105
<211> LENGTH: 272
<212> TYPE: PRT
<213> ORGANISM: Artificial Sequence
<220> FEATURE:
<223> OTHER INFORMATION: TCR amino acid sequence, Donor HD7

<400> SEQUENCE: 105

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Arg Leu Asn Thr Asp Lys Leu Ile Phe Gly Thr Gly Thr Arg Leu Gln
        115                 120                 125

Val Phe Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 106
<211> LENGTH: 5
<212> TYPE: PRT
<213> ORGANISM: Artificial Sequence
<220> FEATURE:
<223> OTHER INFORMATION: TCR amino acid sequence, Donor HD7

<400> SEQUENCE: 106

Asp Ser Val Asn Asn
1               5

-continued

```
<210> SEQ ID NO 107
<211> LENGTH: 5
<212> TYPE: PRT
<213> ORGANISM: Artificial Sequence
<220> FEATURE:
<223> OTHER INFORMATION: TCR amino acid sequence, Donor HD7

<400> SEQUENCE: 107

Ile Pro Ser Gly Thr
1               5

<210> SEQ ID NO 108
<211> LENGTH: 14
<212> TYPE: PRT
<213> ORGANISM: Artificial Sequence
<220> FEATURE:
<223> OTHER INFORMATION: TCR amino acid sequence, Donor HD7

<400> SEQUENCE: 108

Cys Ala Val Glu Ala Thr Asp Ser Trp Gly Lys Leu Gln Phe
1               5                   10

<210> SEQ ID NO 109
<211> LENGTH: 131
<212> TYPE: PRT
<213> ORGANISM: Artificial Sequence
<220> FEATURE:
<223> OTHER INFORMATION: TCR amino acid sequence, Donor HD7

<400> SEQUENCE: 109

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30

Leu Gln Glu Gly Ala Asn Ser Thr Leu Arg Cys Asn Phe Ser Asp Ser
        35                  40                  45

Val Asn Asn Leu Gln Trp Phe His Gln Asn Pro Trp Gly Gln Leu Ile
    50                  55                  60

Asn Leu Phe Tyr Ile Pro Ser Gly Thr Lys Gln Asn Gly Arg Leu Ser
65                  70                  75                  80

Ala Thr Thr Val Ala Thr Glu Arg Tyr Ser Leu Leu Tyr Ile Ser Ser
                85                  90                  95

Ser Gln Thr Thr Asp Ser Gly Val Tyr Phe Cys Ala Val Glu Ala Thr
            100                 105                 110

Asp Ser Trp Gly Lys Leu Gln Phe Gly Ala Gly Thr Gln Val Val Val
        115                 120                 125

Thr Pro Asp
    130

<210> SEQ ID NO 110
<211> LENGTH: 271
<212> TYPE: PRT
<213> ORGANISM: Artificial Sequence
<220> FEATURE:
<223> OTHER INFORMATION: TCR amino acid sequence, Donor HD7

<400> SEQUENCE: 110

Met Lys Arg Ile Leu Gly Ala Leu Leu Gly Leu Leu Ser Ala Gln Val
1               5                   10                  15

Cys Cys Val Arg Gly Ile Gln Val Glu Gln Ser Pro Pro Asp Leu Ile
            20                  25                  30
```

```
Leu Gln Glu Gly Ala Asn Ser Thr Leu Arg Cys Asn Phe Ser Asp Ser
            35                  40                  45

Val Asn Asn Leu Gln Trp Phe His Gln Asn Pro Trp Gly Gln Leu Ile
 50                  55                  60

Asn Leu Phe Tyr Ile Pro Ser Gly Thr Lys Gln Asn Gly Arg Leu Ser
 65                  70                  75                  80

Ala Thr Thr Val Ala Thr Glu Arg Tyr Ser Leu Leu Tyr Ile Ser Ser
                 85                  90                  95

Ser Gln Thr Thr Asp Ser Gly Val Tyr Phe Cys Ala Val Glu Ala Thr
                100                 105                 110

Asp Ser Trp Gly Lys Leu Gln Phe Gly Ala Gly Thr Gln Val Val Val
            115                 120                 125

Thr Pro Asp Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
            210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 111
<211> LENGTH: 6
<212> TYPE: PRT
<213> ORGANISM: Artificial Sequence
<220> FEATURE:
<223> OTHER INFORMATION: TCR amino acid sequence, Donor HD7

<400> SEQUENCE: 111

Asp Ser Ala Ser Asn Tyr
1               5

<210> SEQ ID NO 112
<211> LENGTH: 7
<212> TYPE: PRT
<213> ORGANISM: Artificial Sequence
<220> FEATURE:
<223> OTHER INFORMATION: TCR amino acid sequence, Donor HD7

<400> SEQUENCE: 112

Ile Arg Ser Asn Val Gly Glu
1               5

<210> SEQ ID NO 113
<211> LENGTH: 12
<212> TYPE: PRT
<213> ORGANISM: Artificial Sequence
<220> FEATURE:
<223> OTHER INFORMATION: TCR amino acid sequence, Donor HD7
```

```
<400> SEQUENCE: 113

Cys Ala Val Arg Thr Ser Tyr Asp Lys Val Ile Phe
1               5                   10

<210> SEQ ID NO 114
<211> LENGTH: 131
<212> TYPE: PRT
<213> ORGANISM: Artificial Sequence
<220> FEATURE:
<223> OTHER INFORMATION: TCR amino acid sequence, Donor HD7

<400> SEQUENCE: 114

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Val Arg
            100                 105                 110

Thr Ser Tyr Asp Lys Val Ile Phe Gly Pro Gly Thr Ser Leu Ser Val
        115                 120                 125

Ile Pro Asn
    130

<210> SEQ ID NO 115
<211> LENGTH: 15
<212> TYPE: PRT
<213> ORGANISM: Artificial Sequence
<220> FEATURE:
<223> OTHER INFORMATION: Wilms tumour 1 (WT1) peptide 40

<400> SEQUENCE: 115

Ala Ala Gln Trp Ala Pro Val Leu Asp Phe Ala Pro Pro Gly Ala
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: WT1 peptide 41

<400> SEQUENCE: 116

Ala Pro Val Leu Asp Phe Ala Pro Pro Gly Ala Ser Ala Tyr Gly
1               5                   10                  15

<210> SEQ ID NO 117
<211> LENGTH: 11
<212> TYPE: PRT
<213> ORGANISM: Artificial Sequence
<220> FEATURE:
<223> OTHER INFORMATION: WT1 peptide Overlapping sequence
```

<400> SEQUENCE: 117

Ala Pro Val Leu Asp Phe Ala Pro Pro Gly Ala
1               5                   10

<210> SEQ ID NO 118
<211> LENGTH: 15
<212> TYPE: PRT
<213> ORGANISM: Artificial Sequence
<220> FEATURE:
<223> OTHER INFORMATION: WT1 peptide 54

<400> SEQUENCE: 118

Gln Cys Leu Ser Ala Phe Thr Val His Phe Ser Gly Gln Phe Thr
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: WT1 peptide 77

<400> SEQUENCE: 119

Glu Asp Pro Met Gly Gln Gln Gly Ser Leu Gly Glu Gln Gln Tyr
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: WT1 peptide 90

<400> SEQUENCE: 120

Ser Gln Leu Glu Cys Met Thr Trp Asn Gln Met Asn Leu Gly Ala
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: WT1 peptide 17

<400> SEQUENCE: 121

Thr Cys Val Pro Glu Pro Ala Ser Gln His Thr Leu Arg Ser Gly
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: WT1 peptide 18

<400> SEQUENCE: 122

Glu Pro Ala Ser Gln His Thr Leu Arg Ser Gly Pro Gly Cys Leu
1               5                   10                  15

<210> SEQ ID NO 123
<211> LENGTH: 11
<212> TYPE: PRT
<213> ORGANISM: Artificial Sequence
<220> FEATURE:
<223> OTHER INFORMATION: WT1 peptide Overlapping sequence

```
<400> SEQUENCE: 123

Glu Pro Ala Ser Gln His Thr Leu Arg Ser Gly
1               5                   10

<210> SEQ ID NO 124
<211> LENGTH: 15
<212> TYPE: PRT
<213> ORGANISM: Artificial Sequence
<220> FEATURE:
<223> OTHER INFORMATION: WT1 peptide 99

<400> SEQUENCE: 124

His Ser Thr Gly Tyr Glu Ser Asp Asn His Thr Thr Pro Ile Leu
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: WT1 peptide 100

<400> SEQUENCE: 125

Tyr Glu Ser Asp Asn His Thr Thr Pro Ile Leu Cys Gly Ala Gln
1               5                   10                  15

<210> SEQ ID NO 126
<211> LENGTH: 11
<212> TYPE: PRT
<213> ORGANISM: Artificial Sequence
<220> FEATURE:
<223> OTHER INFORMATION: WT1 peptide Overlapping sequence

<400> SEQUENCE: 126

Tyr Glu Ser Asp Asn His Thr Thr Pro Ile Leu
1               5                   10

<210> SEQ ID NO 127
<211> LENGTH: 15
<212> TYPE: PRT
<213> ORGANISM: Artificial Sequence
<220> FEATURE:
<223> OTHER INFORMATION: WT1 peptide 101

<400> SEQUENCE: 127

Asn His Thr Thr Pro Ile Leu Cys Gly Ala Gln Tyr Arg Ile His
1               5                   10                  15

<210> SEQ ID NO 128
<211> LENGTH: 140
<212> TYPE: PRT
<213> ORGANISM: Artificial Sequence
<220> FEATURE:
<223> OTHER INFORMATION: sequence of an alpha chain constant domain
      encoded by a TRAC gene

<400> SEQUENCE: 128

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60
```

```
Ser Asn Lys Ser Asp Phe Ala Cys Ala Asn Ala Phe Asn Asn Ser Ile
 65                  70                  75                  80

Ile Pro Glu Asp Thr Phe Phe Pro Ser Pro Glu Ser Ser Cys Asp Val
                 85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
130                 135                 140
```

<210> SEQ ID NO 129
<211> LENGTH: 176
<212> TYPE: PRT
<213> ORGANISM: Artificial Sequence
<220> FEATURE:
<223> OTHER INFORMATION: sequence of a beta chain constant domain
      encoded by a TRBC1 gene

<400> SEQUENCE: 129

```
Asp Leu Asn Lys Val Phe Pro Pro Glu Val Ala Val Phe Glu Pro Ser
  1               5                  10                  15

Glu Ala Glu Ile Ser His Thr Gln Lys Ala Thr Leu Val Cys Leu Ala
             20                  25                  30

Thr Gly Phe Phe Pro Asp His Val Glu Leu Ser Trp Trp Val Asn Gly
         35                  40                  45

Lys Glu Val His Ser Gly Val Ser Thr Asp Pro Gln Pro Leu Lys Glu
 50                  55                  60

Gln Pro Ala Leu Asn Asp Ser Arg Tyr Cys Leu Ser Ser Arg Leu Arg
 65                  70                  75                  80

Val Ser Ala Thr Phe Trp Gln Asn Pro Arg Asn His Phe Arg Cys Gln
                 85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175
```

<210> SEQ ID NO 130
<211> LENGTH: 178
<212> TYPE: PRT
<213> ORGANISM: Artificial Sequence
<220> FEATURE:
<223> OTHER INFORMATION: sequence of a beta chain constant domain
      encoded by a TRBC2 gene

<400> SEQUENCE: 130

```
Asp Leu Lys Asn Val Phe Pro Pro Glu Val Ala Val Phe Glu Pro Ser
  1               5                  10                  15

Glu Ala Glu Ile Ser His Thr Gln Lys Ala Thr Leu Val Cys Leu Ala
             20                  25                  30

Thr Gly Phe Tyr Pro Asp His Val Glu Leu Ser Trp Trp Val Asn Gly
         35                  40                  45
```

Lys Glu Val His Ser Gly Val Ser Thr Asp Pro Gln Pro Leu Lys Glu
 50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                 85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 131
<211> LENGTH: 575
<212> TYPE: PRT
<213> ORGANISM: Artificial Sequence
<220> FEATURE:
<223> OTHER INFORMATION: WT1 protein sequence

<400> SEQUENCE: 131

Ser Arg Gln Arg Pro His Pro Gly Ala Leu Arg Asn Pro Thr Ala Cys
1               5                   10                  15

Pro Leu Pro His Phe Pro Pro Ser Leu Pro Pro Thr His Ser Pro Thr
            20                  25                  30

His Pro Pro Arg Ala Gly Thr Ala Ala Gln Ala Pro Gly Pro Arg Arg
        35                  40                  45

Leu Leu Ala Ala Ile Leu Asp Phe Leu Leu Leu Gln Asp Pro Ala Ser
    50                  55                  60

Thr Cys Val Pro Glu Pro Ala Ser Gln His Thr Leu Arg Ser Gly Pro
65                  70                  75                  80

Gly Cys Leu Gln Gln Pro Glu Gln Gln Gly Val Arg Asp Pro Gly Gly
                85                  90                  95

Ile Trp Ala Lys Leu Gly Ala Ala Glu Ala Ser Ala Glu Arg Leu Gln
            100                 105                 110

Gly Arg Arg Ser Arg Gly Ala Ser Gly Ser Glu Pro Gln Gln Met Gly
        115                 120                 125

Ser Asp Val Arg Asp Leu Asn Ala Leu Leu Pro Ala Val Pro Ser Leu
    130                 135                 140

Gly Gly Gly Gly Gly Cys Ala Leu Pro Val Ser Gly Ala Ala Gln Trp
145                 150                 155                 160

Ala Pro Val Leu Asp Phe Ala Pro Pro Gly Ala Ser Ala Tyr Gly Ser
                165                 170                 175

Leu Gly Gly Pro Ala Pro Pro Pro Ala Pro Pro Pro Pro Pro Pro Pro
            180                 185                 190

Pro Pro His Ser Phe Ile Lys Gln Glu Pro Ser Trp Gly Gly Ala Glu
        195                 200                 205

Pro His Glu Glu Gln Cys Leu Ser Ala Phe Thr Val His Phe Ser Gly
    210                 215                 220

```
Gln Phe Thr Gly Thr Ala Gly Ala Cys Arg Tyr Gly Pro Phe Gly Pro
225                 230                 235                 240

Pro Pro Pro Ser Gln Ala Ser Ser Gly Gln Ala Arg Met Phe Pro Asn
            245                 250                 255

Ala Pro Tyr Leu Pro Ser Cys Leu Glu Ser Gln Pro Ala Ile Arg Asn
            260                 265                 270

Gln Gly Tyr Ser Thr Val Thr Phe Asp Gly Thr Pro Ser Tyr Gly His
            275                 280                 285

Thr Pro Ser His His Ala Ala Gln Phe Pro Asn His Ser Phe Lys His
            290                 295                 300

Glu Asp Pro Met Gly Gln Gln Gly Ser Leu Gly Glu Gln Gln Tyr Ser
305                 310                 315                 320

Val Pro Pro Pro Val Tyr Gly Cys His Thr Pro Thr Asp Ser Cys Thr
                325                 330                 335

Gly Ser Gln Ala Leu Leu Leu Arg Thr Pro Tyr Ser Ser Asp Asn Leu
            340                 345                 350

Tyr Gln Met Thr Ser Gln Leu Glu Cys Met Thr Trp Asn Gln Met Asn
            355                 360                 365

Leu Gly Ala Thr Leu Lys Gly Val Ala Ala Gly Ser Ser Ser Ser Val
370                 375                 380

Lys Trp Thr Glu Gly Gln Ser Asn His Ser Thr Gly Tyr Glu Ser Asp
385                 390                 395                 400

Asn His Thr Thr Pro Ile Leu Cys Gly Ala Gln Tyr Arg Ile His Thr
                405                 410                 415

His Gly Val Phe Arg Gly Ile Gln Asp Val Arg Arg Val Pro Gly Val
            420                 425                 430

Ala Pro Thr Leu Val Arg Ser Ala Ser Glu Thr Ser Glu Lys Arg Pro
            435                 440                 445

Phe Met Cys Ala Tyr Pro Gly Cys Asn Lys Arg Tyr Phe Lys Leu Ser
450                 455                 460

His Leu Gln Met His Ser Arg Lys His Thr Gly Glu Lys Pro Tyr Gln
465                 470                 475                 480

Cys Asp Phe Lys Asp Cys Glu Arg Arg Phe Ser Arg Ser Asp Gln Leu
                485                 490                 495

Lys Arg His Gln Arg Arg His Thr Gly Val Lys Pro Phe Gln Cys Lys
            500                 505                 510

Thr Cys Gln Arg Lys Phe Ser Arg Ser Asp His Leu Lys Thr His Thr
            515                 520                 525

Arg Thr His Thr Gly Lys Thr Ser Glu Lys Pro Phe Ser Cys Arg Trp
530                 535                 540

Pro Ser Cys Gln Lys Lys Phe Ala Arg Ser Asp Glu Leu Val Arg His
545                 550                 555                 560

His Asn Met His Gln Arg Asn Met Thr Lys Leu Gln Leu Ala Leu
                565                 570                 575

<210> SEQ ID NO 132
<211> LENGTH: 816
<212> TYPE: DNA
<213> ORGANISM: Artificial Sequence
<220> FEATURE:
<223> OTHER INFORMATION: Nucleotide sequence encoding TCR, Donor HD1

<400> SEQUENCE: 132
atggagactc tcctgaaagt gctttcaggc accttgttgt ggcagttgac ctgggtgaga    60
agccaacaac cagtgcagag tcctcaagcc gtgatcctcc gagaagggga agatgctgtc   120
```

```
atcaactgca gttcctccaa ggctttatat tctgtacact ggtacaggca gaagcatggt      180
gaagcacccg tcttcctgat gatattactg aagggtggag aacagaaggg tcatgaaaaa      240
atatctgctt catttaatga aaaaagcag caaagctccc tgtaccttac ggcctcccag       300
ctcagttact caggaaccta cttctgcggc acagcttgga ttaacgacta caagctcagc      360
tttggagccg aaccacagt aactgtaaga gcaaatatcc agaaccctga ccctgccgtg       420
taccagctga gagactctaa atccagtgac aagtctgtct gcctattcac cgatttgat      480 tctcaaacaa atgtgtcaca agtaaggat tctgatgtgt atatcacaga caaaactgtg       540
ctagacatga ggtctatgga cttcaagagc aacagtgctg tggcctggag caacaaatct      600
gactttgcat gtgcaaacgc cttcaacaac agcattattc agaagacac cttcttcccc       660 agcccagaaa gttcctgtga tgtcaagctg gtcgagaaaa gctttgaaac agatacgaac      720
ctaaactttc aaaacctgtc agtgattggg ttccgaatcc tcctcctgaa agtggccggg      780
tttaatctgc tcatgacgct gcggctgtgg tccagc                                816
```

<210> SEQ ID NO 133
<211> LENGTH: 936
<212> TYPE: DNA
<213> ORGANISM: Artificial Sequence
<220> FEATURE:
<223> OTHER INFORMATION: Nucleotide sequence encoding TCR, Donor HD1

<400> SEQUENCE: 133

```
atgggctcct ggaccctctg ctgtgtgtcc ctttgcatcc tggtagcaaa gcacacagat       60
gctggagtta tccagtcacc ccggcacgag gtgacagaga tgggacaaga agtgactctg      120
agatgtaaac caatttcagg acacgactac ctttttctggt acagacagac catgatgcgg      180
ggactggagt tgctcattta ctttaacaac aacgttccga tagatgattc agggatgccc      240
gaggatcgat tctcagctaa gatgcctaat gcatcattct ccactctgaa gatccagccc      300
tcagaaccca gggactcagc tgtgtacttc tgtgccagca aaaaaccgg gggatatagc      360 aatcagcccc agcattttgg tgatgggact cgactctcca tcctagagga cctgaacaag      420
gtgttcccac ccgaggtcgc tgtgtttgag ccatcagaag cagagatctc cacacccaa      480 aaggccacac tggtgtgcct ggccacaggc ttcttccccg accacgtgga gctgagctgg      540
tgggtgaatg gaaggaggt gcacagtggg gtcagcacgg acccgcagcc cctcaaggag      600
cagcccgccc tcaatgactc cagatactgc ctgagcagcc gcctgagggt ctcggccacc      660
ttctggcaga accccgcaa ccacttccgc tgtcaagtcc agttctacgg gctctcggag      720
aatgacgagt ggacccagga tagggccaaa cccgtcaccc agatcgtcag cgccgaggcc      780
tggggtagag cagactgtgg ctttacctcg gtgtcctacc agcaaggggt cctgtctgcc      840
accatcctct atgagatcct gctagggaag gccaccctgt atgctgtgct ggtcagcgcc      900
cttgtgttga tggccatggt caagagaaag gatttc                                936
```

<210> SEQ ID NO 134
<211> LENGTH: 942
<212> TYPE: DNA
<213> ORGANISM: Artificial Sequence
<220> FEATURE:
<223> OTHER INFORMATION: Nucleotide sequence encoding TCR, Donor HD1

<400> SEQUENCE: 134

```
atgggctcct ggaccctctg ctgtgtgtcc ctttgcatcc tggtagcaaa gcacacagat      60
gctggagtta tccagtcacc ccggcacgag gtgacagaga tgggacaaga agtgactctg     120
agatgtaaac caatttcagg acacgactac ctttctggt acagacagac catgatgcgg     180
ggactggagt tgctcattta ctttaacaac aacgttccga tagatgattc agggatgccc     240
gaggatcgat tctcagctaa gatgcctaat gcatcattct ccactctgaa gatccagccc     300
tcagaaccca gggactcagc tgtgtacttc tgtgccagca gaaaaaccgg gggatatagc     360
aatcagcccc agcattttgg tgatgggact cgactctcca tcctagagga cctgaaaaac     420
gtgttcccac ccgaggtcgc tgtgtttgag ccatcagaag cagagatctc ccacacccaa     480
aaggccacac tggtgtgcct ggccacaggc ttctaccccg accacgtgga gctgagctgg     540
tgggtgaatg ggaaggaggt gcacagtggg gtcagcacag acccgcagcc cctcaaggag     600
cagccccgcc tcaatgactc cagatactgc ctgagcagcc gctgagggt tcggccacc      660
ttctggcaga accccgcaa ccacttccgc tgtcaagtcc agttctacgg gctctcggag      720
aatgacgagt ggacccagga tagggccaaa cctgtcaccc agatcgtcag cgccgaggcc     780
tggggtagag cagactgtgg cttcacctcc gagtcttacc agcaagggg cctgtctgcc     840
accatcctct atgagatctt gctagggaag gccaccttgt atgccgtgct ggtcagtgcc     900
ctcgtgctga tggccatggt caagagaaag gattccagag gc                       942
```

<210> SEQ ID NO 135
<211> LENGTH: 822
<212> TYPE: DNA
<213> ORGANISM: Artificial Sequence
<220> FEATURE:
<223> OTHER INFORMATION: Nucleotide sequence encoding TCR, Donor HD2-1

<400> SEQUENCE: 135

```
atgctcctgc tgctcgtccc agtgctcgag gtgattttta ccctgggagg aaccagagcc      60
cagtcggtga cccagcttgg cagccacgtc tctgtctctg aaggagccct ggttctgctg     120
aggtgcaact actcatcgtc tgttccacca tatctcttct ggtatgtgca atacccaac      180
caaggactcc agcttctcct gaagtacaca tcagcggcca ccctggttaa aggcatcaac     240
ggttttgagg ctgaatttaa gaagagtgaa acctccttcc acctgacgaa accctcagcc     300
catatgagcg acgcggctga gtacttctgt gctgtgagat tatctggttc tgcaaggcaa     360
ctgaccttg gatctgggac acaattgact gttttacctg atatccagaa ccctgaccct     420
gccgtgtacc agctgagaga ctctaaatcc agtgacaagt ctgtctgcct attcaccgat     480
tttgattctc aaacaaatgt gtcacaaagt aaggattctg atgtgtatat cacagacaaa     540
actgtgctag acatgaggtc tatggacttc aagagcaaca gtgctgtggc ctggagcaac     600
aaatctgact tgcatgtgc aaacgccttc aacaacagca ttattccaga agacaccttc     660
ttccccagcc agaaagttc ctgtgatgtc aagctggtcg agaaaagctt tgaaacagat     720
acgaacctaa actttcaaaa cctgtcagtg attgggttcc gaatcctcct cctgaaagtg     780
gccgggttta atctgctcat gacgctgcgg ctgtggtcca gc                       822
```

<210> SEQ ID NO 136
<211> LENGTH: 924
<212> TYPE: DNA
<213> ORGANISM: Artificial Sequence
<220> FEATURE:

<223> OTHER INFORMATION: Nucleotide sequence encoding TCR, Donor HD2-1

<400> SEQUENCE: 136

```
atgggcacca ggctcctctg ctgggcggcc ctctgtctcc tgggagcaga actcacagaa      60
gctggagttg cccagtctcc cagatataag attatagaga aaaggcagag tgtggctttt     120
tggtgcaatc ctatatctgg ccatgctacc ctttactggt accagcagat cctgggacag     180
ggcccaaagc ttctgattca gtttcagaat aacggtgtag tggatgattc acagttgcct     240
aaggatcgat tttctgcaga gaggctcaaa ggagtagact ccactctcaa gatccagcct     300
gcaaagcttg aggactcggc cgtgtatctc tgtgccagca gcttactggg agacgagcag     360
tacttcgggc cgggcaccag gctcacggtc acagaggacc tgaacaaggt gttcccaccc     420
gaggtcgctg tgtttgagcc atcagaagca gagatctccc acacccaaaa ggccacactg     480
gtgtgcctgg ccacaggctt cttccccgac cacgtggagc tgagctggtg ggtgaatggg     540
aaggaggtgc acagtggggt cagcacggac ccgcagcccc tcaaggagca gcccgccctc     600
aatgactcca gatactgcct gagcagccgc ctgagggtct cggccacctt ctggcagaac     660
ccccgcaacc acttccgctg tcaagtccag ttctacgggc tctcggagaa tgacgagtgg     720
acccaggata gggccaaacc cgtcacccag atcgtcagcg ccgaggcctg ggtagagca      780
gactgtggct ttacctcggt gtcctaccag caaggggtcc tgtctgccac catcctctat     840
gagatcctgc tagggaaggc caccctgtat gctgtgctgg tcagcgccct tgtgttgatg     900
gccatggtca agagaaagga tttc                                            924
```

<210> SEQ ID NO 137
<211> LENGTH: 930
<212> TYPE: DNA
<213> ORGANISM: Artificial Sequence
<220> FEATURE:
<223> OTHER INFORMATION: Nucleotide sequence encoding TCR, Donor HD2-1

<400> SEQUENCE: 137

```
atgggcacca ggctcctctg ctgggcggcc ctctgtctcc tgggagcaga actcacagaa      60
gctggagttg cccagtctcc cagatataag attatagaga aaaggcagag tgtggctttt     120
tggtgcaatc ctatatctgg ccatgctacc ctttactggt accagcagat cctgggacag     180
ggcccaaagc ttctgattca gtttcagaat aacggtgtag tggatgattc acagttgcct     240
aaggatcgat tttctgcaga gaggctcaaa ggagtagact ccactctcaa gatccagcct     300
gcaaagcttg aggactcggc cgtgtatctc tgtgccagca gcttactggg agacgagcag     360
tacttcgggc cgggcaccag gctcacggtc acagaggacc tgaaaaacgt gttcccaccc     420
gaggtcgctg tgtttgagcc atcagaagca gagatctccc acacccaaaa ggccacactg     480
gtgtgcctgg ccacaggctt ctaccccgac cacgtggagc tgagctggtg ggtgaatggg     540
aaggaggtgc acagtggggt cagcacagac ccgcagcccc tcaaggagca gcccgccctc     600
aatgactcca gatactgcct gagcagccgc ctgagggtct cggccacctt ctggcagaac     660
ccccgcaacc acttccgctg tcaagtccag ttctacgggc tctcggagaa tgacgagtgg     720
acccaggata gggccaaacc tgtcacccag atcgtcagcg ccgaggcctg ggtagagca      780
gactgtggct tcacctccga gtcttaccag caaggggtcc tgtctgccac catcctctat     840
gagatcttgc taggggaaggc caccttgtat gccgtgctgg tcagtgccct cgtgctgatg     900
gccatggtca agagaaagga ttccagaggc                                      930
```

<210> SEQ ID NO 138
<211> LENGTH: 828
<212> TYPE: DNA
<213> ORGANISM: Artificial Sequence
<220> FEATURE:
<223> OTHER INFORMATION: Nucleotide sequence encoding TCR, Donor HD2-2

<400> SEQUENCE: 138

```
atggcatgcc ctggcttcct gtgggcactt gtgatctcca cctgtcttga atttagcatg      60
gctcagacag tcactcagtc tcaaccagag atgtctgtgc aggaggcaga gaccgtgacc     120
ctgagctgca catatgacac cagtgagagt gattattatt tattctggta caagcagcct     180
cccagcaggc agatgattct cgttattcgc caagaagctt ataagcaaca gaatgcaaca     240
gagaatcgtt tctctgtgaa cttccagaaa gcagccaaat ccttcagtct caagatctca     300
gactcacagc tgggggatgc cgcgatgtat ttctgtgctt ataggagtct aaaatatgga     360
aacaaactgg tctttggcgc aggaaccatt ctgagagtca agtcctatat ccagaaccct     420
gaccctgccg tgtaccagct gagagactct aaatccagtg acaagtctgt ctgcctattc     480
accgattttg attctcaaac aaatgtgtca caaagtaagg attctgatgt gtatatcaca     540
gacaaaactg tgctagacat gaggtctatg gacttcaaga gcaacagtgc tgtggcctgg     600
agcaacaaat ctgactttgc atgtgcaaac gccttcaaca acagcattat tccagaagac     660
accttcttcc ccagcccaga aagttcctgt gatgtcaagc tggtcgagaa aagctttgaa     720
acagatacga acctaaactt tcaaaaacctg tcagtgattg ggttccgaat cctcctcctg     780
aaagtggccg ggtttaatct gctcatgacg ctgcggctgt ggtccagc                  828
```

<210> SEQ ID NO 139
<211> LENGTH: 936
<212> TYPE: DNA
<213> ORGANISM: Artificial Sequence
<220> FEATURE:
<223> OTHER INFORMATION: Nucleotide sequence encoding TCR, Donor HD2-2

<400> SEQUENCE: 139

```
atgggcacca ggctcctctt ctgggtggcc ttctgtctcc tgggggcaga tcacacagga      60
gctggagtct cccagtcccc cagtaacaag gtcacagaga agggaaagga tgtagagctc     120
aggtgtgatc caatttcagg tcatactgcc ctttactggt accgacagag cctggggcag     180
ggcctggagt tttttaattta cttccaaggc aacagtgcac cagacaaatc agggctgccc     240
agtgatcgct tctctgcaga gaggactggg ggatccgtct ccactctgac gatccagcgc     300
acacagcagg aggactcggc cgtgtatctc tgtgccagca gcttggtagc tttacaggga     360
gcgggcgagc agtacttcgg ccgggcacc aggctcacgg tcacagagga cctgaacaag     420
gtgttcccac ccgaggtcgc tgtgtttgag ccatcagaag cagagatctc cacacccaa     480
aaggccacac tggtgtgcct ggccacaggc ttcttccccg accacgtgga gctgagctgg     540
tgggtgaatg gaaggaggt gcacagtggg gtcagcacgg accgcagcc cctcaaggag     600
cagcccgccc tcaatgactc cagatactgc ctgagcagcc gcctgagggt ctcggccacc     660
ttctggcaga accccgcaa ccacttccgc tgtcaagtcc agttctacgg gctctcggag     720
aatgacgagt ggacccagga tagggccaaa cccgtcaccc cagatcgtcag cgccgaggcc     780
tggggtagag cagactgtgg ctttacctcg gtgtcctacc agcaaggggt cctgtctgcc     840
accatcctct atgagatcct gctagggaag gccaccctgt atgctgtgct ggtcagcgcc     900
cttgtgttga tggccatggt caagagaaag gatttc                               936
```

```
<210> SEQ ID NO 140
<211> LENGTH: 942
<212> TYPE: DNA
<213> ORGANISM: Artificial Sequence
<220> FEATURE:
<223> OTHER INFORMATION: Nucleotide sequence encoding TCR, Donor HD2-2

<400> SEQUENCE: 140
atgggcacca ggctcctctt ctgggtggcc ttctgtctcc tgggggcaga tcacacagga      60
gctggagtct cccagtcccc cagtaacaag gtcacagaga agggaaagga tgtagagctc     120
aggtgtgatc caatttcagg tcatactgcc ctttactggt accgacagag cctggggcag     180
ggcctggagt ttttaattta cttccaaggc aacagtgcac cagacaaatc agggctgccc     240
agtgatcgct tctctgcaga gaggactggg ggatccgtct ccactctgac gatccagcgc     300
acacagcagg aggactcggc cgtgtatctc tgtgccagca gcttggtagc tttacagggt     360
gcgggcgagc agtacttcgg ccgggcacc aggctcacgg tcacagagga cctgaaaaac      420
gtgttcccac ccgaggtcgc tgtgtttgag ccatcagaag cagagatctc ccacacccaa     480
aaggccacac tggtgtgcct ggccacaggc ttctacccg accacgtgga gctgagctgg      540
tgggtgaatg gaaggaggt gcacagtggg gtcagcacag acccgcagcc cctcaaggag      600
cagcccgccc tcaatgactc cagatactgc ctgagcagcc gcctgagggt ctcggccacc     660
ttctggcaga accccgcaa ccacttccgc tgtcaagtcc agttctacgg gctctcggag      720
aatgacgagt ggacccagga tagggccaaa cctgtcaccc agatcgtcag cgccgaggcc     780
tggggtagag cagactgtgg cttcacctcc gagtcttacc agcaagggg cctgtctgcc      840 accatcctct atgagatctt gctagggaag gccaccttgt atgccgtgct ggtcagtgcc     900
ctcgtgctga tggccatggt caagagaaag gattccagag gc                        942

<210> SEQ ID NO 141
<211> LENGTH: 822
<212> TYPE: DNA
<213> ORGANISM: Artificial Sequence
<220> FEATURE:
<223> OTHER INFORMATION: Nucleotide sequence encoding TCR, Donor HD3

<400> SEQUENCE: 141
atgatatcct tgagagtttt actggtgatc ctgtggcttc agttaagctg ggtttggagc      60
caacggaagg aggtggagca ggatcctgga cccttcaatg ttccagaggg agccactgtc     120
gctttcaact gtacttacag caacagtgct tctcagtctt tcttctggta cagacaggat     180
tgcaggaaag aacctaagtt gctgatgtcc gtatactcca gtggtaatga agatggaagg     240
tttacagcac agctcaatag agccagccag tatatttccc tgctcatcag agactccaag     300
ctcagtgatt cagccaccta cctctgtgtg gtgaacctcc tgtctaacca gggaggaaag     360
cttatcttcg gacagggaac ggagttatct gtgaaaccca atatccagaa ccctgaccct     420
gccgtgtacc agctgagaga ctctaaatcc agtgacaagt ctgtctgcct attcaccgat     480
tttgattctc aaacaaatgt gtcacaaagt aaggattctg atgtgtatat cacagacaaa     540
actgtgctag acatgaggtc tatggacttc aagagcaaca gtgctgtggc ctggagcaac     600
aaatctgact ttgcatgtgc aaacgccttc aacaacagca ttattccaga agacaccttc     660
ttccccagcc cagaaagttc ctgtgatgtc aagctggtcg agaaaagctt tgaaacagat     720
acgaacctaa actttcaaaa cctgtcagtg attgggttcc gaatcctcct cctgaaagtg     780
gccgggttta atctgctcat gacgctgcgg ctgtggtcca gc                        822
```

<210> SEQ ID NO 142
<211> LENGTH: 942
<212> TYPE: DNA
<213> ORGANISM: Artificial Sequence
<220> FEATURE:
<223> OTHER INFORMATION: Nucleotide sequence encoding TCR, Donor HD3

<400> SEQUENCE: 142

| | | | | | |
|---|---|---|---|---|---|
| atgggctgca | ggctgctctg | ctgtgcggtt | ctctgtctcc | tgggagcggg | tgagttggtc | 60 |
| cccatggaaa | cgggagttac | gcagacacca | agacacctgg | tcatgggaat | gacaaataag | 120 |
| aagtctttga | aatgtgaaca | acatctgggt | cataacgcta | tgtattggta | caagcaaagt | 180 |
| gctaagaagc | cactggagct | catgtttgtc | tacagtcttg | aagaacgggt | tgaaaacaac | 240 |
| agtgtgccaa | gtcgcttctc | acctgaatgc | cccaacagct | ctcacttatt | ccttcaccta | 300 |
| cacaccctgc | agccagaaga | ctcggccctg | tatctctgcg | ccagcagcca | agattacttg | 360 |
| gtttctaatg | aaaaactgtt | ttttggcagt | ggaacccagc | tctctgtctt | ggaggacctg | 420 |
| aacaaggtgt | tcccacccga | ggtcgctgtg | tttgagccat | cagaagcaga | gatctcccac | 480 |
| acccaaaagg | ccacactggt | gtgcctggcc | acaggcttct | tccccgacca | cgtggagctg | 540 |
| agctggtggg | tgaatgggaa | ggaggtgcac | agtggggtca | gcacggaccc | gcagcccctc | 600 |
| aaggagcagc | ccgccctcaa | tgactccaga | tactgcctga | gcagccgcct | gagggtctcg | 660 |
| gccaccttct | ggcagaaccc | ccgcaaccac | ttccgctgtc | aagtccagtt | ctacgggctc | 720 |
| tcggagaatg | acgagtggac | ccaggatagg | gccaaacccg | tcacccagat | cgtcagcgcc | 780 |
| gaggcctggg | gtagagcaga | ctgtggcttt | acctcggtgt | cctaccagca | aggggtcctg | 840 |
| tctgccacca | tcctctatga | gatcctgcta | gggaaggcca | ccctgtatgc | tgtgctggtc | 900 |
| agcgccttg | tgttgatggc | catggtcaag | agaaaggatt | tc | | 942 |

<210> SEQ ID NO 143
<211> LENGTH: 948
<212> TYPE: DNA
<213> ORGANISM: Artificial Sequence
<220> FEATURE:
<223> OTHER INFORMATION: Nucleotide sequence encoding TCR, Donor HD3

<400> SEQUENCE: 143

| | | | | | |
|---|---|---|---|---|---|
| atgggctgca | ggctgctctg | ctgtgcggtt | ctctgtctcc | tgggagcggg | tgagttggtc | 60 |
| cccatggaaa | cgggagttac | gcagacacca | agacacctgg | tcatgggaat | gacaaataag | 120 |
| aagtctttga | aatgtgaaca | acatctgggt | cataacgcta | tgtattggta | caagcaaagt | 180 |
| gctaagaagc | cactggagct | catgtttgtc | tacagtcttg | aagaacgggt | tgaaaacaac | 240 |
| agtgtgccaa | gtcgcttctc | acctgaatgc | cccaacagct | ctcacttatt | ccttcaccta | 300 |
| cacaccctgc | agccagaaga | ctcggccctg | tatctctgcg | ccagcagcca | agattacttg | 360 |
| gtttctaatg | aaaaactgtt | ttttggcagt | ggaacccagc | tctctgtctt | ggaggacctg | 420 |
| aaaaacgtgt | tcccacccga | ggtcgctgtg | tttgagccat | cagaagcaga | gatctcccac | 480 |
| acccaaaagg | ccacactggt | gtgcctggcc | acaggcttct | accccgacca | cgtggagctg | 540 |
| agctggtggg | tgaatgggaa | ggaggtgcac | agtggggtca | gcacagaccc | gcagcccctc | 600 |
| aaggagcagc | ccgccctcaa | tgactccaga | tactgcctga | gcagccgcct | gagggtctcg | 660 |
| gccaccttct | ggcagaaccc | ccgcaaccac | ttccgctgtc | aagtccagtt | ctacgggctc | 720 |
| tcggagaatg | acgagtggac | ccaggatagg | gccaaacctg | tcacccagat | cgtcagcgcc | 780 |

```
gaggcctggg gtagagcaga ctgtggcttc acctccgagt cttaccagca agggGtcctg    840
tctgccacca tcctctatga gatcttgcta gggaaggcca ccttgtatgc cgtgctggtc    900
agtgccctcg tgctgatggc catggtcaag agaaaggatt ccagaggc                 948
```

<210> SEQ ID NO 144
<211> LENGTH: 819
<212> TYPE: DNA
<213> ORGANISM: Artificial Sequence
<220> FEATURE:
<223> OTHER INFORMATION: Nucleotide sequence encoding TCR, Donor HD4-1

<400> SEQUENCE: 144

```
atggaaactc tcctgggagt gtctttggtg attctatggc ttcaactggc tagggtgaac    60
agtcaacagg gagaagagga tcctcaggcc ttgagcatcc aggagggtga aaatgccacc   120
atgaactgca gttacaaaac tagtataaac aatttacagt ggtatagaca aaattcaggt   180
agaggccttg tccacctaat tttaatacgt tcaaatgaaa agagagaaca cagtggaaga   240
ttaagagtca cgcttgacac ttccaagaaa agcagttcct tgttgatcac ggcttcccgg   300
gcagcagaca ctgcttctta cttctgtgct acggacgcgt attcaggaaa cacacctctt   360
gtctttggaa agggcacaag actttctgtg attgcaaata tccagaaccc tgaccctgcc   420
gtgtaccagc tgagagactc taaatccagt gacaagtctg tctgcctatt caccgatttt   480
gattctcaaa caaatgtgtc acaaagtaag gattctgatg tgtatatcac agacaaaact   540
gtgctagaca tgaggtctat ggacttcaag agcaacagtg ctgtggcctg agcaacaaa    600 tctgactttg catgtgcaaa cgccttcaac aacagcatta ttccagaaga cacctttctc   660
cccagcccag aaagttcctg tgatgtcaag ctggtcgaga aaagctttga aacagatacg   720
aacctaaact ttcaaaacct gtcagtgatt gggttccgaa tcctcctcct gaaagtggcc   780
gggtttaatc tgctcatgac gctgcggctg tggtccagc                          819
```

<210> SEQ ID NO 145
<211> LENGTH: 927
<212> TYPE: DNA
<213> ORGANISM: Artificial Sequence
<220> FEATURE:
<223> OTHER INFORMATION: Nucleotide sequence encoding TCR, Donor HD4-1

<400> SEQUENCE: 145

```
atgagcatcg ggctcctgtg ctgtgtggcc ttttctctcc tgtgggcaag tccagtgaat    60
gctggtgtca ctcagacccc aaaattccag gtcctgaaga ggacagagag catgacactg   120
cagtgtgccc aggatatgaa ccataactcc atgtactggt atcgacaaga cccaggcatg   180
ggactgaggc tgatttatta ctcagcttct gagggtacca ctgacaaagg agaagtcccc   240
aatggctaca atgtctccag attaaacaaa cgggagttct cgctcaggct ggagtcggct   300
gctccctccc agacatctgt gtacttctgt gccagcaggg cagcagggtt ggacactgaa   360
gctttctttg gacaaggcac cagactcaca gttgtagagg acctgaacaa ggtgttccca   420
cccgaggtcg ctgtgtttga gccatcagaa gcagagatct cccacaccca aaaggccaca   480
ctggtgtgcc tggccacagg cttcttcccc gaccacgtgg agctgagctg gtgggtgaat   540
gggaaggagg tgcacagtgg ggtcagcacg gacccgcagc cctcaaggaa gcagcccgcc   600
ctcaatgact ccagatactg cctgagcagc cgcctgaggg tctcggccac cttctggcag   660 aaccccgca accacttccg ctgtcaagtc cagttctacg gctctcggaa gaatgacgag   720
tggacccagg ataggccaa acccgtcacc cagatcgtca gcgccgaggc ctggggtaga   780
```

```
gcagactgtg gctttacctc ggtgtcctac cagcaagggg tcctgtctgc caccatcctc      840
tatgagatcc tgctagggaa ggccaccctg tatgctgtgc tggtcagcgc ccttgtgttg      900
atggccatgg tcaagagaaa ggatttc                                          927
```

<210> SEQ ID NO 146
<211> LENGTH: 933
<212> TYPE: DNA
<213> ORGANISM: Artificial Sequence
<220> FEATURE:
<223> OTHER INFORMATION: Nucleotide sequence encoding TCR, Donor HD4-1

<400> SEQUENCE: 146

```
atgagcatcg ggctcctgtg ctgtgtggcc ttttctctcc tgtgggcaag tccagtgaat      60
gctggtgtca ctcagacccc aaaattccag gtcctgaaga caggacagag catgacactg     120
cagtgtgccc aggatatgaa ccataactcc atgtactggt atcgacaaga cccaggcatg     180
ggactgaggc tgatttatta ctcagcttct gagggtacca ctgacaaagg agaagtcccc     240
aatggctaca atgtctccag attaaacaaa cgggagttct cgctcaggct ggagtcggct     300
gctccctccc agacatctgt gtacttctgt gccagcaggg cagcagggtt ggacactgaa     360
gctttctttg gacaaggcac cagactcaca gttgtagagg acctgaaaaa cgtgttccca     420
cccgaggtcg ctgtgtttga gccatcagaa gcagagatct cccacaccca aaaggccaca     480
ctggtgtgcc tggccacagg cttctacccc gaccacgtgg agctgagctg gtgggtgaat     540
gggaaggagg tgcacagtgg ggtcagcaca gacccgcagc ccctcaagga gcagcccgcc     600
ctcaatgact ccagatactg cctgagcagc cgcctgaggg tctcggccac cttctggcag     660 aaccccccgca accacttccg ctgtcaagtc cagttctacg gctctcggga gaatgacgag     720
tggacccagg atagggccaa acctgtcacc cagatcgtca gcgccgaggc tgggggtaga     780
gcagactgtg gcttcacctc cgagtcttac cagcaagggg tcctgtctgc caccatcctc     840
tatgagatct tgctagggaa ggccaccttg tatgccgtgc tggtcagtgc cctcgtgctg     900
atggccatgg tcaagagaaa ggattccaga ggc                                  933
```

<210> SEQ ID NO 147
<211> LENGTH: 825
<212> TYPE: DNA
<213> ORGANISM: Artificial Sequence
<220> FEATURE:
<223> OTHER INFORMATION: Nucleotide sequence encoding TCR, Donor HD4-2

<400> SEQUENCE: 147

```
atggagaccc tcttgggcct gcttatcctt tggctgcagc tgcaatgggt gagcagcaaa      60
caggaggtga cgcagattcc tgcagctctg agtgtcccag aaggagaaaa cttggttctc     120
aactgcagtt tcactgatag cgctatttac aacctccagt ggtttaggca ggaccctggg     180
aaaggtctca catctctgtt gcttattcag tcaagtcaga gagagcaaac aagtggaaga     240
cttaatgcct cgctggataa atcatcagga cgtagtactt tatacattgc agcttctcag     300
cctggtgact cagccaccta cctctgtgct gtccgggcag agatttataa ccagggagga     360
aagcttatct tcggacaggg aacgagttat ctgtgaaac ccaatatcca gaaccctgac     420
cctgccgtgt accagctgag agactctaaa tccagtgaca gtctgtctg cctattcacc     480 gattttgatt ctcaaacaaa tgtgtcacaa agtaaggatt ctgatgtgta tatcacagac     540
aaaactgtgc tagacatgag gtcatatgga cttcaagagca acagtgctgt ggcctggagc     600
```

```
aacaaatctg actttgcatg tgcaaacgcc ttcaacaaca gcattattcc agaagacacc    660
ttcttcccca gcccagaaag ttcctgtgat gtcaagctgg tcgagaaaag ctttgaaaca    720
gatacgaacc taaactttca aaacctgtca gtgattgggt tccgaatcct cctcctgaaa    780
gtggccgggt ttaatctgct catgacgctg cggctgtggt ccagc                    825

<210> SEQ ID NO 148
<211> LENGTH: 921
<212> TYPE: DNA
<213> ORGANISM: Artificial Sequence
<220> FEATURE:
<223> OTHER INFORMATION: Nucleotide sequence encoding TCR, Donor HD4-2

<400> SEQUENCE: 148
atgagcatca gcctcctgtg ctgtgcagcc tttcctctcc tgtgggcagg tccagtgaat     60
gctggtgtca ctcagacccc aaaattccgc atcctgaaga taggacagag catgacactg    120
cagtgtaccc aggatatgaa ccataactac atgtactggt atcgacaaga cccaggcatg    180
gggctgaagc tgatttatta ttcagttggt gctggtatca ctgataaagg agaagtcccg    240
aatggctaca acgtctccag atcaaccaca gaggatttcc cgctcaggct ggagttggct    300
gctccctccc agacatctgt gtacttctgt gccagtaccc aaaactccct acgagcagtac   360 ttcgggccgg gcaccaggct cacggtcaca gaggacctga caaggtgtt cccacccgag    420 gtcgctgtgt ttgagccatc agaagcagag atctcccaca cccaaaaggc cacactggtg    480
tgcctggcca caggcttctt ccccgaccac gtggagctga gctggtgggt gaatgggaag    540
gaggtgcaca gtggggtcag cacggacccg cagcccctca aggagcagcc cgccctcaat    600
gactccagat actgcctgag cagccgcctg agggtctcgg ccaccttctg gcagaacccc    660
cgcaaccact ccgctgtgca gtccagttc tacgggctct cggagaatga cgagtggacc    720
caggataggg ccaaacccgt cacccagatc gtcagcgccg aggcctgggg tagagcagac    780
tgtggcttta cctcggtgtc ctaccagcaa ggggtcctgt ctgccaccat cctctatgag    840
atcctgctag ggaaggccac cctgtatgct gtgctggtca gcgcccttgt gttgatggcc    900
atggtcaaga gaaaggattt c                                              921

<210> SEQ ID NO 149
<211> LENGTH: 927
<212> TYPE: DNA
<213> ORGANISM: Artificial Sequence
<220> FEATURE:
<223> OTHER INFORMATION: Nucleotide sequence encoding TCR, Donor HD4-2

<400> SEQUENCE: 149
atgagcatca gcctcctgtg ctgtgcagcc tttcctctcc tgtgggcagg tccagtgaat     60
gctggtgtca ctcagacccc aaaattccgc atcctgaaga taggacagag catgacactg    120
cagtgtaccc aggatatgaa ccataactac atgtactggt atcgacaaga cccaggcatg    180
gggctgaagc tgatttatta ttcagttggt gctggtatca ctgataaagg agaagtcccg    240
aatggctaca acgtctccag atcaaccaca gaggatttcc cgctcaggct ggagttggct    300
gctccctccc agacatctgt gtacttctgt gccagtaccc aaaactccct acgagcagtac   360 ttcgggccgg gcaccaggct cacggtcaca gaggacctga aaaacgtgtt cccacccgag    420
gtcgctgtgt ttgagccatc agaagcagag atctcccaca cccaaaaggc cacactggtg    480
tgcctggcca caggcttcta ccccgaccac gtggagctga gctggtgggt gaatgggaag    540
gaggtgcaca gtggggtcag cacagacccg cagcccctca aggagcagcc cgccctcaat    600
```

```
gactccagat actgcctgag cagccgcctg agggtctcgg ccaccttctg gcagaacccc    660
cgcaaccact tccgctgtca agtccagttc tacgggctct cggagaatga cgagtggacc    720
caggataggg ccaaacctgt cacccagatc gtcagcgccg aggcctgggg tagagcagac    780
tgtggcttca cctccgagtc ttaccagcaa ggggtcctgt ctgccaccat cctctatgag    840
atcttgctag ggaaggccac cttgtatgcc gtgctggtca gtgccctcgt gctgatggcc    900
atggtcaaga gaaaggattc cagaggc                                         927
```

<210> SEQ ID NO 150
<211> LENGTH: 933
<212> TYPE: DNA
<213> ORGANISM: Artificial Sequence
<220> FEATURE:
<223> OTHER INFORMATION: Nucleotide sequence encoding TCR, Donor HD4-2

<400> SEQUENCE: 150

```
atggactcct ggaccttctg ctgtgtgtcc ctttgcatcc tggtagcgaa gcatacagat     60
gctggagtta tccagtcacc ccgccatgag gtgacagaga tgggacaaga agtgactctg    120
agatgtaaac caatttcagg ccacaactcc cttttctggt acagacagac catgatgcgg    180
ggactggagt tgctcattta ctttaacaac aacgttccga tagatgattc agggatgccc    240
gaggatcgat tctcagctaa gatgcctaat gcatcattct ccactctgaa gatccagccc    300
tcagaaccca gggactcagc tgtgtacttc tgtgccagca gcacagtggg aggggaggat    360
tatggctaca ccttcggttc ggggaccagg ttaaccgttg tagaggacct gaacaaggtg    420
ttcccacccg aggtcgctgt gtttgagcca tcagaagcag agatctccca cacccaaaag    480
gccacactgg tgtgcctggc cacaggcttc ttccccgacc acgtggagct gagctggtgg    540
gtgaatggga aggaggtgca cagtggggtc agcacggacc cgcagcccct caaggagcag    600
cccgccctca tgactccaga tactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt tacctcggtg tcctaccagc aaggggtcct gtctgccacc    840
atcctctatg agatcctgct agggaaggcc accctgtatg ctgtgctggt cagcgccctt    900
gtgttgatgg ccatggtcaa gagaaaggat ttc                                  933
```

<210> SEQ ID NO 151
<211> LENGTH: 939
<212> TYPE: DNA
<213> ORGANISM: Artificial Sequence
<220> FEATURE:
<223> OTHER INFORMATION: Nucleotide sequence encoding TCR, Donor HD4-2

<400> SEQUENCE: 151

```
atggactcct ggaccttctg ctgtgtgtcc ctttgcatcc tggtagcgaa gcatacagat     60
gctggagtta tccagtcacc ccgccatgag gtgacagaga tgggacaaga agtgactctg    120
agatgtaaac caatttcagg ccacaactcc cttttctggt acagacagac catgatgcgg    180
ggactggagt tgctcattta ctttaacaac aacgttccga tagatgattc agggatgccc    240
gaggatcgat tctcagctaa gatgcctaat gcatcattct ccactctgaa gatccagccc    300
tcagaaccca gggactcagc tgtgtacttc tgtgccagca gcacagtggg aggggaggat    360
tatggctaca ccttcggttc ggggaccagg ttaaccgttg tagaggacct gaaaaacgtg    420
```

```
ttcccacccg aggtcgctgt gtttgagcca tcagaagcag agatctccca cacccaaaag    480
gccacactgg tgtgcctggc cacaggcttc tacccc gacc acgtgagct gagctggtgg    540 gtgaatggga aggaggtgca cagtggggtc agcacagacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaacct gtcacccaga tcgtcagcgc cgaggcctgg    780
ggtagagcag actgtggctt cacctccgag tcttaccagc aagggg tcct gtctgccacc    840 atcctctatg agatcttgct agggaaggcc accttgtatg ccgtgctggt cagtgccctc    900
gtgctgatgg ccatggtcaa agaaaggat tccagaggc                            939

<210> SEQ ID NO 152
<211> LENGTH: 822
<212> TYPE: DNA
<213> ORGANISM: Artificial Sequence
<220> FEATURE:
<223> OTHER INFORMATION: Nucleotide sequence encoding TCR, Donor HD5

<400> SEQUENCE: 152
atgacatcca ttcgagctgt atttatattc ctgtggctgc agctggactt ggtgaatgga     60
gagaatgtgg agcagcatcc ttcaaccctg agtgtccagg agggagacag cgctgttatc    120
aagtgtactt attcagacag tgcctcaaac tacttccctt ggtataagca agaacttgga    180
aaaagacctc agcttattat agacattcgt tcaaatgtgg gcgaaaagaa agaccaacga    240
attgctgtta cattgaacaa gacagccaaa catttctccc tgcacatcac agagacccaa    300
cctgaagact cggctgtcta cttctgtgca gcaagtatgg ctggggctgg gagttaccaa    360 ctcacttcg ggaaggggac caaactctcg gtcataccaa atatccagaa ccctgaccct    420
gccgtgtacc agctgagaga ctctaaatcc agtgacaagt ctgtctgcct attcaccgat    480
tttgattctc aaacaaatgt gtcacaaagt aaggattctg atgtgtatat cacagacaaa    540
actgtgctag acatgaggtc tatggacttc aagagcaaca gtgctgtggc ctggagcaac    600
aaatctgact tgcatgtgc aaacgccttc aacaacagca ttattccaga agacaccttc    660
ttccccagcc cagaaagttc ctgtgatgtc aagctggtcg agaaaagctt tgaaacagat    720
acgaacctaa actttcaaaa cctgtcagtg attgggttcc gaatcctcct cctgaaagtg    780
gccgggttta tctgctcat gacgctgcgg ctgtggtcca gc                        822

<210> SEQ ID NO 153
<211> LENGTH: 930
<212> TYPE: DNA
<213> ORGANISM: Artificial Sequence
<220> FEATURE:
<223> OTHER INFORMATION: Nucleotide sequence encoding TCR, Donor HD5

<400> SEQUENCE: 153
atgggcacaa ggttgttctt ctatgtggcc ctttgtctcc tgtggacagg acacatggat     60
gctggaatca cccagagccc aagacacaag gtcacagaga caggaacacc agtgactctg    120
agatgtcacc agactgagaa ccaccgctat atgtactggt atcgacaaga cccgggggcat    180 gggctgaggc tgatccatta ctcatatggt gttaaagata ctgacaaagg agaagtctca    240
gatggctata gtgtctctag atcaaagaca gaggattttc ctctcactct ggagtccgct    300
accagctccc agacatctgt gtacttctgt gccatctcgg tggacagggg gccctctac    360 gagcagtact cgggccgggg caccaggctc acggtcacag aggacctgaa caaggtgttc    420
```

```
ccacccgagg tcgctgtgtt tgagccatca gaagcagaga tctcccacac ccaaaaggcc    480
acactggtgt gcctggccac aggcttcttc cccgaccacg tggagctgag ctggtgggtg    540
aatgggaagg aggtgcacag tggggtcagc acggacccgc agcccctcaa ggagcagccc    600
gccctcaatg actccagata ctgcctgagc agccgcctga ggtctcggc caccttctgg     660 cagaaccccc gcaaccactt ccgctgtcaa gtccagttct acgggctctc ggagaatgac    720
gagtggaccc aggatagggc caaacccgtc acccagatcg tcagcgccga ggcctggggt    780
agagcagact gtggctttac ctcggtgtcc taccagcaag gggtcctgtc tgccaccatc    840
ctctatgaga tcctgctagg gaaggccacc ctgtatgctg tgctggtcag cgcccttgtg    900
ttgatggcca tggtcaagag aaaggatttc                                     930
```

<210> SEQ ID NO 154
<211> LENGTH: 936
<212> TYPE: DNA
<213> ORGANISM: Artificial Sequence
<220> FEATURE:
<223> OTHER INFORMATION: Nucleotide sequence encoding TCR, Donor HD5

<400> SEQUENCE: 154

```
atgggcacaa ggttgttctt ctatgtggcc ctttgtctcc tgtggacagg acacatggat     60
gctggaatca cccagagccc aagacacaag gtcacagaga caggaacacc agtgactctg    120
agatgtcacc agactgagaa ccaccgctat atgtactggt atcgacaaga cccggggcat    180
gggctgaggc tgatccatta ctcatatggt gttaaagata ctgacaaagg agaagtctca    240
gatggctata gtgtctctag atcaaagaca gaggatttcc tcctcactct ggagtccgct    300
accagctccc agacatctgt gtacttctgt gccatctcgg tgggacaggg ggccctctac    360
gagcagtact cgggccgggg caccaggctc acggtcacag gacctgaa aaacgtgttc     420 ccacccgagg tcgctgtgtt tgagccatca gaagcagaga tctcccacac ccaaaaggcc    480
acactggtgt gcctggccac aggcttctac cccgaccacg tggagctgag ctggtgggtg    540
aatgggaagg aggtgcacag tggggtcagc acagacccgc agcccctcaa ggagcagccc    600
gccctcaatg actccagata ctgcctgagc agccgcctga ggtctcggc caccttctgg     660 cagaaccccc gcaaccactt ccgctgtcaa gtccagttct acgggctctc ggagaatgac    720
gagtggaccc aggatagggc caaacctgtc acccagatcg tcagcgccga ggcctggggt    780
agagcagact gtggcttcac ctccgagtct taccagcaag gggtcctgtc tgccaccatc    840
ctctatgaga tcttgctagg gaaggccacc ttgtatgccg tgctggtcag tgccctcgtg    900
ctgatggcca tggtcaagag aaaggattcc agaggc                              936
```

<210> SEQ ID NO 155
<211> LENGTH: 933
<212> TYPE: DNA
<213> ORGANISM: Artificial Sequence
<220> FEATURE:
<223> OTHER INFORMATION: Nucleotide sequence encoding TCR, Donor HD5

<400> SEQUENCE: 155

```
atgggcttca ggctcctctg ctgtgtggcc ttttgtctcc tgggagcagg cccagtggat     60
tctggagtca cacaaacccc aaagcacctg atcacagcaa ctggacagcg agtgacgctg    120
agatgctccc ctaggtctgg agacctctct gtgtactggt accaacagag cctggaccag    180
ggcctccagt tcctcattca gtattataat ggagaagaga gagcaaaagg aaacattctt    240
```

```
gaacgattct ccgcacaaca gttccctgac ttgcactctg aactaaacct gagctctctg      300
gagctggggg actcagcttt gtatttctgt gccagcagcg tagctcggga caggcggaac      360
tatggctaca ccttcggttc ggggaccagg ttaaccgttg tagaggacct gaacaaggtg      420
ttcccacccg aggtcgctgt gtttgagcca tcagaagcag agatctccca cacccaaaag      480
gccacactgg tgtgcctggc cacaggcttc ttccccgacc acgtggagct gagctggtgg      540
gtgaatggga aggaggtgca cagtggggtc agcacggacc cgcagcccct caaggagcag      600
cccgccctca atgactccag atactgcctg agcagccgcc tgagggtctc ggccaccttc      660
tggcagaacc cccgcaacca cttccgctgt caagtccagt tctacgggct ctcggagaat      720
gacgagtgga cccaggatag ggccaaaccc gtcacccaga tcgtcagcgc cgaggcctgg      780
ggtagagcag actgtggctt tacctcggtg tcctaccagc aagggtcct gtctgccacc       840 atcctctatg agatcctgct agggaaggcc accctgtatg ctgtgctggt cagcgccctt      900
gtgttgatgg ccatggtcaa gagaaaggat ttc                                   933
```

<210> SEQ ID NO 156
<211> LENGTH: 939
<212> TYPE: DNA
<213> ORGANISM: Artificial Sequence
<220> FEATURE:
<223> OTHER INFORMATION: Nucleotide sequence encoding TCR, Donor HD5

<400> SEQUENCE: 156

```
atgggcttca ggctcctctg ctgtgtggcc ttttgtctcc tgggagcagg cccagtggat       60
tctggagtca cacaaacccc aaagcacctg atcacagcaa ctggacagcg agtgacgctg      120
agatgctccc ctaggtctgg agacctctct gtgtactggt accaacagag cctggaccag      180
ggcctccagt tcctcattca gtattataat ggagaagaga gagcaaaagg aaacattctt      240
gaacgattct ccgcacaaca gttccctgac ttgcactctg aactaaacct gagctctctg      300
gagctggggg actcagcttt gtatttctgt gccagcagcg tagctcggga caggcggaac      360
tatggctaca ccttcggttc ggggaccagg ttaaccgttg tagaggacct gaaaaacgtg      420
ttcccacccg aggtcgctgt gtttgagcca tcagaagcag agatctccca cacccaaaag      480
gccacactgg tgtgcctggc cacaggcttc taccccgacc acgtggagct gagctggtgg      540
gtgaatggga aggaggtgca cagtggggtc agcacggacc cgcagcccct caaggagcag      600
cccgccctca atgactccag atactgcctg agcagccgcc tgagggtctc ggccaccttc      660
tggcagaacc cccgcaacca cttccgctgt caagtccagt tctacgggct ctcggagaat      720
gacgagtgga cccaggatag ggccaaacct gtcacccaga tcgtcagcgc cgaggcctgg      780
ggtagagcag actgtggctt cacctccgag tcttaccagc aagggtcct gtctgccacc       840 atcctctatg agatcttgct agggaaggcc accttgtatg ccgtgctggt cagtgccctc      900
gtgctgatgg ccatggtcaa gagaaaggat tccagaggc                             939
```

<210> SEQ ID NO 157
<211> LENGTH: 9
<212> TYPE: PRT
<213> ORGANISM: Artificial Sequence
<220> FEATURE:
<223> OTHER INFORMATION: nonamer peptide VLD
<400> SEQUENCE: 157

Val Leu Asp Phe Ala Pro Pro Gly Ala
1               5

```
<210> SEQ ID NO 158
<211> LENGTH: 9
<212> TYPE: PRT
<213> ORGANISM: Artificial Sequence
<220> FEATURE:
<223> OTHER INFORMATION: nonamer peptide PVL

<400> SEQUENCE: 158

Pro Val Leu Asp Phe Ala Pro Pro Gly
1               5

<210> SEQ ID NO 159
<211> LENGTH: 9
<212> TYPE: PRT
<213> ORGANISM: Artificial Sequence
<220> FEATURE:
<223> OTHER INFORMATION: nonamer peptide LDF

<400> SEQUENCE: 159

Leu Asp Phe Ala Pro Pro Gly Ala Ser
1               5

<210> SEQ ID NO 160
<211> LENGTH: 271
<212> TYPE: PRT
<213> ORGANISM: Artificial Sequence
<220> FEATURE:
<223> OTHER INFORMATION: TCR amino acid sequence, Donor HD7

<400> SEQUENCE: 160

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
        50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Val Arg
            100                 105                 110

Thr Ser Tyr Asp Lys Val Ile Phe Gly Pro Gly Thr Ser Leu Ser Val
        115                 120                 125

Ile Pro Asn Ile Gln Asn Pro Asp Pro Ala Val Tyr Gln Leu Arg Asp
        130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
        210                 215                 220
```

```
Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
                260                 265                 270

<210> SEQ ID NO 161
<211> LENGTH: 6
<212> TYPE: PRT
<213> ORGANISM: Artificial Sequence
<220> FEATURE:
<223> OTHER INFORMATION: TCR amino acid sequence, Donor HD7

<400> SEQUENCE: 161

Asp Phe Gln Ala Thr Thr
1               5

<210> SEQ ID NO 162
<211> LENGTH: 7
<212> TYPE: PRT
<213> ORGANISM: Artificial Sequence
<220> FEATURE:
<223> OTHER INFORMATION: TCR amino acid sequence, Donor HD7

<400> SEQUENCE: 162

Ser Asn Glu Gly Ser Lys Ala
1               5

<210> SEQ ID NO 163
<211> LENGTH: 14
<212> TYPE: PRT
<213> ORGANISM: Artificial Sequence
<220> FEATURE:
<223> OTHER INFORMATION: TCR amino acid sequence, Donor HD7

<400> SEQUENCE: 163

Cys Ser Ala Arg Asp Ser Val Ser Gly Asn Thr Ile Tyr Phe
1               5                   10

<210> SEQ ID NO 164
<211> LENGTH: 142
<212> TYPE: PRT
<213> ORGANISM: Artificial Sequence
<220> FEATURE:
<223> OTHER INFORMATION: TCR amino acid sequence, Donor HD7

<400> SEQUENCE: 164

Met Leu Leu Leu Leu Leu Leu Gly Pro Gly Ile Ser Leu Leu
1               5                   10                  15

Pro Gly Ser Leu Ala Gly Ser Gly Leu Gly Ala Val Val Ser Gln His
                20                  25                  30

Pro Ser Trp Val Ile Cys Lys Ser Gly Thr Ser Val Lys Ile Glu Cys
            35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
                85                  90                  95

Ala Ser Leu Thr Leu Ser Thr Leu Thr Val Thr Ser Ala His Pro Glu
                100                 105                 110
```

Asp Ser Ser Phe Tyr Ile Cys Ser Ala Arg Asp Ser Val Ser Gly Asn
        115                 120                 125

Thr Ile Tyr Phe Gly Glu Gly Ser Trp Leu Thr Val Val Glu
    130                 135                 140

<210> SEQ ID NO 165
<211> LENGTH: 318
<212> TYPE: PRT
<213> ORGANISM: Artificial Sequence
<220> FEATURE:
<223> OTHER INFORMATION: TCR amino acid sequence, Donor HD7

<400> SEQUENCE: 165

Met Leu Leu Leu Leu Leu Leu Gly Pro Gly Ile Ser Leu Leu Leu
1               5                   10                  15

Pro Gly Ser Leu Ala Gly Ser Gly Leu Gly Ala Val Val Ser Gln His
            20                  25                  30

Pro Ser Trp Val Ile Cys Lys Ser Gly Thr Ser Val Lys Ile Glu Cys
        35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
                85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Arg Asp Ser Val Ser Gly Asn
        115                 120                 125

Thr Ile Tyr Phe Gly Glu Gly Ser Trp Leu Thr Val Val Glu Asp Leu
    130                 135                 140

Asn Lys Val Phe Pro Pro Glu Val Ala Val Phe Glu Pro Ser Glu Ala
145                 150                 155                 160

Glu Ile Ser His Thr Gln Lys Ala Thr Leu Val Cys Leu Ala Thr Gly
                165                 170                 175

Phe Phe Pro Asp His Val Glu Leu Ser Trp Trp Val Asn Gly Lys Glu
            180                 185                 190

Val His Ser Gly Val Ser Thr Asp Pro Gln Pro Leu Lys Glu Gln Pro
        195                 200                 205

Ala Leu Asn Asp Ser Arg Tyr Cys Leu Ser Ser Arg Leu Arg Val Ser
    210                 215                 220

Ala Thr Phe Trp Gln Asn Pro Arg Asn His Phe Arg Cys Gln Val Gln
225                 230                 235                 240

Phe Tyr Gly Leu Ser Glu Asn Asp Glu Trp Thr Gln Asp Arg Ala Lys
                245                 250                 255

Pro Val Thr Gln Ile Val Ser Ala Glu Ala Trp Gly Arg Ala Asp Cys
            260                 265                 270

Gly Phe Thr Ser Val Ser Tyr Gln Gln Gly Val Leu Ser Ala Thr Ile
        275                 280                 285

Leu Tyr Glu Ile Leu Leu Gly Lys Ala Thr Leu Tyr Ala Val Leu Val
    290                 295                 300

Ser Ala Leu Val Leu Met Ala Met Val Lys Arg Lys Asp Phe
305                 310                 315

<210> SEQ ID NO 166

```
<211> LENGTH: 320
<212> TYPE: PRT
<213> ORGANISM: Artificial Sequence
<220> FEATURE:
<223> OTHER INFORMATION: TCR amino acid sequence, Donor HD7

<400> SEQUENCE: 166
```

Met Leu Leu Leu Leu Leu Leu Gly Pro Gly Ile Ser Leu Leu Leu
1               5                   10                  15

Pro Gly Ser Leu Ala Gly Ser Gly Leu Gly Ala Val Val Ser Gln His
            20                  25                  30

Pro Ser Trp Val Ile Cys Lys Ser Gly Thr Ser Val Lys Ile Glu Cys
            35                  40                  45

Arg Ser Leu Asp Phe Gln Ala Thr Thr Met Phe Trp Tyr Arg Gln Phe
            50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
            85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Arg Asp Ser Val Ser Gly Asn
            115                 120                 125

Thr Ile Tyr Phe Gly Glu Gly Ser Trp Leu Thr Val Val Glu Asp Leu
            130                 135                 140

Lys Asn Val Phe Pro Pro Glu Val Ala Val Phe Glu Pro Ser Glu Ala
145                 150                 155                 160

Glu Ile Ser His Thr Gln Lys Ala Thr Leu Val Cys Leu Ala Thr Gly
            165                 170                 175

Phe Tyr Pro Asp His Val Glu Leu Ser Trp Trp Val Asn Gly Lys Glu
            180                 185                 190

Val His Ser Gly Val Ser Thr Asp Pro Gln Pro Leu Lys Glu Gln Pro
            195                 200                 205

Ala Leu Asn Asp Ser Arg Tyr Cys Leu Ser Ser Arg Leu Arg Val Ser
            210                 215                 220

Ala Thr Phe Trp Gln Asn Pro Arg Asn His Phe Arg Cys Gln Val Gln
225                 230                 235                 240

Phe Tyr Gly Leu Ser Glu Asn Asp Glu Trp Thr Gln Asp Arg Ala Lys
            245                 250                 255

Pro Val Thr Gln Ile Val Ser Ala Glu Ala Trp Gly Arg Ala Asp Cys
            260                 265                 270

Gly Phe Thr Ser Glu Ser Tyr Gln Gln Gly Val Leu Ser Ala Thr Ile
            275                 280                 285

Leu Tyr Glu Ile Leu Leu Gly Lys Ala Thr Leu Tyr Ala Val Leu Val
            290                 295                 300

Ser Ala Leu Val Leu Met Ala Met Val Lys Arg Lys Asp Ser Arg Gly
305                 310                 315                 320

```
<210> SEQ ID NO 167
<211> LENGTH: 5
<212> TYPE: PRT
<213> ORGANISM: Artificial Sequence
<220> FEATURE:
<223> OTHER INFORMATION: TCR amino acid sequence, Donor HD7
```

```
<400> SEQUENCE: 167

Ser Gln Val Thr Met
1               5

<210> SEQ ID NO 168
<211> LENGTH: 7
<212> TYPE: PRT
<213> ORGANISM: Artificial Sequence
<220> FEATURE:
<223> OTHER INFORMATION: TCR amino acid sequence, Donor HD7

<400> SEQUENCE: 168

Ala Asn Gln Gly Ser Glu Ala
1               5

<210> SEQ ID NO 169
<211> LENGTH: 14
<212> TYPE: PRT
<213> ORGANISM: Artificial Sequence
<220> FEATURE:
<223> OTHER INFORMATION: TCR amino acid sequence, Donor HD7

<400> SEQUENCE: 169

Cys Ser Val Gly Gly Ser Gly Ser Tyr Asn Glu Gln Phe Phe
1               5                   10

<210> SEQ ID NO 170
<211> LENGTH: 131
<212> TYPE: PRT
<213> ORGANISM: Artificial Sequence
<220> FEATURE:
<223> OTHER INFORMATION: TCR amino acid sequence, Donor HD7

<400> SEQUENCE: 170

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
                100                 105                 110

Ser Gly Ser Tyr Asn Glu Gln Phe Phe Gly Pro Gly Thr Arg Leu Thr
            115                 120                 125

Val Leu Glu
    130

<210> SEQ ID NO 171
<211> LENGTH: 307
<212> TYPE: PRT
<213> ORGANISM: Artificial Sequence
<220> FEATURE:
<223> OTHER INFORMATION: TCR amino acid sequence, Donor HD7
```

<400> SEQUENCE: 171

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ser Gly Ser Tyr Asn Glu Gln Phe Phe Gly Pro Gly Thr Arg Leu Thr
            115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
            195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
            275                 280                 285

Tyr Ala Val Leu Val Ser Ala Leu Val Leu Met Ala Met Val Lys Arg
290                 295                 300

Lys Asp Phe
305

<210> SEQ ID NO 172
<211> LENGTH: 309
<212> TYPE: PRT
<213> ORGANISM: Artificial Sequence
<220> FEATURE:
<223> OTHER INFORMATION: TCR amino acid sequence, Donor HD7

<400> SEQUENCE: 172

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
                35                  40                  45
Trp Tyr Arg Gln Gln Pro Gly Gln Ser Leu Thr Leu Ile Ala Thr Ala
    50                  55                  60
Asn Gln Gly Ser Glu Ala Thr Tyr Glu Ser Gly Phe Val Ile Asp Lys
65                  70                  75                  80
Phe Pro Ile Ser Arg Pro Asn Leu Thr Phe Ser Thr Leu Thr Val Ser
                85                  90                  95
Asn Met Ser Pro Glu Asp Ser Ser Ile Tyr Leu Cys Ser Val Gly Gly
            100                 105                 110
Ser Gly Ser Tyr Asn Glu Gln Phe Phe Gly Pro Gly Thr Arg Leu Thr
        115                 120                 125
Val Leu Glu Asp Leu Lys Asn Val Phe Pro Pro Glu Val Ala Val Phe
    130                 135                 140
Glu Pro Ser Glu Ala Glu Ile Ser His Thr Gln Lys Ala Thr Leu Val
145                 150                 155                 160
Cys Leu Ala Thr Gly Phe Tyr Pro Asp His Val Glu Leu Ser Trp Trp
                165                 170                 175
Val Asn Gly Lys Glu Val His Ser Gly Val Ser Thr Asp Pro Gln Pro
            180                 185                 190
Leu Lys Glu Gln Pro Ala Leu Asn Asp Ser Arg Tyr Cys Leu Ser Ser
        195                 200                 205
Arg Leu Arg Val Ser Ala Thr Phe Trp Gln Asn Pro Arg Asn His Phe
    210                 215                 220
Arg Cys Gln Val Gln Phe Tyr Gly Leu Ser Glu Asn Asp Glu Trp Thr
225                 230                 235                 240
Gln Asp Arg Ala Lys Pro Val Thr Gln Ile Val Ser Ala Glu Ala Trp
                245                 250                 255
Gly Arg Ala Asp Cys Gly Phe Thr Ser Glu Ser Tyr Gln Gln Gly Val
            260                 265                 270
Leu Ser Ala Thr Ile Leu Tyr Glu Ile Leu Leu Gly Lys Ala Thr Leu
        275                 280                 285
Tyr Ala Val Leu Val Ser Ala Leu Val Leu Met Ala Met Val Lys Arg
    290                 295                 300
Lys Asp Ser Arg Gly
305

<210> SEQ ID NO 173
<211> LENGTH: 5
<212> TYPE: PRT
<213> ORGANISM: Artificial Sequence
<220> FEATURE:
<223> OTHER INFORMATION: TCR amino acid sequence, Donor HD8

<400> SEQUENCE: 173

Val Gly Ile Ser Ala
1               5

<210> SEQ ID NO 174
<211> LENGTH: 5
<212> TYPE: PRT
<213> ORGANISM: Artificial Sequence
<220> FEATURE:
<223> OTHER INFORMATION: TCR amino acid sequence, Donor HD8

<400> SEQUENCE: 174

Leu Ser Ser Gly Lys
1               5

<210> SEQ ID NO 175
<211> LENGTH: 11
<212> TYPE: PRT
<213> ORGANISM: Artificial Sequence
<220> FEATURE:
<223> OTHER INFORMATION: TCR amino acid sequence, Donor HD8

<400> SEQUENCE: 175

Cys Ala Val Thr Val Gly Asn Lys Leu Val Phe
1               5                   10

<210> SEQ ID NO 176
<211> LENGTH: 130
<212> TYPE: PRT
<213> ORGANISM: Artificial Sequence
<220> FEATURE:
<223> OTHER INFORMATION: TCR amino acid sequence, Donor HD8

<400> SEQUENCE: 176

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Thr
            100                 105                 110

Val Gly Asn Lys Leu Val Phe Gly Ala Gly Thr Ile Leu Arg Val Lys
        115                 120                 125

Ser Tyr
    130

<210> SEQ ID NO 177
<211> LENGTH: 270
<212> TYPE: PRT
<213> ORGANISM: Artificial Sequence
<220> FEATURE:
<223> OTHER INFORMATION: TCR amino acid sequence, Donor HD8

<400> SEQUENCE: 177

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                85                  90                  95

-continued

```
Thr Ala Ser His Pro Arg Asp Ser Ala Val Tyr Ile Cys Ala Val Thr
                100                 105                 110
Val Gly Asn Lys Leu Val Phe Gly Ala Gly Thr Ile Leu Arg Val Lys
        115                 120                 125
Ser Tyr Ile Gln Asn Pro Asp Pro Ala Val Tyr Gln Leu Arg Asp Ser
130                 135                 140
Lys Ser Ser Asp Lys Ser Val Cys Leu Phe Thr Asp Phe Asp Ser Gln
145                 150                 155                 160
Thr Asn Val Ser Gln Ser Lys Asp Ser Asp Val Tyr Ile Thr Asp Lys
                165                 170                 175
Thr Val Leu Asp Met Arg Ser Met Asp Phe Lys Ser Asn Ser Ala Val
            180                 185                 190
Ala Trp Ser Asn Lys Ser Asp Phe Ala Cys Ala Asn Ala Phe Asn Asn
        195                 200                 205
Ser Ile Ile Pro Glu Asp Thr Phe Phe Pro Ser Pro Glu Ser Ser Cys
    210                 215                 220
Asp Val Lys Leu Val Glu Lys Ser Phe Glu Thr Asp Thr Asn Leu Asn
225                 230                 235                 240
Phe Gln Asn Leu Ser Val Ile Gly Phe Arg Ile Leu Leu Leu Lys Val
                245                 250                 255
Ala Gly Phe Asn Leu Leu Met Thr Leu Arg Leu Trp Ser Ser
            260                 265                 270

<210> SEQ ID NO 178
<211> LENGTH: 5
<212> TYPE: PRT
<213> ORGANISM: Artificial Sequence
<220> FEATURE:
<223> OTHER INFORMATION: TCR amino acid sequence, Donor HD8

<400> SEQUENCE: 178

Met Asn His Asn Ser
1               5

<210> SEQ ID NO 179
<211> LENGTH: 6
<212> TYPE: PRT
<213> ORGANISM: Artificial Sequence
<220> FEATURE:
<223> OTHER INFORMATION: TCR amino acid sequence, Donor HD8

<400> SEQUENCE: 179

Ser Ala Ser Glu Gly Thr
1               5

<210> SEQ ID NO 180
<211> LENGTH: 11
<212> TYPE: PRT
<213> ORGANISM: Artificial Sequence
<220> FEATURE:
<223> OTHER INFORMATION: TCR amino acid sequence, Donor HD8

<400> SEQUENCE: 180

Cys Ala Ser Arg Gly Trp Arg Glu Gln Phe Phe
1               5                   10

<210> SEQ ID NO 181
<211> LENGTH: 130
<212> TYPE: PRT
<213> ORGANISM: Artificial Sequence
<220> FEATURE:
<223> OTHER INFORMATION: TCR amino acid sequence, Donor HD8
```

<400> SEQUENCE: 181

Met Ser Ile Gly Leu Leu Cys Cys Val Ala Phe Ser Leu Leu Trp Ala
1               5                   10                  15

Ser Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Asn Ser Met Tyr Trp Tyr Arg Gln Asp Pro Gly Met Gly Leu Arg Leu
    50                  55                  60

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
            100                 105                 110

Arg Gly Trp Arg Glu Gln Phe Phe Gly Pro Gly Thr Arg Leu Thr Val
        115                 120                 125

Leu Glu
    130

<210> SEQ ID NO 182
<211> LENGTH: 306
<212> TYPE: PRT
<213> ORGANISM: Artificial Sequence
<220> FEATURE:
<223> OTHER INFORMATION: TCR amino acid sequence, Donor HD8

<400> SEQUENCE: 182

Met Ser Ile Gly Leu Leu Cys Cys Val Ala Phe Ser Leu Leu Trp Ala
1               5                   10                  15

Ser Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Asn Ser Met Tyr Trp Tyr Arg Gln Asp Pro Gly Met Gly Leu Arg Leu
    50                  55                  60

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
            100                 105                 110

Arg Gly Trp Arg Glu Gln Phe Phe Gly Pro Gly Thr Arg Leu Thr Val
        115                 120                 125

Leu Glu Asp Leu Asn Lys Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Phe Pro Asp His Val Glu Leu Ser Trp Trp Val
                165                 170                 175

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

```
Leu Arg Val Ser Ala Thr Phe Trp Gln Asn Pro Arg Asn His Phe Arg
210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Val Ser Tyr Gln Gln Gly Val Leu
                260                 265                 270

Ser Ala Thr Ile Leu Tyr Glu Ile Leu Leu Gly Lys Ala Thr Leu Tyr
                275                 280                 285

Ala Val Leu Val Ser Ala Leu Val Leu Met Ala Met Val Lys Arg Lys
290                 295                 300

Asp Phe
305

<210> SEQ ID NO 183
<211> LENGTH: 308
<212> TYPE: PRT
<213> ORGANISM: Artificial Sequence
<220> FEATURE:
<223> OTHER INFORMATION: TCR amino acid sequence, Donor HD8

<400> SEQUENCE: 183

Met Ser Ile Gly Leu Leu Cys Cys Val Ala Phe Ser Leu Leu Trp Ala
1               5                   10                  15

Ser Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
                35                  40                  45

Asn Ser Met Tyr Trp Tyr Arg Gln Asp Pro Gly Met Gly Leu Arg Leu
50                  55                  60

Ile Tyr Tyr Ser Ala Ser Glu Gly Thr Thr Asp Lys Gly Glu Val Pro
65                  70                  75                  80

Asn Gly Tyr Asn Val Ser Arg Leu Asn Lys Arg Glu Phe Ser Leu Arg
                85                  90                  95

Leu Glu Ser Ala Ala Pro Ser Gln Thr Ser Val Tyr Phe Cys Ala Ser
                100                 105                 110

Arg Gly Trp Arg Glu Gln Phe Phe Gly Pro Gly Thr Arg Leu Thr Val
                115                 120                 125

Leu Glu Asp Leu Lys Asn Val Phe Pro Pro Glu Val Ala Val Phe Glu
130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp His Val Glu Leu Ser Trp Trp Val
                165                 170                 175

Asn Gly Lys Glu Val His Ser Gly Val Ser Thr Asp Pro Gln Pro Leu
                180                 185                 190

Lys Glu Gln Pro Ala Leu Asn Asp Ser Arg Tyr Cys Leu Ser Ser Arg
                195                 200                 205

Leu Arg Val Ser Ala Thr Phe Trp Gln Asn Pro Arg Asn His Phe Arg
210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255
```

-continued

```
Arg Ala Asp Cys Gly Phe Thr Ser Glu Ser Tyr Gln Gln Gly Val Leu
                260                 265                 270

Ser Ala Thr Ile Leu Tyr Glu Ile Leu Leu Gly Lys Ala Thr Leu Tyr
            275                 280                 285

Ala Val Leu Val Ser Ala Leu Val Leu Met Ala Met Val Lys Arg Lys
        290                 295                 300

Asp Ser Arg Gly
305

<210> SEQ ID NO 184
<211> LENGTH: 5
<212> TYPE: PRT
<213> ORGANISM: Artificial Sequence
<220> FEATURE:
<223> OTHER INFORMATION: TCR amino acid sequence, Donor HD9

<400> SEQUENCE: 184

Val Gly Ile Ser Ala
1               5

<210> SEQ ID NO 185
<211> LENGTH: 5
<212> TYPE: PRT
<213> ORGANISM: Artificial Sequence
<220> FEATURE:
<223> OTHER INFORMATION: TCR amino acid sequence, Donor HD9

<400> SEQUENCE: 185

Leu Ser Ser Gly Lys
1               5

<210> SEQ ID NO 186
<211> LENGTH: 13
<212> TYPE: PRT
<213> ORGANISM: Artificial Sequence
<220> FEATURE:
<223> OTHER INFORMATION: TCR amino acid sequence, Donor HD9

<400> SEQUENCE: 186

Cys Ala Ala Arg Ser Tyr Asn Thr Asp Lys Leu Ile Phe
1               5                   10

<210> SEQ ID NO 187
<211> LENGTH: 132
<212> TYPE: PRT
<213> ORGANISM: Artificial Sequence
<220> FEATURE:
<223> OTHER INFORMATION: TCR amino acid sequence, Donor HD9

<400> SEQUENCE: 187

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys His Gly Arg
65                  70                  75                  80

Leu Ile Ala Thr Ile Asn Ile Gln Glu Lys His Ser Ser Leu His Ile
                85                  90                  95
```

```
Thr Ala Ser His Pro Arg Asp Ser Ala Val Tyr Ile Cys Ala Ala Arg
            100                 105                 110

Ser Tyr Asn Thr Asp Lys Leu Ile Phe Gly Thr Gly Thr Arg Leu Gln
        115                 120                 125

Val Phe Pro Asn
        130

<210> SEQ ID NO 188
<211> LENGTH: 272
<212> TYPE: PRT
<213> ORGANISM: Artificial Sequence
<220> FEATURE:
<223> OTHER INFORMATION: TCR amino acid sequence, Donor HD9

<400> SEQUENCE: 188

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Ala Arg
            100                 105                 110

Ser Tyr Asn Thr Asp Lys Leu Ile Phe Gly Thr Gly Thr Arg Leu Gln
        115                 120                 125

Val Phe Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 189
<211> LENGTH: 6
<212> TYPE: PRT
<213> ORGANISM: Artificial Sequence
<220> FEATURE:
<223> OTHER INFORMATION: TCR amino acid sequence, Donor HD9
```

<400> SEQUENCE: 189

Asn Ser Met Phe Asp Tyr
1               5

<210> SEQ ID NO 190
<211> LENGTH: 7
<212> TYPE: PRT
<213> ORGANISM: Artificial Sequence
<220> FEATURE:
<223> OTHER INFORMATION: TCR amino acid sequence, Donor HD9

<400> SEQUENCE: 190

Ile Ser Ser Ile Lys Asp Lys
1               5

<210> SEQ ID NO 191
<211> LENGTH: 12
<212> TYPE: PRT
<213> ORGANISM: Artificial Sequence
<220> FEATURE:
<223> OTHER INFORMATION: TCR amino acid sequence, Donor HD9

<400> SEQUENCE: 191

Cys Ala Ala Ser Tyr Asn Asn Ala Arg Leu Met Phe
1               5                   10

<210> SEQ ID NO 192
<211> LENGTH: 138
<212> TYPE: PRT
<213> ORGANISM: Artificial Sequence
<220> FEATURE:
<223> OTHER INFORMATION: TCR amino acid sequence, Donor HD9

<400> SEQUENCE: 192

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Tyr Asn Asn Ala Arg Leu Met Phe Gly
        115                 120                 125

Asp Gly Thr Gln Leu Val Val Lys Pro Asn
    130                 135

<210> SEQ ID NO 193
<211> LENGTH: 278
<212> TYPE: PRT
<213> ORGANISM: Artificial Sequence
<220> FEATURE:
<223> OTHER INFORMATION: TCR amino acid sequence, Donor HD9

<400> SEQUENCE: 193

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
            35                  40                  45

Cys Asp Tyr Thr Asn Ser Met Phe Asp Tyr Phe Leu Trp Tyr Lys Lys
50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
                100                 105                 110

Val Tyr Phe Cys Ala Ala Ser Tyr Asn Asn Ala Arg Leu Met Phe Gly
                115                 120                 125

Asp Gly Thr Gln Leu Val Val Lys Pro Asn Ile Gln Asn Pro Asp Pro
130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
                180                 185                 190

Asp Phe Lys Ser Asn Ser Ala Val Ala Trp Ser Asn Lys Ser Asp Phe
                195                 200                 205

Ala Cys Ala Asn Ala Phe Asn Asn Ser Ile Ile Pro Glu Asp Thr Phe
                210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
                260                 265                 270

Leu Arg Leu Trp Ser Ser
                275

<210> SEQ ID NO 194
<211> LENGTH: 5
<212> TYPE: PRT
<213> ORGANISM: Artificial Sequence
<220> FEATURE:
<223> OTHER INFORMATION: TCR amino acid sequence, Donor HD9

<400> SEQUENCE: 194

Ser Gly His Thr Ser
1               5

<210> SEQ ID NO 195
<211> LENGTH: 6
<212> TYPE: PRT
<213> ORGANISM: Artificial Sequence
<220> FEATURE:
<223> OTHER INFORMATION: TCR amino acid sequence, Donor HD9

<400> SEQUENCE: 195

Tyr Asp Glu Gly Glu Glu
1               5

<210> SEQ ID NO 196
<211> LENGTH: 13
<212> TYPE: PRT
<213> ORGANISM: Artificial Sequence
<220> FEATURE:
<223> OTHER INFORMATION: TCR amino acid sequence, Donor HD9

<400> SEQUENCE: 196

Cys Ala Ser Ser Trp Gly Tyr Gln Glu Thr Gln Tyr Phe
1               5                   10

<210> SEQ ID NO 197
<211> LENGTH: 132
<212> TYPE: PRT
<213> ORGANISM: Artificial Sequence
<220> FEATURE:
<223> OTHER INFORMATION: TCR amino acid sequence, Donor HD9

<400> SEQUENCE: 197

Met Gly Pro Arg Leu Leu Phe Trp Ala Leu Leu Cys Leu Leu Gly Thr
1               5                   10                  15

Gly Pro Val Glu Ala Gly Val Thr Gln Ser Pro Thr His Leu Ile Lys
            20                  25                  30

Thr Arg Gly Gln Gln Ala Thr Leu Arg Cys Ser Pro Ile Ser Gly His
        35                  40                  45

Thr Ser Val Tyr Trp Tyr Gln Gln Ala Leu Gly Leu Gly Leu Gln Phe
    50                  55                  60

Leu Leu Trp Tyr Asp Glu Gly Glu Glu Arg Asn Arg Gly Asn Phe Pro
65                  70                  75                  80

Pro Arg Phe Ser Gly Arg Gln Phe Pro Asn Tyr Ser Ser Glu Leu Asn
                85                  90                  95

Val Asn Ala Leu Glu Leu Glu Asp Ser Ala Leu Tyr Leu Cys Ala Ser
            100                 105                 110

Ser Trp Gly Tyr Gln Glu Thr Gln Tyr Phe Gly Pro Gly Thr Arg Leu
        115                 120                 125

Leu Val Leu Glu
    130

<210> SEQ ID NO 198
<211> LENGTH: 308
<212> TYPE: PRT
<213> ORGANISM: Artificial Sequence
<220> FEATURE:
<223> OTHER INFORMATION: TCR amino acid sequence, Donor HD9

<400> SEQUENCE: 198

Met Gly Pro Arg Leu Leu Phe Trp Ala Leu Leu Cys Leu Leu Gly Thr
1               5                   10                  15

Gly Pro Val Glu Ala Gly Val Thr Gln Ser Pro Thr His Leu Ile Lys
            20                  25                  30

Thr Arg Gly Gln Gln Ala Thr Leu Arg Cys Ser Pro Ile Ser Gly His
        35                  40                  45

Thr Ser Val Tyr Trp Tyr Gln Gln Ala Leu Gly Leu Gly Leu Gln Phe
    50                  55                  60

Leu Leu Trp Tyr Asp Glu Gly Glu Arg Asn Arg Gly Asn Phe Pro
65                  70                  75                  80

Pro Arg Phe Ser Gly Arg Gln Phe Pro Asn Tyr Ser Ser Glu Leu Asn
                85                  90                  95

Val Asn Ala Leu Glu Leu Glu Asp Ser Ala Leu Tyr Leu Cys Ala Ser
            100                 105                 110

Ser Trp Gly Tyr Gln Glu Thr Gln Tyr Phe Gly Pro Gly Thr Arg Leu
            115                 120                 125

Leu Val Leu Glu Asp Leu Asn Lys Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
            290                 295                 300

Arg Lys Asp Phe
305

<210> SEQ ID NO 199
<211> LENGTH: 310
<212> TYPE: PRT
<213> ORGANISM: Artificial Sequence
<220> FEATURE:
<223> OTHER INFORMATION: TCR amino acid sequence, Donor HD9

<400> SEQUENCE: 199

Met Gly Pro Arg Leu Leu Phe Trp Ala Leu Leu Cys Leu Leu Gly Thr
1               5                   10                  15

Gly Pro Val Glu Ala Gly Val Thr Gln Ser Pro Thr His Leu Ile Lys
            20                  25                  30

Thr Arg Gly Gln Gln Ala Thr Leu Arg Cys Ser Pro Ile Ser Gly His
            35                  40                  45

Thr Ser Val Tyr Trp Tyr Gln Gln Ala Leu Gly Leu Gly Leu Gln Phe
        50                  55                  60

Leu Leu Trp Tyr Asp Glu Gly Glu Arg Asn Arg Gly Asn Phe Pro
65                  70                  75                  80

Pro Arg Phe Ser Gly Arg Gln Phe Pro Asn Tyr Ser Ser Glu Leu Asn
                85                  90                  95

Val Asn Ala Leu Glu Leu Glu Asp Ser Ala Leu Tyr Leu Cys Ala Ser
            100                 105                 110

-continued

```
Ser Trp Gly Tyr Gln Glu Thr Gln Tyr Phe Gly Pro Gly Thr Arg Leu
        115                 120                 125

Leu Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 200
<211> LENGTH: 5
<212> TYPE: PRT
<213> ORGANISM: Artificial Sequence
<220> FEATURE:
<223> OTHER INFORMATION: TCR amino acid sequence, Donor HD9

<400> SEQUENCE: 200

Lys Gly His Ser His
1               5

<210> SEQ ID NO 201
<211> LENGTH: 6
<212> TYPE: PRT
<213> ORGANISM: Artificial Sequence
<220> FEATURE:
<223> OTHER INFORMATION: TCR amino acid sequence, Donor HD9

<400> SEQUENCE: 201

Leu Gln Lys Glu Asn Ile
1               5

<210> SEQ ID NO 202
<211> LENGTH: 15
<212> TYPE: PRT
<213> ORGANISM: Artificial Sequence
<220> FEATURE:
<223> OTHER INFORMATION: TCR amino acid sequence, Donor HD9

<400> SEQUENCE: 202

Cys Ala Ser Ser Pro Thr Gly Gly Glu Tyr Tyr Gly Tyr Thr Phe
1               5                   10                  15
```

<210> SEQ ID NO 203
<211> LENGTH: 135
<212> TYPE: PRT
<213> ORGANISM: Artificial Sequence
<220> FEATURE:
<223> OTHER INFORMATION: TCR amino acid sequence, Donor HD9

<400> SEQUENCE: 203

```
Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
                20                  25                  30

Arg Arg Gly Gln Glu Ala Arg Leu Arg Cys Ser Pro Met Lys Gly His
            35                  40                  45

Ser His Val Tyr Trp Tyr Arg Gln Leu Pro Glu Glu Gly Leu Lys Phe
        50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Thr Gly Gly Glu Tyr Tyr Gly Tyr Thr Phe Gly Ser Gly
        115                 120                 125

Thr Arg Leu Thr Val Val Glu
    130                 135
```

<210> SEQ ID NO 204
<211> LENGTH: 311
<212> TYPE: PRT
<213> ORGANISM: Artificial Sequence
<220> FEATURE:
<223> OTHER INFORMATION: TCR amino acid sequence, Donor HD9

<400> SEQUENCE: 204

```
Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
                20                  25                  30

Arg Arg Gly Gln Glu Ala Arg Leu Arg Cys Ser Pro Met Lys Gly His
            35                  40                  45

Ser His Val Tyr Trp Tyr Arg Gln Leu Pro Glu Glu Gly Leu Lys Phe
        50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Thr Gly Gly Glu Tyr Tyr Gly Tyr Thr Phe Gly Ser Gly
        115                 120                 125

Thr Arg Leu Thr Val Val Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175
```

```
Leu Ser Trp Trp Val Asn Gly Lys Glu Val His Ser Gly Val Ser Thr
                180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
                260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
290                 295                 300

Met Val Lys Arg Lys Asp Phe
305                 310

<210> SEQ ID NO 205
<211> LENGTH: 313
<212> TYPE: PRT
<213> ORGANISM: Artificial Sequence
<220> FEATURE:
<223> OTHER INFORMATION: TCR amino acid sequence, Donor HD9

<400> SEQUENCE: 205

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
        35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Thr Gly Gly Glu Tyr Tyr Gly Tyr Thr Phe Gly Ser Gly
        115                 120                 125

Thr Arg Leu Thr Val Val Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
210                 215                 220
```

-continued

```
Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Glu Ser Tyr
        260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
        290                 295                 300

Met Val Lys Arg Lys Asp Ser Arg Gly
305                 310

<210> SEQ ID NO 206
<211> LENGTH: 5
<212> TYPE: PRT
<213> ORGANISM: Artificial Sequence
<220> FEATURE:
<223> OTHER INFORMATION: TCR amino acid sequence, Donor HD9

<400> SEQUENCE: 206

Met Asn His Glu Tyr
1               5

<210> SEQ ID NO 207
<211> LENGTH: 6
<212> TYPE: PRT
<213> ORGANISM: Artificial Sequence
<220> FEATURE:
<223> OTHER INFORMATION: TCR amino acid sequence, Donor HD9

<400> SEQUENCE: 207

Ser Val Gly Ala Gly Ile
1               5

<210> SEQ ID NO 208
<211> LENGTH: 22
<212> TYPE: PRT
<213> ORGANISM: Artificial Sequence
<220> FEATURE:
<223> OTHER INFORMATION: TCR amino acid sequence, Donor HD9

<400> SEQUENCE: 208

Cys Ala Ser Ser Ser Tyr Pro Leu Arg Thr Gly Arg Tyr Asn Ser Tyr
1               5                   10                  15

Asn Ser Pro Leu His Phe
            20

<210> SEQ ID NO 209
<211> LENGTH: 141
<212> TYPE: PRT
<213> ORGANISM: Artificial Sequence
<220> FEATURE:
<223> OTHER INFORMATION: TCR amino acid sequence, Donor HD9

<400> SEQUENCE: 209

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45
```

Glu Tyr Met Ser Trp Tyr Arg Gln Asp Pro Gly Met Gly Leu Arg Leu
            50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Ser Tyr Pro Leu Arg Thr Gly Arg Tyr Asn Ser Tyr Asn Ser Pro
        115                 120                 125

Leu His Phe Gly Asn Gly Thr Arg Leu Thr Val Thr Glu
        130                 135                 140

<210> SEQ ID NO 210
<211> LENGTH: 317
<212> TYPE: PRT
<213> ORGANISM: Artificial Sequence
<220> FEATURE:
<223> OTHER INFORMATION: TCR amino acid sequence, Donor HD9

<400> SEQUENCE: 210

Met Ser Ile Gly Leu Cys Cys Ala Ala Leu Ser Leu Leu Trp Ala
1                   5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
            50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Ser Tyr Pro Leu Arg Thr Gly Arg Tyr Asn Ser Tyr Asn Ser Pro
        115                 120                 125

Leu His Phe Gly Asn Gly Thr Arg Leu Thr Val Thr Glu Asp Leu Asn
        130                 135                 140

Lys Val Phe Pro Pro Glu Val Ala Val Phe Glu Pro Ser Glu Ala Glu
145                 150                 155                 160

Ile Ser His Thr Gln Lys Ala Thr Leu Val Cys Leu Ala Thr Gly Phe
                165                 170                 175

Phe Pro Asp His Val Glu Leu Ser Trp Trp Val Asn Gly Lys Glu Val
            180                 185                 190

His Ser Gly Val Ser Thr Asp Pro Gln Pro Leu Lys Glu Gln Pro Ala
        195                 200                 205

Leu Asn Asp Ser Arg Tyr Cys Leu Ser Ser Arg Leu Arg Val Ser Ala
        210                 215                 220

Thr Phe Trp Gln Asn Pro Arg Asn His Phe Arg Cys Gln Val Gln Phe
225                 230                 235                 240

Tyr Gly Leu Ser Glu Asn Asp Glu Trp Thr Gln Asp Arg Ala Lys Pro
                245                 250                 255

Val Thr Gln Ile Val Ser Ala Glu Ala Trp Gly Arg Ala Asp Cys Gly
            260                 265                 270

Phe Thr Ser Val Ser Tyr Gln Gln Gly Val Leu Ser Ala Thr Ile Leu
            275                 280                 285

Tyr Glu Ile Leu Leu Gly Lys Ala Thr Leu Tyr Ala Val Leu Val Ser
        290                 295                 300

Ala Leu Val Leu Met Ala Met Val Lys Arg Lys Asp Phe
305                 310                 315

<210> SEQ ID NO 211
<211> LENGTH: 319
<212> TYPE: PRT
<213> ORGANISM: Artificial Sequence
<220> FEATURE:
<223> OTHER INFORMATION: TCR amino acid sequence, Donor HD9

<400> SEQUENCE: 211

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Ser Tyr Pro Leu Arg Thr Gly Arg Tyr Asn Ser Tyr Asn Ser Pro
        115                 120                 125

Leu His Phe Gly Asn Gly Thr Arg Leu Thr Val Thr Glu Asp Leu Lys
    130                 135                 140

Asn Val Phe Pro Pro Glu Val Ala Val Phe Glu Pro Ser Glu Ala Glu
145                 150                 155                 160

Ile Ser His Thr Gln Lys Ala Thr Leu Val Cys Leu Ala Thr Gly Phe
                165                 170                 175

Tyr Pro Asp His Val Glu Leu Ser Trp Trp Val Asn Gly Lys Glu Val
            180                 185                 190

His Ser Gly Val Ser Thr Asp Pro Gln Pro Leu Lys Glu Gln Pro Ala
        195                 200                 205

Leu Asn Asp Ser Arg Tyr Cys Leu Ser Ser Arg Leu Arg Val Ser Ala
    210                 215                 220

Thr Phe Trp Gln Asn Pro Arg Asn His Phe Arg Cys Gln Val Gln Phe
225                 230                 235                 240

Tyr Gly Leu Ser Glu Asn Asp Glu Trp Thr Gln Asp Arg Ala Lys Pro
                245                 250                 255

Val Thr Gln Ile Val Ser Ala Glu Ala Trp Gly Arg Ala Asp Cys Gly
            260                 265                 270

Phe Thr Ser Glu Ser Tyr Gln Gln Gly Val Leu Ser Ala Thr Ile Leu
        275                 280                 285

Tyr Glu Ile Leu Leu Gly Lys Ala Thr Leu Tyr Ala Val Leu Val Ser
    290                 295                 300

Ala Leu Val Leu Met Ala Met Val Lys Arg Lys Asp Ser Arg Gly
305                 310                 315

<210> SEQ ID NO 212
<211> LENGTH: 6
<212> TYPE: PRT
<213> ORGANISM: Artificial Sequence
<220> FEATURE:
<223> OTHER INFORMATION: TCR amino acid sequence, Donor HD10

<400> SEQUENCE: 212

Asn Ser Met Phe Asp Tyr
1               5

<210> SEQ ID NO 213
<211> LENGTH: 7
<212> TYPE: PRT
<213> ORGANISM: Artificial Sequence
<220> FEATURE:
<223> OTHER INFORMATION: TCR amino acid sequence, Donor HD10

<400> SEQUENCE: 213

Ile Ser Ser Ile Lys Asp Lys
1               5

<210> SEQ ID NO 214
<211> LENGTH: 13
<212> TYPE: PRT
<213> ORGANISM: Artificial Sequence
<220> FEATURE:
<223> OTHER INFORMATION: TCR amino acid sequence, Donor HD10

<400> SEQUENCE: 214

Cys Ala Ala Ser Gly Gly Arg Asp Asp Lys Ile Ile Phe
1               5                   10

<210> SEQ ID NO 215
<211> LENGTH: 139
<212> TYPE: PRT
<213> ORGANISM: Artificial Sequence
<220> FEATURE:
<223> OTHER INFORMATION: TCR amino acid sequence, Donor HD10

<400> SEQUENCE: 215

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly Gly Arg Asp Asp Lys Ile Ile Phe
        115                 120                 125

Gly Lys Gly Thr Arg Leu His Ile Leu Pro Asn
    130                 135

<210> SEQ ID NO 216

<211> LENGTH: 279
<212> TYPE: PRT
<213> ORGANISM: Artificial Sequence
<220> FEATURE:
<223> OTHER INFORMATION: TCR amino acid sequence, Donor HD10

<400> SEQUENCE: 216

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly Gly Arg Asp Asp Lys Ile Ile Phe
        115                 120                 125

Gly Lys Gly Thr Arg Leu His Ile Leu Pro Asn Ile Gln Asn Pro Asp
130                 135                 140

Pro Ala Val Tyr Gln Leu Arg Asp Ser Lys Ser Ser Asp Lys Ser Val
145                 150                 155                 160

Cys Leu Phe Thr Asp Phe Asp Ser Gln Thr Asn Val Ser Gln Ser Lys
                165                 170                 175

Asp Ser Asp Val Tyr Ile Thr Asp Lys Thr Val Leu Asp Met Arg Ser
            180                 185                 190

Met Asp Phe Lys Ser Asn Ser Ala Val Ala Trp Ser Asn Lys Ser Asp
        195                 200                 205

Phe Ala Cys Ala Asn Ala Phe Asn Asn Ser Ile Ile Pro Glu Asp Thr
    210                 215                 220

Phe Phe Pro Ser Pro Glu Ser Ser Cys Asp Val Lys Leu Val Glu Lys
225                 230                 235                 240

Ser Phe Glu Thr Asp Thr Asn Leu Asn Phe Gln Asn Leu Ser Val Ile
                245                 250                 255

Gly Phe Arg Ile Leu Leu Leu Lys Val Ala Gly Phe Asn Leu Leu Met
            260                 265                 270

Thr Leu Arg Leu Trp Ser Ser
        275

<210> SEQ ID NO 217
<211> LENGTH: 5
<212> TYPE: PRT
<213> ORGANISM: Artificial Sequence
<220> FEATURE:
<223> OTHER INFORMATION: TCR amino acid sequence, Donor HD10

<400> SEQUENCE: 217

Met Asn His Glu Tyr
1               5

<210> SEQ ID NO 218
<211> LENGTH: 6
<212> TYPE: PRT

```
<213> ORGANISM: Artificial Sequence
<220> FEATURE:
<223> OTHER INFORMATION: TCR amino acid sequence, Donor HD10

<400> SEQUENCE: 218

Ser Val Gly Ala Gly Ile
1               5

<210> SEQ ID NO 219
<211> LENGTH: 16
<212> TYPE: PRT
<213> ORGANISM: Artificial Sequence
<220> FEATURE:
<223> OTHER INFORMATION: TCR amino acid sequence, Donor HD10

<400> SEQUENCE: 219

Cys Ala Ser Ser Tyr Ser Arg Thr Glu Ser Thr Asp Thr Gln Tyr Phe
1               5                   10                  15

<210> SEQ ID NO 220
<211> LENGTH: 135
<212> TYPE: PRT
<213> ORGANISM: Artificial Sequence
<220> FEATURE:
<223> OTHER INFORMATION: TCR amino acid sequence, Donor HD10

<400> SEQUENCE: 220

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
        50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Ser Arg Thr Glu Ser Asp Thr Gln Tyr Phe Gly Pro Gly
        115                 120                 125

Thr Arg Leu Thr Val Leu Glu
    130                 135

<210> SEQ ID NO 221
<211> LENGTH: 311
<212> TYPE: PRT
<213> ORGANISM: Artificial Sequence
<220> FEATURE:
<223> OTHER INFORMATION: TCR amino acid sequence, Donor HD10

<400> SEQUENCE: 221

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45
```

Glu Tyr Met Ser Trp Tyr Arg Gln Asp Pro Gly Met Gly Leu Arg Leu
            50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Ser Arg Thr Glu Ser Thr Asp Thr Gln Tyr Phe Gly Pro Gly
            115                 120                 125

Thr Arg Leu Thr Val Leu Glu Asp Leu Asn Lys Val Phe Pro Pro Glu
            130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Phe
305                 310

<210> SEQ ID NO 222
<211> LENGTH: 313
<212> TYPE: PRT
<213> ORGANISM: Artificial Sequence
<220> FEATURE:
<223> OTHER INFORMATION: TCR amino acid sequence, Donor HD10

<400> SEQUENCE: 222

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Ser Arg Thr Glu Ser Thr Asp Thr Gln Tyr Phe Gly Pro Gly
            115                 120                 125

Thr Arg Leu Thr Val Leu Glu Asp Leu Lys Asn Val Phe Pro Pro Glu
        130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser Arg Gly
305                 310

<210> SEQ ID NO 223
<211> LENGTH: 828
<212> TYPE: DNA
<213> ORGANISM: Artificial Sequence
<220> FEATURE:
<223> OTHER INFORMATION: Nucleotide sequence encoding TCR, Donor HD6

<400> SEQUENCE: 223
atggccatgc tcctgggggc atcagtgctg attctgtggc ttcagccaga ctgggtaaac      60
agtcaacaga agaatgatga ccagcaagtt aagcaaaatt caccatccct gagcgtccag     120
gaaggaagaa tttctattct gaactgtgac tatactaaca gcatgtttga ttatttccta     180
tggtacaaaa ataccctgct gaaggtcct acattcctga tatctataag ttccattaag     240
gataaaaatg aagatggaag attcactgtc ttcttaaaca aaagtgccaa gcacctctct     300
ctgcacattg tgccctccca gcctggagac tctgcagtgt acttctgtgc agcaaacaat     360
gccagactca tgtttggaga tggaactcag ctggtggtga agcccaatat ccagaaccct     420
gaccctgccg tgtaccagct gagagactct aaatccagtg acaagtctgt ctgcctattc     480
accgattttg attctcaaac aaatgtgtca caaagtaagg attctgatgt gtatatcaca     540
gacaaaactg tgctagacat gaggtctatg gacttcaaga gcaacagtgc tgtggcctgg     600
agcaacaaat ctgactttgc atgtgcaaac gccttcaaca acagcattat tccagaagac     660
accttcttcc ccagcccaga aagttcctgt gatgtcaagc tggtcgagaa aagctttgaa     720

| acagatacga acctaaactt tcaaaacctg tcagtgattg ggttccgaat cctcctcctg | 780 |
| aaagtggccg ggtttaatct gctcatgacg ctgcggctgt ggtccagc | 828 |

<210> SEQ ID NO 224
<211> LENGTH: 927
<212> TYPE: DNA
<213> ORGANISM: Artificial Sequence
<220> FEATURE:
<223> OTHER INFORMATION: Nucleotide sequence encoding TCR, Donor HD6

<400> SEQUENCE: 224

| atggactcct ggaccttctg ctgtgtgtcc ctttgcatcc tggtagcgaa gcatacagat | 60 |
| gctggagtta tccagtcacc ccgccatgag gtgacagaga tgggacaaga agtgactctg | 120 |
| agatgtaaac caatttcagg ccacaactcc cttttctggt acagacagac catgatgcgg | 180 |
| ggactggagt tgctcattta ctttaacaac aacgttccga tagatgattc agggatgccc | 240 |
| gaggatcgat tctcagctaa gatgcctaat gcatcattct ccactctgaa gatccagccc | 300 |
| tcagaaccca gggactcagc tgtgtacttc tgtgccagca gtgataccag ggcccgggag | 360 |
| cagttcttcg gccagggac acggctcacc gtgctagagg acctgaacaa ggtgttccca | 420 |
| cccgaggtcg ctgtgtttga gccatcagaa gcagagatct cccacaccca aaaggccaca | 480 |
| ctggtgtgcc tggccacagg cttcttcccc gaccacgtgg agctgagctg gtgggtgaat | 540 |
| gggaaggagg tgcacagtgg ggtcagcacg gacccgcagc cctcaagga gcagcccgcc | 600 |
| ctcaatgact ccagatactg cctgagcagc cgcctgaggg tctcggccac cttctgcag | 660 |
| aacccccgca accacttccg ctgtcaagtc cagttctacg gctctcgga gaatgacgag | 720 |
| tggacccagg atagggccaa acccgtcacc cagatcgtca gcgccgaggc ctggggtaga | 780 |
| gcagactgtg gctttacctc ggtgtcctac cagcaagggg tcctgtctgc caccatcctc | 840 |
| tatgagatcc tgctagggaa ggccacccct tatgctgtgc tggtcagcgc ccttgtgttg | 900 |
| atggccatgg tcaagagaaa ggatttc | 927 |

<210> SEQ ID NO 225
<211> LENGTH: 933
<212> TYPE: DNA
<213> ORGANISM: Artificial Sequence
<220> FEATURE:
<223> OTHER INFORMATION: Nucleotide sequence encoding TCR, Donor HD6

<400> SEQUENCE: 225

| atggactcct ggaccttctg ctgtgtgtcc ctttgcatcc tggtagcgaa gcatacagat | 60 |
| gctggagtta tccagtcacc ccgccatgag gtgacagaga tgggacaaga agtgactctg | 120 |
| agatgtaaac caatttcagg ccacaactcc cttttctggt acagacagac catgatgcgg | 180 |
| ggactggagt tgctcattta ctttaacaac aacgttccga tagatgattc agggatgccc | 240 |
| gaggatcgat tctcagctaa gatgcctaat gcatcattct ccactctgaa gatccagccc | 300 |
| tcagaaccca gggactcagc tgtgtacttc tgtgccagca gtgataccag ggcccgggag | 360 |
| cagttcttcg gccagggac acggctcacc gtgctagagg acctgaaaaa cgtgttccca | 420 |
| cccgaggtcg ctgtgtttga gccatcagaa gcagagatct cccacaccca aaaggccaca | 480 |
| ctggtgtgcc tggccacagg cttctacccc gaccacgtgg agctgagctg gtgggtgaat | 540 |
| gggaaggagg tgcacagtgg ggtcagcaca gacccgcagc cctcaagga gcagcccgcc | 600 |
| ctcaatgact ccagatactg cctgagcagc cgcctgaggg tctcggccac cttctgcag | 660 |

```
aacccccgca accacttccg ctgtcaagtc cagttctacg ggctctcgga gaatgacgag    720
tggacccagg atagggccaa acctgtcacc cagatcgtca gcgccgaggc ctggggtaga    780
gcagactgtg gcttcacctc cgagtcttac cagcaagggg tcctgtctgc caccatcctc    840
tatgagatct tgctagggaa ggccaccttg tatgccgtgc tggtcagtgc cctcgtgctg    900
atggccatgg tcaagagaaa ggattccaga ggc                                 933
```

<210> SEQ ID NO 226
<211> LENGTH: 816
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 226

```
atgaagacat ttgctggatt ttcgttcctg tttttgtggc tgcagctgga ctgtatgagt     60
agaggagagg atgtggagca gagtctttc ctgagtgtcc gagagggaga cagctccgtt    120
ataaactgca cttacacaga cagctcctcc acctacttat actggtataa gcaagaacct    180
ggagcaggtc tccagttgct gacgtatatt ttttcaaata tggacatgaa acaagaccaa    240
agactcactg ttctattgaa taaaaaggat aaacatctgt ctctgcgcat tgcagacacc    300
cagactgggg actcagctat ctacttctgt gcagagaggc ttaacaccga caagctcatc    360
tttgggactg gaccagatt acaagtcttt ccaaatatcc agaaccctga ccctgccgtg    420
taccagctga gagactctaa atccagtgac aagtctgtct gcctattcac cgattttgat    480
tctcaaacaa atgtgtcaca agtaaggat tctgatgtgt atatcacaga caaaactgtg    540
ctagacatga ggtctatgga cttcaagagc aacagtgctg tggcctggag caacaaatct    600
gactttgcat gtgcaaacgc cttcaacaac agcattattc cagaagacac cttcttcccc    660
agcccagaaa gttcctgtga tgtcaagctg gtcgagaaaa gctttgaaac agatacgaac    720
ctaaactttc aaaacctgtc agtgattggg ttccgaatcc tcctcctgaa agtggccggg    780
tttaatctgc tcatgacgct gcggctgtgg tccagc                              816
```

<210> SEQ ID NO 227
<211> LENGTH: 813
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 227

```
atgaagagga tatgggagc tctgctgggg ctcttgagtg cccaggtttg ctgtgtgaga     60
ggaatacaag tggagcagag tcctccagac ctgattctcc aggagggagc caattccacg    120
ctgcggtgca attttctga ctctgtgaac aatttgcagt ggtttcatca aaacccttgg    180
ggacagctca tcaacctgtt ttacattccc tcagggacaa aacagaatgg aagattaagc    240
gccacgactg tcgctacgga acgctacagc ttattgtaca tttcctcttc ccagaccaca    300
gactcaggcg tttatttctg tgctgtggag gcaactgaca gctgggggaa attgcagttt    360
ggagcaggga cccaggttgt ggtcaccca gatatccaga accctgaccc tgccgtgtac    420
cagctgagag actctaaatc cagtgacaag tctgtctgcc tattcaccga ttttgattct    480
caaacaaatg tgtcacaaag taaggattct gatgtgtata tcacagacaa aactgtgcta    540
gacatgaggt ctatggactt caagagcaac agtgctgtgg cctggagcaa caaatctgac    600
tttgcatgtg caaacgcctt caacaacagc attattccag aagacaccttc cttccccagc    660
```

```
ccagaaagtt cctgtgatgt caagctggtc gagaaaagct ttgaaacaga tacgaaccta    720
aactttcaaa acctgtcagt gattgggttc cgaatcctcc tcctgaaagt ggccgggttt    780
aatctgctca tgacgctgcg gctgtggtcc agc                                 813
```

<210> SEQ ID NO 228
<211> LENGTH: 813
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 228

```
atgacatcca ttcgagctgt atttatattc ctgtggctgc agctggactt ggtgaatgga     60
gagaatgtgg agcagcatcc ttcaaccctg agtgtccagg agggagacag cgctgttatc    120
aagtgtactt attcagacag tgcctcaaac tacttcccct tggtataagca agaacttgga   180 aaaagacctc agcttattat agacattcgt tcaaatgtgg gcgaaaagaa agaccaacga    240
attgctgtta cattgaacaa gacagccaaa catttctccc tgcacatcac agagacccaa    300
cctgaagact cggctgtcta cttctgtgca gtacgaacct cctacgacaa ggtgatattt    360
gggccaggga caagcttatc agtcattcca aatatccaga accctgaccc tgccgtgtac    420
cagctgagag actctaaatc cagtgacaag tctgtctgcc tattcaccga ttttgattct    480
caaacaaatg tgtcacaaag taaggattct gatgtgtata tcacagacaa aactgtgcta    540
gacatgaggt ctatggactt caagagcaac agtgctgtgg cctggagcaa caaatctgac    600
tttgcatgtg caaacgcctt caacaacagc attattccag aagacacctt cttccccagc    660
ccagaaagtt cctgtgatgt caagctggtc gagaaaagct ttgaaacaga tacgaaccta    720
aactttcaaa acctgtcagt gattgggttc cgaatcctcc tcctgaaagt ggccgggttt    780
aatctgctca tgacgctgcg gctgtggtcc agc                                 813
```

<210> SEQ ID NO 229
<211> LENGTH: 954
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 229

```
atgctgctgc ttctgctgct tctggggcca ggtataagcc tccttctacc tgggagcttg     60
gcaggctccg ggcttggtgc tgtcgtctct caacatccga gctgggttat ctgtaagagt    120
ggaacctctg tgaagatcga gtgccgttcc ctggacttte aggccacaac tatgttttgg    180
tatcgtcagt tcccgaaaca gagtctcatg ctgatggcaa cttccaatga gggctccaag    240
gccacatacg agcaaggcgt cgagaaggac aagtttctca tcaaccatgc aagcctgacc    300
ttgtccactc tgacagtgac cagtgcccat cctgaagaca gcagcttcta catctgcagt    360
gctagggaca gtgtgtctgg aaacaccata tattttggag agggaagttg gctcactgtt    420
gtagaggacc tgaacaaggt gttcccaccc gaggtcgctg tgtttgagcc atcagaagca    480
gagatctccc acacccaaaa ggccacactg gtgtgcctgg ccacaggctt cttccccgac    540
cacgtggagc tgagctggtg ggtgaatggg aaggaggtgc acagtggggt cagcacggac    600
ccgcagcccc tcaaggagca gcccgccctc aatgactcca gatactgcct gagcagccgc    660
ctgagggtct cggccacctt ctggcagaac ccccgcaacc acttccgctg tcaagtccag    720
```

```
ttctacgggc tctcggagaa tgacgagtgg acccaggata gggccaaacc cgtcacccag    780
atcgtcagcg ccgaggcctg ggtagagca gactgtggct ttacctcggt gtcctaccag     840 caagggtcc tgtctgccac catcctctat gagatcctgc tagggaaggc caccctgtat    900
gctgtgctgg tcagcgccct tgtgttgatg gccatggtca agagaaagga tttc         954
```

<210> SEQ ID NO 230
<211> LENGTH: 960
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 230

```
atgctgctgc ttctgctgct tctggggcca ggtataagcc tccttctacc tgggagcttg     60
gcaggctccg ggcttggtgc tgtcgtctct caacatccga gctgggttat ctgtaagagt    120
ggaacctctg tgaagatcga gtgccgttcc ctggactttc aggccacaac tatgttttgg    180
tatcgtcagt tcccgaaaca gagtctcatg ctgatgcaa cttccaatga gggctccaag    240
gccacatacg agcaaggcgt cgagaaggac aagtttctca tcaaccatgc aagcctgacc    300
ttgtccactc tgacagtgac cagtgccat cctgaagaca gcagcttcta catctgcagt    360
gctagggaca gtgtgtctgg aaacaccata tattttggag agggaagttg gctcactgtt    420
gtagaggacc tgaaaaacgt gttcccaccc gaggtcgctg tgtttgagcc atcagaagca    480
gagatctccc acacccaaaa ggccacactg gtgtgcctgg ccacaggctt ctaccccgac    540
cacgtggagc tgagctggtg ggtgaatggg aaggaggtgc acagtggggt cagcacagac    600
ccgcagcccc tcaaggagca gcccgccctc aatgactcca gatactgcct gagcagccgc    660
ctgagggtct cggccacctt ctggcagaac cccgcaacc acttccgctg tcaagtccag    720
ttctacgggc tctcggagaa tgacgagtgg acccaggata gggccaaacc tgtcacccag    780
atcgtcagcg ccgaggcctg ggtagagca gactgtggct tcacctccga gtcttaccag    840 caagggtcc tgtctgccac catcctctat gagatcttgc tagggaaggc caccttgtat    900
gccgtgctgg tcagtgccct cgtgctgatg gccatggtca agagaaagga ttccagaggc    960
```

<210> SEQ ID NO 231
<211> LENGTH: 921
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 231

```
atgctgagtc ttctgctcct tctcctggga ctaggtctg tgttcagtgc tgtcatctct     60
caaaagccaa gcagggatat ctgtcaacgt ggaacctccc tgacgatcca gtgtcaagtc   120
gatagccaag tcaccatgat gttctggtac cgtcagcaac ctggacagag cctgacactg   180
atcgcaactg caaatcaggg ctctgaggcc acatatgaga gtggatttgt cattgacaag   240
tttcccatca gccgcccaaa cctaacattc tcaactctga ctgtgagcaa catgagccct    300
gaagacagca gcatatatct ctgcagcgtt gggggtagcg ggagttacaa tgagcagttc    360
ttcgggccag ggacacggct caccgtgcta gaggacctga acaaggtgtt cccacccgag    420
gtcgctgtgt ttgagccatc agaagcagag atctcccaca cccaaaaggc cacactggtg    480
tgcctggcca caggcttctt ccccgaccac gtggagctga gctggtgggt gaatgggaag    540
gaggtgcaca gtgggtcag cacggaccccg cagcccctca aggagcagcc cgccctcaat    600
```

```
gactccagat actgcctgag cagccgcctg agggtctcgg ccaccttctg gcagaacccc    660
cgcaaccact tccgctgtca agtccagttc tacgggctct cggagaatga cgagtggacc    720
caggataggg ccaaacccgt cacccagatc gtcagcgccg aggcctgggg tagagcagac    780
tgtggcttta cctcggtgtc ctaccagcaa ggggtcctgt ctgccaccat cctctatgag    840
atcctgctag ggaaggccac cctgtatgct gtgctggtca gcgcccttgt gttgatggcc    900
atggtcaaga gaaaggattt c                                              921
```

<210> SEQ ID NO 232
<211> LENGTH: 927
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 232

```
atgctgagtc ttctgctcct tctcctggga ctaggctctg tgttcagtgc tgtcatctct     60
caaaagccaa gcagggatat ctgtcaacgt ggaacctccc tgacgatcca gtgtcaagtc    120
gatagccaag tcaccatgat gttctggtac cgtcagcaac tggacagag cctgacactg     180 atcgcaactg caaatcaggg ctctgaggcc acatatgaga gtggatttgt cattgacaag    240
tttcccatca gccgcccaaa cctaacattc tcaactctga ctgtgagcaa catgagccct    300
gaagacagca gcatatatct ctgcagcgtt gggggtagcg ggagttacaa tgagcagttc    360
ttcgggccag ggacacggct caccgtgcta gaggacctga aaacgtgtt cccacccgag     420 gtcgctgtgt ttgagccatc agaagcagag atctcccaca cccaaaaggc cacactggtg    480
tgcctggcca caggcttcta cccggaccac gtggagctga gctggtgggt gaatgggaag    540
gaggtgcaca gtggggtcag cacagacccg cagcccctca aggagcagcc cgccctcaat    600
gactccagat actgcctgag cagccgcctg agggtctcgg ccaccttctg gcagaacccc    660
cgcaaccact tccgctgtca agtccagttc tacgggctct cggagaatga cgagtggacc    720
caggataggg ccaaacctgt cacccagatc gtcagcgccg aggcctgggg tagagcagac    780
tgtggcttca cctccgagtc ttaccagcaa ggggtcctgt ctgccaccat cctctatgag    840
atcttgctag ggaaggccac cttgtatgcc gtgctggtca gtgccctcgt gctgatggcc    900
atggtcaaga gaaaggattc cagaggc                                        927
```

<210> SEQ ID NO 233
<211> LENGTH: 810
<212> TYPE: DNA
<213> ORGANISM: Artificial Sequence
<220> FEATURE:
<223> OTHER INFORMATION: Nucleotide sequence encoding TCR, Donor HD8

<400> SEQUENCE: 233

```
atggtgaaga tccggcaatt tttgttggct attttgtggc ttcagctaag ctgtgtaagt     60
gccgccaaaa atgaagtgga gcagagtcct cagaacctga ctgcccagga aggagaattt    120
atcacaatca actgcagtta ctcggtagga ataagtgcct tacactggct gcaacagcat    180
ccaggaggag gcattgtttc cttgtttatg ctgagctcag ggaagaagaa gcatggaaga    240
ttaattgcca caataaacat acaggaaaag cacagctccc tgcacatcac agcctcccat    300
cccagagact ctgccgtcta catctgtgct gtcacagtcg aaacaaaact ggtctttggc    360
gcaggaacca ttctgagagt caagtcctat atccagaacc ctgaccctgc cgtgtaccag    420
```

```
ctgagagact ctaaatccag tgacaagtct gtctgcctat tcaccgattt tgattctcaa    480
acaaatgtgt cacaaagtaa ggattctgat gtgtatatca cagacaaaac tgtgctagac    540
atgaggtcta tggacttcaa gagcaacagt gctgtggcct ggagcaacaa atctgacttt    600
gcatgtgcaa acgccttcaa caacagcatt attccagaag acaccttctt ccccagccca    660
gaaagttcct gtgatgtcaa gctggtcgag aaaagctttg aaacagatac gaacctaaac    720
tttcaaaacc tgtcagtgat tgggttccga atcctcctcc tgaaagtggc cgggtttaat    780
ctgctcatga cgctgcggct gtggtccagc                                     810

<210> SEQ ID NO 234
<211> LENGTH: 918
<212> TYPE: DNA
<213> ORGANISM: Artificial Sequence
<220> FEATURE:
<223> OTHER INFORMATION: Nucleotide sequence encoding TCR, Donor HD8

<400> SEQUENCE: 234
atgagcatcg ggctcctgtg ctgtgtggcc ttttctctcc tgtgggcaag tccagtgaat     60
gctggtgtca ctcagacccc aaaattccag gtcctgaaga caggacagag catgacactg    120
cagtgtgccc aggatatgaa ccataactcc atgtactggt atcgacaaga cccaggcatg    180
ggactgaggc tgatttatta ctcagcttct gagggtacca ctgacaaagg agaagtcccc    240
aatggctaca atgtctccag attaaacaaa cgggagttct cgctcaggct ggagtcggct    300
gctccctccc agacatctgt gtacttctgt gccagcaggg ggtggcgtga gcagttcttc    360
gggccaggga cacggctcac cgtgctagag gacctgaaca aggtgttccc acccgaggtc    420
gctgtgtttg agccatcaga agcagagatc tcccacaccc aaaaggccac actggtgtgc    480
ctggccacag gcttcttccc cgaccacgtg gagctgagct ggtgggtgaa tgggaaggag    540
gtgcacagtg gggtcagcac ggacccgcag cccctcaagg agcagcccgc cctcaatgac    600
tccagatact gcctgagcag ccgcctgagg gtctcggcca ccttctggca gaaccccgc     660 aaccacttcc gctgtcaagt ccagttctac gggctctcgg agaatgacga gtggacccag    720
gatagggcca aacccgtcac ccagatcgtc agcgccgagg cctggggtag cagactgt      780 ggctttacct cggtgtccta ccagcaaggg gtcctgtctg ccaccatcct ctatgagatc    840
ctgctaggga aggccaccct gtatgctgtg ctggtcagcg cccttgtgtt gatggccatg    900
gtcaagagaa aggatttc                                                  918

<210> SEQ ID NO 235
<211> LENGTH: 924
<212> TYPE: DNA
<213> ORGANISM: Artificial Sequence
<220> FEATURE:
<223> OTHER INFORMATION: Nucleotide sequence encoding TCR, Donor HD8

<400> SEQUENCE: 235
atgagcatcg ggctcctgtg ctgtgtggcc ttttctctcc tgtgggcaag tccagtgaat     60
gctggtgtca ctcagacccc aaaattccag gtcctgaaga caggacagag catgacactg    120
cagtgtgccc aggatatgaa ccataactcc atgtactggt atcgacaaga cccaggcatg    180
ggactgaggc tgatttatta ctcagcttct gagggtacca ctgacaaagg agaagtcccc    240
aatggctaca atgtctccag attaaacaaa cgggagttct cgctcaggct ggagtcggct    300
gctccctccc agacatctgt gtacttctgt gccagcaggg ggtggcgtga gcagttcttc    360
gggccaggga cacggctcac cgtgctagag gacctgaaaa acgtgttccc acccgaggtc    420
```

```
gctgtgtttg agccatcaga agcagagatc tcccacaccc aaaaggccac actggtgtgc    480
ctggccacag gcttctaccc cgaccacgtg gagctgagct ggtgggtgaa tgggaaggag    540
gtgcacagtg gggtcagcac agacccgcag cccctcaagg agcagcccgc cctcaatgac    600
tccagatact gcctgagcag ccgcctgagg gtctcggcca ccttctggca gaaccccgc    660 aaccacttcc gctgtcaagt ccagttctac gggctctcgg agaatgacga gtggacccag    720
gatagggcca aacctgtcac ccagatcgtc agcgccgagg cctggggtag agcagactgt    780
ggcttcacct ccgagtctta ccagcaaggg gtcctgtctg ccaccatcct ctatgagatc    840
ttgctaggga aggccacctt gtatgccgtg ctggtcagtg ccctcgtgct gatggccatg    900
gtcaagagaa aggattccag aggc                                          924
```

<210> SEQ ID NO 236
<211> LENGTH: 816
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 236

```
atggtgaaga tccggcaatt tttgttggct attttgtggc ttcagctaag ctgtgtaagt     60
gccgccaaaa atgaagtgga gcagagtcct cagaacctga ctgccagga aggagaattt    120 atcacaatca actgcagtta ctcggtagga ataagtgcct acactggct gcaacagcat    180 ccaggaggag gcattgtttc cttgtttatg ctgagctcag ggaagaagaa gcatggaaga    240
ttaattgcca caataaacat acaggaaaag cacagctccc tgcacatcac agcctcccat    300
cccagagact ctgccgtcta catctgtgct gcccgatctt ataacaccga caagctcatc    360
tttgggactg ggaccagatt acaagtcttt ccaaatatcc agaaccctga ccctgccgtg    420
taccagctga gagactctaa atccagtgac aagtctgtct gcctattcac cgattttgat    480
tctcaaacaa atgtgtcaca agtaaggat tctgatgtgt atatcacaga caaaactgtg    540
ctagacatga ggtctatgga cttcaagagc aacagtgctg tggcctggag caacaaatct    600
gactttgcat gtgcaaacgc cttcaacaac agcattattc cagaagacac cttcttcccc    660
agcccagaaa gttcctgtga tgtcaagctg gtcgagaaaa gctttgaaac agatacgaac    720
ctaaactttc aaaacctgtc agtgattggg ttccgaatcc tcctcctgaa agtggccggg    780
tttaatctgc tcatgacgct gcggctgtgg tccagc                              816
```

<210> SEQ ID NO 237
<211> LENGTH: 834
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 237

```
atggccatgc tcctgggggc atcagtgctg attctgtggc ttcagccaga ctgggtaaac     60
agtcaacaga gaatgatga ccagcaagtt aagcaaaatt caccatccct gagcgtccag    120
gaaggaagaa tttctattct gaactgtgac tatactaaca gcatgtttga ttatttccta    180
tggtacaaaa ataccctgc tgaaggtcct acattcctga tctctataag ttccattaag    240
gataaaaatg aagatggaag attcactgtc ttcttaaaca aaagtgccaa gcacctctct    300
ctgcacattg tgccctccca gcctggagac tctgcagtgt acttctgtgc agcaagttac    360
```

```
aacaatgcca gactcatgtt tggagatgga actcagctgg tggtgaagcc caatatccag    420
aaccctgacc ctgccgtgta ccagctgaga gactctaaat ccagtgacaa gtctgtctgc    480
ctattcaccg attttgattc tcaaacaaat gtgtcacaaa gtaaggattc tgatgtgtat    540
atcacagaca aaactgtgct agacatgagg tctatggact caagagcaa cagtgctgtg     600 gcctggagca acaaatctga cttttgcatgt gcaaacgcct caacaacag cattattcca    660 gaagacacct tcttcccag cccagaaagt tcctgtgatg tcaagctggt cgagaaaagc     720
tttgaaacag atacgaacct aaactttcaa aacctgtcag tgattgggtt ccgaatcctc    780
ctcctgaaag tggccgggtt taatctgctc atgacgctgc ggctgtggtc cagc          834

<210> SEQ ID NO 238
<211> LENGTH: 834
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 238
atggccatgc tcctgggggc atcagtgctg attctgtggc ttcagccaga ctgggtaaac    60
agtcaacaga gaatgatga ccagcaagtt aagcaaaatt caccatccct gagcgtccag     120
gaaggaagaa tttctattct gaactgtgac tatactaaca gcatgtttga ttatttccta    180
tggtacaaaa ataccctgc tgaaggtcct acattcctga tatctataag ttccattaag     240
gataaaaatg aagatggaag attcactgtc ttcttaaaca aaagtgccaa gcacctctct    300
ctgcacattg tgccctccca gcctggagac tctgcagtgt acttctgtgc agcaagttac    360
aacaatgcca gactcatgtt tggagatgga actcagctgg tggtgaagcc caatatccag    420
aaccctgacc ctgccgtgta ccagctgaga gactctaaat ccagtgacaa gtctgtctgc    480
ctattcaccg attttgattc tcaaacaaat gtgtcacaaa gtaaggattc tgatgtgtat    540
atcacagaca aaactgtgct agacatgagg tctatggact caagagcaa cagtgctgtg     600 gcctggagca acaaatctga cttttgcatgt gcaaacgcct caacaacag cattattcca    660 gaagacacct tcttcccag cccagaaagt tcctgtgatg tcaagctggt cgagaaaagc     720
tttgaaacag atacgaacct aaactttcaa aacctgtcag tgattgggtt ccgaatcctc    780
ctcctgaaag tggccgggtt taatctgctc atgacgctgc ggctgtggtc cagc          834

<210> SEQ ID NO 239
<211> LENGTH: 924
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 239
atgggaccca ggctcctctt ctgggcactg ctttgtctcc tcggaacagg cccagtggag    60
gctggagtca cacaaagtcc cacacacctg atcaaaacga gaggacagca agcgactctg    120
agatgctctc ctatctctgg gcacaccagt gtgtactggt accaacaggc cctgggtctg    180
ggcctccagt tcctcctttg gtatgacgag ggtgaagaga gaaacagagg aaacttccct    240
cctagatttt caggtcgcca gttccctaat tatagctctg agctgaatgt gaacgccttg    300
gagctggagg actcggccct gtatctctgt gccagcagct gggggtacca agagacccag    360
tacttcgggc caggcacgcg gctcctggtg ctcgaggacc tgaacaaggt gttcccaccc    420
gaggtcgctg tgtttgagcc atcagaagca gagatctccc acacccaaaa ggccacactg    480
```

-continued

```
gtgtgcctgg ccacaggctt cttccccgac cacgtggagc tgagctggtg ggtgaatggg      540
aaggaggtgc acagtggggt cagcacggac ccgcagcccc tcaaggagca gcccgccctc      600
aatgactcca gatactgcct gagcagccgc ctgagggtct cggccacctt ctggcagaac      660
ccccgcaacc acttccgctg tcaagtccag ttctacgggc tctcggagaa tgacgagtgg      720
acccaggata gggccaaacc cgtcacccag atcgtcagcg ccgaggcctg gggtagagca      780
gactgtggct ttacctcggt gtcctaccag caaggggtcc tgtctgccac catcctctat      840
gagatcctgc tagggaaggc caccctgtat gctgtgctgg tcagcgccct tgtgttgatg      900
gccatggtca agagaaagga tttc                                             924
```

<210> SEQ ID NO 240
<211> LENGTH: 930
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 240

```
atgggaccca ggctcctctt ctgggcactg ctttgtctcc tcggaacagg cccagtggag       60
gctggagtca cacaaagtcc cacacacctg atcaaaacga gaggacagca agcgactctg      120
agatgctctc ctatctctgg gcacaccagt gtgtactggt accaacaggc cctgggtctg      180
ggcctccagt tcctcctttg gtatgacgag ggtgaagaga gaaacagagg aaacttccct      240
cctagatttt caggtcgcca gttccctaat tatagctctg agctgaatgt gaacgccttg      300
gagctggagg actcggccct gtatctctgt gccagcagct gggggtacca agagacccag      360
tacttcgggc caggcacgcg gctcctggtg ctcgaggacc tgaaaaacgt gttcccaccc      420
gaggtcgctg tgtttgagcc atcagaagca gagatctccc acacccaaaa ggccacactg      480
gtgtgcctgg ccacaggctt ctaccccgac cacgtggagc tgagctggtg ggtgaatggg      540
aaggaggtgc acagtggggt cagcacggac ccgcagcccc tcaaggagca gcccgccctc      600
aatgactcca gatactgcct gagcagccgc ctgagggtct cggccacctt ctggcagaac      660
ccccgcaacc acttccgctg tcaagtccag ttctacgggc tctcggagaa tgacgagtgg      720
acccaggata gggccaaacc tgtcacccag atcgtcagcg ccgaggcctg ggtagagca      780 gactgtggct tcacctccga gtcttaccag caaggggtcc tgtctgccac catcctctat      840
gagatcttgc tagggaaggc caccttgtat gccgtgctgg tcagtgccct cgtgctgatg      900
gccatggtca agagaaagga ttccagaggc                                       930
```

<210> SEQ ID NO 241
<211> LENGTH: 933
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 241

```
atggacacca gagtactctg ctgtgcggtc atctgtcttc tgggggcagg tctctcaaat       60
gccggcgtca tgcagaaccc aagacacctg gtcaggagga gggacagga ggcaagactg      120 agatgcagcc caatgaaagg acacagtcat gtttactggt atcggcagct cccagaggaa      180
ggtctgaaat tcatggttta tctccagaaa gaaaatatca tagatgagtc aggaatgcca      240
aaggaacgat tttctgctga atttcccaaa gagggcccca gcatcctgag gatccagcag      300
```

```
gtagtgcgag gagattcggc agcttatttc tgtgccagct caccgacagg tggcgagtac    360
tatggctaca ccttcggttc ggggaccagg ttaaccgttg tagaggacct gaacaaggtg    420
ttcccacccg aggtcgctgt gtttgagcca tcagaagcag agatctccca cacccaaaag    480
gccacactgg tgtgcctggc cacaggcttc tcccccgacc acgtggagct gagctggtgg    540
gtgaatggga aggaggtgca cagtggggtc agcacggacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt tacctcggtg tcctaccagc aaggggtcct gtctgccacc    840
atcctctatg agatcctgct agggaaggcc accctgtatg ctgtgctggt cagcgccctt    900
gtgttgatgg ccatggtcaa gagaaaggat ttc    933

<210> SEQ ID NO 242
<211> LENGTH: 939
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 242
atggacacca gagtactctg ctgtgcggtc atctgtcttc tgggggcagg tctctcaaat    60
gccggcgtca tgcagaaccc aagacacctg gtcaggagga ggggacagga ggcaagactg    120
agatgcagcc aatgaaaagg acacagtcat gtttactggt atcggcagct cccagaggaa    180
ggtctgaaat tcatggttta tctccagaaa gaaaatatca tagatgagtc aggaatgcca    240
aaggaacgat tttctgctga atttcccaaa gagggcccca gcatcctgag gatccagcag    300
gtagtgcgag gagattcggc agcttatttc tgtgccagct caccgacagg tggcgagtac    360
tatggctaca ccttcggttc ggggaccagg ttaaccgttg tagaggacct gaaaaacgtg    420
ttcccacccg aggtcgctgt gtttgagcca tcagaagcag agatctccca cacccaaaag    480
gccacactgg tgtgcctggc cacaggcttc taccccgacc acgtggagct gagctggtgg    540
gtgaatggga aggaggtgca cagtggggtc agcacagacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaacct gtcacccaga tcgtcagcgc cgaggcctgg    780
ggtagagcag actgtggctt cacctccgag tcttaccagc aaggggtcct gtctgccacc    840
atcctctatg agatcttgct agggaaggcc accttgtatg ccgtgctggt cagtgccctc    900
gtgctgatgg ccatggtcaa gagaaaggat tccagaggc    939

<210> SEQ ID NO 243
<211> LENGTH: 954
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 243
atgagcatcg gcctcctgtg ctgtgcagcc ttgtctctcc tgtgggcagg tccagtgaat    60
gctggtgtca ctcagacccc aaaattccag gtcctgaaga caggacagag catgacactg    120
cagtgtgccc aggatatgaa ccatgaatac atgtcctggt atcgacaaga cccaggcatg    180
```

```
gggctgaggc tgattcatta ctcagttggt gctggtatca ctgaccaagg agaagtcccc    240
aatggctaca atgtctccag atcaaccaca gaggatttcc cgctcaggct gctgtcggct    300
gctccctccc agacatctgt gtacttctgt gccagcagtt catacccct tcggacaggg     360 cgatacaact cctataattc acccctccac tttgggaacg ggaccaggct cactgtgaca    420
gaggacctga acaaggtgtt cccacccgag gtcgctgtgt ttgagccatc agaagcagag    480
atctcccaca cccaaaaggc cacactggtg tgcctggcca caggcttctt ccccgaccac    540
gtggagctga gctggtgggt gaatgggaag gaggtgcaca gtggggtcag cacggacccg    600
cagcccctca aggagcagcc cgccctcaat gactccagat actgcctgag cagccgcctg    660
agggtctcgg ccaccttctg gcagaacccc cgcaaccact ccgctgtca agtccagttc      720 tacgggctct cggagaatga cgagtggacc caggataggg ccaaacccgt cacccagatc    780
gtcagcgccg aggcctgggg tagagcagac tgtggctta cctcggtgtc ctaccagcaa     840
ggggtcctgt ctgccaccat cctctatgag atcctgctag ggaaggccac cctgtatgct    900
gtgctggtca gcgcccttgt gttgatggcc atggtcaaga gaaaggattt ctga           954
```

<210> SEQ ID NO 244
<211> LENGTH: 957
<212> TYPE: DNA
<213> ORGANISM: Artificial Sequence
<220> FEATURE:
<223> OTHER INFORMATION: Nucleotide sequence encoding TCR, Donor HD9

<400> SEQUENCE: 244

```
atgagcatcg gcctcctgtg ctgtgcagcc ttgtctctcc tgtgggcagg tccagtgaat     60
gctggtgtca ctcagacccc aaaattccag gtcctgaaga caggacagag catgacactg    120
cagtgtgccc aggatatgaa ccatgaatac atgtcctggt atcgacaaga cccaggcatg    180
gggctgaggc tgattcatta ctcagttggt gctggtatca ctgaccaagg agaagtcccc    240
aatggctaca atgtctccag atcaaccaca gaggatttcc cgctcaggct gctgtcggct    300
gctccctccc agacatctgt gtacttctgt gccagcagtt catacccct tcggacaggg     360 cgatacaact cctataattc acccctccac tttgggaacg ggaccaggct cactgtgaca    420
gaggacctga aaacgtgtt cccacccgag gtcgctgtgt ttgagccatc agaagcagag     480
atctcccaca cccaaaaggc cacactggtg tgcctggcca caggcttcta ccccgaccac    540
gtggagctga gctggtgggt gaatgggaag gaggtgcaca gtggggtcag cacagacccg    600
cagcccctca aggagcagcc cgccctcaat gactccagat actgcctgag cagccgcctg    660
agggtctcgg ccaccttctg gcagaacccc cgcaaccact ccgctgtca agtccagttc      720 tacgggctct cggagaatga cgagtggacc caggataggg ccaaacctgt cacccagatc    780
gtcagcgccg aggcctgggg tagagcagac tgtggcttca cctccgagtc ttaccagcaa    840
ggggtcctgt ctgccaccat cctctatgag atcttgctag ggaaggccac cttgtatgcc    900
gtgctggtca gtgccctcgt gctgatggcc atggtcaaga gaaaggattc cagaggc        957
```

<210> SEQ ID NO 245
<211> LENGTH: 837
<212> TYPE: DNA
<213> ORGANISM: Artificial Sequence
<220> FEATURE:
<223> OTHER INFORMATION: Nucleotide sequence encoding TCR, Donor HD10

<400> SEQUENCE: 245

```
atggccatgc tcctgggggc atcagtgctg attctgtggc ttcagccaga ctgggtaaac    60
agtcaacaga agaatgatga ccagcaagtt aagcaaaatt caccatccct gagcgtccag   120
gaaggaagaa tttctattct gaactgtgac tatactaaca gcatgtttga ttatttccta   180
tggtacaaaa aataccctgc tgaaggtcct acattcctga tatctataag ttccattaag   240
gataaaaatg aagatggaag attcactgtc ttcttaaaca aaagtgccaa gcacctctct   300
ctgcacattg tgccctccca gcctggagac tctgcagtgt acttctgtgc agcaagcgga   360
ggaagagatg acaagatcat ctttggaaaa gggacacgac ttcatattct ccccaatatc   420
cagaaccctg accctgccgt gtaccagctg agagactcta atccagtga caagtctgtc   480
tgcctattca ccgattttga ttctcaaaca aatgtgtcac aaagtaagga ttctgatgtg   540
tatatcacag acaaaactgt gctagacatg aggtctatgg acttcaagag caacagtgct   600
gtggcctgga gcaacaaatc tgactttgca tgtgcaaacg ccttcaacaa cagcattatt   660
ccagaagaca ccttcttccc cagcccagaa agttcctgtg atgtcaagct ggtcgagaaa   720
agctttgaaa cagatacgaa cctaaacttt caaaacctgt cagtgattgg gttccgaatc   780
ctcctcctga aagtggccgg gtttaatctg ctcatgacgc tgcggctgtg gtccagc     837
```

<210> SEQ ID NO 246
<211> LENGTH: 933
<212> TYPE: DNA
<213> ORGANISM: Artificial Sequence
<220> FEATURE:
<223> OTHER INFORMATION: Nucleotide sequence encoding TCR, Donor HD10

<400> SEQUENCE: 246

```
atgagcatcg gcctcctgtg ctgtgcagcc ttgtctctcc tgtgggcagg tccagtgaat    60
gctggtgtca ctcagacccc aaaattccag gtcctgaaga caggacagag catgacactg   120
cagtgtgccc aggatatgaa ccatgaatac atgtcctggt atcgacaaga cccaggcatg   180
gggctgaggc tgattcatta ctcagttggt gctggtatca ctgaccaagg agaagtcccc   240
aatggctaca atgtctccag atcaaccaca gaggatttcc cgctcaggct gctgtcggct   300
gctcccctcc agacatctgt gtacttctgt gccagcagct actcccggac agagagcaca   360
gatacgcagt attttggccc aggcaccagg ctgacagtgc tcgaggacct gaacaaggtg   420
ttcccacccg aggtcgctgt gtttgagcca tcagaagcag atctcccca cacccaaaag   480
gccacactgg tgtgcctggc cacaggcttc ttccccgacc acgtggagct gagctggtgg   540
gtgaatggga aggaggtgca cagtggggtc agcacggacc cgcagcccct caaggagcag   600
cccgccctca tgactccag atactgcctg agcagccgcc tgagggtctc ggccaccttc   660
tggcagaacc cccgcaacca cttccgctgt caagtccagt tctacgggct ctcggagaat   720
gacgagtgga cccaggatag ggccaaaccc gtcacccaga tcgtcagcgc cgaggcctgg   780
ggtagagcag actgtggctt tacctcggtg tcctaccagc aaggggtcct gtctgccacc   840
atcctctatg agatcctgct agggaaggcc accctgtatg ctgtgctggt cagcgccctt   900
gtgttgatgg ccatggtcaa gagaaaggat ttc                                933
```

<210> SEQ ID NO 247
<211> LENGTH: 939
<212> TYPE: DNA
<213> ORGANISM: Artificial Sequence
<220> FEATURE:

<223> OTHER INFORMATION: Nucleotide sequence encoding TCR, Donor HD10

<400> SEQUENCE: 247

```
atgagcatcg gcctcctgtg ctgtgcagcc ttgtctctcc tgtgggcagg tccagtgaat      60
gctggtgtca ctcagacccc aaaattccag gtcctgaaga caggacagag catgacactg     120
cagtgtgccc aggatatgaa ccatgaatac atgtcctggt atcgacaaga cccaggcatg     180
gggctgaggc tgattcatta ctcagttggt gctggtatca ctgaccaagg agaagtcccc     240
aatggctaca atgtctccag atcaaccaca gaggatttcc cgctcaggct gctgtcggct     300
gctccctccc agacatctgt gtacttctgt gccagcagct actccggac agagagcaca     360
gatacgcagt attttggccc aggcacccgg ctgacagtgc tcgaggacct gaaaaacgtg     420
ttcccacccg aggtcgctgt gtttgagcca tcagaagcag agatctccca cacccaaaag     480
gccacactgg tgtgcctggc cacaggcttc taccccgacc acgtggagct gagctggtgg     540
gtgaatggga aggaggtgca cagtgggctc agcacagacc cgcagcccct caaggagcag     600
cccgccctca atgactccag atactgcctg agcagccgcc tgagggtctc ggccaccttc     660
tggcagaacc cccgcaacca cttccgctgt caagtccagt tctacgggct ctcggagaat     720
gacgagtgga cccaggatag gccaaacct gtcacccaga tcgtcagcgc cgaggcctgg     780
ggtagagcag actgtggctt cacctccgag tcttaccagc aaggggtcct gtctgccacc     840
atcctctatg agatcttgct agggaaggcc accttgtatg ccgtgctggt cagtgccctc     900
gtgctgatgg ccatggtcaa gagaaaggat tccagaggc                            939
```

<210> SEQ ID NO 248
<211> LENGTH: 15
<212> TYPE: PRT
<213> ORGANISM: Artificial Sequence
<220> FEATURE:
<223> OTHER INFORMATION: WT1 peptide 91

<400> SEQUENCE: 248

Cys Met Thr Trp Asn Gln Met Asn Leu Gly Ala Thr Leu Lys Gly
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: WT1 peptide 92

<400> SEQUENCE: 249

Asn Gln Met Asn Leu Gly Ala Thr Leu Lys Gly Val Ala Ala Gly
1               5                   10                  15

<210> SEQ ID NO 250
<211> LENGTH: 11
<212> TYPE: PRT
<213> ORGANISM: Artificial Sequence
<220> FEATURE:
<223> OTHER INFORMATION: WT1 peptide Overlapping sequence

<400> SEQUENCE: 250

Asn Gln Met Asn Leu Gly Ala Thr Leu Lys Gly
1               5                   10

<210> SEQ ID NO 251
<211> LENGTH: 15
<212> TYPE: PRT

```
<213> ORGANISM: Artificial Sequence
<220> FEATURE:
<223> OTHER INFORMATION: WT1 peptide 24

<400> SEQUENCE: 251

Asp Pro Gly Gly Ile Trp Ala Lys Leu Gly Ala Ala Glu Ala Ser
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: WT1 peptide 101

<400> SEQUENCE: 252

Asn His Thr Thr Pro Ile Leu Cys Gly Ala Gln Tyr Arg Ile His
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: WT1 peptide 125

<400> SEQUENCE: 253

Lys Arg His Gln Arg Arg His Thr Gly Val Lys Pro Phe Gln Cys
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: WT1 peptide 137

<400> SEQUENCE: 254

Pro Ser Cys Gln Lys Lys Phe Ala Arg Ser Asp Glu Leu Val Arg
1               5                   10                  15

<210> SEQ ID NO 255
<211> LENGTH: 9
<212> TYPE: PRT
<213> ORGANISM: Artificial Sequence
<220> FEATURE:
<223> OTHER INFORMATION: WT1 126-134 epitope

<400> SEQUENCE: 255

Arg Met Phe Pro Asn Ala Pro Tyr Leu
1               5

<210> SEQ ID NO 256
<211> LENGTH: 816
<212> TYPE: DNA
<213> ORGANISM: Artificial Sequence
<220> FEATURE:
<223> OTHER INFORMATION: HD1a TCR sequence

<400> SEQUENCE: 256
atggaaaccc tgctgaaggt gctgagcggc acactgctgt ggcagctgac atgggtccga      60
tctcagcagc ctgtgcagtc tcctcaggcc gtgattctga gaagaggcga ggacgccgtg     120
atcaactgca gcagctctaa ggcccctgta cagcgtgcact ggtacagaca gaagcacggc    180
gaggcccctg tgttcctgat gatcctgctg aaaggcggcg agcagaaggg ccacgagaag     240
```

```
atcagcgcca gcttcaacga gaagaagcag cagtccagcc tgtacctgac agccagccag   300
ctgagctaca gcggcaccta cttttgtggc accgcctgga tcaacgacta caagctgtct   360
ttcggagccg gcaccacagt gacagtgcgg gccaatattc agaaccccga tcctgccgtg   420
taccagctga gagacagcaa gagcagcgac aagagcgtgt gcctgttcac cgacttcgac   480
agccagacca acgtgtccca gagcaaggac agcgacgtgt acatcaccga taagtgcgtg   540
ctggacatgc ggagcatgga cttcaagagc aacagcgccg tggcctggtc caacaagagc   600
gatttcgcct gcgccaacgc cttcaacaac agcattatcc ccgaggacac attcttccca   660
agtcctgaga gcagctgcga cgtgaagctg gtggaaaaga gcttcgagac agacaccaac   720
ctgaacttcc agaacctgag cgtgatcggc ttcagaatcc tgctgctcaa ggtggccggc   780
ttcaacctgc tgatgaccct gagactgtgg tccagc                            816
```

<210> SEQ ID NO 257
<211> LENGTH: 272
<212> TYPE: PRT
<213> ORGANISM: Artificial Sequence
<220> FEATURE:
<223> OTHER INFORMATION: HD1a TCR sequence

<400> SEQUENCE: 257

```
Met Glu Thr Leu Leu Lys Val Leu Ser Gly Thr Leu Leu Trp Gln Leu
1               5                   10                  15

Thr Trp Val Arg Ser Gln Gln Pro Val Gln Ser Pro Gln Ala Val Ile
            20                  25                  30

Leu Arg Glu Gly Glu Asp Ala Val Ile Asn Cys Ser Ser Ser Lys Ala
        35                  40                  45

Leu Tyr Ser Val His Trp Tyr Arg Gln Lys His Gly Glu Ala Pro Val
    50                  55                  60

Phe Leu Met Ile Leu Leu Lys Gly Gly Glu Gln Lys Gly His Glu Lys
65                  70                  75                  80

Ile Ser Ala Ser Phe Asn Glu Lys Lys Gln Gln Ser Ser Leu Tyr Leu
                85                  90                  95

Thr Ala Ser Gln Leu Ser Tyr Ser Gly Thr Tyr Phe Cys Gly Thr Ala
            100                 105                 110

Trp Ile Asn Asp Tyr Lys Leu Ser Phe Gly Ala Gly Thr Thr Val Thr
        115                 120                 125

Val Arg Ala Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Cys Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255
```

Lys Val Ala Gly Phe Asn Leu Leu Met Thr Leu Arg Leu Trp Ser Ser
                260                 265                 270

<210> SEQ ID NO 258
<211> LENGTH: 942
<212> TYPE: DNA
<213> ORGANISM: Artificial Sequence
<220> FEATURE:
<223> OTHER INFORMATION: HD1b TCR sequence

<400> SEQUENCE: 258
atgggatctt ggacactgtg ttgcgtgtcc ctgtgcatcc tggtggccaa gcacacagat    60
gccggcgtga tccagtctcc tagacacgaa gtgaccgaga tgggccaaga agtgaccctg   120
cgctgcaagc ctatcagcgg ccacgattac ctgttctggt acagacagac catgatgaga   180
ggcctggaac tgctgatcta cttcaacaac aacgtgccca tcgacgacag cggcatgccc   240
gaggatagat tcagcgccaa gatgcccaac gccagcttca gcaccctgaa gatccagcct   300
agcgagccca gagatagcgc cgtgtacttc tgcgccagca aaagacaggc ggctacagc   360 aatcagcccc agcactttgg agatggcacc cggctgagca tcctggaaga tctgaagaac   420
gtgttcccac ctgaggtggc cgtgttcgag ccttctgagg ccgagatcag ccacacacag   480
aaagccacac tcgtgtgtct ggccaccggc ttctatcccg atcacgtgga actgtcttgg   540
tgggtcaacg gcaaagaggt gcacagcggc gtctgtaccg atcctcagcc tctgaaagag   600
cagcccgctc tgaacgacag cagatactgc ctgagcagca gactgagagt gtccgccacc   660
ttctggcaga accccagaaa ccacttcaga tgccaggtgc agttctacgg cctgagcgag   720
aacgatgagt ggacccagga tagagccaag cctgtgacac agatcgtgtc tgccgaagcc   780
tggggcagag ccgattgtgg ctttaccagc gagagctacc agcagggcgt gctgtctgcc   840
acaatcctgt acgagatcct gctgggcaaa gccactctgt acgccgtgct ggtgtctgcc   900
ctggtgctga tggccatggt caagcggaag gatagcaggg gc                       942

<210> SEQ ID NO 259
<211> LENGTH: 314
<212> TYPE: PRT
<213> ORGANISM: Artificial Sequence
<220> FEATURE:
<223> OTHER INFORMATION: HD1b TCR sequence

<400> SEQUENCE: 259

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asp Tyr Leu Phe Trp Tyr Arg Gln Thr Met Met Arg Gly Leu Glu Leu
        50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Lys Thr Gly Gly Tyr Ser Asn Gln Pro Gln His Phe Gly Asp
        115                 120                 125

Gly Thr Arg Leu Ser Ile Leu Glu Asp Leu Lys Asn Val Phe Pro Pro
        130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Cys
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
290                 295                 300

Ala Met Val Lys Arg Lys Asp Ser Arg Gly
305                 310

<210> SEQ ID NO 260
<211> LENGTH: 822
<212> TYPE: DNA
<213> ORGANISM: Artificial Sequence
<220> FEATURE:
<223> OTHER INFORMATION: HD3a TCR sequence

<400> SEQUENCE: 260
atgatcagcc tgagagtgct gctggtcatc ctgtggctgc agctgtcttg ggtctggtcc      60
cagcggaaag aggtggaaca ggaccccgga cctttcaatg tgcctgaagg cgccaccgtg     120
gccttcaact gcacctacag caatagcgcc agccagagct tcttctggta cagacaggac     180
tgccggaaag aacccaagct gctgatgagc gtgtacagca gcggcaacga ggacggcaga     240
ttcacagccc agctgaacag agccagccag tacatcagcc tgctgatccg ggatagcaag     300
ctgagcgata gcgccaccta cctgtgcgtg gtcaacctgc tgtctaatca aggcggcaag     360
ctgatcttcg ccagggcac agagctgagc gtgaagccca acattcagaa ccccgatcct     420
gccgtgtacc agctgagaga cagcaagagc agcgacaaga gcgtgtgcct gttcaccgac     480
ttcgacagcc agaccaacgt gtcccagagc aaggacagcg acgtgtacat caccgataag     540
tgcgtgctgg acatgcggag catggacttc aagagcaaca cgccgtggc ctggtccaac     600 aagagcgatt tcgcctgcgc caacgccttc aacaacagca ttatccccga ggacacattc     660
ttcccaagtc ctgagagcag ctgcgacgtg aagctggtgg aaaagagctt cgagacagac     720
accaacctga acttccagaa cctgtccgtg atcggcttcc ggatcctgct gctgaaagtg     780
gccggcttca acctcctgat gaccctgaga ctgtggtcca gc                       822

<210> SEQ ID NO 261
<211> LENGTH: 274
<212> TYPE: PRT

<213> ORGANISM: Artificial Sequence
<220> FEATURE:
<223> OTHER INFORMATION: HD3a TCR sequence

<400> SEQUENCE: 261

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Leu Leu Ser Asn Gln Gly Gly Lys Leu Ile Phe Gly Gln Gly Thr Glu
        115                 120                 125

Leu Ser Val Lys Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 262
<211> LENGTH: 948
<212> TYPE: DNA
<213> ORGANISM: Artificial Sequence
<220> FEATURE:
<223> OTHER INFORMATION: HD3b TCR sequence

<400> SEQUENCE: 262
atgggatgta gacttctgtg ttgcgccgtg ctgtgtctgc ttggagctgg cgaactggtg      60
cctatggaaa ccggcgtgac ccagacacct agacacctgg tcatgggcat gacaaacaag     120
aaaagcctga agtgcgagca gcacctgggc acaatgcca tgtactggta caagcagagc      180
gccaagaaac ccctggaact gatgttcgtg tacagcctgg aagagaggt cgagaacaac      240 agcgtgccca gcagattcag ccctgagtgc cctaatagca gccacctgtt tctgcatctg     300

```
cacaccctgc agcctgagga ctctgccctg tatctgtgtg ccagcagcca ggactacctg    360
gtgtccaacg agaagctgtt cttcggcagc ggcacacagc tgagcgtgct ggaagatctg    420
aagaacgtgt tcccacctga ggtggccgtg ttcgagcctt ctgaggccga gatcagccac    480
acacagaaag ccacactcgt gtgtctggcc accggcttct atcccgatca cgtggaactg    540
tcttggtggg tcaacggcaa agaggtgcac agcggcgtct gtaccgatcc tcagcctctg    600
aaagagcagc ccgctctgaa cgacagcaga tactgcctga gcagcagact gagagtgtcc    660
gccaccttct ggcagaaccc cagaaaccac ttcagatgcc aggtgcagtt ctacggcctg    720
agcgagaacg atgagtggac ccaggataga gccaagcctg tgacacagat cgtgtctgcc    780
gaagcctggg gcagagccga ttgtggcttt accagcgaga gctaccagca gggcgtgctg    840
tctgccacaa tcctgtacga gatcctgctg ggaaaagcca ctctgtacgc tgtgctggtg    900
tccgctctgg tgctgatggc catggtcaag cggaaggata gcaggggc                 948
```

<210> SEQ ID NO 263
<211> LENGTH: 316
<212> TYPE: PRT
<213> ORGANISM: Artificial Sequence
<220> FEATURE:
<223> OTHER INFORMATION: HD3b TCR sequence

<400> SEQUENCE: 263

```
Met Gly Cys Arg Leu Leu Cys Cys Ala Val Leu Cys Leu Leu Gly Ala
1               5                   10                  15
Gly Glu Leu Val Pro Met Glu Thr Gly Val Thr Gln Thr Pro Arg His
            20                  25                  30
Leu Val Met Gly Met Thr Asn Lys Lys Ser Leu Lys Cys Glu Gln His
        35                  40                  45
Leu Gly His Asn Ala Met Tyr Trp Tyr Lys Gln Ser Ala Lys Lys Pro
    50                  55                  60
Leu Glu Leu Met Phe Val Tyr Ser Leu Glu Glu Arg Val Glu Asn Asn
65                  70                  75                  80
Ser Val Pro Ser Arg Phe Ser Pro Glu Cys Pro Asn Ser Ser His Leu
                85                  90                  95
Phe Leu His Leu His Thr Leu Gln Pro Glu Asp Ser Ala Leu Tyr Leu
            100                 105                 110
Cys Ala Ser Ser Gln Asp Tyr Leu Val Ser Asn Glu Lys Leu Phe Phe
        115                 120                 125
Gly Ser Gly Thr Gln Leu Ser Val Leu Glu Asp Leu Lys Asn Val Phe
    130                 135                 140
Pro Pro Glu Val Ala Val Phe Glu Pro Ser Glu Ala Glu Ile Ser His
145                 150                 155                 160
Thr Gln Lys Ala Thr Leu Val Cys Leu Ala Thr Gly Phe Tyr Pro Asp
                165                 170                 175
His Val Glu Leu Ser Trp Trp Val Asn Gly Lys Glu Val His Ser Gly
            180                 185                 190
Val Cys Thr Asp Pro Gln Pro Leu Lys Glu Gln Pro Ala Leu Asn Asp
        195                 200                 205
Ser Arg Tyr Cys Leu Ser Ser Arg Leu Arg Val Ser Ala Thr Phe Trp
    210                 215                 220
Gln Asn Pro Arg Asn His Phe Arg Cys Gln Val Gln Phe Tyr Gly Leu
225                 230                 235                 240
Ser Glu Asn Asp Glu Trp Thr Gln Asp Arg Ala Lys Pro Val Thr Gln
                245                 250                 255
```

Ile Val Ser Ala Glu Ala Trp Gly Arg Ala Asp Cys Gly Phe Thr Ser
                260                 265                 270

Glu Ser Tyr Gln Gln Gly Val Leu Ser Ala Thr Ile Leu Tyr Glu Ile
            275                 280                 285

Leu Leu Gly Lys Ala Thr Leu Tyr Ala Val Leu Val Ser Ala Leu Val
        290                 295                 300

Leu Met Ala Met Val Lys Arg Lys Asp Ser Arg Gly
305                 310                 315

<210> SEQ ID NO 264
<211> LENGTH: 6
<212> TYPE: PRT
<213> ORGANISM: Artificial Sequence
<220> FEATURE:
<223> OTHER INFORMATION: TCR amino acid sequence, Donor HD6

<400> SEQUENCE: 264

Asn Ser Met Phe Asp Tyr
1               5

<210> SEQ ID NO 265
<211> LENGTH: 7
<212> TYPE: PRT
<213> ORGANISM: Artificial Sequence
<220> FEATURE:
<223> OTHER INFORMATION: TCR amino acid sequence, Donor HD6

<400> SEQUENCE: 265

Ile Ser Ser Ile Lys Asp Lys
1               5

<210> SEQ ID NO 266
<211> LENGTH: 12
<212> TYPE: PRT
<213> ORGANISM: Artificial Sequence
<220> FEATURE:
<223> OTHER INFORMATION: TCR amino acid sequence, Donor HD6

<400> SEQUENCE: 266

Cys Ala Ala Ser Ala Thr Gly Asn Gln Phe Tyr Phe
1               5                   10

<210> SEQ ID NO 267
<211> LENGTH: 138
<212> TYPE: PRT
<213> ORGANISM: Artificial Sequence
<220> FEATURE:
<223> OTHER INFORMATION: TCR amino acid sequence, Donor HD6

<400> SEQUENCE: 267

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

```
Lys His Leu Ser Leu His Ile Val Pro Ser Gln Pro Gly Asp Ser Ala
            100                 105                 110

Val Tyr Phe Cys Ala Ala Ser Ala Thr Gly Asn Gln Phe Tyr Phe Gly
            115                 120                 125

Thr Gly Thr Ser Leu Thr Val Ile Pro Asn
            130                 135

<210> SEQ ID NO 268
<211> LENGTH: 278
<212> TYPE: PRT
<213> ORGANISM: Artificial Sequence
<220> FEATURE:
<223> OTHER INFORMATION: TCR amino acid sequence, Donor HD6

<400> SEQUENCE: 268

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
            35                  40                  45

Cys Asp Tyr Thr Asn Ser Met Phe Asp Tyr Phe Leu Trp Tyr Lys Lys
        50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Ala Thr Gly Asn Gln Phe Tyr Phe Gly
            115                 120                 125

Thr Gly Thr Ser Leu Thr Val Ile Pro Asn Ile Gln Asn Pro Asp Pro
            130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
            195                 200                 205

Ala Cys Ala Asn Ala Phe Asn Asn Ser Ile Ile Pro Glu Asp Thr Phe
        210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
            275

<210> SEQ ID NO 269
<211> LENGTH: 5
<212> TYPE: PRT
<213> ORGANISM: Artificial Sequence
```

<220> FEATURE:
<223> OTHER INFORMATION: TCR amino acid sequence, Donor HD6

<400> SEQUENCE: 269

Ser Gly His Arg Ser
1               5

<210> SEQ ID NO 270
<211> LENGTH: 6
<212> TYPE: PRT
<213> ORGANISM: Artificial Sequence
<220> FEATURE:
<223> OTHER INFORMATION: TCR amino acid sequence, Donor HD6

<400> SEQUENCE: 270

Tyr Phe Ser Glu Thr Gln
1               5

<210> SEQ ID NO 271
<211> LENGTH: 13
<212> TYPE: PRT
<213> ORGANISM: Artificial Sequence
<220> FEATURE:
<223> OTHER INFORMATION: TCR amino acid sequence, Donor HD6

<400> SEQUENCE: 271

Cys Ala Ser Ser Pro Gly Gln His Gly Glu Leu Phe Phe
1               5                   10

<210> SEQ ID NO 272
<211> LENGTH: 132
<212> TYPE: PRT
<213> ORGANISM: Artificial Sequence
<220> FEATURE:
<223> OTHER INFORMATION: TCR amino acid sequence, Donor HD6

<400> SEQUENCE: 272

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
                20                  25                  30

Thr Arg Gly Gln Gln Val Thr Leu Ser Cys Ser Pro Ile Ser Gly His
                35                  40                  45

Arg Ser Val Ser Trp Tyr Gln Gln Thr Pro Gly Gln Gly Leu Gln Phe
            50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
                100                 105                 110

Ser Pro Gly Gln His Gly Glu Leu Phe Phe Gly Glu Gly Ser Arg Leu
            115                 120                 125

Thr Val Leu Glu
        130

<210> SEQ ID NO 273
<211> LENGTH: 308
<212> TYPE: PRT
<213> ORGANISM: Artificial Sequence
<220> FEATURE:
<223> OTHER INFORMATION: TCR amino acid sequence, Donor HD6

<400> SEQUENCE: 273

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
    50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
            100                 105                 110

Ser Pro Gly Gln His Gly Glu Leu Phe Phe Gly Glu Gly Ser Arg Leu
        115                 120                 125

Thr Val Leu Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
290                 295                 300

Arg Lys Asp Phe
305

<210> SEQ ID NO 274
<211> LENGTH: 310
<212> TYPE: PRT
<213> ORGANISM: Artificial Sequence
<220> FEATURE:
<223> OTHER INFORMATION: TCR amino acid sequence, Donor HD6

<400> SEQUENCE: 274

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

```
Thr Arg Gly Gln Gln Val Thr Leu Ser Cys Ser Pro Ile Ser Gly His
            35                  40                  45
Arg Ser Val Ser Trp Tyr Gln Gln Thr Pro Gly Gln Gly Leu Gln Phe
 50                  55                  60
Leu Phe Glu Tyr Phe Ser Glu Thr Gln Arg Asn Lys Gly Asn Phe Pro
65                  70                  75                  80
Gly Arg Phe Ser Gly Arg Gln Phe Ser Asn Ser Arg Ser Glu Met Asn
                85                  90                  95
Val Ser Thr Leu Glu Leu Gly Asp Ser Ala Leu Tyr Leu Cys Ala Ser
            100                 105                 110
Ser Pro Gly Gln His Gly Glu Leu Phe Gly Glu Gly Ser Arg Leu
                115                 120                 125
Thr Val Leu Glu Asp Leu Lys Asn Val Phe Pro Pro Glu Val Ala Val
            130                 135                 140
Phe Glu Pro Ser Glu Ala Glu Ile Ser His Thr Gln Lys Ala Thr Leu
145                 150                 155                 160
Val Cys Leu Ala Thr Gly Phe Tyr Pro Asp His Val Glu Leu Ser Trp
                165                 170                 175
Trp Val Asn Gly Lys Glu Val His Ser Gly Val Ser Thr Asp Pro Gln
                180                 185                 190
Pro Leu Lys Glu Gln Pro Ala Leu Asn Asp Ser Arg Tyr Cys Leu Ser
                195                 200                 205
Ser Arg Leu Arg Val Ser Ala Thr Phe Trp Gln Asn Pro Arg Asn His
            210                 215                 220
Phe Arg Cys Gln Val Gln Phe Tyr Gly Leu Ser Glu Asn Asp Glu Trp
225                 230                 235                 240
Thr Gln Asp Arg Ala Lys Pro Val Thr Gln Ile Val Ser Ala Glu Ala
                245                 250                 255
Trp Gly Arg Ala Asp Cys Gly Phe Thr Ser Glu Ser Tyr Gln Gln Gly
                260                 265                 270
Val Leu Ser Ala Thr Ile Leu Tyr Glu Ile Leu Leu Gly Lys Ala Thr
            275                 280                 285
Leu Tyr Ala Val Leu Val Ser Ala Leu Val Leu Met Ala Met Val Lys
290                 295                 300
Arg Lys Asp Ser Arg Gly
305                 310

<210> SEQ ID NO 275
<211> LENGTH: 5
<212> TYPE: PRT
<213> ORGANISM: Artificial Sequence
<220> FEATURE:
<223> OTHER INFORMATION: TCR amino acid sequence, Donor HD7

<400> SEQUENCE: 275

Thr Ser Ile Asn Asn
1               5

<210> SEQ ID NO 276
<211> LENGTH: 7
<212> TYPE: PRT
<213> ORGANISM: Artificial Sequence
<220> FEATURE:
<223> OTHER INFORMATION: TCR amino acid sequence, Donor HD7
```

<400> SEQUENCE: 276

Ile Arg Ser Asn Glu Arg Glu
1               5

<210> SEQ ID NO 277
<211> LENGTH: 13
<212> TYPE: PRT
<213> ORGANISM: Artificial Sequence
<220> FEATURE:
<223> OTHER INFORMATION: TCR amino acid sequence, Donor HD7

<400> SEQUENCE: 277

Cys Ala Thr Asp Gly Asp Ser Ser Tyr Lys Leu Ile Phe
1               5                   10

<210> SEQ ID NO 278
<211> LENGTH: 132
<212> TYPE: PRT
<213> ORGANISM: Artificial Sequence
<220> FEATURE:
<223> OTHER INFORMATION: TCR amino acid sequence, Donor HD7

<400> SEQUENCE: 278

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asp
            100                 105                 110

Gly Asp Ser Ser Tyr Lys Leu Ile Phe Gly Ser Gly Thr Arg Leu Leu
        115                 120                 125

Val Arg Pro Asp
    130

<210> SEQ ID NO 279
<211> LENGTH: 272
<212> TYPE: PRT
<213> ORGANISM: Artificial Sequence
<220> FEATURE:
<223> OTHER INFORMATION: TCR amino acid sequence, Donor HD7

<400> SEQUENCE: 279

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
            85                  90                  95

Thr Ala Ser Arg Ala Ala Asp Thr Ala Ser Tyr Phe Cys Ala Thr Asp
            100                 105                 110

Gly Asp Ser Ser Tyr Lys Leu Ile Phe Gly Ser Gly Thr Arg Leu Leu
            115                 120                 125

Val Arg Pro Asp Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 280
<211> LENGTH: 6
<212> TYPE: PRT
<213> ORGANISM: Artificial Sequence
<220> FEATURE:
<223> OTHER INFORMATION: TCR amino acid sequence, Donor HD7

<400> SEQUENCE: 280

Asp Phe Gln Ala Thr Thr
1               5

<210> SEQ ID NO 281
<211> LENGTH: 7
<212> TYPE: PRT
<213> ORGANISM: Artificial Sequence
<220> FEATURE:
<223> OTHER INFORMATION: TCR amino acid sequence, Donor HD7

<400> SEQUENCE: 281

Ser Asn Glu Gly Ser Lys Ala
1               5

<210> SEQ ID NO 282
<211> LENGTH: 15
<212> TYPE: PRT
<213> ORGANISM: Artificial Sequence
<220> FEATURE:
<223> OTHER INFORMATION: TCR amino acid sequence, Donor HD7

<400> SEQUENCE: 282

Cys Ser Ala Arg Asp Val Leu Thr Gly Asp Tyr Gly Tyr Thr Phe
1               5                   10                  15

-continued

<210> SEQ ID NO 283
<211> LENGTH: 142
<212> TYPE: PRT
<213> ORGANISM: Artificial Sequence
<220> FEATURE:
<223> OTHER INFORMATION: TCR amino acid sequence, Donor HD7

<400> SEQUENCE: 283

```
Met Leu Leu Leu Leu Leu Leu Gly Pro Gly Ile Ser Leu Leu Leu
1               5                   10                  15

Pro Gly Ser Leu Ala Gly Ser Gly Leu Gly Ala Val Val Ser Gln His
            20                  25                  30

Pro Ser Trp Val Ile Cys Lys Ser Gly Thr Ser Val Lys Ile Glu Cys
            35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
                85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Arg Asp Val Leu Thr Gly Asp
        115                 120                 125

Tyr Gly Tyr Thr Phe Gly Ser Gly Thr Arg Leu Thr Val Val
    130                 135                 140
```

<210> SEQ ID NO 284
<211> LENGTH: 319
<212> TYPE: PRT
<213> ORGANISM: Artificial Sequence
<220> FEATURE:
<223> OTHER INFORMATION: TCR amino acid sequence, Donor HD7

<400> SEQUENCE: 284

```
Met Leu Leu Leu Leu Leu Leu Gly Pro Gly Ile Ser Leu Leu Leu
1               5                   10                  15

Pro Gly Ser Leu Ala Gly Ser Gly Leu Gly Ala Val Val Ser Gln His
            20                  25                  30

Pro Ser Trp Val Ile Cys Lys Ser Gly Thr Ser Val Lys Ile Glu Cys
            35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
                85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Arg Asp Val Leu Thr Gly Asp
        115                 120                 125

Tyr Gly Tyr Thr Phe Gly Ser Gly Thr Arg Leu Thr Val Val Glu Asp
    130                 135                 140

Leu Asn Lys Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175
```

```
Gly Phe Phe Pro Asp His Val Glu Leu Ser Trp Trp Val Asn Gly Lys
            180                 185                 190

Glu Val His Ser Gly Val Ser Thr Asp Pro Gln Pro Leu Lys Glu Gln
        195                 200                 205

Pro Ala Leu Asn Asp Ser Arg Tyr Cys Leu Ser Ser Arg Leu Arg Val
    210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
            260                 265                 270

Cys Gly Phe Thr Ser Val Ser Tyr Gln Gln Gly Val Leu Ser Ala Thr
        275                 280                 285

Ile Leu Tyr Glu Ile Leu Leu Gly Lys Ala Thr Leu Tyr Ala Val Leu
    290                 295                 300

Val Ser Ala Leu Val Leu Met Ala Met Val Lys Arg Lys Asp Phe
305                 310                 315

<210> SEQ ID NO 285
<211> LENGTH: 321
<212> TYPE: PRT
<213> ORGANISM: Artificial Sequence
<220> FEATURE:
<223> OTHER INFORMATION: TCR amino acid sequence, Donor HD7

<400> SEQUENCE: 285

Met Leu Leu Leu Leu Leu Leu Leu Gly Pro Gly Ile Ser Leu Leu Leu
1               5                   10                  15

Pro Gly Ser Leu Ala Gly Ser Gly Leu Gly Ala Val Val Ser Gln His
            20                  25                  30

Pro Ser Trp Val Ile Cys Lys Ser Gly Thr Ser Val Lys Ile Glu Cys
        35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
                85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Arg Asp Val Leu Thr Gly Asp
        115                 120                 125

Tyr Gly Tyr Thr Phe Gly Ser Gly Thr Arg Leu Thr Val Val Glu Asp
    130                 135                 140

Leu Lys Asn Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Tyr Pro Asp His Val Glu Leu Ser Trp Trp Val Asn Gly Lys
            180                 185                 190

Glu Val His Ser Gly Val Ser Thr Asp Pro Gln Pro Leu Lys Glu Gln
        195                 200                 205

Pro Ala Leu Asn Asp Ser Arg Tyr Cys Leu Ser Ser Arg Leu Arg Val
    210                 215                 220
```

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
            245                 250                 255

Lys Pro Val Thr Gln Ile Val Ser Ala Glu Ala Trp Gly Arg Ala Asp
        260                 265                 270

Cys Gly Phe Thr Ser Glu Ser Tyr Gln Gln Gly Val Leu Ser Ala Thr
            275                 280                 285

Ile Leu Tyr Glu Ile Leu Leu Gly Lys Ala Thr Leu Tyr Ala Val Leu
        290                 295                 300

Val Ser Ala Leu Val Leu Met Ala Met Val Lys Arg Lys Asp Ser Arg
305                 310                 315                 320

Gly

<210> SEQ ID NO 286
<211> LENGTH: 5
<212> TYPE: PRT
<213> ORGANISM: Artificial Sequence
<220> FEATURE:
<223> OTHER INFORMATION: TCR amino acid sequence, Donor HD7

<400> SEQUENCE: 286

Ser Gly His Asp Tyr
1               5

<210> SEQ ID NO 287
<211> LENGTH: 6
<212> TYPE: PRT
<213> ORGANISM: Artificial Sequence
<220> FEATURE:
<223> OTHER INFORMATION: TCR amino acid sequence, Donor HD7

<400> SEQUENCE: 287

Phe Asn Asn Asn Val Pro
1               5

<210> SEQ ID NO 288
<211> LENGTH: 16
<212> TYPE: PRT
<213> ORGANISM: Artificial Sequence
<220> FEATURE:
<223> OTHER INFORMATION: TCR amino acid sequence, Donor HD7

<400> SEQUENCE: 288

Cys Ala Ser Ser Leu Gly Leu Ser Ile Ser Gln Glu Thr Gln Tyr Phe
1               5                   10                  15

<210> SEQ ID NO 289
<211> LENGTH: 136
<212> TYPE: PRT
<213> ORGANISM: Artificial Sequence
<220> FEATURE:
<223> OTHER INFORMATION: TCR amino acid sequence, Donor HD7

<400> SEQUENCE: 289

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

```
Asp Tyr Leu Phe Trp Tyr Arg Gln Thr Met Met Arg Gly Leu Glu Leu
         50                  55                  60

Leu Ile Tyr Phe Asn Asn Asn Val Pro Ile Asp Asp Ser Gly Met Pro
 65              70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
                100                 105                 110

Ser Ser Leu Gly Leu Ser Ile Ser Gln Glu Thr Gln Tyr Phe Gly Pro
            115                 120                 125

Gly Thr Arg Leu Leu Val Leu Glu
        130                 135
```

<210> SEQ ID NO 290
<211> LENGTH: 312
<212> TYPE: PRT
<213> ORGANISM: Artificial Sequence
<220> FEATURE:
<223> OTHER INFORMATION: TCR amino acid sequence, Donor HD7

<400> SEQUENCE: 290

```
Met Gly Ser Trp Thr Leu Cys Cys Val Ser Leu Cys Ile Leu Val Ala
 1               5                  10                  15

Lys His Thr Asp Ala Gly Val Ile Gln Ser Pro Arg His Glu Val Thr
                 20                  25                  30

Glu Met Gly Gln Glu Val Thr Leu Arg Cys Lys Pro Ile Ser Gly His
             35                  40                  45

Asp Tyr Leu Phe Trp Tyr Arg Gln Thr Met Met Arg Gly Leu Glu Leu
         50                  55                  60

Leu Ile Tyr Phe Asn Asn Asn Val Pro Ile Asp Asp Ser Gly Met Pro
 65              70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
                100                 105                 110

Ser Ser Leu Gly Leu Ser Ile Ser Gln Glu Thr Gln Tyr Phe Gly Pro
            115                 120                 125

Gly Thr Arg Leu Leu Val Leu Glu Asp Leu Asn Lys Val Phe Pro Pro
        130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270
```

Tyr Gln Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
    290                 295                 300

Ala Met Val Lys Arg Lys Asp Phe
305                 310

<210> SEQ ID NO 291
<211> LENGTH: 314
<212> TYPE: PRT
<213> ORGANISM: Artificial Sequence
<220> FEATURE:
<223> OTHER INFORMATION: TCR amino acid sequence, Donor HD7

<400> SEQUENCE: 291

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Leu Gly Leu Ser Ile Ser Gln Glu Thr Gln Tyr Phe Gly Pro
        115                 120                 125

Gly Thr Arg Leu Leu Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 292
<211> LENGTH: 837
<212> TYPE: DNA
<213> ORGANISM: Artificial Sequence
<220> FEATURE:
<223> OTHER INFORMATION: Nucleotide sequence encoding TCR, Donor HD6

<400> SEQUENCE: 292

```
atggccatgc tcctgggggc atcagtgctg attctgtggc ttcagccaga ctgggtaaac      60
agtcaacaga agaatgatga ccagcaagtt aagcaaaatt caccatccct gagcgtccag     120
gaaggaagaa tttctattct gaactgtgac tatactaaca gcatgtttga ttatttccta     180
tggtacaaaa ataccctgc tgaaggtcct acattcctga tatctataag ttccattaag     240
gataaaaatg aagatggaag attcactgtc ttcttaaaca aaagtgccaa gcacctctct     300
ctgcacattg tgccctccca gcctggagac tctgcagtgt acttctgtgc agcaagcgct     360
accggtaacc agttctattt tgggacaggg acaagtttga cggtcattcc aaatatccag     420
aaccctgacc ctgccgtgta ccagctgaga gactctaaat ccagtgacaa gtctgtctgc     480
ctattcaccg attttgattc tcaaacaaat gtgtcacaaa gtaaggattc tgatgtgtat     540
atcacagaca aaactgtgct agacatgagg tctatggact caagagcaa cagtgctgtg     600
gcctggagca caaatctga ctttgcatgt gcaaacgcct tcaacaacag cattattcca     660
gaagacacct tcttccccag cccagaaagt tcctgtgatg tcaagctggt cgagaaaagc     720
tttgaaacag atacgaacct aaactttcaa aacctgtcag tgattgggtt ccgaatcctc     780
ctcctgaaag tggccgggtt taatctgctc atgacgctgc ggctgtggtc cagctga       837
```

<210> SEQ ID NO 293
<211> LENGTH: 924
<212> TYPE: DNA
<213> ORGANISM: Artificial Sequence
<220> FEATURE:
<223> OTHER INFORMATION: Nucleotide sequence encoding TCR, Donor HD6

<400> SEQUENCE: 293

```
atgggctcca ggctgctctg ttgggtgctg cttttgtctcc tgggagcagg cccagtaaag      60
gctggagtca ctcaaactcc aagatatctg atcaaaacga gaggacagca gtgacactg      120
agctgctccc ctatctctgg cataggagt gtatcctggt accaacagac cccaggacag      180
ggccttcagt tcctctttga atacttcagt gagacacaga gaaacaaagg aaacttccct      240
ggtcgattct cagggcgcca gttctctaac tctcgctctg agatgaatgt gagcaccttg      300
gagctggggg actcggccct ttatctttgc gccagcagcc tggacagca ggggagctg       360
tttttttggag aaggctctag gctgaccgta ctggaggacc tgaacaaggt gttcccaccc     420
gaggtcgctg tgtttgagcc atcagaagca gagatctccc acacccaaaa ggccacactg     480
gtgtgcctgg ccacaggctt cttccccgac cacgtggagc tgagctggtg ggtgaatggg     540
aaggaggtgc acagtggggt cagcacggac ccgcagcccc tcaaggagca gcccgccctc     600
aatgactcca gatactgcct gagcagccgc ctgagggtct cggccacctt ctggcagaac     660
ccccgcaacc acttccgctg tcaagtccag ttctacgggc tctcggagaa tgacgagtgg     720
acccaggata gggccaaacc cgtcacccag atcgtcagcg ccgaggcctg ggtagagca      780
gactgtggct ttacctcggt gtcctaccag caagggtcc tgtctgccac catcctctat     840
gagatcctgc tagggaaggc caccctgtat gctgtgctgg tcagcgccct tgtgttgatg     900
gccatggtca agagaaagga tttc                                            924
```

<210> SEQ ID NO 294
<211> LENGTH: 930
<212> TYPE: DNA
<213> ORGANISM: Artificial Sequence
<220> FEATURE:
<223> OTHER INFORMATION: Nucleotide sequence encoding TCR, Donor HD6

<400> SEQUENCE: 294

| | |
|---|---|
| atgggctcca ggctgctctg ttgggtgctg ctttgtctcc tgggagcagg cccagtaaag | 60 |
| gctggagtca ctcaaactcc aagatatctg atcaaaacga gaggacagca agtgacactg | 120 |
| agctgctccc ctatctctgg cataggagt gtatcctggt accaacagac cccaggacag | 180 |
| ggccttcagt tcctctttga atacttcagt gagacacaga gaaacaaagg aaacttccct | 240 |
| ggtcgattct cagggcgcca gttctctaac tctcgctctg agatgaatgt gagccccttg | 300 |
| gagctggggg actcggccct ttatctttgc gccagcagcc ctggacagca cggggagctg | 360 |
| ttttttggag aaggctctag gctgaccgta ctggaggacc tgaaaaacgt gttcccaccc | 420 |
| gaggtcgctg tgtttgagcc atcagaagca gagatctccc acacccaaaa ggccacactg | 480 |
| gtgtgcctgg ccacaggctt ctaccccgac cacgtggagc tgagctggtg ggtgaatggg | 540 |
| aaggaggtgc acagtggggt cagcacagac ccgcagcccc tcaaggagca gcccgccctc | 600 |
| aatgactcca gatactgcct gagcagccgc ctgagggtct cggccacctt ctggcagaac | 660 |
| ccccgcaacc acttccgctg tcaagtccag ttctacgggc tctcggagaa tgacgagtgg | 720 |
| acccaggata gggccaaacc tgtcacccag atcgtcagcg ccgaggcctg ggtagagca | 780 |
| gactgtggct tcacctccga gtcttaccag caagggtcc tgtctgccac catcctctat | 840 |
| gagatcttgc tagggaaggc caccttgtat gccgtgctgg tcagtgccct cgtgctgatg | 900 |
| gccatggtca agagaaagga ttccagaggc | 930 |

<210> SEQ ID NO 295
<211> LENGTH: 816
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 295

| | |
|---|---|
| atggaaactc tcctgggagt gtctttggtg attctatggc ttcaactggc tagggtgaac | 60 |
| agtcaacagg agaagagga tcctcaggcc ttgagcatcc aggagggtga aaatgccacc | 120 |
| atgaactgca gttacaaaac tagtataaac aatttacagt ggtatagaca aaattcaggt | 180 |
| agaggccttg tccacctaat tttaatacgt tcaaatgaaa gagagaaaca cagtggaaga | 240 |
| ttaagagtca cgcttgacac ttccaagaaa agcagttcct tgttgatcac ggcttcccgg | 300 |
| gcagcagaca ctgcttctta cttctgtgct acggacgggg atagcagcta taattgatc | 360 |
| ttcgggagtg ggaccagact gctggtcagg cctgatatcc agaaccctga ccctgccgtg | 420 |
| taccagctga gagactctaa atccagtgac aagtctgtct gcctattcac cgattttgat | 480 |
| tctcaaacaa atgtgtcaca agtaaggat tctgatgtgt atatcacaga caaaactgtg | 540 |
| ctagacatga ggtctatgga cttcaagagc aacagtgctg tggcctggag caacaaatct | 600 |
| gactttgcat gtgcaacgc cttcaacaac agcattattc agaagacac cttcttcccc | 660 |
| agcccagaaa gttcctgtga tgtcaagctg gtcgagaaaa gctttgaaac agatacgaac | 720 |

```
ctaaactttc aaaacctgtc agtgattggg ttccgaatcc tcctcctgaa agtggccggg    780
tttaatctgc tcatgacgct gcggctgtgg tccagc                              816
```

<210> SEQ ID NO 296
<211> LENGTH: 957
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 296

```
atgctgctgc ttctgctgct tctggggcca ggtataagcc tccttctacc tgggagcttg     60
gcaggctccg ggcttggtgc tgtcgtctct caacatccga gctgggttat ctgtaagagt    120
ggaacctctg tgaagatcga gtgccgttcc ctggactttc aggccacaac tatgttttgg    180
tatcgtcagt tcccgaaaca gagtctcatg ctgatggcaa cttccaatga gggctccaag    240
gccacatacg agcaaggcgt cgagaaggac aagtttctca tcaaccatgc aagcctgacc    300
ttgtccactc tgacagtgac cagtgcccat cctgaagaca gcagcttcta catctgcagt    360
gctagagacg tactgacagg ggactatggc tacaccttcg gttcggggac caggttaacc    420
gttgtagagg acctgaacaa ggtgttccca cccgaggtcg ctgtgtttga gccatcagaa    480
gcagagatct cccacaccca aaaggccaca ctggtgtgcc tggccacagg cttcttcccc    540
gaccacgtgg agctgagctg gtgggtgaat gggaaggagg tgcacagtgg ggtcagcacg    600
gacccgcagc ccctcaagga gcagcccgcc ctcaatgact ccagatactg cctgagcagc    660
cgcctgaggg tctcggccac cttctggcag aaccccgca accacttccg ctgtcaagtc    720
cagttctacg gctctcgga gaatgacgag tggacccagg atagggccaa acccgtcacc    780
cagatcgtca gcgccgaggc ctggggtaga gcagactgtg ctttacctc ggtgtcctac    840 cagcaagggg tcctgtctgc caccatcctc tatgagatcc tgctagggaa ggccaccctg    900
tatgctgtgc tggtcagcgc ccttgtgttg atggccatgg tcaagagaaa ggatttc      957
```

<210> SEQ ID NO 297
<211> LENGTH: 963
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 297

```
atgctgctgc ttctgctgct tctggggcca ggtataagcc tccttctacc tgggagcttg     60
gcaggctccg ggcttggtgc tgtcgtctct caacatccga gctgggttat ctgtaagagt    120
ggaacctctg tgaagatcga gtgccgttcc ctggactttc aggccacaac tatgttttgg    180
tatcgtcagt tcccgaaaca gagtctcatg ctgatggcaa cttccaatga gggctccaag    240
gccacatacg agcaaggcgt cgagaaggac aagtttctca tcaaccatgc aagcctgacc    300
ttgtccactc tgacagtgac cagtgcccat cctgaagaca gcagcttcta catctgcagt    360
gctagagacg tactgacagg ggactatggc tacaccttcg gttcggggac caggttaacc    420
gttgtagagg acctgaaaaa cgtgttccca cccgaggtcg ctgtgtttga gccatcagaa    480
gcagagatct cccacaccca aaaggccaca ctggtgtgcc tggccacagg cttctacccc    540
gaccacgtgg agctgagctg gtgggtgaat gggaaggagg tgcacagtgg ggtcagcaca    600
gacccgcagc ccctcaagga gcagcccgcc ctcaatgact ccagatactg cctgagcagc    660
```

```
cgcctgaggg tctcggccac cttctggcag aaccccccgca accacttccg ctgtcaagtc    720
cagttctacg ggctctcgga gaatgacgag tggacccagg atagggccaa acctgtcacc    780
cagatcgtca gcgccgaggc ctggggtaga gcagactgtg gcttcacctc cgagtcttac    840
cagcaagggg tcctgtctgc caccatcctc tatgagatct gctagggaa ggccaccttg    900 tatgccgtgc tggtcagtgc cctcgtgctg atggccatgg tcaagagaaa ggattccaga    960
ggc                                                                  963
```

<210> SEQ ID NO 298
<211> LENGTH: 936
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 298

```
atgggctcct ggaccctctg ctgtgtgtcc ctttgcatcc tggtagcaaa gcacacagat     60
gctggagtta tccagtcacc ccggcacgag gtgacagaga tggacaaga agtgactctg    120 agatgtaaac caatttcagg acacgactac cttttctggt acagacagac catgatgcgg    180
ggactggagt tgctcattta ctttaacaac aacgttccga tagatgattc agggatgccc    240
gaggatcgat tctcagctaa gatgcctaat gcatcattct ccactctgaa gatccagccc    300
tcagaaccca gggactcagc tgtgtacttc tgtgccagca gtttaggact gagcatttcc    360
caagagaccc agtacttcgg gccaggcacg cggctcctgg tgctcgagga cctgaacaag    420
gtgttcccac ccgaggtcgc tgtgtttgag ccatcagaag cagagatctc cacacccaa    480 aaggccacac tggtgtgcct ggccacaggc ttcttcccg accacgtgga gctgagctgg    540
tgggtgaatg gaaaggaggt gcacagtggg gtcagcacgg accgcagcc cctcaaggag    600 cagcccgccc tcaatgactc cagatactgc ctgagcagcc gcctgagggt ctcggccacc    660
ttctggcaga accccgcaa ccacttccg tgtcaagtcc agttctacgg gctctcggag    720
aatgacgagt ggacccagga tagggccaaa cccgtcaccc agatcgtcag cgccgaggcc    780
tggggtagag cagactgtgg ctttacctcg gtgtcctacc agcaaggggt cctgtctgcc    840
accatcctct atgagatcct gctagggaag gccacctgt atgctgtgct ggtcagcgcc    900
cttgtgttga tggccatggt caagagaaag gatttc                               936
```

<210> SEQ ID NO 299
<211> LENGTH: 942
<212> TYPE: DNA
<213> ORGANISM: Artificial Sequence
<220> FEATURE:
<223> OTHER INFORMATION: Nucleotide sequence encoding TCR, Donor HD7

<400> SEQUENCE: 299

```
atgggctcct ggaccctctg ctgtgtgtcc ctttgcatcc tggtagcaaa gcacacagat     60
gctggagtta tccagtcacc ccggcacgag gtgacagaga tggacaaga agtgactctg    120 agatgtaaac caatttcagg acacgactac cttttctggt acagacagac catgatgcgg    180
ggactggagt tgctcattta ctttaacaac aacgttccga tagatgattc agggatgccc    240
gaggatcgat tctcagctaa gatgcctaat gcatcattct ccactctgaa gatccagccc    300
tcagaaccca gggactcagc tgtgtacttc tgtgccagca gtttaggact gagcatttcc    360
caagagaccc agtacttcgg gccaggcacg cggctcctgg tgctcgagga cctgaaaaac    420
gtgttcccac ccgaggtcgc tgtgtttgag ccatcagaag cagagatctc cacacccaa    480
```

```
aaggccacac tggtgtgcct ggccacaggc ttctaccccg accacgtgga gctgagctgg      540
tgggtgaatg ggaaggaggt gcacagtggg gtcagcacag acccgcagcc cctcaaggag      600
cagcccgccc tcaatgactc cagatactgc ctgagcagcc gcctgagggt ctcggccacc      660
ttctggcaga accccgcaa ccacttccgc tgtcaagtcc agttctacgg gctctcggag       720
aatgacgagt ggacccagga tagggccaaa cctgtcaccc agatcgtcag cgccgaggcc      780
tggggtagag cagactgtgg cttcacctcc gagtcttacc agcaagggg cctgtctgcc       840 accatcctct atgagatctt gctagggaag gccaccttgt atgccgtgct ggtcagtgcc      900
ctcgtgctga tggccatggt caagagaaag gattccagag gc                         942
```

TCR AND PEPTIDES

CROSS-REFERENCE TO RELATED APPLICATIONS

This application is a U.S. National Phase of International Application No. PCT/EP2018/060477, filed Apr. 24, 2018, which claims the benefit under 35 USC § 119 of U.S. Provisional Application No. 62/489,226, filed Apr. 24, 2017.

INCORPORATION BY REFERENCE OF MATERIAL SUBMITTED ELECTRONICALLY

This application incorporates by reference in its entirety a computer-readable nucleotide/amino acid sequence listing identified as one 332,536 byte ASCII (text) file named "PCT_sequence_listing.TXT," created on Oct. 11, 2020.

FIELD OF THE INVENTION

The present invention relates to T-cell receptors (TCRs) which bind to peptides derived from Wilms tumour 1 protein (WT1) when presented by a major histocompatibility complex. In this regard, the present invention relates to complementarity determining regions (CDRs) which specifically recognise WT1 peptides. The present invention further relates to immunogenic peptides derived from WT1.

BACKGROUND TO THE INVENTION

T cell receptor (TCR) gene therapy is based on the genetic transfer of high-avidity tumour-specific TCR genes into T lymphocytes, thus enabling the specific targeting of the desired tumour-associated antigens and leading to a less toxic and more specific and effective therapy. This approach has shown promise in clinical trials. One of the main barriers limiting the exploitation of TCR gene therapy for clinical treatment of cancers is the lack of tumour-specific T-cells and corresponding TCRs. Thus, the low availability of tumour-specific TCRs still remains an open issue limiting the broad exploitation of TCR-based immunotherapeutic approaches.

The majority of tumour-associated antigens (TAAs) are self antigens, thus T-cells specific for such molecules are either destroyed or anergized due to central and peripheral tolerance. Despite this, naturally occurring tumour-specific T-cells have been observed in healthy donors and patients, particularly in patients affected by hematological malignancies, after allogeneic hematopoietic stem cell transplantation (allo-HSCT) where frequencies of tumor-specific lymphocytes have been correlated with disease regression (Kapp, M. et al. Bone Marrow Transplantation 43,399-410 (2009); and Tyler, E. M. et al. Blood 121,308-317 (2013)).

The choice of a tumor antigen to be targeted by immunotherapeutic approaches is still a matter of debate. Ideal TAAs are highly expressed on tumor cells while being minimally expressed in healthy tissue.

Wilms tumor 1 (WT1) is an intracellular protein encoding a zinc finger transcription factor that plays an important role in cell growth and differentiation (Yang, L. et al. Leukemia 21, 868-876 (2007)). WT1 is widely expressed on a variety of hematological and solid tumors, while showing limited expression on various healthy tissues (e.g. gonads, uterus, kidney, mesothelium, progenitor cells in different tissues). Recent evidence suggests a role for WT1 in leukemogenesis and tumorigenesis.

Several ongoing clinical trials rely on the generation of cytotoxic T lymphocyte (CTL) responses upon vaccination with WT1 peptides. However, despite the recognition that WT1 is useful for immunotherapy, a small number of WT1 epitopes, which are restricted to a limited number of HLA alleles, are presently used for vaccination purposes (Di Stasi, A. et al. Front. Immunol. (2015)). One such epitope is the WT1 126-134 epitope (RMFPNAPYL; SEQ ID NO: 255), which is presented by MHC encoded by the HLA-A*0201 allele (i.e. the epitope is HLA-A*0201 restricted).

HLA-A*0201 restricted epitopes and corresponding TCRs are of interest since major histocompatibility complex (MHC) having the HLA-A*0201 haplotype are expressed in the vast majority (60%) of the Caucasian population. Accordingly, TCRs that target HLA-A*0201-restricted WT1 epitopes are particularly advantageous since an immunotherapy making use of such TCRs may be widely applied.

The WT1 126-134 epitope has been widely studied in several trials, alone or in combination with additional tumor antigens. However, recent reports have highlighted a major concern regarding the processing of this particular epitope, which may impair its use for immunotherapy purposes. Notably, the WT1 126-134 epitope is more efficiently processed by the immunoproteasome compared with standard proteasomes (Jaigirdar, A. et al. J Immunother. 39(3):105-16 (2016)), which leads to poor recognition of many HLA-A*0201 tumour cell lines or primary leukemia cells that endogenously express WT1.

Thus, there remains a need for new WT1 epitopes, particularly those presented by MHC with prevalent HLA haplotypes (e.g. HLA-A*0201).

One naturally processed HLA-A*0201 restricted epitope that has been identified is WT1 37-45, which has the amino acid sequence VLDFAPPGA (SEQ ID NO: 157, see e.g. Smithgall et al 2001; Blood 98 (11 Part 1): 121a). However, few TCR amino acid sequences, particularly CDR sequences, specific for this peptide sequence have been reported (Schmitt, T. M. et al. (2017) Nat Biotechnol 35: 1188-1195).

Accordingly, there remains a need for new WT1 epitopes, particularly those restricted to common HLA alleles and a need for new TCRs capable of binding to WT1 epitopes.

SUMMARY OF THE INVENTION

We have identified novel TCRs that bind to WT1 peptides when presented by an MHC. Further, we have determined the amino acid sequences of the TCRs, including the amino acid sequences of their CDR regions, which are responsible for binding specificity for WT1. Moreover, we have demonstrated that T-cells expressing TCRs according to the present invention specifically target and kill cells that overexpress the WT1 protein. In addition, it has been shown that the TCRs of the present invention are restricted to MHC encoded by HLA class 1 and 2 alleles common in the Caucasian population, such as HLA-A*0201 and HLA-B*3501 or HLA-B*3502.

Accordingly, in a first aspect, the present invention provides a T-cell receptor (TCR), which binds to a Wilms tumour 1 protein (WT1) peptide when presented by a major histocompatibility complex (MHC), wherein the TCR:

(i) comprises a CDR3α comprising the amino acid sequence of CGTAWINDYKLSF (SEQ ID NO: 3) or a variant thereof having up to three amino acid substitutions, additions or deletions, and a CDR3β comprising the amino acid sequence of CASRKTG- GYSNQPQHF (SEQ ID NO: 8) or a variant thereof having up to three amino acid substitutions, additions or deletions;

(ii) comprises a CDR3α comprising the amino acid sequence of CVVNLLSNQGGKLIF (SEQ ID NO: 36) or a variant thereof having up to three amino acid substitutions, additions or deletions, and a CDR3β comprising the amino acid sequence of CASSQDYLVSNEKLFF (SEQ ID NO: 41) or a variant thereof having up to three amino acid substitutions, additions or deletions;

(iii) comprises a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions;

(iv) comprises a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions;

(v) comprises a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions;

(vi) comprises a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions;

(vii) comprises a CDR3α comprising the amino acid sequence of CATDAYSGNTPLVF (SEQ ID NO: 47) or a variant thereof having up to three amino acid substitutions, additions or deletions, and a CDR3β comprising the amino acid sequence of CASRAAGLDTEAFF (SEQ ID NO: 57) or a variant thereof having up to three amino acid substitutions, additions or deletions;

(viii) comprises a CDR3α comprising the amino acid sequence of CATDAYSGNTPLVF (SEQ ID NO: 47) or a variant thereof having up to three amino acid substitutions, additions or deletions, and a CDR3β comprising the amino acid sequence of CASTQTPYEQYF (SEQ ID NO: 63) or a variant thereof having up to three amino acid substitutions, additions or deletions;

(ix) comprises a CDR3α comprising the amino acid sequence of CATDAYSGNTPLVF (SEQ ID NO: 47) or a variant thereof having up to three amino acid substitutions, additions or deletions, and a CDR3β comprising the amino acid sequence of CASSTVGGEDYGYTF (SEQ ID NO: 69) or a variant thereof having up to three amino acid substitutions, additions or deletions;

(x) comprises a CDR3α comprising the amino acid sequence of CAVRAEIYNQGGKLIF (SEQ ID NO: 52) or a variant thereof having up to three amino acid substitutions, additions or deletions, and a CDR3β comprising the amino acid sequence of CASRAAGLDTEAFF (SEQ ID NO:57) or a variant thereof having up to three amino acid substitutions, additions or deletions;

(xi) comprises a CDR3α comprising the amino acid sequence of CAVRAEIYNQGGKLIF (SEQ ID NO: 52) or a variant thereof having up to three amino acid substitutions, additions or deletions, and a CDR3β comprising the amino acid sequence of CASTQTPYEQYF (SEQ ID NO: 63) or a variant thereof having up to three amino acid substitutions, additions or deletions;

(xii) comprises a CDR3α comprising the amino acid sequence of CAVRAEIYNQGGKLIF (SEQ ID NO: 52) or a variant thereof having up to three amino acid substitutions, additions or deletions, and a CDR3β comprising the amino acid sequence of CASSTVGGEDYGYTF (SEQ ID NO: 69) or a variant thereof having up to three amino acid substitutions, additions or deletions;

(xiii) comprises a CDR3α comprising the amino acid sequence of CAASMAGAGSYQLTF (SEQ ID NO: 75) or a variant thereof having up to three amino acid substitutions, additions or deletions, and a CDR3β comprising the amino acid sequence of CAISVGQGALYEQYF (SEQ ID NO: 80) or a variant thereof having up to three amino acid substitutions, additions or deletions;

(xiv) comprises a CDR3α comprising the amino acid sequence of CAASMAGAGSYQLTF (SEQ ID NO: 75) or a variant thereof having up to three amino acid substitutions, additions or deletions, and a CDR3β comprising the amino acid sequence of CASSVARDRRNYGYTF (SEQ ID NO: 86) or a variant thereof having up to three amino acid substitutions, additions or deletions;

(xv) comprises a CDR3α comprising the amino acid sequence of CAANNARLMF (SEQ ID NO: 92) or a variant thereof having up to three amino acid substitutions, additions or deletions, and a CDR3β comprising the amino acid sequence of CASSDTRAREQFF (SEQ ID NO: 97) or a variant thereof having up to three amino acid substitutions, additions or deletions;

(xvi) comprises a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions;

(xvii) comprises a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSVGGSGSYNEQFF (SEQ ID NO: 169) or a variant thereof having up to three amino acid substitutions, additions or deletions;

(xviii) comprises a CDR3α comprising the amino acid sequence of CAVEATDSWGKLQF (SEQ ID NO: 108) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions;

(xix) comprises a CDR3α comprising the amino acid sequence of CAVEATDSWGKLQF (SEQ ID NO: 108) or a variant thereof having up to three amino acid substitutions, additions or deletions, and a CDR3β comprising the amino acid sequence of CSVGGSGSYNEQFF (SEQ ID NO: 169) or a variant thereof having up to three amino acid substitutions, additions or deletions;

(xx) comprises a CDR3α comprising the amino acid sequence of CAVRTSYDKVIF (SEQ ID NO: 113) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions;

(xxi) comprises a CDR3α comprising the amino acid sequence of CAVRTSYDKVIF (SEQ ID NO: 113) or a variant thereof having up to three amino acid substitutions, additions or deletions, and a CDR3β comprising the amino acid sequence of CSVGGSGSYNEQFF (SEQ ID NO: 169) or a variant thereof having up to three amino acid substitutions, additions or deletions;

(xxii) comprises a CDR3α comprising the amino acid sequence of CAVTVGNKLVF (SEQ ID NO: 175) or a variant thereof having up to three amino acid substitutions, additions or deletions, and a CDR3β comprising the amino acid sequence of CASRGWREQFF (SEQ ID NO: 180) or a variant thereof having up to three amino acid substitutions, additions or deletions;

(xxiii) comprises a CDR3α comprising the amino acid sequence of CAARSYNTDKLIF (SEQ ID NO: 186) or a variant thereof having up to three amino acid substitutions, additions or deletions, and a CDR3β comprising the amino acid sequence of CASSWGYQETQYF (SEQ ID NO: 196) or a variant thereof having up to three amino acid substitutions, additions or deletions;

(xxiv) comprises a CDR3α comprising the amino acid sequence of CAARSYNTDKLIF (SEQ ID NO: 186) or a variant thereof having up to three amino acid substitutions, additions or deletions, and a CDR3β comprising the amino acid sequence of CASSPTGGEYYGYTF (SEQ ID NO: 202) or a variant thereof having up to three amino acid substitutions, additions or deletions;

(xxv) comprises a CDR3α comprising the amino acid sequence of CAARSYNTDKLIF (SEQ ID NO: 186) or a variant thereof having up to three amino acid substitutions, additions or deletions, and a CDR3β comprising the amino acid sequence of CASSSYPLRTGRYNSYNSPLHF (SEQ ID NO: 208) or a variant thereof having up to three amino acid substitutions, additions or deletions;

(xxvi) comprises a CDR3α comprising the amino acid sequence of CAASYNNARLMF (SEQ ID NO: 191) or a variant thereof having up to three amino acid substitutions, additions or deletions, and a CDR3β comprising the amino acid sequence of CASSWGYQETQYF (SEQ ID NO: 196) or a variant thereof having up to three amino acid substitutions, additions or deletions;

(xxvii) comprises a CDR3α comprising the amino acid sequence of CAASYNNARLMF (SEQ ID NO: 191) or a variant thereof having up to three amino acid substitutions, additions or deletions, and a CDR3β comprising the amino acid sequence of CASSPTGGEYYGYTF (SEQ ID NO: 202) or a variant thereof having up to three amino acid substitutions, additions or deletions;

(xxviii) comprises a CDR3α comprising the amino acid sequence of CAASYNNARLMF (SEQ ID NO: 191) or a variant thereof having up to three amino acid substitutions, additions or deletions, and a CDR3β comprising the amino acid sequence of CASSSYPLRTGRYNSYNSPLHF (SEQ ID NO: 208) or a variant thereof having up to three amino acid substitutions, additions or deletions;

(xxix) comprises a CDR3α comprising the amino acid sequence of CAASGGRDDKIIF (SEQ ID NO: 214) or a variant thereof having up to three amino acid substitutions, additions or deletions, and a CDR3β comprising the amino acid sequence of CASSYSRTESTDTQYF (SEQ ID NO: 219) or a variant thereof having up to three amino acid substitutions, additions or deletions;

(xxx) comprises a CDR3α comprising the amino acid sequence of CAANNARLMF (SEQ ID NO: 92) or a variant thereof having up to three amino acid substitutions, additions or deletions, and a CDR3β comprising the amino acid sequence of CASSPGQHGELFF (SEQ ID NO: 271) or a variant thereof having up to three amino acid substitutions, additions or deletions;

(xxxi) comprises a CDR3α comprising the amino acid sequence of CAASATGNQFYF (SEQ ID NO: 266) or a variant thereof having up to three amino acid substitutions, additions or deletions, and a CDR3β comprising the amino acid sequence of CASSDTRAREQFF (SEQ ID NO: 97) or a variant thereof having up to three amino acid substitutions, additions or deletions;

(xxxii) comprises a CDR3α comprising the amino acid sequence of CAASATGNQFYF (SEQ ID NO: 266) or a variant thereof having up to three amino acid substitutions, additions or deletions, and a CDR3β comprising the amino acid sequence of CASSPGQHGELFF (SEQ ID NO: 271) or a variant thereof having up to three amino acid substitutions, additions or deletions;

(xxxiii) comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions;

(xxxiv) comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSVGGSGSYNEQFF (SEQ ID NO: 169) or a variant thereof having up to three amino acid substitutions, additions or deletions;

(xxxv) comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions;

(xxxvi) comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CASSLGLSISQETQYF (SEQ ID NO: 288) or a variant thereof having up to three amino acid substitutions, additions or deletions;

(xxxvii) comprises a CDR3α comprising the amino acid sequence of CAERLNTDKLIF (SEQ ID NO: 103) or a variant thereof having up to three amino acid substitutions, additions or deletions, and a CDR3β comprising the amino acid sequence of CASSLGLSISQETQYF (SEQ ID NO: 288) or a variant thereof having up to three amino acid substitutions, additions or deletions;

(xxxviii) comprises a CDR3α comprising the amino acid sequence of CAVEATDSWGKLQF (SEQ ID NO: 108) or a variant thereof having up to three amino acid substitutions, additions or deletions, and a CDR3β comprising the amino acid sequence of CASSLGLSISQETQYF (SEQ ID NO: 288) or a variant thereof having up to three amino acid substitutions, additions or deletions;

(xxxix) comprises a CDR3α comprising the amino acid sequence of CAVRTSYDKVIF (SEQ ID NO: 113) or a variant thereof having up to three amino acid substitutions, additions or deletions, and a CDR3β comprising the amino acid sequence of CASSLGLSISQETQYF (SEQ ID NO: 288) or a variant thereof having up to three amino acid substitutions, additions or deletions;

(xxxx) comprises a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions;

(xxxxi) comprises a CDR3α comprising the amino acid sequence of CAVEATDSWGKLQF (SEQ ID NO: 108) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions; or (xxxxii) comprises a CDR3α comprising the amino acid sequence of CAVRTSYDKVIF (SEQ ID NO: 113) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions.

In one embodiment, the present invention provides a TCR of the present invention comprising the following CDR sequences:

(i)
CDR1α - KALYS, (SEQ ID NO: 1)

CDR2α - LLKGGEQ, (SEQ ID NO: 2)

CDR3α - CGTAWINDYKLSF, (SEQ ID NO: 3)

CDR1β - SGHDY, (SEQ ID NO: 6)

CDR2β - FNNNVP, (SEQ ID NO: 7)
and

CDR3β - CASRKTGGYSNQPQHF, (SEQ ID NO: 8)

or variants thereof each having up to three amino acid substitutions, additions or deletions;

(ii)
CDR1α - NSASQS, (SEQ ID NO: 34)

CDR2α - VYSSGN, (SEQ ID NO: 35)

CDR3α - CVVNLLSNQGGKLIF, (SEQ ID NO: 36)

CDR1β - LGHNA, (SEQ ID NO: 39)

CDR2β - YSLEER, (SEQ ID NO: 40)
and

CDR3β - CASSQDYLVSNEKLFF, (SEQ ID NO: 41)

or variants thereof each having up to three amino acid substitutions, additions or deletions;

(iii)
CDR1α-
SSVPPY, (SEQ ID NO: 12)

CDR2α-
YTSAATLV, (SEQ ID NO: 13)

CDR3α-
CAVRLSGSARQLTF, (SEQ ID NO: 14)

CDR1β-
SGHAT, (SEQ ID NO: 22)

CDR2β-
FQNNGV, (SEQ ID NO: 23)
and

CDR3β-
CASSLLGDEQYF, (SEQ ID NO: 24)

or variants thereof each having up to three amino acid substitutions, additions or deletions;

(iv)
CDR1α-
SSVPPY, (SEQ ID NO: 12)

CDR2α-
YTSAATLV, (SEQ ID NO: 13)

CDR3α-
CAVRLSGSARQLTF, (SEQ ID NO: 14)

CDR1β-
SGHTA, (SEQ ID NO: 28)

-continued

CDR2β-
FQGNSA, (SEQ ID NO: 29)
and

CDR3β-
CASSLVALQGAGEQYF, (SEQ ID NO: 30)

or variants thereof each having up to three amino acid substitutions, additions or deletions;

(v)
CDR1α-
TSESDYY, (SEQ ID NO: 17)

CDR2α-
QEAYKQQN, (SEQ ID NO: 18)

CDR3α-
CAYRSLKYGNKLVF, (SEQ ID NO: 19)

CDR1β-
SGHAT, (SEQ ID NO: 22)

CDR2β-
FQNNGV, (SEQ ID NO: 23)
and

CDR3β-
CASSLLGDEQYF, (SEQ ID NO: 24)

or variants thereof each having up to three amino acid substitutions, additions or deletions;

(vi)
CDR1α-
TSESDYY, (SEQ ID NO: 17)

CDR2α-
QEAYKQQN, (SEQ ID NO: 18)

CDR3α-
CAYRSLKYGNKLVF, (SEQ ID NO: 19)

CDR1β-
SGHTA, (SEQ ID NO: 28)

CDR2β-
FQGNSA, (SEQ ID NO: 29)
and

CDR3β-
CASSLVALQGAGEQYF, (SEQ ID NO: 30)

or variants thereof each having up to three amino acid substitutions, additions or deletions;

(vii)
CDR1α-
TSINN, (SEQ ID NO: 45)

CDR2α-
IRSNERE, (SEQ ID NO: 46)

CDR3α-
CATDAYSGNTPLVF, (SEQ ID NO: 47)

CDR1β-
MNHNS, (SEQ ID NO: 55)

CDR2β-
SASEGT, (SEQ ID NO: 56)
and

CDR3β-
CASRAAGLDTEAFF, (SEQ ID NO: 57)

or variants thereof each having up to three amino acid substitutions, additions or deletions;

(viii)
CDR1α-
TSINN, (SEQ ID NO: 45)

CDR2α-
IRSNERE, (SEQ ID NO: 46)

CDR3α-
CATDAYSGNTPLVF, (SEQ ID NO: 47)

CDR1β-
MNHNY, (SEQ ID NO: 61)

CDR2β-
SVGAGI, (SEQ ID NO: 62)
and

CDR3β-
CASTQTPYEQYF, (SEQ ID NO: 63)

or variants thereof each having up to three amino acid substitutions, additions or deletions;

(ix)
CDR1α-
TSINN, (SEQ ID NO: 45)

CDR2α-
IRSNERE, (SEQ ID NO: 46)

CDR3α-
CATDAYSGNTPLVF, (SEQ ID NO: 47)

CDR1β-
SGHNS, (SEQ ID NO: 67)

CDR2β-
FNNNVP, (SEQ ID NO: 68)
and

CDR3β-
CASSTVGGEDYGYTF, (SEQ ID NO: 69)

or variants thereof each having up to three amino acid substitutions, additions or deletions;

(x)
CDR1α-
(SEQ ID NO: 50)
DSAIYN,

CDR2α-
(SEQ ID NO: 51)
IQSSQRE,

CDR3α-
(SEQ ID NO: 52)
CAVRAEIYNQGGKLIF,

CDR1β-
(SEQ ID NO: 55)
MNHNS,

CDR2β-
(SEQ ID NO: 56)
SASEGT,
and

CDR3β-
(SEQ ID NO: 57)
CASRAAGLDTEAFF, or variants thereof each having up to three amino acid substitutions, additions or deletions;

(xi)
CDR1α-
(SEQ ID NO: 50)
DSAIYN,

CDR2α-
(SEQ ID NO: 51)
IQSSQRE,

CDR3α-
(SEQ ID NO: 52)
CAVRAEIYNQGGKLIF,

CDR1β-
(SEQ ID NO: 61)
MNHNY,

CDR2β-
(SEQ ID NO: 62)
SVGAGI,
and

CDR3β-
(SEQ ID NO: 63)
CASTQTPYEQYF, or variants thereof each having up to three amino acid substitutions, additions or deletions;

(xii)
CDR1α-
(SEQ ID NO: 50)
DSAIYN,

CDR2α-
(SEQ ID NO: 51)
IQSSQRE,

CDR3α-
(SEQ ID NO: 52)
CAVRAEIYNQGGKLIF,

CDR1β-
(SEQ ID NO: 67)
SGHNS,

CDR2β-
(SEQ ID NO: 68)
FNNNVP,
and

CDR3β-
(SEQ ID NO: 69)
CASSTVGGEDYGYTF, or variants thereof each having up to three amino acid substitutions, additions or deletions;

(xiii)
CDR1α-
(SEQ ID NO: 73)
DSASNY,

CDR2α-
(SEQ ID NO: 74)
IRSNVGE,

CDR3α-
(SEQ ID NO: 75)
CAASMAGAGSYQLTF,

CDR1β-
(SEQ ID NO: 78)
ENHRY,

CDR2β-
(SEQ ID NO: 79)
SYGVKD,
and

CDR3β-
(SEQ ID NO: 80)
CAISVGQGALYEQYF, or variants thereof each having up to three amino acid substitutions, additions or deletions;

(xiv)
CDR1α-
(SEQ ID NO: 73)
DSASNY,

CDR2α-
(SEQ ID NO: 74)
IRSNVGE,

CDR3α-
(SEQ ID NO: 75)
CAASMAGAGSYQLTF,

CDR1β-
(SEQ ID NO: 84)
SGDLS,

CDR2β-
(SEQ ID NO: 85)
YYNGEE,
and

CDR3β-
(SEQ ID NO: 86)
CASSVARDRRNYGYTF, or variants thereof each having up to three amino acid substitutions, additions or deletions;

(xv)
CDR1α-
(SEQ ID NO: 90)
NSMFDY,

-continued

CDR2α-
(SEQ ID NO: 91)
ISSIKDK,

CDR3α-
(SEQ ID NO: 92)
CAANNARLMF,

CDR1β-
(SEQ ID NO: 95)
SGHNS,

CDR2β-
(SEQ ID NO: 96)
FNNNVP,
and

CDR3β-
(SEQ ID NO: 97)
CASSDTRAREQFF, or variants thereof each having up to three amino acid substitutions, additions or deletions;

(xvi)
CDR1α-
(SEQ ID NO: 101)
DSSSTY,

CDR2α-
(SEQ ID NO: 102)
IFSNMDM,

CDR3α-
(SEQ ID NO: 103)
CAERLNTDKLIF,

CDR1β-
(SEQ ID NO: 161)
DFQATT,

CDR2β-
(SEQ ID NO: 162)
SNEGSKA,
and

CDR3β-
(SEQ ID NO: 163)
CSARDSVSGNTIYF, or variants thereof each having up to three amino acid substitutions, additions or deletions;

(xvii)
CDR1α-
(SEQ ID NO: 101)
DSSSTY,

CDR2α-
(SEQ ID NO: 102)
IFSNMDM,

CDR3α-
(SEQ ID NO: 103)
CAERLNTDKLIF,

CDR1β-
(SEQ ID NO: 167)
SQVTM,

CDR2β-
(SEQ ID NO: 168)
ANQGSEA,
and

CDR3β-
(SEQ ID NO: 169)
CSVGGSGSYNEQFF, or variants thereof each having up to three amino acid substitutions, additions or deletions;

(xviii)
CDR1α - DSVNN, (SEQ ID NO: 106)

CDR2α - IPSGT, (SEQ ID NO: 107)

CDR3α - CAVEATDSWGKLQF, (SEQ ID NO: 108)

CDR1β - DFQATT, (SEQ ID NO: 161)

CDR2β - SNEGSKA, (SEQ ID NO: 162)
and

CDR3β - CSARDSVSGNTIYF, (SEQ ID NO: 163)

or variants thereof each having up to three amino acid substitutions, additions or deletions;

(xix)
CDR1α - DSVNN, (SEQ ID NO: 106)

CDR2α - IPSGT, (SEQ ID NO: 107)

CDR3α - CAVEATDSWGKLQF, (SEQ ID NO: 108)

CDR1β - SQVTM, (SEQ ID NO: 167)

CDR2β - ANQGSEA, (SEQ ID NO: 168)
and

CDR3β - CSVGGSGSYNEQFF, (SEQ ID NO: 169)

or variants thereof each having up to three amino acid substitutions, additions or deletions;

(xx)
CDR1α - DSASNY, (SEQ ID NO: 111)

CDR2α - IRSNVGE, (SEQ ID NO: 112)

CDR3α - CAVRTSYDKVIF, (SEQ ID NO: 113)

CDR1β - DFQATT, (SEQ ID NO: 161)

CDR2β - SNEGSKA, (SEQ ID NO: 162)
and

CDR3β - CSARDSVSGNTIYF, (SEQ ID NO: 163)

or variants thereof each having up to three amino acid substitutions, additions or deletions;

(xxi)
CDR1α - DSASNY, (SEQ ID NO: 111)

CDR2α - IRSNVGE, (SEQ ID NO: 112)

CDR3α - CAVRTSYDKVIF, (SEQ ID NO: 113)

CDR1β - SQVTM, (SEQ ID NO: 167)

CDR2β - ANQGSEA, (SEQ ID NO: 168)
and

CDR3β - CSVGGSGSYNEQFF, (SEQ ID NO: 169)

or variants thereof each having up to three amino acid substitutions, additions or deletions;

(xxii)
CDR1α - VGISA, (SEQ ID NO: 173)

CDR2α - LSSGK, (SEQ ID NO: 174)

CDR3α - CAVTVGNKLVF, (SEQ ID NO: 175)

CDR1β - MNHNS, (SEQ ID NO: 178)

CDR2β - SASEGT, (SEQ ID NO: 179)
and

CDR3β - CASRGWREQFF, (SEQ ID NO: 180)

or variants thereof each having up to three amino acid substitutions, additions or deletions;

(xxiii)
CDR1α - VGISA, (SEQ ID NO: 184)

CDR2α - LSSGK, (SEQ ID NO: 185)

CDR3α - CAARSYNTDKLIF, (SEQ ID NO: 186)

CDR1β - SGHTS, (SEQ ID NO: 194)

CDR2β - YDEGEE, (SEQ ID NO: 195)
and

CDR3β - CASSWGYQETQYF, (SEQ ID NO: 196)

or variants thereof each having up to three amino acid substitutions, additions or deletions;

(xxiv)
CDR1α - VGISA, (SEQ ID NO: 184)

CDR2α - LSSGK, (SEQ ID NO: 185)

CDR3α - CAARSYNTDKLIF, (SEQ ID NO: 186)

CDR1β - KGHSH, (SEQ ID NO: 200)

CDR2β - LQKENI, (SEQ ID NO: 201)
and

CDR3β - CASSPTGGEYYGYTF, (SEQ ID NO: 202)

or variants thereof each having up to three amino acid substitutions, additions or deletions;

(xxv)
CDR1α - VGISA, (SEQ ID NO: 184)

CDR2α - LSSGK, (SEQ ID NO: 185)

CDR3α - CAARSYNTDKLIF, (SEQ ID NO: 186)

CDR1β - MNHEY, (SEQ ID NO: 206)

CDR2β - SVGAGI, (SEQ ID NO: 207)
and

CDR3β - CASSSYPLRTGRYNSYNSPLHF, (SEQ ID NO: 208)

or variants thereof each having up to three amino acid substitutions, additions or deletions;

(xxvi)
CDR1α - NSMFDY, (SEQ ID NO: 189)

CDR2α - ISSIKDK, (SEQ ID NO: 190)

CDR3α - CAASYNNARLMF, (SEQ ID NO: 191)

CDR1β - SGHTS, (SEQ ID NO: 194)

CDR2β - YDEGEE, (SEQ ID NO: 195)
and

CDR3β - CASSWGYQETQYF, (SEQ ID NO: 196)

or variants thereof each having up to three amino acid substitutions, additions or deletions;

(xxvii)
CDR1α - NSMFDY, (SEQ ID NO: 189)

CDR2α - ISSIKDK, (SEQ ID NO: 190)

CDR3α - CAASYNNARLMF, (SEQ ID NO: 191)

CDR1β - KGHSH, (SEQ ID NO: 200)

CDR2β - LQKENI, (SEQ ID NO: 201)
and

CDR3β - CASSPTGGEYYGYTF, (SEQ ID NO: 202)

or variants thereof each having up to three amino acid substitutions, additions or deletions;

(xxviii)
CDR1α - NSMFDY, (SEQ ID NO: 189)

CDR2α - ISSIKDK, (SEQ ID NO: 190)

CDR3α - CAASYNNARLMF, (SEQ ID NO: 191)

CDR1β - MNHEY, (SEQ ID NO: 206)

CDR2β - SVGAGI, (SEQ ID NO: 207)
and

CDR3β - CASSSYPLRTGRYNSYNSPLHF, (SEQ ID NO: 208)

or variants thereof each having up to three amino acid substitutions, additions or deletions;

(xxix)
CDR1α - NSMFDY, (SEQ ID NO: 212)

CDR2α - ISSIKDK, (SEQ ID NO: 213)

CDR3α - CAASGGRDDKIIF, (SEQ ID NO: 214)

CDR1β - MNHEY, (SEQ ID NO: 217)

CDR2β - SVGAGI, (SEQ ID NO: 218)
and

CDR3β - CASSYSRTESTDTQYF, (SEQ ID NO: 219)

or variants thereof each having up to three amino acid substitutions, additions or deletions;

(xxx)
CDR1α - NSMFDY, (SEQ ID NO: 90)

CDR2α - ISSIKDK, (SEQ ID NO: 91)

CDR3α - CAANNARLMF, (SEQ ID NO: 92)

CDR1β - SGHRS, (SEQ ID NO: 269)

CDR2β - YFSETQ, (SEQ ID NO: 270)
and

CDR3β - CASSPGQHGELFF, (SEQ ID NO: 271)

or variants thereof each having up to three amino acid substitutions, additions or deletions;

(xxxi)
CDR1α - NSMFDY, (SEQ ID NO: 264)

CDR2α - ISSIKDK, (SEQ ID NO: 265)

CDR3α - CAASATGNQFYF, (SEQ ID NO: 266)

CDR1β - SGHNS, (SEQ ID NO: 95)

CDR2β - FNNNVP, (SEQ ID NO: 96)
and

CDR3β - CASSDTRAREQFF, (SEQ ID NO: 97)

or variants thereof each having up to three amino acid substitutions, additions or deletions;

(xxxii)
CDR1α - NSMFDY, (SEQ ID NO: 264)

CDR2α - ISSIKDK, (SEQ ID NO: 265)

CDR3α - CAASATGNQFYF, (SEQ ID NO: 266)

CDR1β - SGHRS, (SEQ ID NO: 269)

CDR2β - YFSETQ, (SEQ ID NO: 270)
and

CDR3β - CASSPGQHGELFF, (SEQ ID NO: 271)

or variants thereof each having up to three amino acid substitutions, additions or deletions;

(xxxiii)
CDR1α - TSINN, (SEQ ID NO: 275)

CDR2α - IRSNERE, (SEQ ID NO: 276)

CDR3α - CATDGDSSYKLIF, (SEQ ID NO: 277)

CDR1β - DFQATT, (SEQ ID NO: 161)

CDR2β - SNEGSKA, (SEQ ID NO: 162)
and

CDR3β - CSARDSVSGNTIYF, (SEQ ID NO: 163)

or variants thereof each having up to three amino acid substitutions, additions or deletions;

(xxxiv)
CDR1α - TSINN, (SEQ ID NO: 275)

-continued

CDR2α - IRSNERE, (SEQ ID NO: 276)

CDR3α - CATDGDSSYKLIF, (SEQ ID NO: 277)

CDR1β - SQVTM, (SEQ ID NO: 167)

CDR2β - ANQGSEA,
and (SEQ ID NO: 168)

CDR3β - CSVGGSGSYNEQFF, (SEQ ID NO: 169)

or variants thereof each having up to three amino acid substitutions, additions or deletions;

(xxxv)

CDR1α - TSINN, (SEQ ID NO: 275)

CDR2α - IRSNERE, (SEQ ID NO: 276)

CDR3α - CATDGDSSYKLIF, (SEQ ID NO: 277)

CDR1β - DFQATT, (SEQ ID NO: 280)

CDR2β - SNEGSKA,
and (SEQ ID NO: 281)

CDR3β - CSARDVLTGDYGYTF, (SEQ ID NO: 282)

or variants thereof each having up to three amino acid substitutions, additions or deletions;

(xxxvi)

CDR1α - TSINN, (SEQ ID NO: 275)

CDR2α - IRSNERE, (SEQ ID NO: 276)

CDR3α - CATDGDSSYKLIF, (SEQ ID NO: 277)

CDR1β - SGHDY, (SEQ ID NO: 286)

CDR2β - FNNNVP,
and (SEQ ID NO: 287)

CDR3β - CASSLGLSISQETQYF, (SEQ ID NO: 288)

or variants thereof each having up to three amino acid substitutions, additions or deletions;

(xxxvii)

CDR1α - DSSSTY, (SEQ ID NO: 101)

CDR2α - IFSNMDM, (SEQ ID NO: 102)

CDR3α - CAERLNTDKLIF, (SEQ ID NO: 103)

CDR1β - SGHDY, (SEQ ID NO: 286)

CDR2β - FNNNVP,
and (SEQ ID NO: 287)

CDR3β - CASSLGLSISQETQYF, (SEQ ID NO: 288)

or variants thereof each having up to three amino acid substitutions, additions or deletions;

(xxxviii)

CDR1α - DSVNN, (SEQ ID NO: 106)

CDR2α - IPSGT, (SEQ ID NO: 107)

CDR3α - CAVEATDSWGKLQF, (SEQ ID NO: 108)

CDR1β - SGHDY, (SEQ ID NO: 286)

CDR2β - FNNNVP,
and (SEQ ID NO: 287)

CDR3β - CASSLGLSISQETQYF, (SEQ ID NO: 288)

or variants thereof each having up to three amino acid substitutions, additions or deletions;

(xxxix)

CDR1α - DSASNY, (SEQ ID NO: 111)

CDR2α - IRSNVGE, (SEQ ID NO: 112)

CDR3α - CAVRTSYDKVIF, (SEQ ID NO: 113)

CDR1β - SGHDY, (SEQ ID NO: 286)

CDR2β - FNNNVP,
and (SEQ ID NO: 287)

CDR3β - CASSLGLSISQETQYF, (SEQ ID NO: 288)

or variants thereof each having up to three amino acid substitutions, additions or deletions;

(xxxx)

CDR1α - DSSSTY, (SEQ ID NO: 101)

CDR2α - IFSNMDM, (SEQ ID NO: 102)

CDR3α - CAERLNTDKLIF, (SEQ ID NO: 103)

CDR1β - DFQATT, (SEQ ID NO: 280)

CDR2β - SNEGSKA,
and (SEQ ID NO: 281)

-continued

```
                                    (SEQ ID NO: 282)
CDR3β - CSARDVLTGDYGYTF,
``` or variants thereof each having up to three amino acid substitutions, additions or deletions;

```
(xxxxi)
                                    (SEQ ID NO: 106)
CDR1α - DSVNN, (SEQ ID NO: 107)
CDR2α - IPSGT, (SEQ ID NO: 108)
CDR3α - CAVEATDSWGKLQF, (SEQ ID NO: 280)
CDR1β - DFQATT, (SEQ ID NO: 281)
CDR2β - SNEGSKA,
and (SEQ ID NO: 282)
CDR3β - CSARDVLTGDYGYTF,
``` or variants thereof each having up to three amino acid substitutions, additions or deletions; or

```
(xxxxii)
                                    (SEQ ID NO: 111)
CDR1α - DSASNY, (SEQ ID NO: 112)
CDR2α - IRSNVGE, (SEQ ID NO: 113)
CDR3α - CAVRTSYDKVIF, (SEQ ID NO: 280)
CDR1β - DFQATT, (SEQ ID NO: 281)
CDR2β - SNEGSKA,
and (SEQ ID NO: 282)
CDR3β - CSARDVLTGDYGYTF,
``` or variants thereof each having up to three amino acid substitutions, additions or deletions.

In one embodiment, the present invention provides a TCR of the present invention comprising:

(i) an α chain variable domain comprising the amino acid sequence of SEQ ID NO: 4 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 9 or a variant thereof having at least 75%, at least 80%, at least 85%, at least 90%, at least 95%, at least 96%, at least 97%, at least 98%, or at least 99%, preferably at least 75%, sequence identity thereto;

(ii) an α chain variable domain comprising the amino acid sequence of SEQ ID NO: 37 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 42 or a variant thereof having at least 75%, at least 80%, at least 85%, at least 90%, at least 95%, at least 96%, at least 97%, at least 98%, or at least 99%, preferably at least 75%, sequence identity thereto;

(iii) an α chain variable domain comprising the amino acid sequence of SEQ ID NO: 15 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 25 or a variant thereof having at least 75%, at least 80%, at least 85%, at least 90%, at least 95%, at least 96%, at least 97%, at least 98%, or at least 99%, preferably at least 75%, sequence identity thereto;

(iv) an α chain variable domain comprising the amino acid sequence of SEQ ID NO: 15 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 31 or a variant thereof having at least 75%, at least 80%, at least 85%, at least 90%, at least 95%, at least 96%, at least 97%, at least 98%, or at least 99%, preferably at least 75%, sequence identity thereto;

(v) an α chain variable domain comprising the amino acid sequence of SEQ ID NO: 20 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 25 or a variant thereof having at least 75%, at least 80%, at least 85%, at least 90%, at least 95%, at least 96%, at least 97%, at least 98%, or at least 99%, preferably at least 75%, sequence identity thereto;

(vi) an α chain variable domain comprising the amino acid sequence of SEQ ID NO: 20 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 31 or a variant thereof having at least 75%, at least 80%, at least 85%, at least 90%, at least 95%, at least 96%, at least 97%, at least 98%, or at least 99%, preferably at least 75%, sequence identity thereto;

(vii) an α chain variable domain comprising the amino acid sequence of SEQ ID NO: 48 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 58 or a variant thereof having at least 75%, at least 80%, at least 85%, at least 90%, at least 95%, at least 96%, at least 97%, at least 98%, or at least 99%, preferably at least 75%, sequence identity thereto;

(viii) an α chain variable domain comprising the amino acid sequence of SEQ ID NO: 48 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 64 or a variant thereof having at least 75%, at least 80%, at least 85%, at least 90%, at least 95%, at least 96%, at least 97%, at least 98%, or at least 99%, preferably at least 75%, sequence identity thereto;

(ix) an α chain variable domain comprising the amino acid sequence of SEQ ID NO: 48 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 70 or a variant thereof having at least 75%, at least 80%, at least 85%, at least 90%, at least 95%, at least 96%, at least 97%, at least 98%, or at least 99%, preferably at least 75%, sequence identity thereto;

(x) an α chain variable domain comprising the amino acid sequence of SEQ ID NO: 53 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 58 or a variant thereof having at least 75%, at least 80%, at least 85%, at least 90%, at least 95%, at least 96%, at least 97%, at least 98%, or at least 99%, preferably at least 75%, sequence identity thereto;

(xi) an α chain variable domain comprising the amino acid sequence of SEQ ID NO: 53 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 64 or a variant thereof having at least 75%, at least 80%, at least 85%, at least 90%, at least 95%, at least 96%, at least 97%, at least 98%, or at least 99%, preferably at least 75%, sequence identity thereto;

(xii) an α chain variable domain comprising the amino acid sequence of SEQ ID NO: 53 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 70 or a variant thereof having at least 75%, at least 80%, at least 85%, at least 90%, at least 95%, at least 96%, at least 97%, at least 98%, or at least 99%, preferably at least 75%, sequence identity thereto;

(xiii) an α chain variable domain comprising the amino acid sequence of SEQ ID NO: 76 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 81 or a variant thereof having at least 75%, at least 80%, at least 85%, at least 90%, at least 95%, at least 96%, at least 97%, at least 98%, or at least 99%, preferably at least 75%, sequence identity thereto;

(xiv) an α chain variable domain comprising the amino acid sequence of SEQ ID NO: 76 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 87 or a variant thereof at least 75%, at least 80%, at least 85%, at least 90%, at least 95%, at least 96%, at least 97%, at least 98%, or at least 99%, preferably at least 75%, sequence identity thereto;

(xv) an α chain variable domain comprising the amino acid sequence of SEQ ID NO: 93 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 98 or a variant thereof having at least 75%, at least 80%, at least 85%, at least 90%, at least 95%, at least 96%, at least 97%, at least 98%, or at least 99%, preferably at least 75%, sequence identity thereto;

(xvi) an α chain variable domain comprising the amino acid sequence of SEQ ID NO: 104 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 164 or a variant thereof having at least 75%, at least 80%, at least 85%, at least 90%, at least 95%, at least 96%, at least 97%, at least 98%, or at least 99%, preferably at least 75%, sequence identity thereto;

(xvii) an α chain variable domain comprising the amino acid sequence of SEQ ID NO: 104 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 170 or a variant thereof having at least 75%, at least 80%, at least 85%, at least 90%, at least 95%, at least 96%, at least 97%, at least 98%, or at least 99%, preferably at least 75%, sequence identity thereto;

(xviii) an α chain variable domain comprising the amino acid sequence of SEQ ID NO: 109 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 164 or a variant thereof having at least 75%, at least 80%, at least 85%, at least 90%, at least 95%, at least 96%, at least 97%, at least 98%, or at least 99%, preferably at least 75%, sequence identity thereto;

(xix) an α chain variable domain comprising the amino acid sequence of SEQ ID NO: 109 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 170 or a variant thereof having at least 75%, at least 80%, at least 85%, at least 90%, at least 95%, at least 96%, at least 97%, at least 98%, or at least 99%, preferably at least 75%, sequence identity thereto;

(xx) an α chain variable domain comprising the amino acid sequence of SEQ ID NO: 114 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 164 or a variant thereof having at least 75%, at least 80%, at least 85%, at least 90%, at least 95%, at least 96%, at least 97%, at least 98%, or at least 99%, preferably at least 75%, sequence identity thereto;

(xxi) an α chain variable domain comprising the amino acid sequence of SEQ ID NO: 114 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 170 or a variant thereof having at least 75%, at least 80%, at least 85%, at least 90%, at least 95%, at least 96%, at least 97%, at least 98%, or at least 99%, preferably at least 75%, sequence identity thereto;

(xxii) an α chain variable domain comprising the amino acid sequence of SEQ ID NO: 176 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 181 or a variant thereof having at least 75%, at least 80%, at least 85%, at least 90%, at least 95%, at least 96%, at least 97%, at least 98%, or at least 99%, preferably at least 75%, sequence identity thereto;

(xxiii) an α chain variable domain comprising the amino acid sequence of SEQ ID NO: 187 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 197 or a variant thereof having at least 75%, at least 80%, at least 85%, at least 90%, at least 95%, at least 96%, at least 97%, at least 98%, or at least 99%, preferably at least 75%, sequence identity thereto;

(xxiv) an α chain variable domain comprising the amino acid sequence of SEQ ID NO: 187 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 203 or a variant thereof having at least 75%, at least 80%, at least 85%, at least 90%, at least 95%, at least 96%, at least 97%, at least 98%, or at least 99%, preferably at least 75%, sequence identity thereto;

(xxv) an α chain variable domain comprising the amino acid sequence of SEQ ID NO: 187 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 209 or a variant thereof having at least 75%, at least 80%, at least 85%, at least 90%, at least 95%, at least 96%, at least 97%, at least 98%, or at least 99%, preferably at least 75%, sequence identity thereto;

(xxvi) an α chain variable domain comprising the amino acid sequence of SEQ ID NO: 192 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 197 or a variant thereof having at least 75%, at least 80%, at least 85%, at least 90%, at least 95%, at least 96%, at least 97%, at least 98%, or at least 99%, preferably at least 75%, sequence identity thereto;

(xxvii) an α chain variable domain comprising the amino acid sequence of SEQ ID NO: 192 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 203 or a variant thereof having at least 75%, at least 80%, at least 85%, at least 90%, at least 95%, at least 96%, at least 97%, at least 98%, or at least 99%, preferably at least 75%, sequence identity thereto;

(xxviii) an α chain variable domain comprising the amino acid sequence of SEQ ID NO: 192 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 209 or a variant thereof having at least 75%, at least 80%, at least 85%, at least 90%, at least 95%, at least 96%, at least 97%, at least 98%, or at least 99%, preferably at least 75%, sequence identity thereto; or (xxix) an α chain variable domain comprising the amino acid sequence of SEQ ID NO: 215 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 220 or a variant thereof having at least 75%, at least 80%, at least 85%, at least 90%, at least 95%, at least 96%, at least 97%, at least 98%, or at least 99%, preferably at least 75%, sequence identity thereto;

(xxx) an α chain variable domain comprising the amino acid sequence of SEQ ID NO: 93 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 272 or a variant thereof having at least 75%, at least 80%, at least 85%, at least 90%, at least 95%, at least 96%, at least 97%, at least 98%, or at least 99%, preferably at least 75%, sequence identity thereto;

(xxxi) an α chain variable domain comprising the amino acid sequence of SEQ ID NO: 267 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 98 or a variant thereof having at least 75%, at least 80%, at least 85%, at least 90%, at least 95%, at least 96%, at least 97%, at least 98%, or at least 99%, preferably at least 75%, sequence identity thereto;

(xxxii) an α chain variable domain comprising the amino acid sequence of SEQ ID NO: 267 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 272 or a variant thereof having at least 75%, at least 80%, at least 85%, at least 90%, at least 95%, at least 96%, at least 97%, at least 98%, or at least 99%, preferably at least 75%, sequence identity thereto;

(xxxiii) an α chain variable domain comprising the amino acid sequence of SEQ ID NO: 278 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 164 or a variant thereof having at least 75%, at least 80%, at least 85%, at least 90%, at least 95%, at least 96%, at least 97%, at least 98%, or at least 99%, preferably at least 75%, sequence identity thereto;

(xxxiv) an α chain variable domain comprising the amino acid sequence of SEQ ID NO: 278 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 170 or a variant thereof having at least 75%, at least 80%, at least 85%, at least 90%, at least 95%, at least 96%, at least 97%, at least 98%, or at least 99%, preferably at least 75%, sequence identity thereto;

(xxxv) an α chain variable domain comprising the amino acid sequence of SEQ ID NO: 278 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 283 or a variant thereof having at least 75%, at least 80%, at least 85%, at least 90%, at least 95%, at least 96%, at least 97%, at least 98%, or at least 99%, preferably at least 75%, sequence identity thereto;

(xxxvi) an α chain variable domain comprising the amino acid sequence of SEQ ID NO: 278 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 289 or a variant thereof having at least 75%, at least 80%, at least 85%, at least 90%, at least 95%, at least 96%, at least 97%, at least 98%, or at least 99%, preferably at least 75%, sequence identity thereto;

(xxxvii) an α chain variable domain comprising the amino acid sequence of SEQ ID NO: 104 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 289 or a variant thereof having at least 75%, at least 80%, at least 85%, at least 90%, at least 95%, at least 96%, at least 97%, at least 98%, or at least 99%, preferably at least 75%, sequence identity thereto;

(xxxviii) an α chain variable domain comprising the amino acid sequence of SEQ ID NO: 109 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 289 or a variant thereof having at least 75%, at least 80%, at least 85%, at least 90%, at least 95%, at least 96%, at least 97%, at least 98%, or at least 99%, preferably at least 75%, sequence identity thereto;

(xxxix) an α chain variable domain comprising the amino acid sequence of SEQ ID NO: 114 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 289 or a variant thereof having at least 75%, at least 80%, at least 85%, at least 90%, at least 95%, at least 96%, at least 97%, at least 98%, or at least 99%, preferably at least 75%, sequence identity thereto;

(xxxx) an α chain variable domain comprising the amino acid sequence of SEQ ID NO: 104 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 283 or a variant thereof having at least 75%, at least 80%, at least 85%, at least 90%, at least 95%, at least 96%, at least 97%, at least 98%, or at least 99%, preferably at least 75%, sequence identity thereto;

(xxxxi) an α chain variable domain comprising the amino acid sequence of SEQ ID NO: 109 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 283 or a variant thereof having at least 75%, at least 80%, at least 85%, at least 90%, at least 95%, at least 96%, at least 97%, at least 98%, or at least 99%, preferably at least 75%, sequence identity thereto; or (xxxxii) an α chain variable domain comprising the amino acid sequence of SEQ ID NO: 114 or a variant thereof having at least 75%, at least 80%, at least 85%, at least 90%, at least 95%, at least 96%, at least 97%, at least 98%, or at least 99%, preferably at least 75%, sequence identity thereto; and a β chain variable domain comprising the amino acid sequence of SEQ ID NO: 283 or a variant thereof having at least 75%, at least 80%, at least 85%, at least 90%, at least 95%, at least 96%, at least 97%, at least 98%, or at least 99%, preferably at least 75%, sequence identity thereto.

In one embodiment, the present invention provides a TCR of the present invention comprising:

(i) an α chain comprising the amino acid sequence of SEQ ID NO: 5 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 10, SEQ ID NO: 11 and variants of SEQ ID NOs: 10 and 11 having at least 75%, at least 80%, at least 85%, at least 90%, at least 95%, at least 96%, at least 97%, at least 98%, or at least 99%, preferably at least 75%, sequence identity thereto;

(ii) an α chain comprising the amino acid sequence of SEQ ID NO: 38 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 43, SEQ ID NO: 44 and variants of SEQ ID NOs: 43 and 44 having at least 75%, at least 80%, at least 85%, at least 90%, at least 95%, at least 96%, at least 97%, at least 98%, or at least 99%, preferably at least 75%, sequence identity thereto;

(iii) an α chain comprising the amino acid sequence of SEQ ID NO: 16 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 26, SEQ ID NO: 27 and variants of SEQ ID NOs: 26 and 27 having at least 75%, at least 80%, at least 85%, at least 90%, at least 95%, at least 96%, at least 97%, at least 98%, or at least 99%, preferably at least 75%, sequence identity thereto;

(iv) an α chain comprising the amino acid sequence of SEQ ID NO: 16 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 32, SEQ ID NO: 33 and variants of SEQ ID NOs: 32 and 33 having at least 75%, at least 80%, at least 85%, at least 90%, at least 95%, at least 96%, at least 97%, at least 98%, or at least 99%, preferably at least 75%, sequence identity thereto;

(v) an α chain comprising the amino acid sequence of SEQ ID NO: 21 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 26, SEQ ID NO: 27 and variants of SEQ ID NOs: 26 and 27 having at least 75%, at least 80%, at least 85%, at least 90%, at least 95%, at least 96%, at least 97%, at least 98%, or at least 99%, preferably at least 75%, sequence identity thereto;

(vi) an α chain comprising the amino acid sequence of SEQ ID NO: 21 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 32, SEQ ID NO: 33 and variants of SEQ ID NOs: 32 and 33 having at least 75%, at least 80%, at least 85%, at least 90%, at least 95%, at least 96%, at least 97%, at least 98%, or at least 99%, preferably at least 75%, sequence identity thereto;

(vii) an α chain comprising the amino acid sequence of SEQ ID NO: 49 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 59, SEQ ID NO: 60 and variants of SEQ ID NOs: 59 and 60 having at least 75%, at least 80%, at least 85%, at least 90%, at least 95%, at least 96%, at least 97%, at least 98%, or at least 99%, preferably at least 75%, sequence identity thereto;

(viii) an α chain comprising the amino acid sequence of SEQ ID NO: 49 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 65, SEQ ID NO: 66 and variants of SEQ ID NOs: 65 and 66 having at least 75%, at least 80%, at least 85%, at least 90%, at least 95%, at least 96%, at least 97%, at least 98%, or at least 99%, preferably at least 75%, sequence identity thereto;

(ix) an α chain comprising the amino acid sequence of SEQ ID NO: 49 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 71, SEQ ID NO: 72 and variants of SEQ ID NOs: 71 and 72 having at least 75%, at least 80%, at least 85%, at least 90%, at least 95%, at least 96%, at least 97%, at least 98%, or at least 99%, preferably at least 75%, sequence identity thereto;

(x) an α chain comprising the amino acid sequence of SEQ ID NO: 54 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 59, SEQ ID NO: 60 and variants of SEQ ID NOs: 59 and 60 having at least 75%, at least 80%, at least 85%, at least 90%, at least 95%, at least 96%, at least 97%, at least 98%, or at least 99%, preferably at least 75%, sequence identity thereto;

(xi) an α chain comprising the amino acid sequence of SEQ ID NO: 54 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 65, SEQ ID NO: 66 and variants of SEQ ID NOs: 65 and 66 having at least 75%, at least 80%, at least 85%, at least 90%, at least 95%, at least 96%, at least 97%, at least 98%, or at least 99%, preferably at least 75%, sequence identity thereto;

(xii) an α chain comprising the amino acid sequence of SEQ ID NO: 54 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 71, SEQ ID NO: 72 and variants of SEQ ID NOs: 71 and 72 having at least 75%, at least 80%, at least 85%, at least 90%, at least 95%, at least 96%, at least 97%, at least 98%, or at least 99%, preferably at least 75%, sequence identity thereto;

(xiii) an α chain comprising the amino acid sequence of SEQ ID NO: 77 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 82, SEQ ID NO: 83 and variants of SEQ ID NOs: 82 and 83 having at least 75%, at least 80%, at least 85%, at least 90%, at least 95%, at least 96%, at least 97%, at least 98%, or at least 99%, preferably at least 75%, sequence identity thereto;

(xiv) an α chain comprising the amino acid sequence of SEQ ID NO: 77 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 88, SEQ ID NO: 89 and variants of SEQ ID NOs: 88 and 89 having at least 75%, at least 80%, at least 85%, at least 90%, at least 95%, at least 96%, at least 97%, at least 98%, or at least 99%, preferably at least 75%, sequence identity thereto;

(xv) an α chain comprising the amino acid sequence of SEQ ID NO: 94 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 99, SEQ ID NO: 100 and variants of SEQ ID NO: 99, SEQ ID NO: 100 having at least 75%, at least 80%, at least 85%, at least 90%, at least 95%, at least 96%, at least 97%, at least 98%, or at least 99%, preferably at least 75%, sequence identity thereto;

(xvi) an α chain comprising the amino acid sequence of SEQ ID NO: 105 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 165, SEQ ID NO: 166 and variants of SEQ ID NOs: 165 and 166 having at least 75%, at least 80%, at least 85%, at least 90%, at least 95%, at least 96%, at least 97%, at least 98%, or at least 99%, preferably at least 75%, sequence identity thereto;

(xvii) an α chain comprising the amino acid sequence of SEQ ID NO: 105 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 171, SEQ ID NO: 172 and variants of SEQ ID NOs: 171 and 172 having at least 75%, at least 80%, at least 85%, at least 90%, at least 95%, at least 96%, at least 97%, at least 98%, or at least 99%, preferably at least 75%, sequence identity thereto;

(xviii) an α chain comprising the amino acid sequence of SEQ ID NO: 110 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 165, SEQ ID NO: 166 and variants of SEQ ID NOs: 165 and 166 having at least 75%, at least 80%, at least 85%, at least 90%, at least 95%, at least 96%, at least 97%, at least 98%, or at least 99%, preferably at least 75%, sequence identity thereto;

(xix) an α chain comprising the amino acid sequence of SEQ ID NO: 110 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 171, SEQ ID NO: 172 and variants of SEQ ID NOs: 171 and 172 having at least 75%, at least 80%, at least 85%, at least 90%, at least 95%, at least 96%, at least 97%, at least 98%, or at least 99%, preferably at least 75%, sequence identity thereto;

(xx) an α chain comprising the amino acid sequence of SEQ ID NO: 160 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 165, SEQ ID NO: 166 and variants of SEQ ID NOs: 165 and 166 having at least 75%, at least 80%, at least 85%, at least 90%, at least 95%, at least 96%, at least 97%, at least 98%, or at least 99%, preferably at least 75%, sequence identity thereto;

(xxi) an α chain comprising the amino acid sequence of SEQ ID NO: 160 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 171, SEQ ID NO: 172 and variants of SEQ ID NOs: 171 and 172 having at least 75%, at least 80%, at least 85%, at least 90%, at least 95%, at least 96%, at least 97%, at least 98%, or at least 99%, preferably at least 75%, sequence identity thereto;

(xxii) an α chain comprising the amino acid sequence of SEQ ID NO: 177 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 182, SEQ ID NO: 183 and variants of SEQ ID NOs: 182 and 183 having at least 75%, at least 80%, at least 85%, at least 90%, at least 95%, at least 96%, at least 97%, at least 98%, or at least 99%, preferably at least 75%, sequence identity thereto;

(xxiii) an α chain comprising the amino acid sequence of SEQ ID NO: 188 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 198, SEQ ID NO: 199 and variants of SEQ ID NOs: 198 and 199 having at least 75%, at least 80%, at least 85%, at least 90%, at least 95%, at least 96%, at least 97%, at least 98%, or at least 99%, preferably at least 75%, sequence identity thereto;

(xxiv) an α chain comprising the amino acid sequence of SEQ ID NO: 188 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 204, SEQ ID NO: 205 and variants of SEQ ID NOs: 204 and 205 having at least 75%, at least 80%, at least 85%, at least 90%, at least 95%, at least 96%, at least 97%, at least 98%, or at least 99%, preferably at least 75%, sequence identity thereto;

(xxv) an α chain comprising the amino acid sequence of SEQ ID NO: 188 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 210, SEQ ID NO: 211 and variants of SEQ ID NOs: 210 and 211 having at least 75%, at least 80%, at least 85%, at least 90%, at least 95%, at least 96%, at least 97%, at least 98%, or at least 99%, preferably at least 75%, sequence identity thereto;

(xxvi) an α chain comprising the amino acid sequence of SEQ ID NO: 193 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 198, SEQ ID NO: 199 and variants of SEQ ID NOs: 198 and 199 having at least 75%, at least 80%, at least 85%, at least 90%, at least 95%, at least 96%, at least 97%, at least 98%, or at least 99%, preferably at least 75%, sequence identity thereto;

(xxvii) an α chain comprising the amino acid sequence of SEQ ID NO: 193 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 204, SEQ ID NO: 205 and variants of SEQ ID NOs: 204 and 205 having at least 75%, at least 80%, at least 85%, at least 90%, at least 95%, at least 96%, at least 97%, at least 98%, or at least 99%, preferably at least 75%, sequence identity thereto;

(xxviii) an α chain comprising the amino acid sequence of SEQ ID NO: 193 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 210, SEQ ID NO: 211 and variants of SEQ ID NOs: 210 and 211 having at least 75%, at least 80%, at least 85%, at least 90%, at least 95%, at least 96%, at least 97%, at least 98%, or at least 99%, preferably at least 75%, sequence identity thereto;

(xxix) an α chain comprising the amino acid sequence of SEQ ID NO: 216 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 221, SEQ ID NO: 222 and variants of SEQ ID NOs: 221 and 222 having at least 75%, at least 80%, at least 85%, at least 90%, at least 95%, at least 96%, at least 97%, at least 98%, or at least 99%, preferably at least 75%, sequence identity thereto;

(xxx) an α chain comprising the amino acid sequence of SEQ ID NO: 94 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 273, SEQ ID NO: 274 and variants of SEQ ID NOs: 273 and 274 having at least 75%, at least 80%, at least 85%, at least 90%, at least 95%, at least 96%, at least 97%, at least 98%, or at least 99%, preferably at least 75%, sequence identity thereto;

(xxxi) an α chain comprising the amino acid sequence of SEQ ID NO: 268 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 99, SEQ ID NO: 100 and variants of SEQ ID NOs: 99 and 100 having at least 75%, at least 80%, at least 85%, at least 90%, at least 95%, at least 96%, at least 97%, at least 98%, or at least 99%, preferably at least 75%, sequence identity thereto;

(xxxii) an α chain comprising the amino acid sequence of SEQ ID NO: 268 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 273, SEQ ID NO: 274 and variants of SEQ ID NOs: 273 and 274 having at least 75%, at least 80%, at least 85%, at least 90%, at least 95%, at least 96%, at least 97%, at least 98%, or at least 99%, preferably at least 75%, sequence identity thereto;

(xxxiii) an α chain comprising the amino acid sequence of SEQ ID NO: 279 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 165, SEQ ID NO: 166 and variants of SEQ ID NOs: 165 and 166 having at least 75%, at least 80%, at least 85%, at least 90%, at least 95%, at least 96%, at least 97%, at least 98%, or at least 99%, preferably at least 75%, sequence identity thereto;

(xxxiv) an α chain comprising the amino acid sequence of SEQ ID NO: 279 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 171, SEQ ID NO: 172 and variants of SEQ ID NOs: 171 and 172 having at least 75%, at least 80%, at least 85%, at least 90%, at least 95%, at least 96%, at least 97%, at least 98%, or at least 99%, preferably at least 75%, sequence identity thereto;

(xxxv) an α chain comprising the amino acid sequence of SEQ ID NO: 279 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 284, SEQ ID NO: 285 and variants of SEQ ID NOs: 284 and 285 having at least 75%, at least 80%, at least 85%, at least 90%, at least 95%, at least 96%, at least 97%, at least 98%, or at least 99%, preferably at least 75%, sequence identity thereto;

(xxxvi) an α chain comprising the amino acid sequence of SEQ ID NO: 279 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 290, SEQ ID NO: 291 and variants of SEQ ID NOs: 290 and 291 having at least 75%, at least 80%, at least 85%, at least 90%, at least 95%, at least 96%, at least 97%, at least 98%, or at least 99%, preferably at least 75%, sequence identity thereto;

(xxxvii) an α chain comprising the amino acid sequence of SEQ ID NO: 105 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 290, SEQ ID NO: 291 and variants of SEQ ID NOs: 290 and 291 having at least 75%, at least 80%, at least 85%, at least 90%, at least 95%, at least 96%, at least 97%, at least 98%, or at least 99%, preferably at least 75%, sequence identity thereto;

(xxxviii) an α chain comprising the amino acid sequence of SEQ ID NO: 110 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 290, SEQ ID NO: 291 and variants of SEQ ID NOs: 290 and 291 having at least 75%, at least 80%, at least 85%, at least 90%, at least 95%, at least 96%, at least 97%, at least 98%, or at least 99%, preferably at least 75%, sequence identity thereto;

(xxxix) an α chain comprising the amino acid sequence of SEQ ID NO: 160 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 290, SEQ ID NO: 291 and variants of SEQ ID NOs: 290 and 291 having at least 75%, at least 80%, at least 85%, at least 90%, at least 95%, at least 96%, at least 97%, at least 98%, or at least 99%, preferably at least 75%, sequence identity thereto;

(xxxx) an α chain comprising the amino acid sequence of SEQ ID NO: 105 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 284, SEQ ID NO: 285 and variants of SEQ ID NOs: 284 and 285 having at least 75%, at least 80%, at least 85%, at least 90%, at least 95%, at least 96%, at least 97%, at least 98%, or at least 99%, preferably at least 75%, sequence identity thereto;

(xxxxi) an α chain comprising the amino acid sequence of SEQ ID NO: 110 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 284, SEQ ID NO: 285 and variants of SEQ ID NOs: 284 and 285 having at least 75%, at least 80%, at least 85%, at least 90%, at least 95%, at least 96%, at least 97%, at least 98%, or at least 99%, preferably at least 75%, sequence identity thereto; or (xxxxii) an α chain comprising the amino acid sequence of SEQ ID NO: 160 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence selected from the group consisting of SEQ ID NO: 284, SEQ ID NO: 285 and variants of SEQ ID NOs: 284 and 285 having at least 75%, at least 80%, at least 85%, at least 90%, at least 95%, at least 96%, at least 97%, at least 98%, or at least 99%, preferably at least 75%, sequence identity thereto.

In one embodiment, the present invention provides a TCR of the present invention comprising an α chain comprising the amino acid sequence of SEQ ID NO: 257 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence of SEQ ID NO: 259 or a variant thereof having at least 75%, at least 80%, at least 85%, at least 90%, at least 95%, at least 96%, at least 97%, at least 98%, or at least 99%, preferably at least 75%, sequence identity thereto.

In one embodiment, the present invention provides a TCR of the present invention comprising an α chain comprising the amino acid sequence of SEQ ID NO: 261 or a variant thereof having at least 75%, at least 80%, at least 85%, at least 90%, at least 95%, at least 96%, at least 97%, at least 98%, or at least 99%, preferably at least 75%, sequence identity thereto; and a β chain comprising an amino acid sequence of SEQ ID NO: 263 or a variant thereof having at least 75%, at least 80%, at least 85%, at least 90%, at least 95%, at least 96%, at least 97%, at least 98%, or at least 99%, preferably at least 75%, sequence identity thereto.

A TCR of the present invention may bind to a WT1 peptide comprising an amino acid sequence selected from the group consisting of EPASQHTLRSG (SEQ ID NO: 123), YESDNHTTPIL (SEQ ID NO: 126), NHTTPILCGAQYRIH (SEQ ID NO: 127), QCLSAFTVHFSGQFT (SEQ ID NO: 118), EDPMGQQGSLGEQQY (SEQ ID NO: 119), SQLECMTWNQMNLGA (SEQ ID NO: 120), APVLDFAPPGA (SEQ ID NO: 117) NQMNLGATLKG (SEQ ID NO: 250), DPGGIWAKLGAAEAS (SEQ ID NO: 251), NHTTPILCGAQYRIH (SEQ ID NO: 252), KRHQRRHTGVKPFQC (SEQ ID NO: 253), PSCQKKFARSDELVR (SEQ ID NO: 254) and variants thereof each having up to three amino acid substitutions, additions or deletions.

In another aspect, the present invention provides a T-cell receptor (TCR), which binds to a Wilms tumour 1 protein (WT1) peptide when presented by a major histocompatibility complex (MHC), wherein the WT1 peptide comprises an amino acid sequence selected from the group consisting of EPASQHTLRSG (SEQ ID NO: 123), YESDNHTTPIL (SEQ ID NO: 126), NHTTPILCGAQYRIH (SEQ ID NO: 127), QCLSAFTVHFSGQFT (SEQ ID NO: 118), EDPMGQQGSLGEQQY (SEQ ID NO: 119), SQLECMTWNQMNLGA (SEQ ID NO: 120), APVLDFAPPGA (SEQ ID NO: 117), NQMNLGATLKG (SEQ ID NO: 250), DPGGIWAKLGAAEAS (SEQ ID NO: 251), NHTTPILCGAQYRIH (SEQ ID NO: 252), KRHQR-RHTGVKPFQC (SEQ ID NO: 253), PSCQKKFARS-DELVR (SEQ ID NO: 254) and variants thereof each having up to three amino acid substitutions, additions or deletions.

In one embodiment, a TCR of the present invention binds to an MHC I and/or MHC II peptide complex.

In one embodiment, a TCR of the present invention is restricted to a human leukocyte antigen (HLA) allele. In one embodiment, a TCR of the present invention is restricted to a HLA-A or a HLA-B allele. In one embodiment, a TCR of the present invention is restricted to a HLA-A allele selected from the group consisting of HLA-A*0201, HLA-A*0101, HLA-A*2402 and HLA-A*0301 or a HLA-B allele selected from the group consisting of HLA-B*0702, HLA-B*3501 and HLA-B*3502.

In one embodiment, a TCR of the present invention is restricted to HLA-A*0201.

In one embodiment, a TCR of the present invention is restricted to HLA-B*3502.

In one embodiment, a TCR of the present invention is restricted to HLA-B*3501.

In one embodiment, a TCR of the present invention is restricted to a HLA-C allele. In one embodiment, a TCR of the present invention is restricted to a HLA-C allele selected from the group consisting of HLA-C*07:01, HLA-C*03:04, HLA-C*04:01, HLA-C*05:01, HLA-C*06:02 and HLA-C*07:02.

In one embodiment, a TCR of the present invention comprises one or more mutations at the α chain/β chain interface, such that when the α chain and the β chain are expressed in a T-cell, the frequency of mispairing between said chains and endogenous TCR α and β chains is reduced.

In one embodiment, a TCR of the present invention comprises one or more mutations at the α chain/β chain interface, such that when the α chain and the β chain are expressed in a T-cell, the level of expression of the TCR α and β chains is increased.

In one embodiment, the one or more mutations introduce a cysteine residue into the constant region domain of each of the α chain and the β chain, wherein the cysteine residues are capable of forming a disulphide bond between the α chain and the β chain.

A TCR of the present invention may comprise a murinized constant region.

In one embodiment, the TCR of the invention is a soluble TCR.

In another aspect, the present invention provides an isolated polynucleotide encoding the α chain of a T-cell receptor (TCR) of the present invention, and/or the β chain of a TCR of the present invention.

In another aspect, the present invention provides an isolated polynucleotide comprising a nucleotide sequence of SEQ ID NO: 256 and/or a nucleotide sequence of SEQ ID NO: 258, or variants thereof having at least 40%, at least 50%, at least 60%, at least 70%, at least 75%, at least 80%, at least 85%, at least 90%, at least 95%, at least 96%, at least 97%, at least 98%, or at least 99% sequence identity thereto.

In another aspect, the present invention provides an isolated polynucleotide comprising a nucleotide sequence of SEQ ID NO: 260 and/or a nucleotide sequence of SEQ ID NO: 262, or variants thereof having at least 40%, at least 50%, at least 60%, at least 70%, at least 75%, at least 80%, at least 85%, at least 90%, at least 95%, at least 96%, at least 97%, at least 98%, or at least 99% sequence identity thereto.

In one embodiment, the isolated polynucleotide encodes the α chain linked to the β chain. In one embodiment, the isolated polynucleotide encodes one or more short interfering RNA (siRNA) sequences and/or one or more other agents capable of reducing or preventing expression of one or more endogenous TCR genes.

In another aspect, the present invention provides a vector comprising a polynucleotide of the present invention. In one embodiment, the vector comprises a polynucleotide which encodes one or more CD3 chains, CD8, a suicide gene, and/or a selectable marker.

In another aspect, the present invention provides a cell comprising a TCR of the present invention, a polynucleotide of the present invention, or a vector of the present invention.

In one embodiment, the cell further comprises a vector which encodes one or more CD3 chains, CD8, a suicide gene and/or a selectable marker.

In one embodiment, the cell is a T-cell, a lymphocyte or a stem cell, such as hematopoietic stem cells or induced pluripotent stem cells (iPS). The T-cell, the lymphocyte, or the stem cell may be selected from the group consisting of CD4 cells, CD8 cells, Th0 cells, Tc0 cells, Th1 cells, Tc1 cells, Th2 cells, Tc2 cells, Th17 cells, Th22 cells, gamma/delta T-cells, natural killer (NK) cells, natural killer T (NKT) cells, double negative T-cells, naive T-cells, memory stem T-cells, central memory T-cells, effector memory T-cells, effector T cells, hematopoietic stem cells and pluripotent stem cells.

In one embodiment, the cell is a T-cell which has been isolated from a subject.

In one embodiment, an endogenous gene encoding a TCR α chain and/or an endogenous gene encoding a TCR β chain in the cell is disrupted, preferably such that the endogenous gene encoding a TCR α chain and/or the endogenous gene encoding a TCR β chain is not expressed. In one embodiment, the endogenous gene encoding a TCR α chain and/or the endogenous gene encoding a TCR β chain is disrupted by insertion of an expression cassette comprising a polynucleotide sequence encoding a TCR of the present invention. In one embodiment, one or more endogenous genes encoding an MHC in the cell is disrupted, preferably wherein the cell is a non-alloreactive universal T-cell. In one embodiment, an endogenous gene involved in persistence, expansion, activity, resistance to exhaustion/senescence/inhibitory signals, homing capacity, or other T-cell functions in the cell is disrupted, preferably wherein the endogenous gene involved in persistence, expansion, activity, resistance to exhaustion/senescence/inhibitory signals, homing capacity, or other T-cell functions is selected from the group consisting of PD1, TIM3, LAG3, 2B4, KLRG1, TGFbR, CD160 and CTLA4. In one embodiment, the endogenous gene involved in persistence, expansion, activity, resistance to exhaustion/senescence/inhibitory signals, homing capacity, or other T-cell functions is disrupted by integration of an expression cassette, wherein the expression cassette comprises a polynucleotide sequence encoding a TCR of the present invention.

In another aspect, the present invention provides a method of preparing a cell, which comprises the step of introducing a vector of the invention into a cell in vitro, ex vivo or in vivo, for example by transfection or transduction.

In another aspect, the present invention provides a method of preparing a cell, which comprises the step of transducing a cell in vitro, ex vivo or in vivo with one or more vectors of the present invention.

In one embodiment, the cell to be transduced with the one or more vectors is selected from the group consisting of T-cells, lymphocytes or stem cells, such as hematopoietic stem cells or induced pluripotent stem cells (iPS), optionally the T-cell, the lymphocyte or the stem cell may be selected from the group consisting of CD4 cells, CD8 cells, Th0 cells, Tc0 cells, Th1 cells, Tc1 cells, Th2 cells, Tc2 cells, Th17 cells, Th22 cells, gamma/delta T-cells, natural killer (NK) cells, natural killer T (NKT) cells, double negative T-cells, naive T-cells, memory stem T-cells, central memory T-cells, effector memory T-cells, effector T cells, hematopoeitic stem cells and pluripotent stem cells.

In one embodiment, the method comprises the step of T-cell editing, which comprises disrupting an endogenous gene, for example an endogenous gene encoding a TCR α chain and/or an endogenous gene encoding a TCR β chain with an artificial nuclease, preferably wherein the artificial nuclease is selected from the group consisting of zinc finger nucleases (ZFN), transcription activator-like effector nucleases (TALEN) and CRISPR/Cas system.

In one embodiment, the method comprises the step of T-cell editing, which comprises disrupting an endogenous gene encoding a TCR α chain and/or an endogenous gene encoding a TCR β chain with an artificial nuclease, preferably wherein the artificial nuclease is selected from the group consisting of zinc finger nucleases (ZFN), transcription activator-like effector nucleases (TALEN) and CRISPR/Cas system.

In one embodiment, the method comprises the step of targeted integration of an expression cassette into the endogenous gene encoding the TCR α chain gene and/or the endogenous gene encoding the TCR β chain disrupted by the artificial nuclease, wherein the expression cassette comprises a polynucleotide encoding a TCR of the present invention or a polynucleotide sequence of the present invention.

In one embodiment, the method comprises the step of disrupting one or more endogenous genes encoding an MHC, preferably wherein the cell prepared by the method is a non-alloreactive universal T-cell.

In one embodiment, the method comprises the step of disrupting one or more endogenous MHC genes, preferably wherein the cell prepared by the method is a non-alloreactive universal T-cell.

In one embodiment, the method comprises the step of disrupting one or more endogenous genes to modify the persistence, expansion, activity, resistance to exhaustion/senescence/inhibitory signals, homing capacity, or other T-cell functions, preferably wherein the method comprises the step of targeted integration of an expression cassette into an endogenous gene involved in persistence, expansion, activity, resistance to exhaustion/senescence/inhibitory signals, homing capacity, or other T-cell functions disrupted by an artificial nuclease, wherein the expression cassette comprises a polynucleotide sequence encoding a TCR of the present invention, preferably wherein the endogenous gene is selected from the group consisting of PD1, TIM3, LAG3, 2B4, KLRG1, TGFbR, CD160 and CTLA4.

In another aspect, the present invention provides a cell of the present invention or a cell prepared by a method of the present invention for use in adoptive cell transfer, preferably adoptive T-cell transfer, optionally the adoptive T-cell transfer may be allogenic adoptive T-cell transfer, universal non-alloreactive T-cell transfer, or autologous adoptive T-cell transfer.

In another aspect, the present invention provides a TCR of the present invention, an isolated polynucleotide of the present invention, a vector of the present invention, a cell of the present invention, a cell prepared by a method of the present invention, or a chimeric molecule of the present invention for use in therapy.

In another aspect, the present invention provides a TCR of the present invention, an isolated polynucleotide of the present invention, a vector of the present invention, a cell of the present invention, a cell prepared by a method the present invention for use in treating and/or preventing a disease associated with expression of WT1.

In another aspect, the present invention provides a T-cell genetically engineered (genetically edited) to modify the persistence, expansion, activity, resistance to exaustion/senescence/inhibitory signals, homing capacity, or other T cell functions, wherein the T-cell expresses a TCR α chain of the present invention and/or a TCR β chain of the present invention.

In another aspect, the present invention provides a T cell genetically engineered (genetically edited) by a protocol which comprises the step of targeted integration of an expression cassette into an endogenous gene involved in persistence, expansion, activity, resistance to exhaustion/senescence/inhibitory signals, homing capacity, or other T-cell functions disrupted by an artificial nuclease, wherein the expression cassette comprises a polynucleotide sequence encoding TCR α chain of the present invention and/or a TCR β chain of the present invention.

In another aspect, the present invention provides a method for treating and/or preventing a disease associated with expression of WT1, which comprises the step of administering a TCR of the present invention, an isolated polynucleotide of the present invention, a vector of the present invention, a cell of the present invention, a cell prepared by a method of the present invention, or a chimeric molecule of the present invention to a subject in need thereof.

The disease associated with expression of WT1 may be a proliferative disorder. Preferably the proliferative disorder may be selected from the group consisting of hematological malignancies, such as acute myeloid leukemia (AML), chronic myeloid leukemia (CML), lymphoblastic leukemia, myelodisplastic syndromes, multiple myeloma, non Hodgkin lymphoma, Hodgkin lymphoma. The proliferative disorder may be selected from the group of solid tumors, such as lung cancer, breast cancer, oesophageal cancer, gastric cancer, colon cancer, cholangiocarcinoma, pancreatic cancer, ovarian cancer, head and neck cancers, synovial sarcoma, angiosarcoma, osteosarcoma, thyroid cancer, endometrial cancer, neuroblastoma, rabdomyosarcoma, liver cancer, melanoma, prostate cancer, renal cancer, soft tissue sarcoma, urothelial cancer, biliary cancer, glioblastoma, mesothelioma, cervical cancer, and colorectal cancer.

In a preferred embodiment, the disease associated with expression of WT1 is acute myeloid leukemia (AML).

In another preferred embodiment, the disease associated with expression of WT1 is chronic myeloid leukemia (CML).

In another aspect, the present invention provides an isolated immunogenic WT1 peptide comprising an amino acid sequence selected from the group consisting of EPASQHTLRSG (SEQ ID NO: 123), YESDNHTTPIL (SEQ ID NO: 126), NHTTPILCGAQYRIH (SEQ ID NO: 127), QCLSAFTVHFSGQFT (SEQ ID NO: 118), EDPMGQQGSLGEQQY (SEQ ID NO: 119), SQLECMTWNQMNLGA (SEQ ID NO: 120), APVLD-FAPPGA (SEQ ID NO: 117), NQMNLGATLKG (SEQ ID NO: 250), DPGGIWAKLGAAEAS (SEQ ID NO: 251), NHTTPILCGAQYRIH (SEQ ID NO: 252), KRHQR-RHTGVKPFQC (SEQ ID NO: 253), PSCQKKFARS- DELVR (SEQ ID NO: 254) and variants thereof each having up to three amino acid substitutions, additions or deletions.

DESCRIPTION OF THE DRAWINGS

FIGS. 2A-2K. Grid and plots showing the identification of WT1-immunogenic peptides by a mapping grid strategy Epitopes recognized by T-cells sensitized in vitro by repeated stimulations with the pool of overlapping WT1 peptides were identified by intracellular staining. In particular, the percentage of specific T-cells responding to the mapping grid of subpools of WT1 pentadecapeptides loaded on APCs was assessed. Additionally, negative (T-cells unstimulated and T-cells co-cultured with APCs loaded with an unrelated peptide pool) and positive (T-cells cultured in the presence of PMA and Ionomycin) controls were included in the experimental setting (T-cells unstimulated and PMA/lono conditions are not shown).

(FIG. 2A) Deconvolution grid indicating the percentage of T-cells expressing IFNγ and CD107a after co-culture with APCs loaded with the different subpools (denoted SP1-24). IFNγ and CD107a values in bold text denote subpools that contain the WT1 epitope recognized by the T-cells. Representative dot plots relative to the co-culture of the T-cells with APCs loaded with the responsive subpools and indicating the expression of IFNγ and CD107a are reported. Dominant responses were observed for: subpools 4, 5, 16 in HD1 (FIG. 2B), HD3 (FIG. 2D), HD6 (FIG. 2G), HD7 (FIG. 2H), HD10 (FIG. 2K); subpools 6, 16, 17, 20, 23 in HD2 (FIG. 2C); subpools 4, 5, 6, 14, 18, 21 in HD4 (FIG. 2E); subpools 5, 11, 12, 21, 22 in HD5 (FIG. 2F); subpools 12, 14 for HD8 (i); subpools 5,13,21 for HD9 (FIG. 2J). For HD7, we also observed an increased IFNγ secretion and CD107a expression in response to subpools 7, 8, 20, even though at lower percentages compared to the response observed with subpools 4, 5, 16. SP, subpools; WT1, Wilms Tumor 1; APC, antigen-presenting cells; PMA, Phorbol 12-myristate 13-acetate; IFNγ, interferon-γ.

FIGS. 3A-3M. Epitope specificity of the WT1-specific T cells generated by sensitization with the pooled peptides.

Figure 3A:
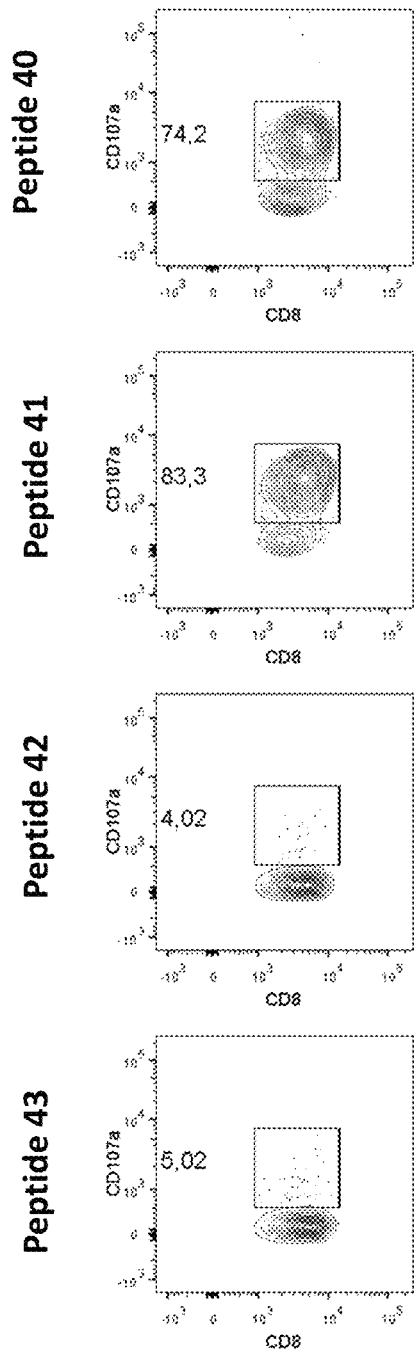
Figure 3B:
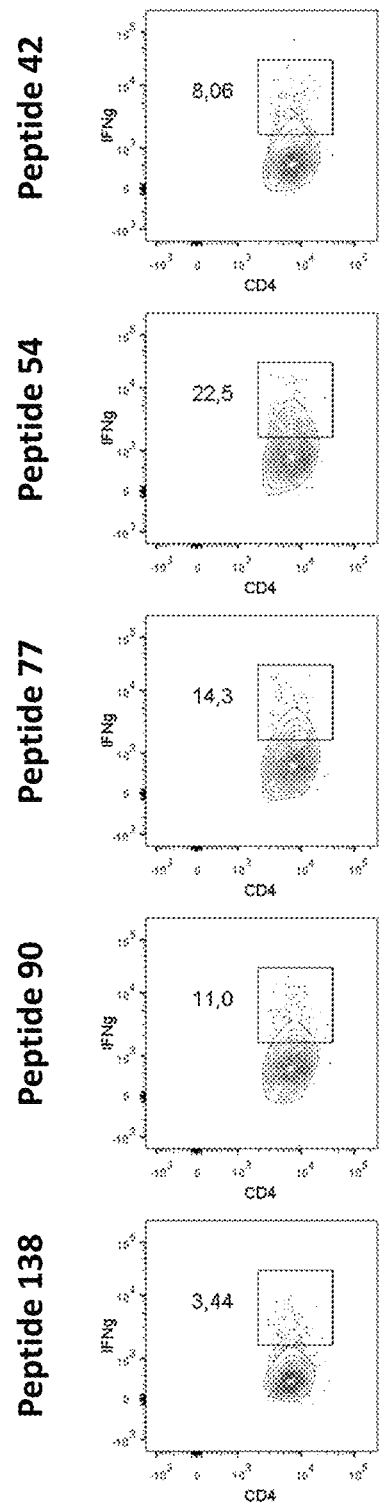
Figure 3C:
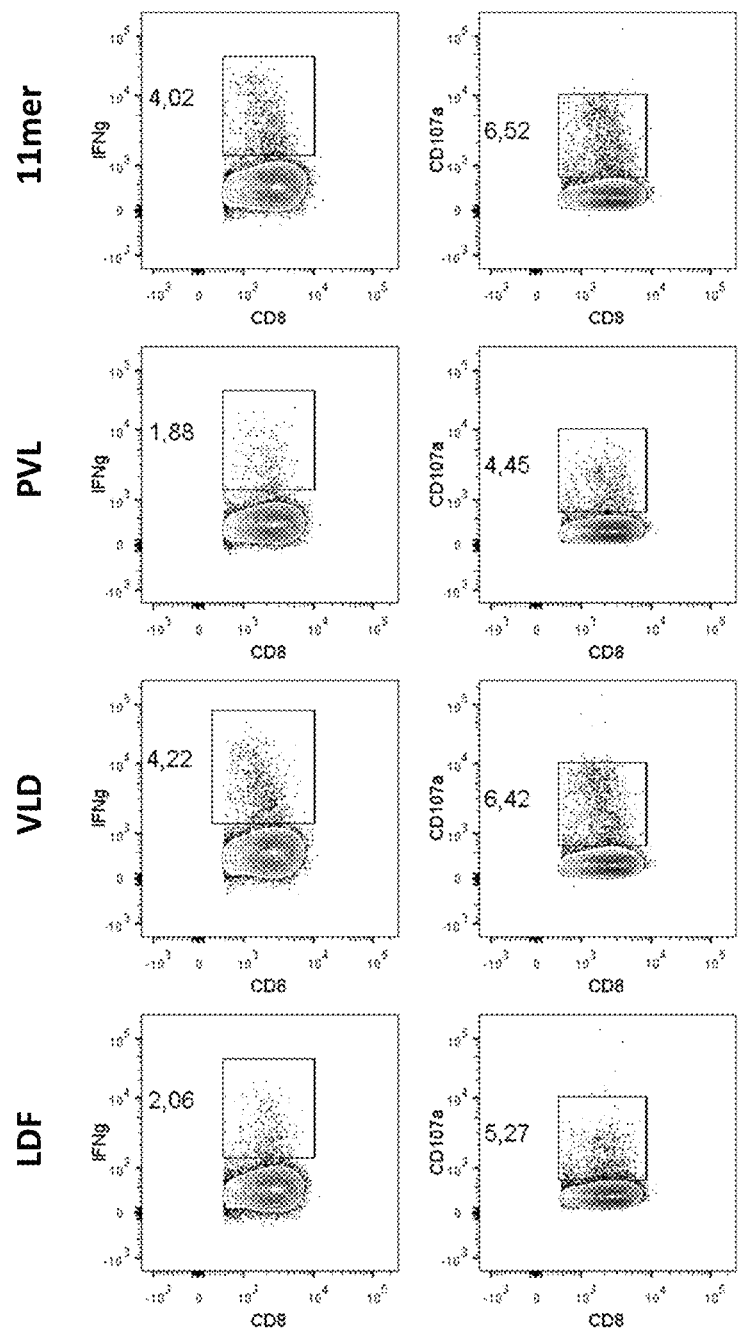
Figure 3D:
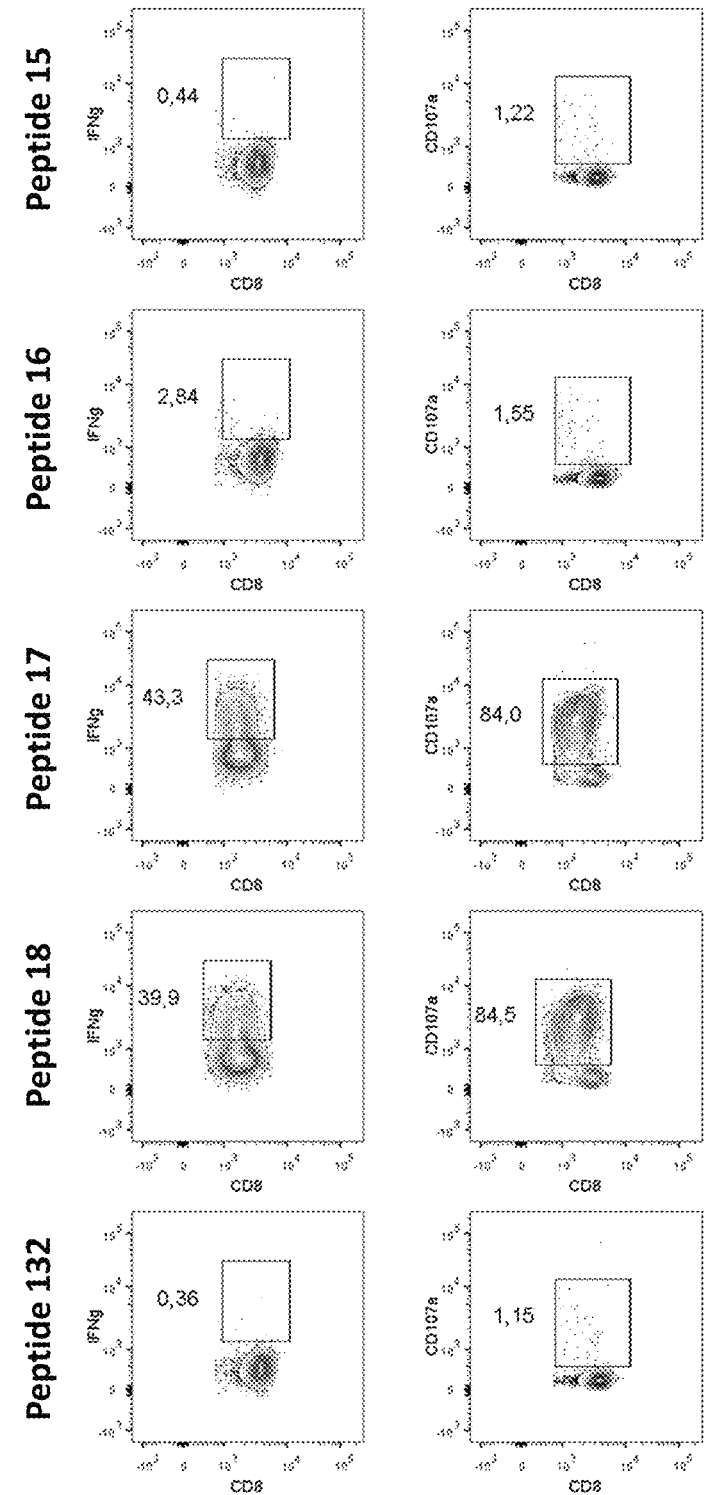
Figure 3E:
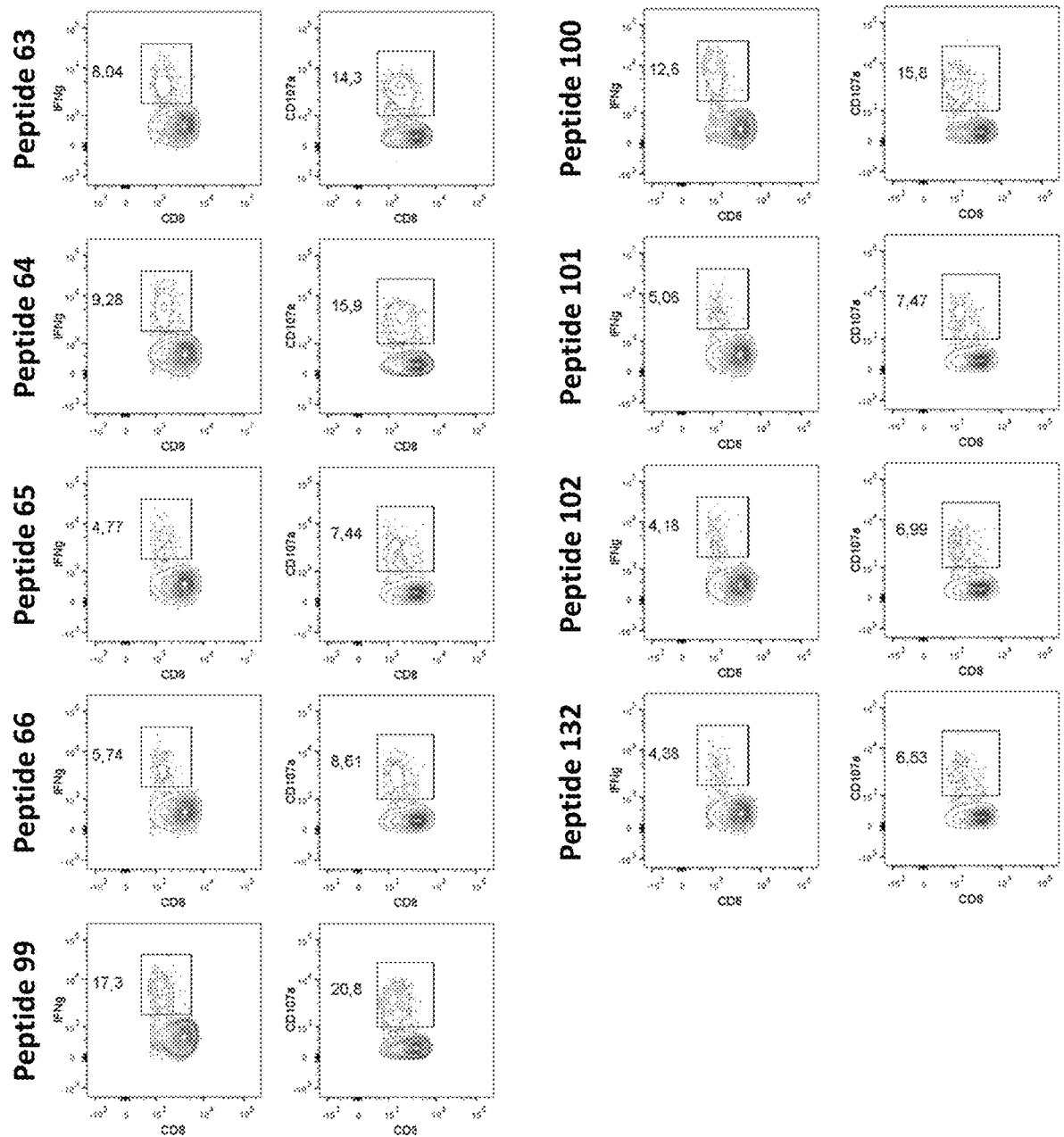
Figure 3F:
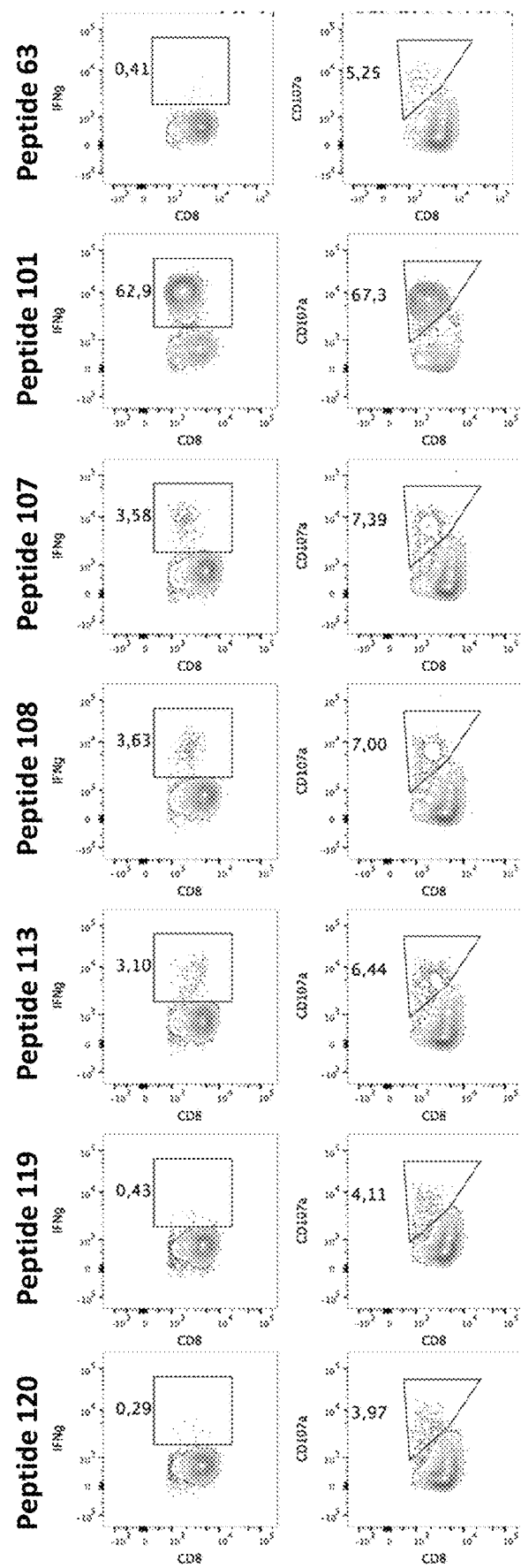
Figure 3G:
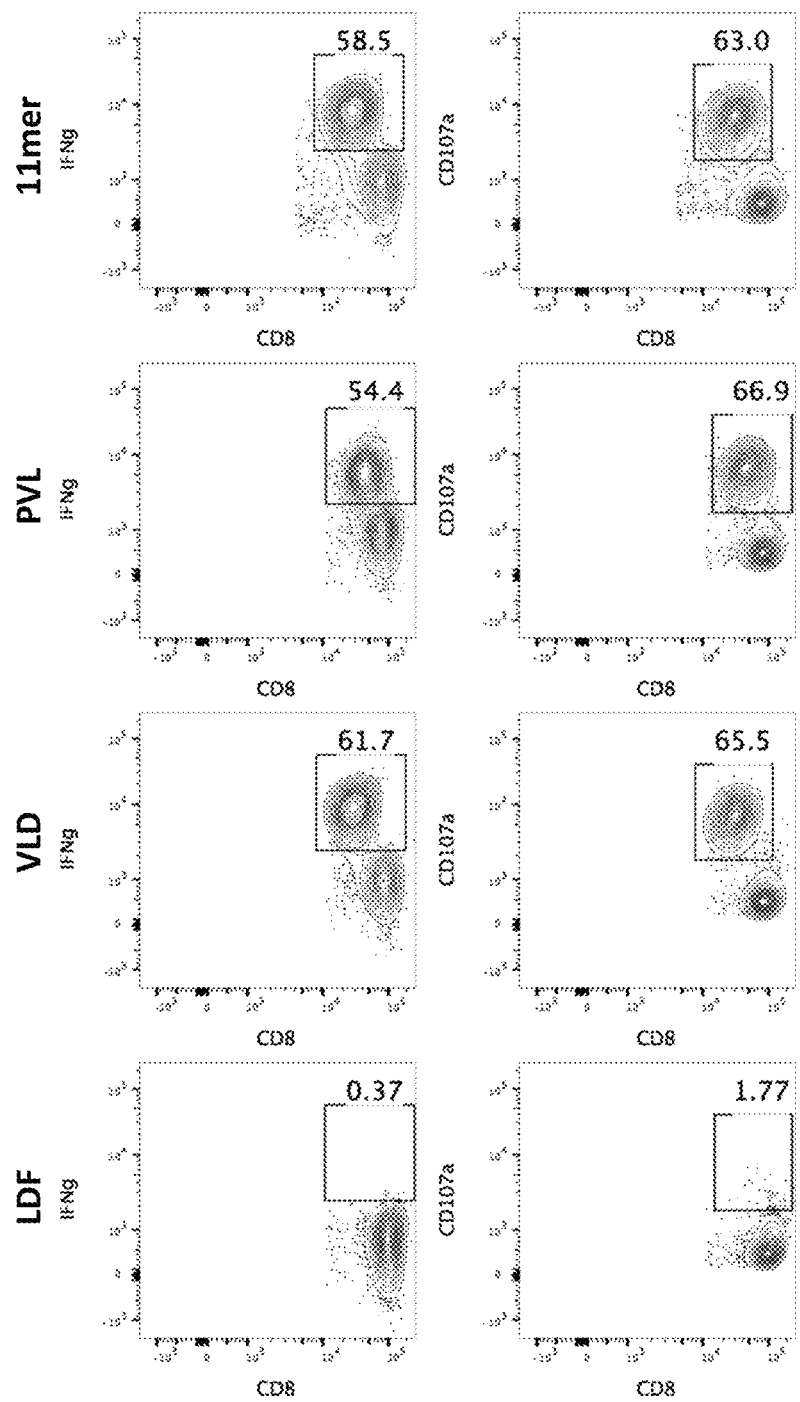
Figure 3H:
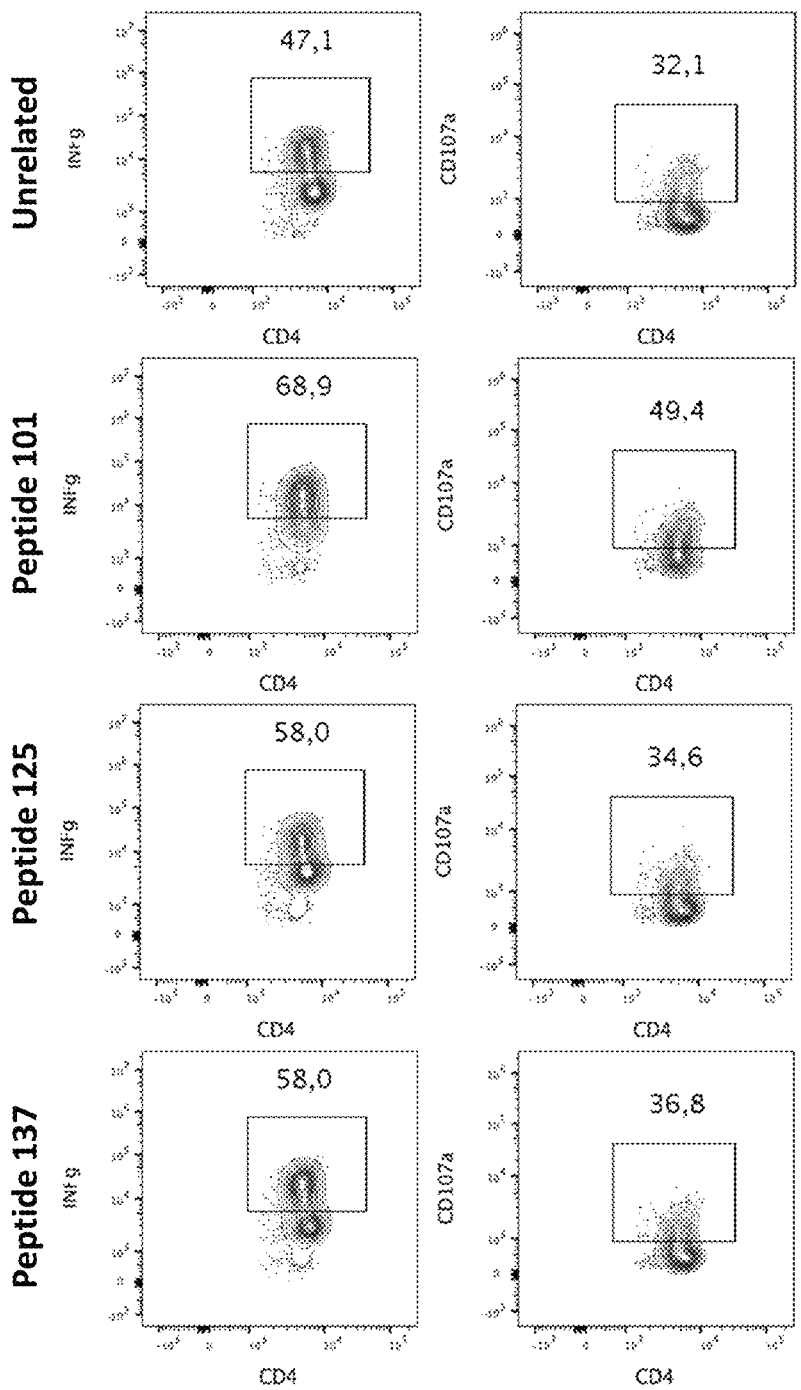

In order to validate the WT1 immunogenic peptides, T-cells expanded from each HD were co-cultured for 6 hours in the presence of APCs loaded with the peptides identified after deconvolution of the mapping grid and with at least one unrelated peptide as negative control. Additionally, negative (T cells unstimulated) and positive (T cells cultured in the presence of PMA and Ionomycin) controls were included in the experimental setting (not shown). Dot plots show for each HD the results of the intracellular staining for IFNγ and/or surface CD107a. Enrichment of CD107a and/or IFNγ positive cells was respectively observed for T-cells co-cultured with peptides 40 and 41 for HD1 (FIG. 3A) and not for peptide 42 and 43 (unrelated peptides); peptides 54, 77, 90 for HD2 (FIG. 3B) and not for peptide 42 and 138 (unrelated peptides); peptide VLDFAPPGA (SEQ ID NO: 157, VLD, which is a nonamer of the peptide represented by SEQ ID NO: 117 (referred to as "11 mer" in FIG. 3c)) for HD3 (FIG. 3C) and low response with peptides PVLDFAPPG (SEQ ID NO: 158, PVL, which is another nonamer of the peptide represented by SEQ ID NO: 117) and LDFAPPGAS (SEQ ID NO: 159, LDF, which is a nonamer of the peptide represented by SEQ ID NO: 116, previously described as an immunogenic peptide (Doubrovina, E. et al. (2012) Blood 120: 1633-1646)); peptides 17, 18, 99, 100 for HD4 (FIG. 3D, FIG. 3E) and not for the unrelated peptides (15, 16, 63-66, 101, 102 and 132); peptide 101 for HD5 (FIG. 3F) and not for the unrelated peptides (63, 107, 108, 113, 119 and 120); peptide VLDFAPPGA (SEQ ID NO: 157, VLD, which is a nonamer of the peptide represented by SEQ ID NO: 117 (referred to as "11 mer" in FIG. 3c)) for HD6 (FIG. 3G) and peptide PVLDFAPPG (SEQ ID NO: 158, PVL, which is another nonamer of the peptide represented by SEQ ID NO: 117) and not for peptide LDFAPPGAS (SEQ ID NO: 159, LDF, which is a nonamer of the peptide represented by SEQ ID NO: 116, previously described as an immunogenic peptide (Doubrovina, E. et al. (2012) Blood 120: 1633-1646)); peptides 101, 125, 137 for HD9 (FIG. 3H); peptide VLDFAPPGA (SEQ ID NO: 157, VLD, which is a nonamer of the peptide represented by SEQ ID NO: 117 (referred to as "11 mer" in FIG. 3c)) for HD10 (FIG. 3I) and not for the unrelated peptide. For HD7 and HD8, due to a reduced fitness of T cells, it was not possible to perform functional tests to verify the peptide predicted by the deconvolution of the mapping grid, i.e. peptides 40, 41, 91, 92 for HD7 and peptide 24 for HD8.

Figure 3I:
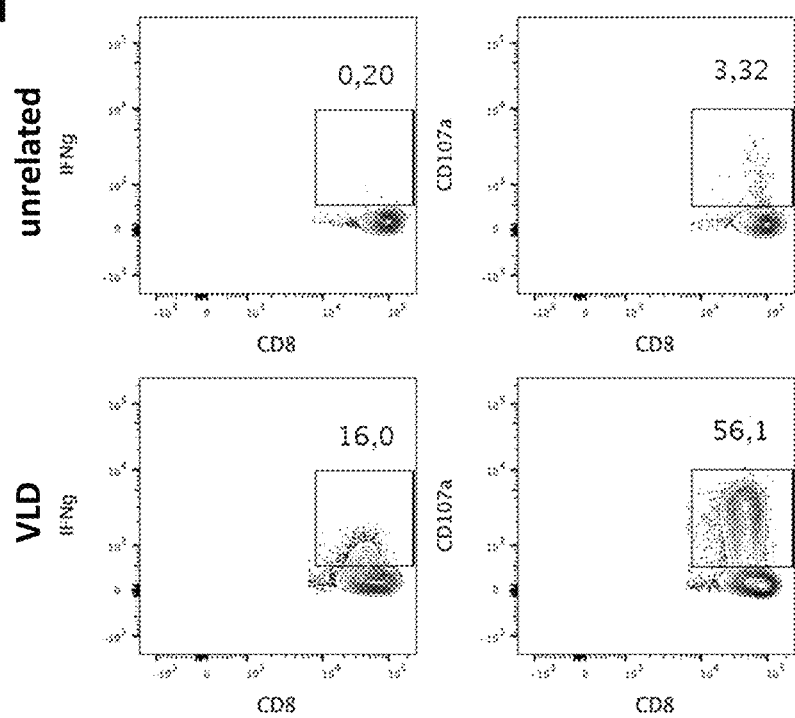
Figure 3J:
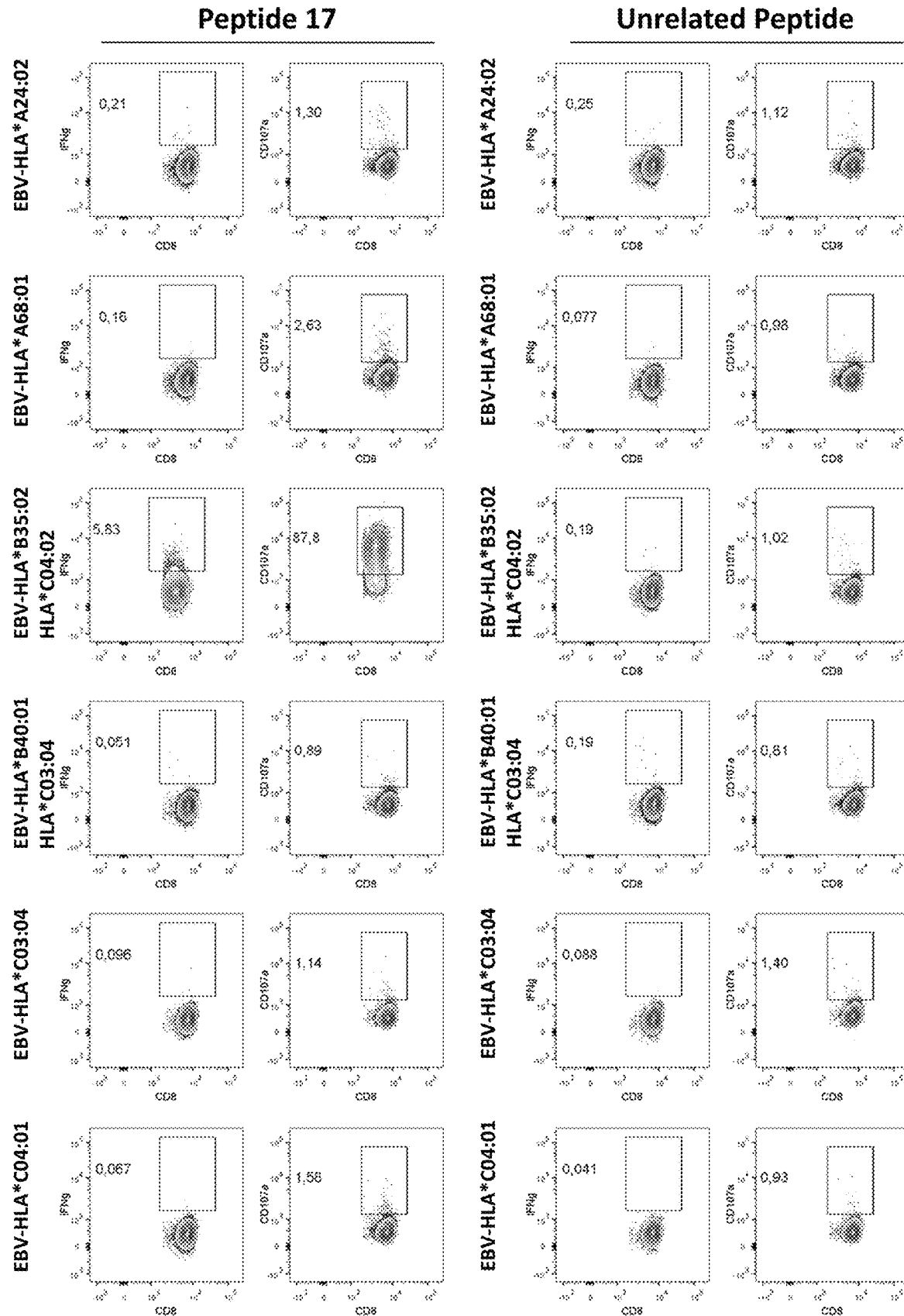
Figure 3K:
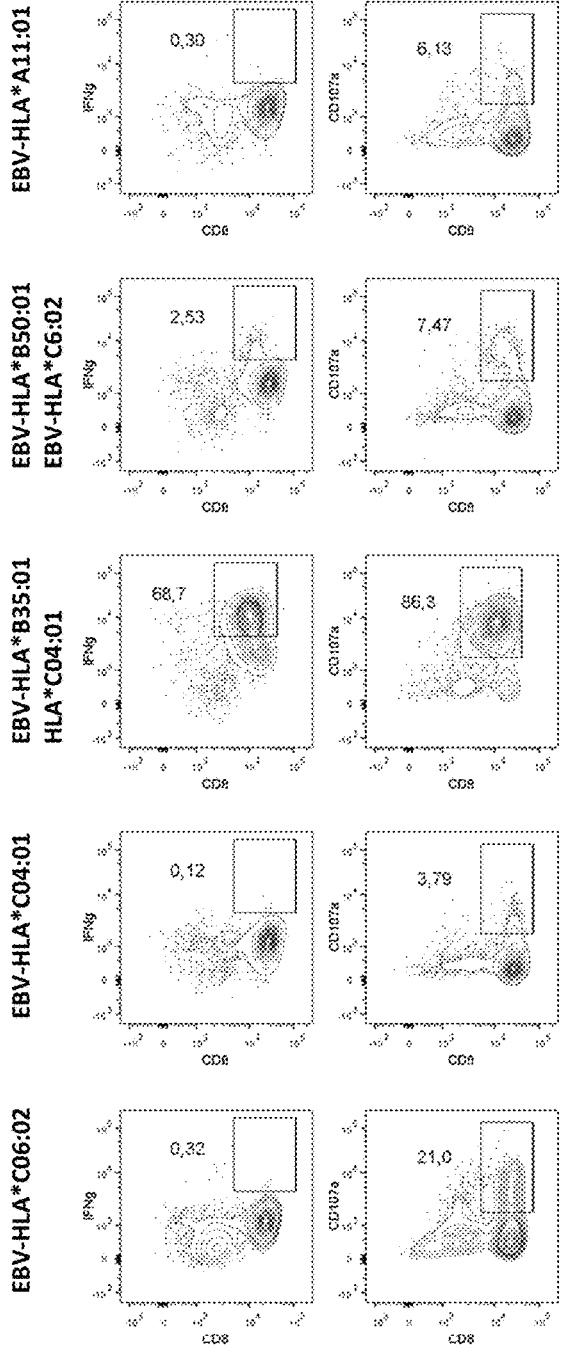
Figure 3K:
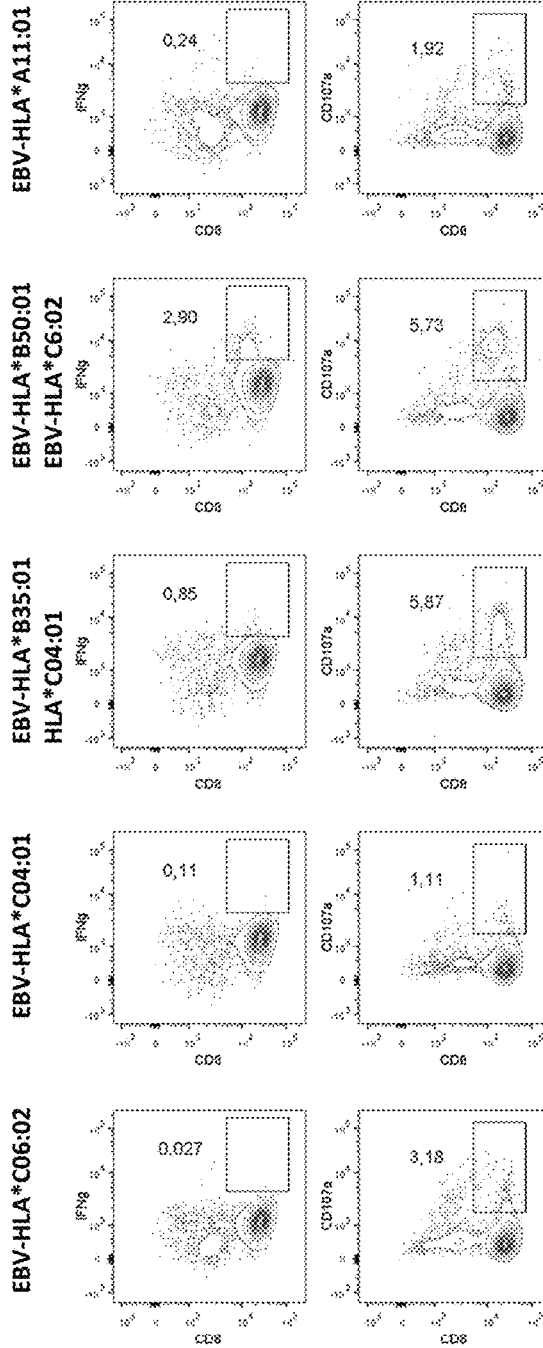
Figure 3L:
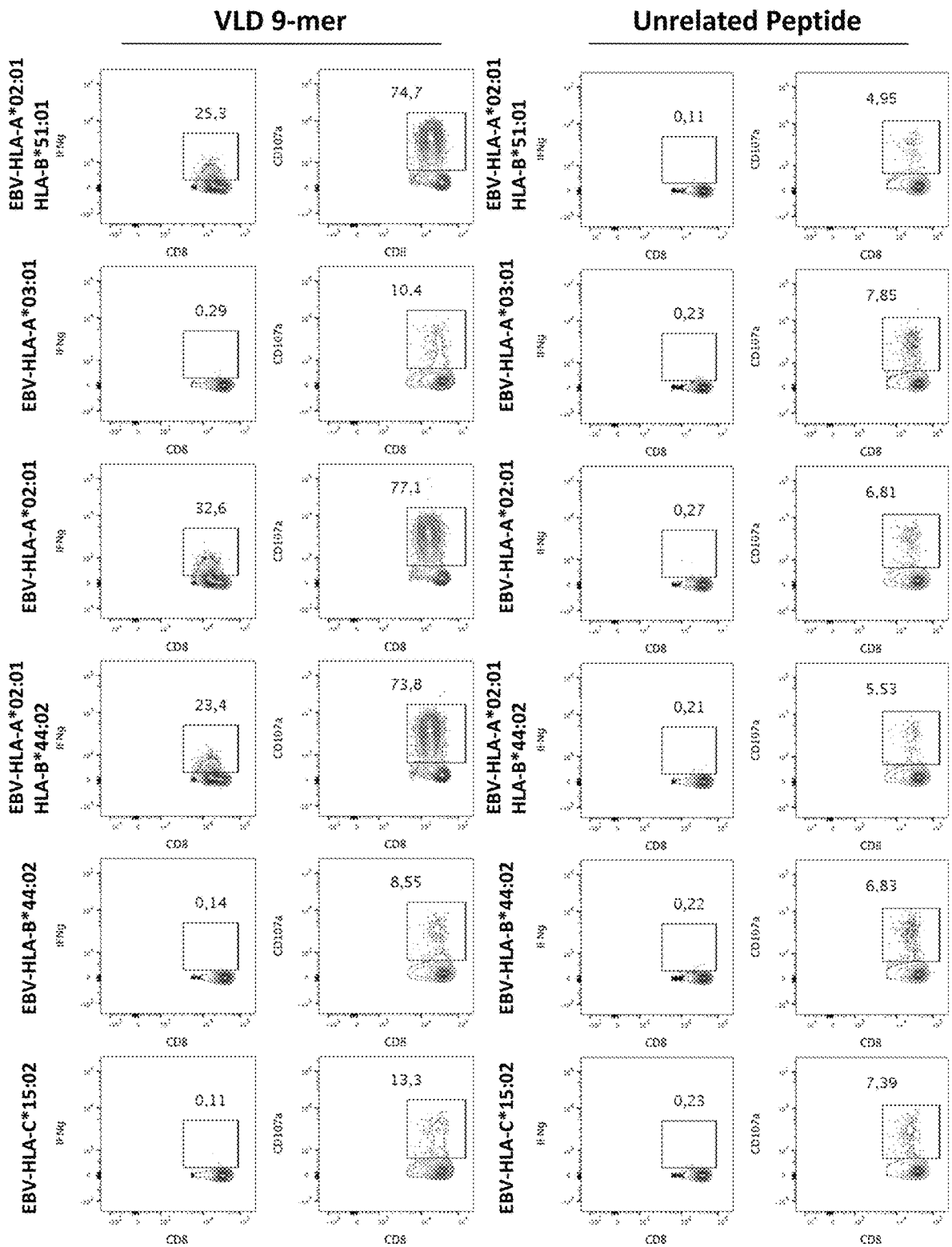

In order to determine the HLA restriction of the WT1 epitopes identified for HD4, HD5 and HD10 T-cells, donor DNA was sequenced to determine the HLA typing. Afterwards, WT1-specific T-cells were co-cultured with different antigen presenting EBV-BLCL cell lines, each one harboring a specific HLA allele of interest that was identified by sequencing of the HD4, HD5 or HD10 DNA. The EBV-BLCL cells were pulsed with peptide 17 for HD4, peptide 101 for HD5 and peptide VLDFAPPGA (SEQ ID NO: 157) or with an unrelated control peptide. After co-culture for 6 hours, we observed a substantial response to WT1 by the WT1-specific T-cells that had been co-cultured with EBV-BLCL cells expressing the HLA-B*3502 allele and pulsed with peptide 17 for HD4 (FIG. 3J), EBV-BLCL cells expressing the HLA-B*3501 allele and pulsed with peptide 101 for HD5 (FIG. 3K) and EBV-BLCL cells expressing the HLA-A*0201 allele and pulsed with peptide VLDFAPPGA (SEQ ID NO: 157) for HD10 (FIG. 3L). (FIG. 3M) Table showing the peptides recognized by T-cells expanded from HD1-HD10. For HD3, HD6 and HD10, the specific nonamer overlapping peptides 40 and 41 and eliciting an immune response is shown. Wilms' Tumor 1; APC, antigen-presenting cells; PMA, 2; Phorbol 12-myristate 13-acetate; IFNγ, interferon-γ; S, stimulation.

Figure 4A:
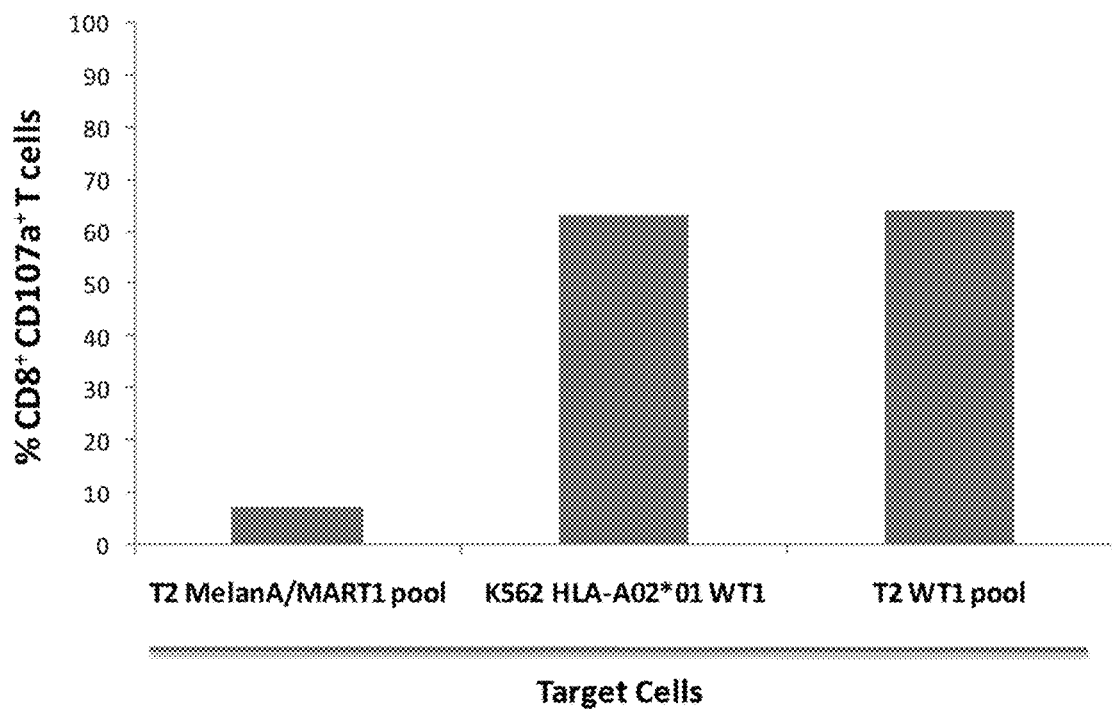
Figure 4B:
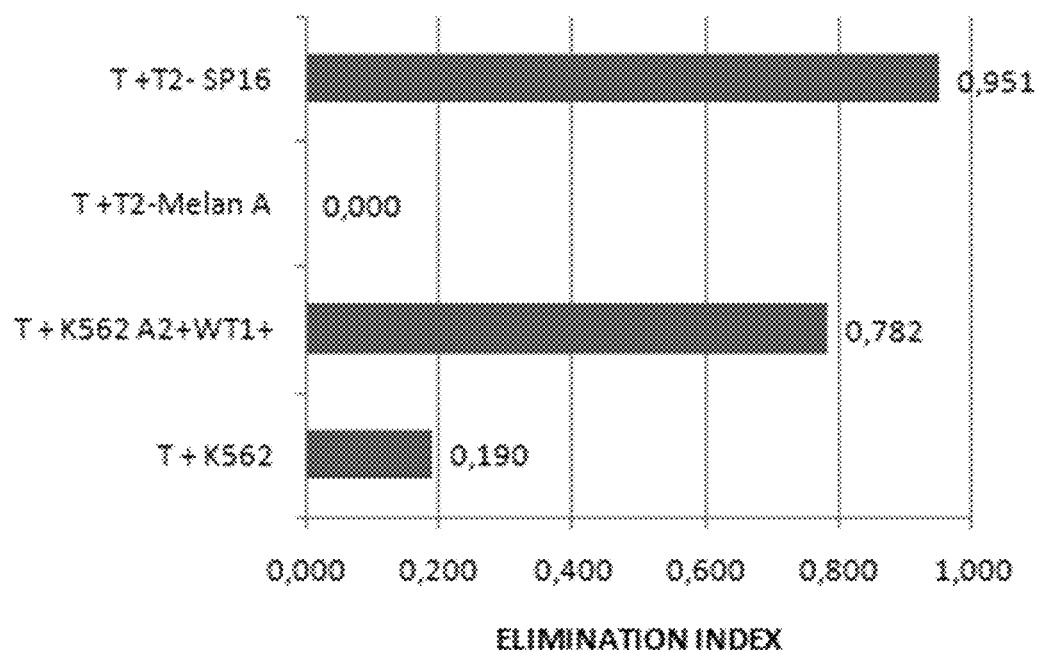
Figure 4C:
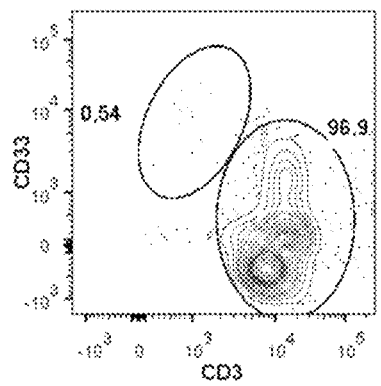
Figure 4C:
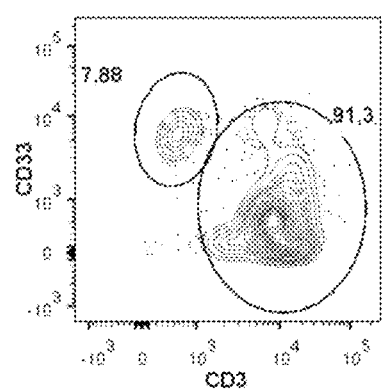

FIGS. 4A-4C. Graphs and plots showing that expanded T-cells of HD1, HD3 and HD4 recognize a naturally processed WT1 epitope (FIG. 4A) Graph depicting CD107 expression by CD8+ T-cells expanded from HD1 following co-culture with T2 cells pulsed with WT1 pool, K562 cells genetically modified to express the HLA-A*0201 allele and to overexpress the WT1 protein, or T2 cells pulsed with the non-specific control MelanA/MART1 pool as a negative control.

(FIG. 4B) Graph depicting the results of experiments to determine the ability of HD3 expanded T-cells to target WT1-expressing cells. The results are represented as an elimination index, which is calculated as the total number of target cells still present after co-culture with the WT1-specific T-cells divided by the total number of target cells alone. HD3 T-cells were co-cultured with T2 cells pulsed with the subpool 16 (SP16) containing the immunogenic peptide eliciting the immune response; T2 cells pulsed with the MelanA/MART1 pool (Melan A) as negative control; K562 cells either wild type (K562) or genetically modified in order to express both the HLA-A*0201 allele and to overexpress the WT1 protein (K562 A2+WT1+).

(FIG. 4C) Plots depicting the results of experiments to determine the ability of WT1-specific T-cells from HD4 to eliminate target cells. HD4 T-cells were co-cultured with primary CD33+ blasts harvested from a HLA-B*3502 patient at a ratio of 10:1 or, as control, with leukemic cells from a patient not harboring the HLA-B*3502 allele. After 3 days of co-culture, results indicate a nearly complete clearance of the CD33+ HLA-B*3502 blasts when seeded with WT1-specific T-cells (CD3+ cells). E, effector; T, target.

Figure 5:
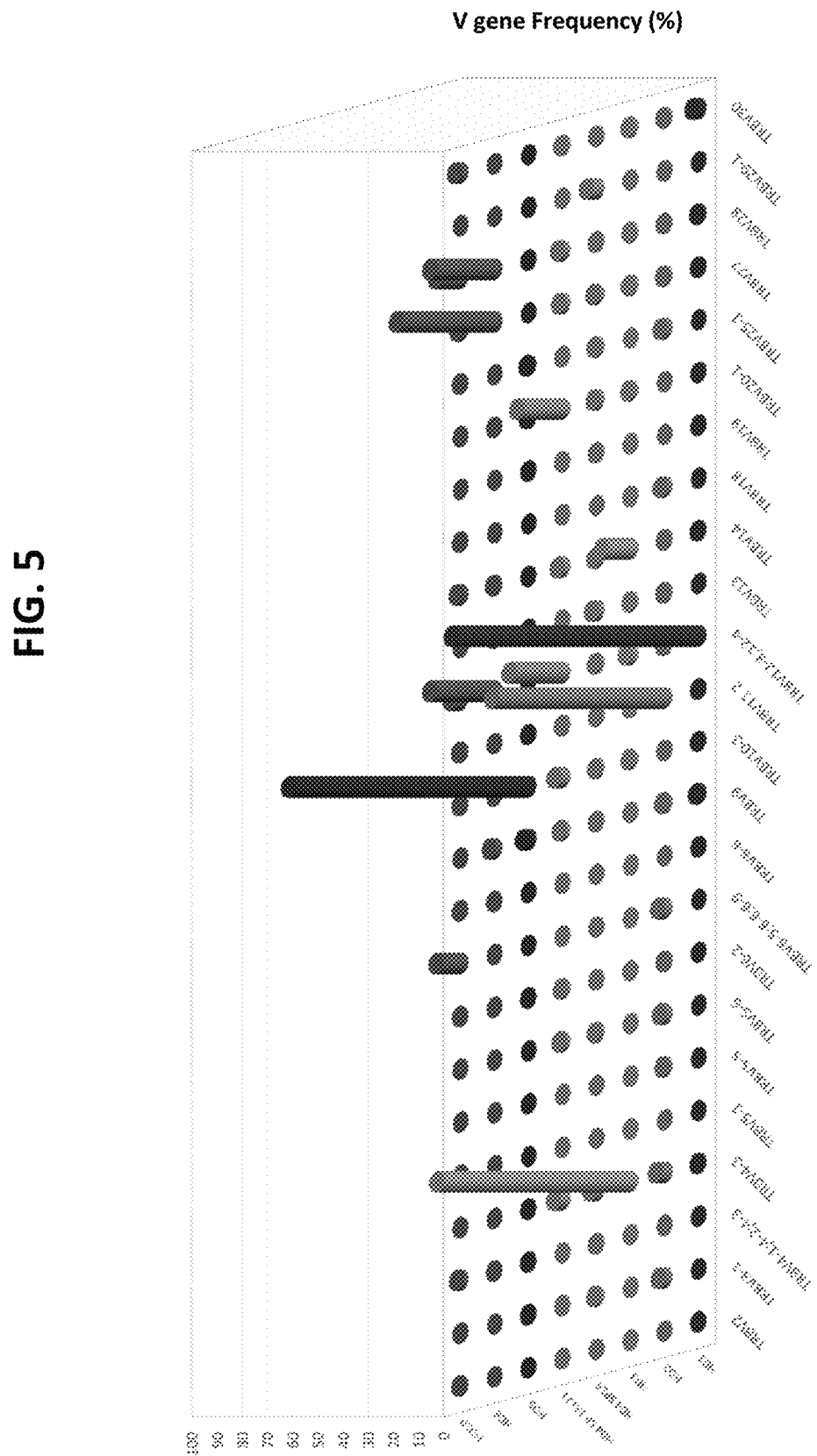

FIG. 5. Graph showing results of Vβ profiling of WT1-specific T-cells

WT1-specific T-cells generated from the different HDs after several stimulations with the WT1 pool were stained with the Vβ Immunoprofiling kit in order to determine the clonality of the population. In particular, the expression of the variable (V) genes of the β-chain was determined by FACS analysis. Results indicate the expression of a highly dominant Vβ gene in HD1 (TRBV12-3; 12-4), HD2 (TRBV11-2), HD3 (TRBV4-3), HD5 (TRBV20-1) whereas for HD4, HD6, HD10 a clear enrichment of a defined Vβ was not detected. HD4 SP14 indicates T cells stimulated with subpool 14 which contains peptides 17-18 eliciting the highest immune response; HD4 SP18+21 indicates T cells stimulated with subpools 18 and 21 which contain peptides 63-64-65-66 and 99-100-101-102, respectively, eliciting a minimal immune response as shown in FIG. 3. For HD7, HD8 and HD9, it was not possible to perform the Vβ Immunoprofiling analysis due to a reduced cell fitness.

Figure 6A:
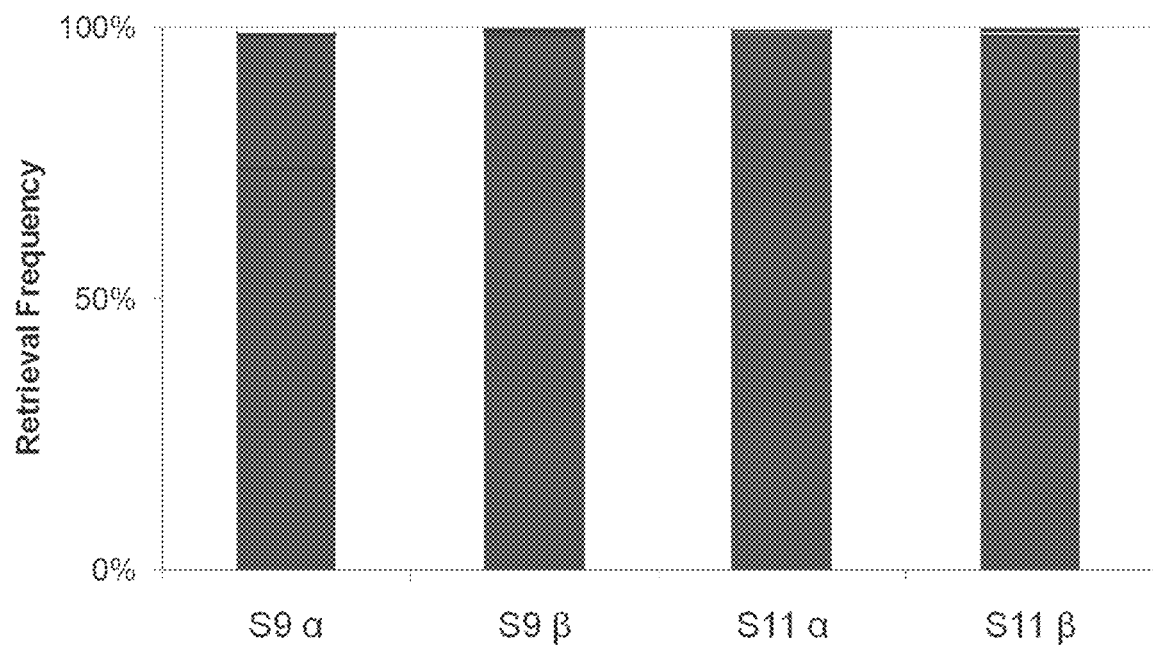
Figure 6B:
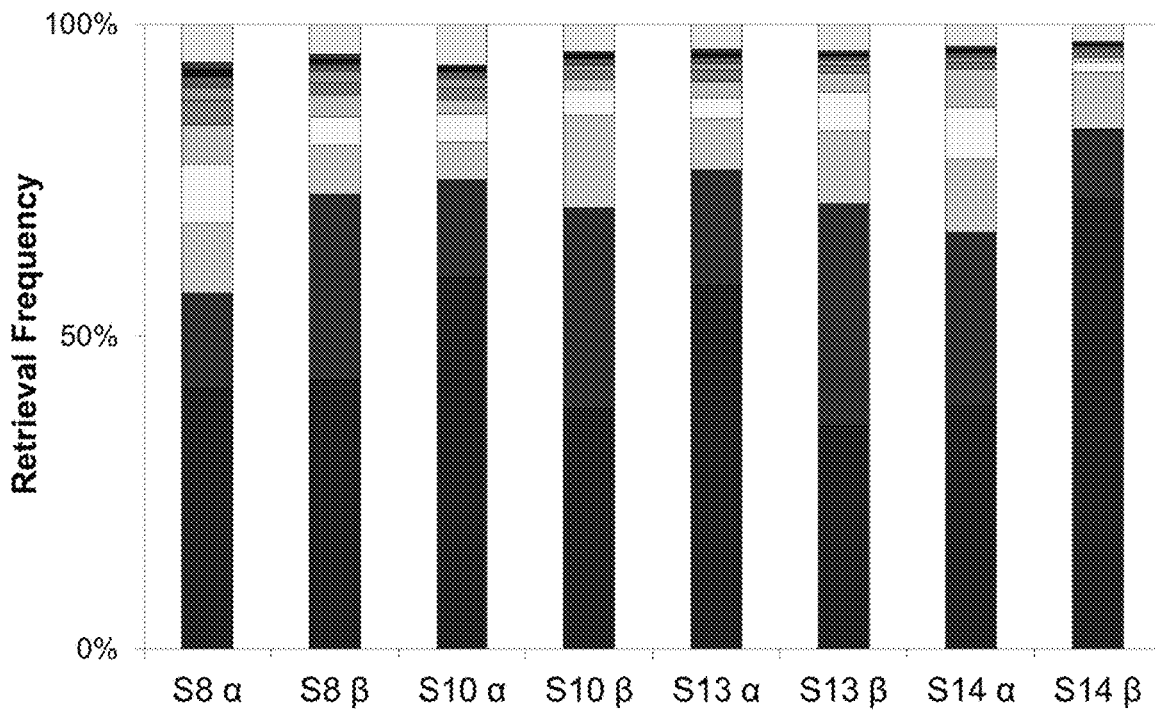
Figure 6C:
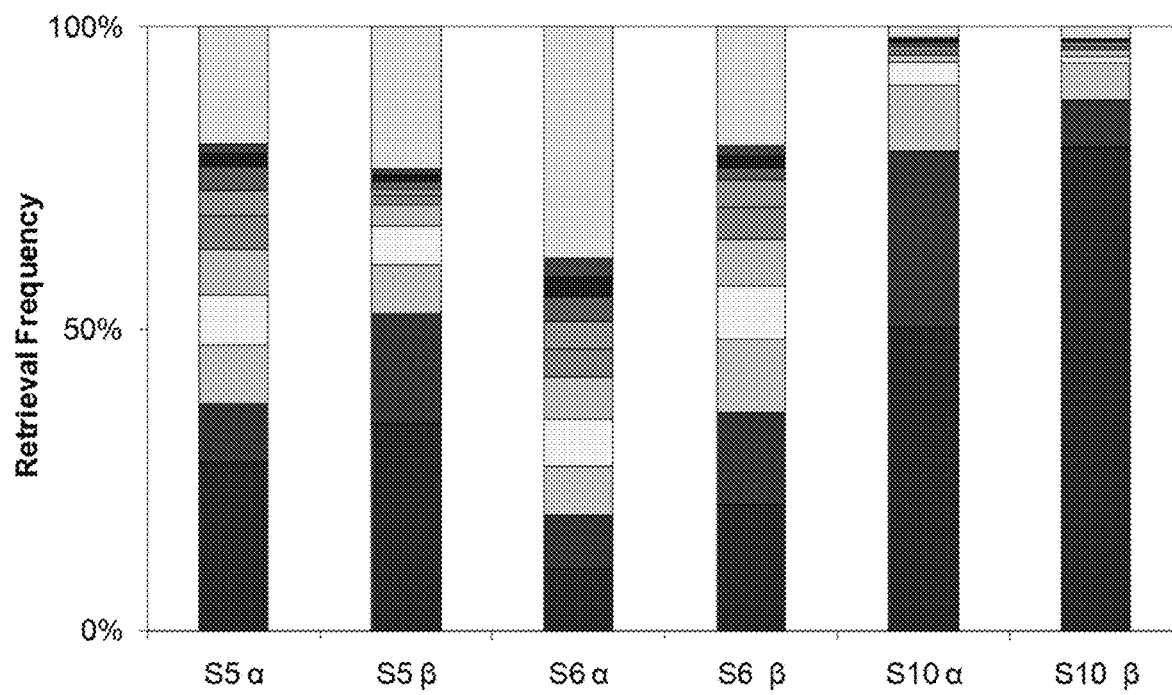
Figure 6D:
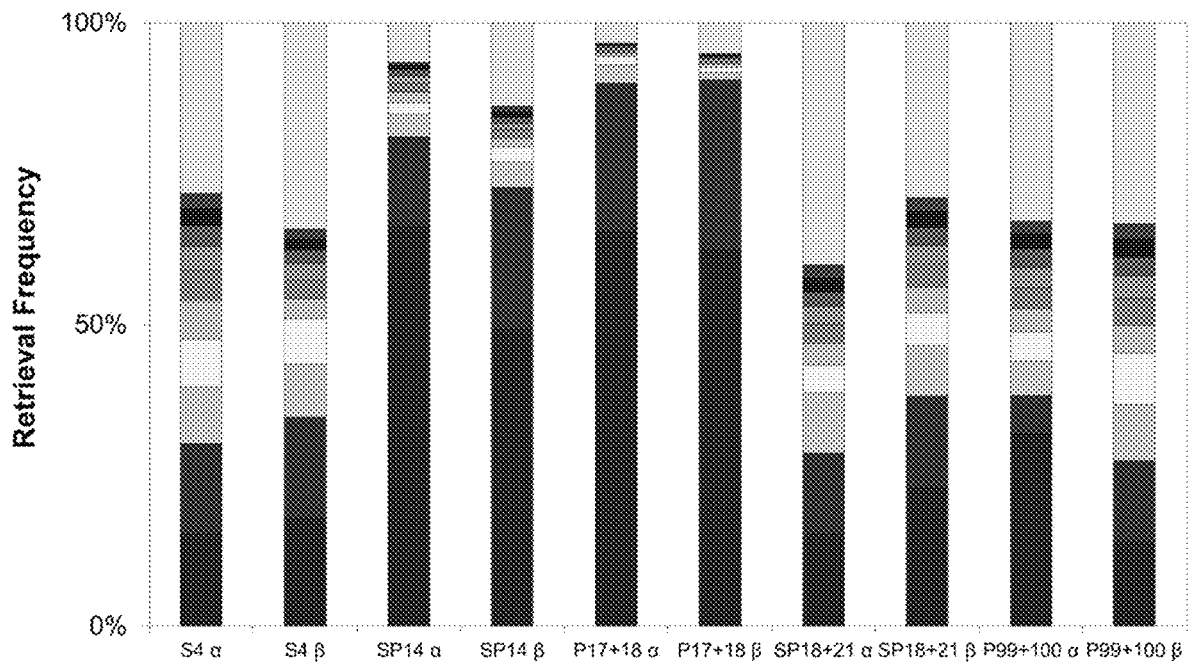
Figure 6E:
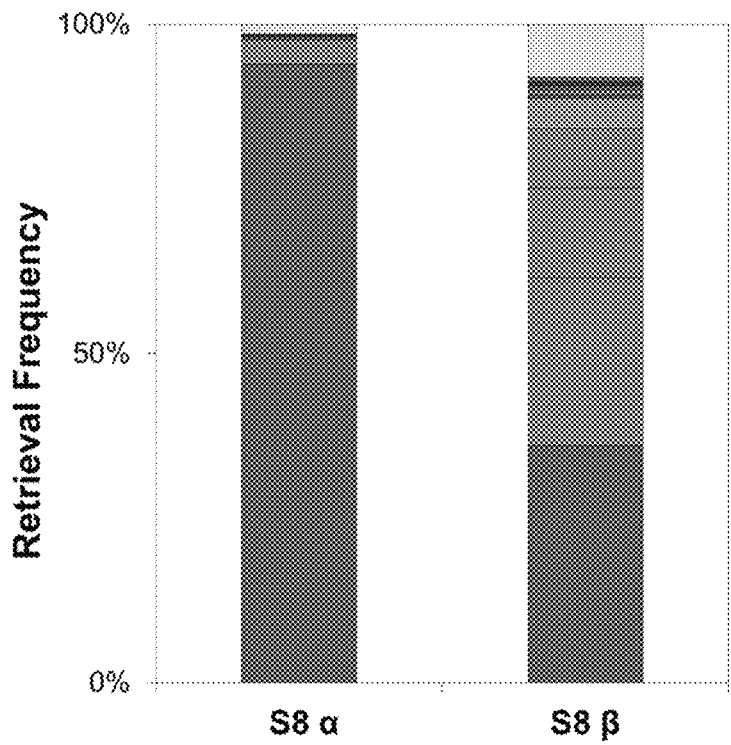
Figure 6F:
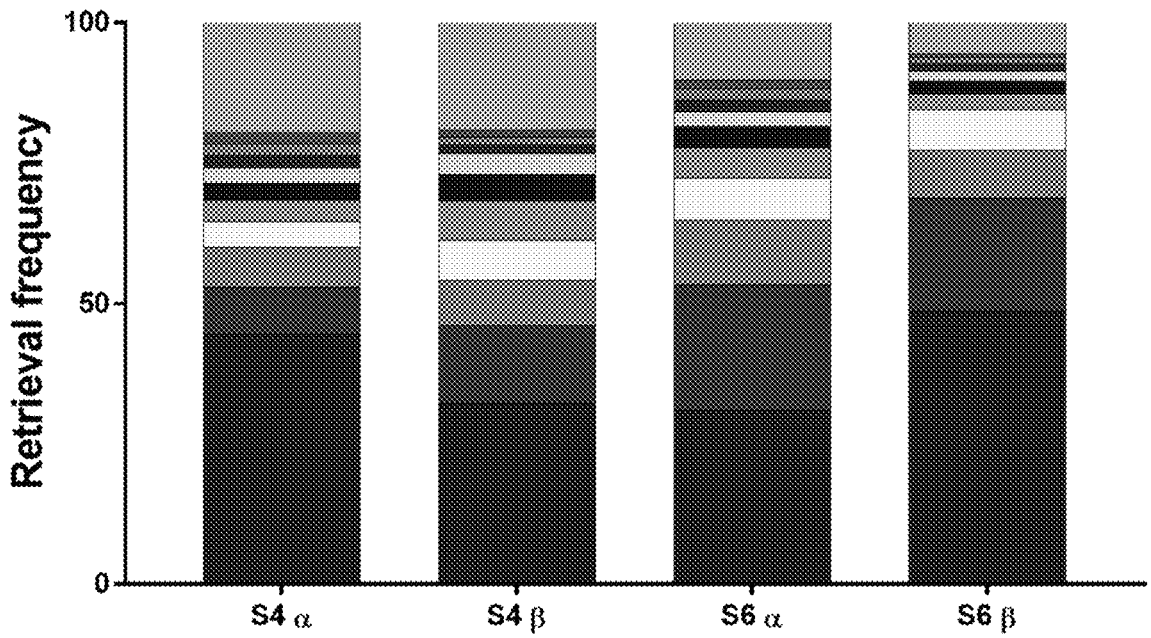
Figure 6H:
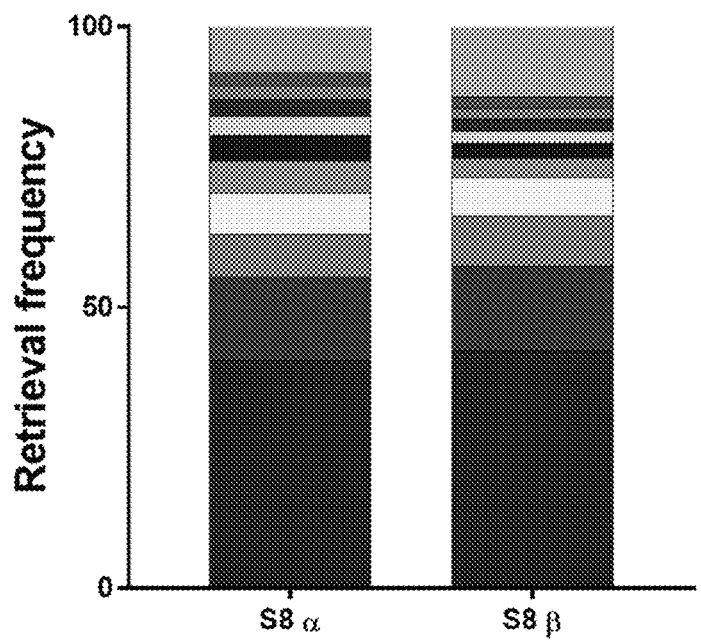
Figure 6I:
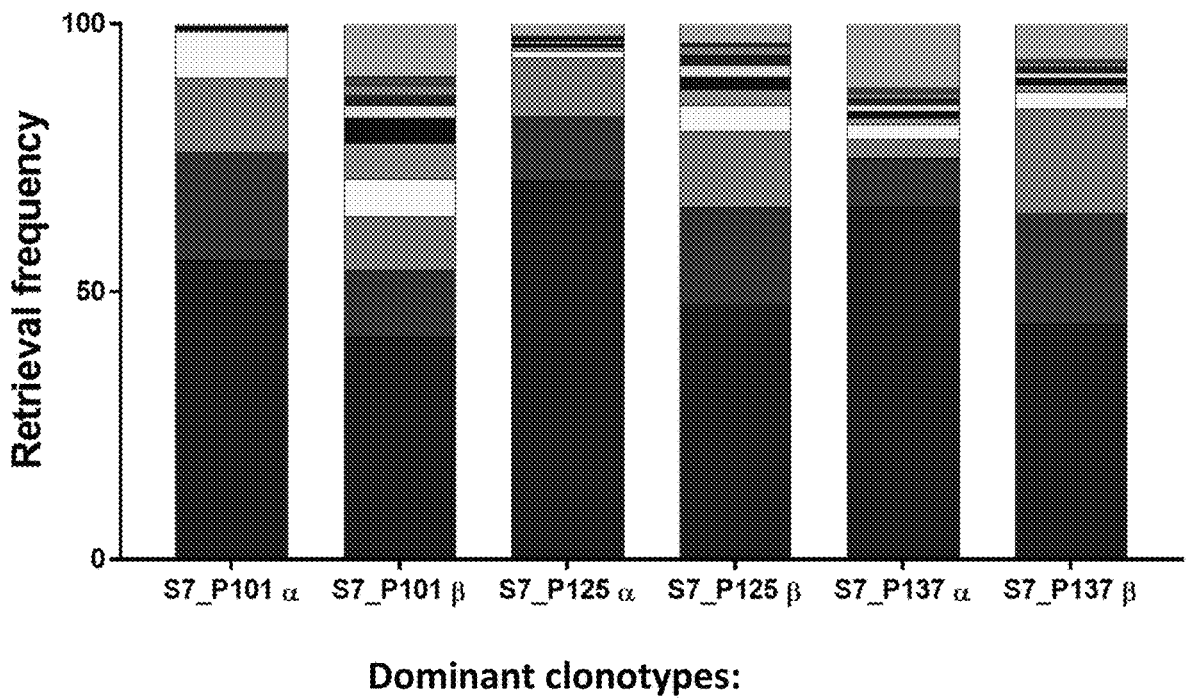
Figure 6J:
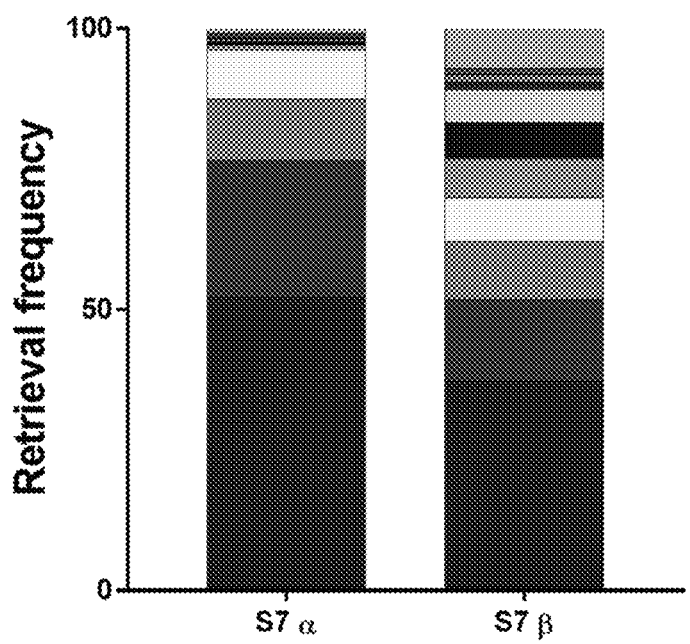

FIGS. 6A-6J. Graphs showing results of TCR sequencing of enriched WT1-specific T-cells over time T-cells generated from each healthy donor included in the experimental setting were characterized by TCR αβ sequencing after several stimulations with the WT1 pool. Sequencing results indicated the presence of predominant clonotypes for HD1 (FIG. 6A), HD2 (FIG. 6B) and HD3 (FIG. 6C), HD4 (FIG. 6D), HD5 (FIG. 6E), HD6 (FIG. 6F), HD7 (FIG. 6G), HD8 (FIG. 6H), HD9 (FIG. 6I), HD10 (FIG. 6J). Bar charts depict the ten most predominant CDR3 amino acid sequences identified at each time point (e.g. S9 corresponds to the sequencing results obtained following the 9$^{th}$ round of stimulation). For each bar, starting from the x-axis, the bottom segment represents the most predominant CDR sequence. The next nine most predominant sequences are stacked above the bottom segment and are ordered by decreasing frequency going upwards. The remaining sequences are grouped together in top segment. WT1, Wilms Tumor 1; CDR3, complementarity determining region 3; S, stimulation.

Figure 7A:
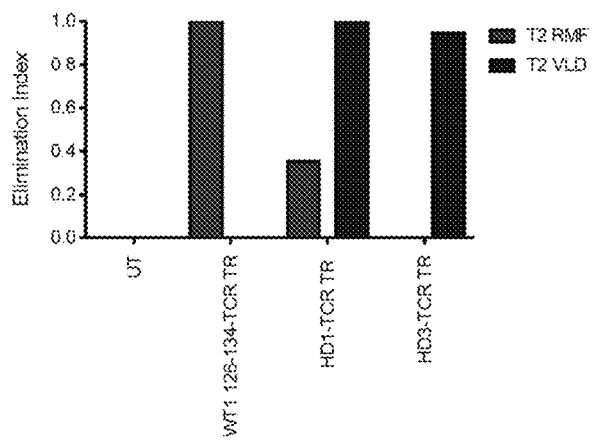
Figure 7B:
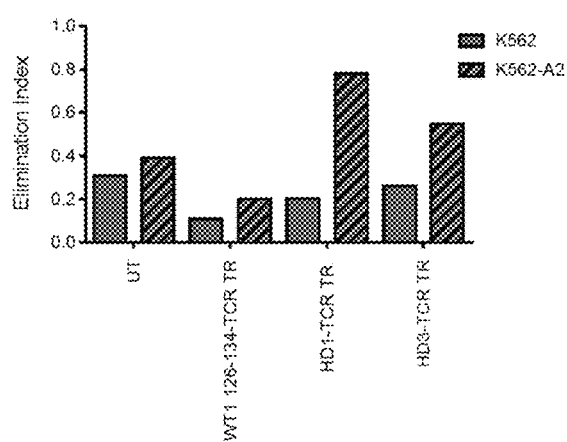
Figure 7C:
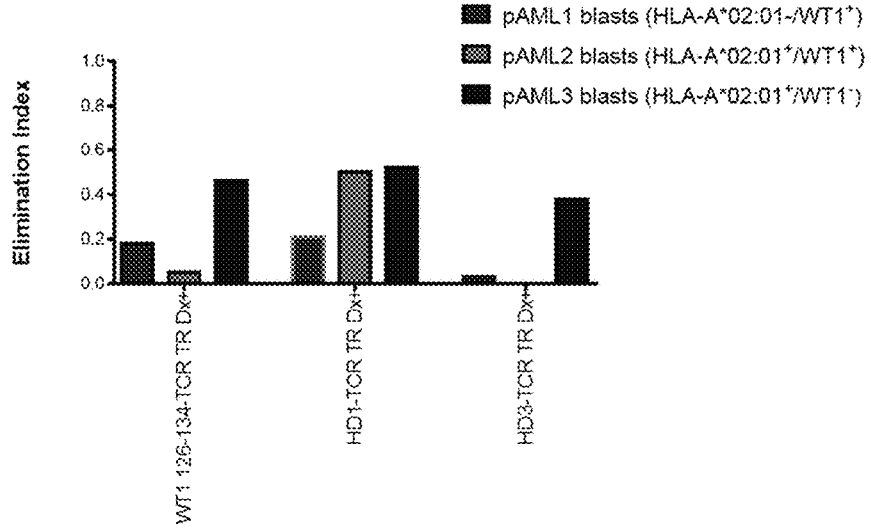

FIGS. 7A-7C. Functional activity of genetically-modified T lymphocytes.

T cells isolated from PBMCs of healthy individuals were transduced with a bidirectional lentiviral vector encoding for the α and the β chain of TCRs isolated from HD1 and HD3. As control we transduced T cells with a previously published TCR recognizing the WT1 126-134 (RMFPNAPYL; SEQ ID NO: 255) peptide when presented by the HLA-A*0201 allele. Transfer (TR) T lymphocytes were co-cultured for 3 days with (a) T2 cells either pulsed or not with the WT1 126-134 peptide or with the VLDFAPPGA (SEQ ID NO: 157) peptide (effector:target ratio=1:1); (b) K562 cells either wild type (K562) or genetically modified in order to express the HLA-A*0201 allele (effector:target ratio=1:1); (c) 3 different primary AML blasts selected according to the expression of the HLA-A*0201 allele and of the WT1 antigen (effector:target ratio=5:1). For the co-culture with T2 and K562 cell lines, we included untransduced T cells as control. Results indicated the ability of each TCR in recognizing the target peptide when presented by the HLA-A*0201 allele (FIG. 7a) and the greater potential of HD1 TCR-transduced T cells in mediating a specific and near complete elimination of K562 cells harbouring the HLA*A0201 allele compared to HD3-TR T cells. Of note, no substantial killing of target cells was observed in the co-culture of K562 HLA*A0201 cells with WT1 126-134 TR T cells (FIG. 7b). These results were further confirmed by the outcome of the co-culture experiment performed using as target cells primary AML blasts derived from 3 different AML patients (pAML1 blasts: WT1-/HLA-A*0201+; pAML2 and pAML3 blasts: WT1+/HLA-A*0201+). In this experimental setting, each individual T cell population was sorted with specific dextramers, before co-culture with targets, to enrich the purity of effector cells. We observed a greater elimination of both pAML blasts harbouring the HLA-A*0201 allele upon co-culture with HD1 TR T cells, whereas only blasts from pAML3 were recognized by HD3 T and WT1 126-134 T cells. UT, untransduced, pAML, primary acute myeloid leukemia; TR, transfer; Dx, dextramer.

DETAILED DESCRIPTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

T-Cell Receptor

During antigen processing, antigens are degraded inside cells and then carried to the cell surface by major histocompatibility complex (MHC) molecules. T-cells are able to recognise this peptide:MHC complex at the surface of the antigen presenting cell. There are two different classes of MHC molecules: MHC I and MHC II, each class delivers peptides from different cellular compartments to the cell surface.

A T cell receptor (TCR) is a molecule which can be found on the surface of T-cells that is responsible for recognizing antigens bound to MHC molecules. The naturally-occurring TCR heterodimer consists of an alpha (α) and beta (β) chain in around 95% of T-cells, whereas around 5% of T-cells have TCRs consisting of gamma (γ) and delta (δ) chains.

Engagement of a TCR with antigen and MHC results in activation of the T lymphocyte on which the TCR is expressed through a series of biochemical events mediated by associated enzymes, co-receptors, and specialized accessory molecules.

Each chain of a natural TCR is a member of the immunoglobulin superfamily and possesses one N-terminal immunoglobulin OM-variable (V) domain, one Ig-constant (C) domain, a transmembrane/cell membrane-spanning region, and a short cytoplasmic tail at the C-terminal end.

The variable domain of both the TCR α chain and β chain have three hypervariable or complementarity determining regions (CDRs). A TCR α chain or β chain, for example, comprises a CDR1, a CDR2, and a CDR3 in amino to carboxy terminal order. In general, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule.

A constant domain of a TCR may consist of short connecting sequences in which a cysteine residue forms a disulfide bond, making a link between the two chains.

An α chain of a TCR of the present invention may have a constant domain encoded by a TRAC gene. An example amino acid sequence of an α chain constant domain encoded by a TRAC gene is a shown below:

(SEQ ID NO: 128)
IQNPDPAVYQLRDSKSSDKSVCLFTDFDSQTNVSQSKDSDVYITDKT

VLDMRSMDFKSNSAVAWSNKSDFACANAFNNSIIPEDTFFPSPESSC

DVKLVEKSFETDTNLNFQNLSVIGFRILLLKVAGFNLLMTLRLWSS

A TCR of the present invention may comprise an α chain comprising the amino acid sequence of SEQ ID NO: 128 or a variant thereof having at least 75%, at least 80%, at least 85%, at least 90%, at least 95%, at least 96%, at least 97%, at least 98%, at least 99% sequence identity thereto, preferably at least 75% sequence identity thereto.

A β chain of a TCR of the present invention may have a constant domain encoded by a TRBC1 or a TRBC2 gene. An example amino acid sequence of a β chain constant domain encoded by a TRBC1 gene is a shown below:

(SEQ ID NO: 129)
DLNKVFPPEVAVFEPSEAEISHTQKATLVCLATGFFPDHVELSWWVN

GKEVHSGVSTDPQPLKEQPALNDSRYCLSSRLRVSATFWQNPRNHFR

CQVQFYGLSENDEWTQDRAKPVTQIVSAEAWGRADCGFTSVSYQQGV

LSATILYEILLGKATLYAVLVSALVLMAMVKRKDF

An example amino acid sequence of a β chain constant domain encoded by a TRBC2 gene is shown below:

(SEQ ID NO: 130)
DLKNVFPPEVAVFEPSEAEISHTQKATLVCLATGFYPDHVELSWWVN

GKEVHSGVSTDPQPLKEQPALNDSRYCLSSRLRVSATFWQNPRNHFR

-continued
CQVQFYGLSENDEWTQDRAKPVTQIVSAEAWGRADCGFTSESYQQGV

LSATILYEILLGKATLYAVLVSALVLMAMVKRKDSRG

A TCR of the present invention may comprise a β chain comprising the amino acid sequence of SEQ ID NO: 129, SEQ ID NO: 130, or variants of SEQ ID NOs: 129 and 130 having at least 75%, at least 80%, at least 85%, at least 90%, at least 95%, at least 96%, at least 97%, at least 98%, at least 99% sequence identity thereto, preferably at least 75% sequence identity thereto.

The TCR of the present invention may have one or more additional cysteine residues in each of the α and β chains such that the TCR may comprise two or more disulphide bonds in the constant domains.

The structure allows the TCR to associate with other molecules like CD3 which possess three distinct chains (γ, δ, and ε) in mammals and the ζ-chain. These accessory molecules have negatively charged transmembrane regions and are vital to propagating the signal from the TCR into the cell. The CD3- and ζ-chains, together with the TCR, form what is known as the T cell receptor complex.

The signal from the T cell complex is enhanced by simultaneous binding of the MHC molecules by a specific co-receptor. For helper T-cells, this co-receptor is CD4 (specific for class II MHC); whereas for cytotoxic T-cells, this co-receptor is CD8 (specific for class I MHC). The co-receptor allows prolonged engagement between the antigen presenting cell and the T cell and recruits essential molecules (e.g., LCK) inside the cell involved in the signalling of the activated T lymphocyte.

Accordingly, as used herein the term "T-cell receptor" (TCR) refers to molecule capable of recognising a peptide when presented by an MHC molecule. The molecule may be a heterodimer of two chains α and β (or optionally γ and δ) or it may be a single chain TCR construct. A TCR of the present invention may be a soluble TCR, e.g. omitting or altering one or more constant domains. A TCR of the present invention may comprise a constant domain.

The present invention also provides an α chain or a β chain from such a T cell receptor.

The TCR of the present invention may be a hybrid TCR comprising sequences derived from more than one species. For example, it has surprisingly been found that murine TCRs are more efficiently expressed in human T-cells than human TCRs. The TCR may therefore comprise a human variable region and murine sequences within a constant region.

A disadvantage of this approach is that the murine constant sequences may trigger an immune response, leading to rejection of the transferred T-cells. However, the conditioning regimens used to prepare patients for adoptive T-cell therapy may result in sufficient immunosuppression to allow the engraftment of T-cells expressing murine sequences.

Complementarity Determining (CDR) Regions

The portion of the TCR that establishes the majority of the contacts with the antigenic peptide bound to the major histocompatibility complex (MHC) is the complementarity determining region 3 (CDR3), which is unique for each T cell clone. The CDR3 region is generated upon somatic rearrangement events occurring in the thymus and involving non-contiguous genes belonging to the variable (V), diversity (D, for β and δ chains) and joining (J) genes. Furthermore, random nucleotides inserted/deleted at the rearranging loci of each TCR chain gene greatly increase diversity of the highly variable CDR3 sequence. Thus, the frequency of a specific CDR3 sequence in a biological sample indicates the abundance of a specific T cell population. The great diversity of the TCR repertoire in healthy human beings provides a wide range protection towards a variety of foreign antigens presented by MHC molecules on the surface of antigen presenting cells. In this regard, it is of note that theoretically up to $10^{15}$ different TCRs can be generated in the thymus.

T-cell receptor diversity is focused on CDR3 and this region is primarily responsible for antigen recognition.

The sequences of the CDR3 regions of the TCR of the present invention may be selected from those set out in Table 1 below. A TCR may comprise CDRs that comprise or consist of a CDR3α and a CDR3β pair described below.

The CDRs may, for example, comprise one, two, or three substitutions, additions or deletions from the given sequence, provided that the TCR retains the capacity to bind a WT1 peptide when presented by an MHC molecule.

As used herein, the term "protein" includes single-chain polypeptide molecules as well as multiple-polypeptide complexes where individual constituent polypeptides are linked by covalent or non-covalent means. As used herein, the term "polypeptide" refers to a polymer in which the monomers are amino acids and are joined together through peptide or disulphide bonds.

Variants, derivatives, analogues, homologues and fragments

In addition to the specific proteins and polynucleotides mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question substantially retains at least one of its endogenous functions. A variant sequence can be obtained by addition, deletion, substitution, modification, replacement and/or variation of at least one residue present in the naturally-occurring protein.

A variant amino acid sequence of the present invention referred to as having up to three amino acid substitutions, additions or deletions may have, for example, one, two or three amino acid substitutions, additions or deletions.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Proteins used in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

A substitution may involve replacement of an amino acid for a similar amino acid (a conservative substitution). A similar amino acid is one which has a side chain moiety with related properties as grouped together, for example as shown below:
 (i) basic side chains: lysine (K), arginine (R), histidine (H);
 (ii) acidic side chains: aspartic acid (D) and glutamic acid (E);
 (iii) uncharged polar side chains: asparagine (N), glutamine (Q), serine (S), threonine (T) and tyrosine (Y); or
 (iv) non-polar side chains: glycine (G), alanine (A), valine (V), leucine (L), isoleucine (I), proline (P), phenylalanine (F), methionine (M), tryptophan (W) and cysteine (C).

Any amino acid changes should maintain the capacity of the TCR to bind WT1 peptide presented by MHC molecules.

Variant sequences may comprise amino acid substitutions, additions, deletions and/or insertions. The variation may be concentrated in one or more regions, such as the constant regions, the linker, or the framework regions of the α or β chains, or they may be spread throughout the TCR molecule.

Conservative substitutions, additions or deletions may be made, for example according to the Table below. Amino acids in the same block in the second column and preferably in the same line in the third column may be substituted for each other:

| ALIPHATIC | Non-polar | GAP |
| | | ILV |
| | Polar—uncharged | CSTM |
| | | NQ |
| | Polar—charged | DE |
| | | KR |
| AROMATIC | | HFWY |

The present invention also encompasses homologous substitution (substitution and replacement are both used herein to mean the interchange of an existing amino acid residue, with an alternative residue), e.g. like-for-like substitution such as basic for basic, acidic for acidic, polar for polar etc. Non-homologous substitution may also occur e.g. from one class of residue to another or alternatively involving the inclusion of unnatural amino acids, such as ornithine.

The term "variant" as used herein may mean an entity having a certain homology with the wild type amino acid sequence or the wild type nucleotide sequence. The term "homology" can be equated with "identity".

A variant sequence may include an amino acid sequence which may be at least 50%, 55%, 65%, 75%, 85% or 90% identical, preferably at least 95%, at least 97%, or at least 99% identical to the subject sequence. Typically, the variants will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

A variant sequence may include a nucleotide sequence which may be at least 40%, 45%, 50%, 55%, 65%, 75%, 85% or 90% identical, preferably at least 95%, at least 97%, or at least 99% identical to the subject sequence. Although homology can also be considered in terms of similarity, in the context of the present invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Identity comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) *Nucleic Acids Res.* 12: 387). Examples of other software that can perform sequence comparisons include, but are not limited to, the BLAST package (see Ausubel et al. (1999) *ibid*—Ch. 18), FASTA (Atschul et al. (1990) *J. Mol. Biol.* 403-410) and the GENEWORKS suite of comparison tools. Both BLAST and FASTA are available for offline and online searching (see Ausubel et al. (1999) *ibid*, pages 7-58 to 7-60). However, for some applications, it is preferred to use the GCG Bestfit program. Another tool, called BLAST 2 Sequences is also available for comparing protein and nucleotide sequences (see FEMS Microbiol. Lett. (1999) 174: 247-50; FEMS Microbiol. Lett. (1999) 177: 187-8).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percentage homology, preferably percentage sequence identity. The software typically does this as part of the sequence comparison and generates a numerical result.

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Major Histocompatability Complex (MHC) Molecules

Typically, TCRs bind to peptides as part of peptide:MHC complex.

The MHC molecule may be an MHC class I or II molecule. The complex may be on the surface of an antigen presenting cell, such as a dendritic cell or a B cell, or any other cell, including cancer cells, or it may be immobilised by, for example, coating on to a bead or plate.

The human leukocyte antigen system (HLA) is the name of the gene complex which encodes major histocompatibility complex (MHC) in humans and includes HLA class I antigens (A, B & C) and HLA class II antigens (DP, DQ, & DR). HLA alleles A, B and C present peptides derived mainly from intracellular proteins, e.g. proteins expressed within the cell. This is of particular relevance since WT1 is an intracellular protein.

During T-cell development in vivo, T-cells undergo a positive selection step to ensure recognition of self MHCs followed by a negative step to remove T-cells that bind too strongly to MHC which present self-antigens. As a consequence, certain T-cells and the TCRs they express will only recognise peptides presented by certain types of MHC molecules—i.e. those encoded by particular HLA alleles. This is known as HLA restriction.

One HLA allele of interest is HLA-A*0201, which is expressed in the vast majority (>50%) of the Caucasian population. Accordingly, TCRs which bind WT1 peptides presented by MHC encoded by HLA-A*0201 (i.e. are HLA-A*0201 restricted) are advantageous since an immunotherapy making use of such TCRs will be suitable for treating a large proportion of the Caucasian population.

Other HLA-A alleles of interest are HLA-A*0101, HLA-A*2402, and HLA-A*0301.

Widely expressed HLA-B alleles of interest are HLA-B*3501, HLA-B*0702 and HLA-B*3502.

A TCR of the present invention may be HLA-A*0201-restricted.

In one aspect, where a TCR of the present invention comprises a CDR3α comprising the amino acid sequence of CGTAWINDYKLSF (SEQ ID NO: 3) or a variant thereof having up to three amino acid substitutions, additions or deletions, and a CDR3β comprising the amino acid sequence of CASRKTGGYSNQPQHF (SEQ ID NO: 8) or a variant thereof having up to three amino acid substitutions, additions or deletions, the TCR is HLA-A*0201 restricted.

In another aspect, where a TCR of the present invention comprises a CDR3α comprising the amino acid sequence of CVVNLLSNQGGKLIF (SEQ ID NO: 36) or a variant thereof having up to three amino acid substitutions, additions or deletions, and a CDR3β comprising the amino acid sequence of CASSQDYLVSNEKLFF (SEQ ID NO: 41) or a variant thereof having up to three amino acid substitutions, additions or deletions, the TCR is HLA-A*0201 restricted.

In another aspect, where a TCR of the present invention comprises a CDR3α comprising the amino acid sequence of CAANNARLMF (SEQ ID NO: 92) or a variant thereof having up to three amino acid substitutions, additions or deletions, and a CDR3β comprising the amino acid sequence of CASSDTRAREQFF (SEQ ID NO: 97) or a variant thereof having up to three amino acid substitutions, additions or deletions, the TCR is HLA-A*0201 restricted.

In another aspect, where a TCR of the present invention comprises a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions, the TCR is HLA-A*0201 restricted.

In another aspect, where a TCR of the present invention comprises a CDR3α comprising the amino acid sequence of CAASGGRDDKIIF (SEQ ID NO: 214) or a variant thereof having up to three amino acid substitutions, additions or deletions, and a CDR3β comprising the amino acid sequence of CASSYSRTESTDTQYF (SEQ ID NO: 219) or a variant thereof having up to three amino acid substitutions, additions or deletions, the TCR is HLA-A*0201 restricted.

In another aspect, where a TCR of the present invention comprises a CDR3α comprising the amino acid sequence of CAANNARLMF (SEQ ID NO: 92) or a variant thereof having up to three amino acid substitutions, additions or deletions, and a CDR3β comprising the amino acid sequence of CASSPGQHGELFF (SEQ ID NO: 271) or a variant thereof having up to three amino acid substitutions, additions or deletions, the TCR is HLA-A*0201 restricted.

In another aspect, where a TCR of the present invention comprises a CDR3α comprising the amino acid sequence of CAASATGNQFYF (SEQ ID NO: 266) or a variant thereof having up to three amino acid substitutions, additions or deletions, and a CDR3β comprising the amino acid sequence of CASSDTRAREQFF (SEQ ID NO: 97) or a variant thereof having up to three amino acid substitutions, additions or deletions, the TCR is HLA-A*0201 restricted.

In another aspect, where a TCR of the present invention comprises a CDR3α comprising the amino acid sequence of CAASATGNQFYF (SEQ ID NO: 266) or a variant thereof having up to three amino acid substitutions, additions or deletions, and a CDR3β comprising the amino acid sequence of CASSPGQHGELFF (SEQ ID NO: 271) or a variant thereof having up to three amino acid substitutions, additions or deletions, the TCR is HLA-A*0201 restricted.

In another aspect, where a TCR of the present invention comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions, the TCR is HLA-A*0201 restricted.

In another aspect, where a TCR of the present invention comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions, the TCR is HLA-A*0201 restricted.

In another aspect, where a TCR of the present invention comprises a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions, the TCR is HLA-A*0201 restricted.

In one embodiment, a TCR of the present invention that is HLA-A*0201 restricted binds to a WT1 peptide comprising amino acid sequence APVLDFAPPGA (SEQ ID NO: 117) or a variant thereof having up to three amino acid substituions, additions or deletions.

In one aspect, the present invention provides a TCR which binds a Wilms tumour 1 protein (WT1) peptide when presented by a major histocompatibility complex (MHC), wherein the TCR comprises a CDR3α comprising the amino acid sequence of CGTAWINDYKLSF (SEQ ID NO: 3) or a variant thereof having up to three amino acid substitutions, additions or deletions, and a CDR3β comprising the amino acid sequence of CASRKTGGYSNQPQHF (SEQ ID NO: 8) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CVVNLLSNQGGKLIF (SEQ ID NO: 36) or a variant thereof having up to three amino acid substitutions, additions or deletions, and a CDR3β comprising the amino acid sequence of CASSQDYLVSNEKLFF (SEQ ID NO: 41) or a variant thereof having up to three amino acid substitutions, additions or deletions, wherein the TCR is HLA-A*0201 restricted, and wherein thew WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CAANNARLMF (SEQ ID NO: 92) or a variant thereof having up to three amino acid substitutions, additions or deletions, and a CDR3β comprising the amino acid sequence of CASSDTRAREQFF (SEQ ID NO: 97) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CAASGGRDDKIIF (SEQ ID NO: 214) or a variant thereof having up to three amino acid substitutions, additions or deletions, and a CDR3β comprising the amino acid sequence of CASSYSRTESTDTQYF (SEQ ID NO: 219) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CAANNARLMF (SEQ ID NO: 92) or a variant thereof having up to three amino acid substitutions, additions or deletions, and a CDR3β comprising the amino acid sequence of CASSPGQHGELFF (SEQ ID NO: 271) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CAASATGNQFYF (SEQ ID NO: 266) or a variant thereof having up to three amino acid substitutions, additions or deletions, and a CDR3β comprising the amino acid sequence of CASSDTRAREQFF (SEQ ID NO: 97) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CAASATGNQFYF (SEQ ID NO: 266) or a variant thereof having up to three amino acid substitutions, additions or deletions, and a CDR3β comprising the amino acid sequence of CASSPGQHGELFF (SEQ ID NO: 271) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

In another aspect, the present invention provides a TCR which binds a Wilms tumour 1 protein (WT1) peptide when presented by a major histocompatibility complex (MHC), wherein the TCR comprises a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions, wherein the TCR is HLA-A*0201 restricted, and wherein the WT1 peptide comprises the amino acid sequence of APVLDFAPPGA (SEQ ID NO: 117) or a variant thereof having up to three amino acid substituions, additions or deletions.

Another widely expressed HLA allele of interest is HLA-B*3501. A TCR of the present invention may be HLA-B*3501 restricted.

In one aspect, where a TCR of the present invention comprises a CDR3α comprising the amino acid sequence of CAASMAGAGSYQLTF (SEQ ID NO: 75) or a variant thereof having up to three amino acid substitutions, additions or deletions, and a CDR3β comprising the amino acid sequence of CAISVGQGALYEQYF (SEQ ID NO: 80) or a variant thereof having up to three amino acid substitutions, additions or deletions, the TCR is HLA-B*3501 restricted.

Thus, in another aspect, the present invention provides a TCR which binds a Wilms tumour 1 protein (WT1) peptide when presented by a major histocompatibility complex (MHC), wherein the TCR comprises a CDR3α comprising the amino acid sequence of CAASMAGAGSYQLTF (SEQ ID NO: 75) or a variant thereof having up to three amino acid substitutions, additions or deletions, and a CDR3β comprising the amino acid sequence of CAISVGQGALY-EQYF (SEQ ID NO: 80) or a variant thereof having up to three amino acid substitutions, additions or deletions, wherein the TCR is HLA-B*3501 restricted, and wherein the WT1 peptide comprises the amino acid sequence of NHTTPILCGAQYRIH (SEQ ID NO: 127) or a variant thereof having up to three amino acid substituions, additions or deletions.

In one aspect, where a TCR of the present invention comprises a CDR3α comprising the amino acid sequence of CAASMAGAGSYQLTF (SEQ ID NO: 75) or a variant thereof having up to three amino acid substitutions, additions or deletions, and a CDR3β comprising the amino acid sequence of CASSVARDRRNYGYTF (SEQ ID NO: 86) or a variant thereof having up to three amino acid substitutions, additions or deletions, the TCR is HLA-B*3501 restricted.

Thus, in another aspect, the present invention provides a TCR which binds a Wilms tumour 1 protein (WT1) peptide when presented by a major histocompatibility complex (MHC), wherein the TCR comprises a CDR3α comprising the amino acid sequence of CAASMAGAGSYQLTF (SEQ ID NO: 75) or a variant thereof having up to three amino acid substitutions, additions or deletions, and a CDR3β comprising the amino acid sequence of CASSVARD-RRNYGYTF (SEQ ID NO: 86) or a variant thereof having up to three amino acid substitutions, additions or deletions, wherein the TCR is HLA-B*3501 restricted, and wherein the WT1 peptide comprises the amino acid sequence of NHTTPILCGAQYRIH (SEQ ID NO: 127) or a variant thereof having up to three amino acid substituions, additions or deletions.

Another widely expressed HLA allele of interest is HLA-B*3502. A TCR of the present invention may be HLA-B*3502 restricted.

In one aspect, where a TCR of the present invention comprises a CDR3α comprising the amino acid sequence of CATDAYSGNTPLVF (SEQ ID NO: 47) or a variant thereof having up to three amino acid substitutions, additions or deletions, and a CDR3β comprising the amino acid sequence of CASRAAGLDTEAFF (SEQ ID NO: 57) or a variant thereof having up to three amino acid substitutions, additions or deletions, the TCR is HLA-B*3502 restricted.

Thus, in one aspect, the present invention provides a TCR which binds a Wilms tumour 1 protein (WT1) peptide when presented by a major histocompatibility complex (MHC), wherein the TCR comprises a CDR3α comprising the amino acid sequence of CATDAYSGNTPLVF (SEQ ID NO: 47) or a variant thereof having up to three amino acid substitutions, additions or deletions, and a CDR3β comprising the amino acid sequence of CASRAAGLDTEAFF (SEQ ID NO: 57) or a variant thereof having up to three amino acid substitutions, additions or deletions, wherein the TCR is HLA-B*3502 restricted, and wherein the WT1 peptide comprises the amino acid sequence of EPASQHTLRSG (SEQ ID NO: 123) or a variant thereof having up to three amino acid substituions, additions or deletions.

We have demonstrated that T-cells expressing TCRs of the present invention which bind to WT1 peptides comprising an amino acid sequence of EPASQHTLRSG (SEQ ID NO: 123) are able to selectively eliminate cancer (AML) cells expressing the HLA-B*3502 allele—see Example 4 and FIG. 4c.

In one aspect, where a TCR of the present invention binds to a WT1 peptide comprising an amino acid sequence of EPASQHTLRSG (SEQ ID NO: 123), or a variant thereof having up to three amino acid substitutions, additions or deletions, the TCR is HLA-B*3502 restricted.

In one embodiment, where a TCR of the present invention binds to a WT1 peptide comprising an amino acid sequence of APVLDFAPPGA (SEQ ID NO: 117) or a variant thereof having up to three amino acid substitutions, additions or deletions, the TCR is HLA-A*0201 restricted.

In one embodiment, where a TCR of the present invention binds to a WT1 peptide comprising an amino acid sequence of NHTTPILCGAQYRIH (SEQ ID NO: 127) or a variant thereof having up to three amino acid substitutions, additions or deletions, the TCR is HLA-B*3501 restricted.

Wilms Tumor 1 (WT1) Protein

Wilms tumor 1 (WT1) is an intracellular protein encoding a zinc finger transcription factor that plays an important role in cell growth and differentiation (Yang, L. et al. *Leukemia* 21, 868-876 (2007)). It is widely expressed on a variety of hematological and solid tumors, while showing limited expression on other tissues (gonads, uterus, kidney, mesothelium, progenitor cells in different tissues). Recent evidence suggests that WT1 plays a role in leukemogenesis and tumorigenesis.

WT1 has several isoforms, some of which result from alternative splicing of mRNA transcripts encoding WT1. The complete amino acid sequence of a WT1 isoform was previously published (Gessler, M. et al. *Nature;* 343(6260): 774-778; (1990)). This particular isoform consists of 575 amino acids and includes a first 126 amino acids at the N terminus which are lacking in the exon 5+ and the KTS+ isoforms of WT1.

An example WT1 protein has the amino acid sequence set out in UniProt entry J3KNN9. Another example WT1 protein has the amino acid sequence set out below:

```
                                        (SEQ ID NO: 131)
SRQRPHPGALRNPTACPLPHFPPSLPPTHSPTHPPRAGTAAQAPGPR

RLLAAILDFLLLQDPASTCVPEPASQHTLRSGPGCLQQPEQQGVRDP

GGIWAKLGAAEASAERLQGRRSRGASGSEPQQMGSDVRDLNALLPAV

PSLGGGGGCALPVSGAAQWAPVLDFAPPGASAYGSLGGPAPPPAPPP

PPPPPPHSFIKQEPSWGGAEPHEEQCLSAFTVHFSGQFTGTAGACRY

GPFGPPPPSQASSGQARMFPNAPYLPSCLESQPAIRNQGYSTVTFDG

TPSYGHTPSHHAAQFPNHSFKHEDPMGQQGSLGEQQYSVPPPVYGCH

TPTDSCTGSQALLLRTPYSSDNLYQMTSQLECMTWNQMNLGATLKGV

AAGSSSSVKWTEGQSNHSTGYESDNHTTPILCGAQYRIHTHGVFRGI

QDVRRVPGVAPTLVRSASETSEKRPFMCAYPGCNKRYFKLSHLQMHS

RKHTGEKPYQCDFKDCERRFSRSDQLKRHQRRHTGVKPFQCKTCQRK

FSRSDHLKTHTRTHTGKTSEKPFSCRWPSCQKKFARSDELVRHHNMH

QRNMTKLQLAL
```

WT1 Peptides

As used herein the term peptide refers to a plurality of amino acid residues linked by peptide bonds. As defined herein a peptide may consist of less than about 30, less than about 25, less than about 20, less than 19, less than 18, less than 17, less than 16, less than 15, less than 14, less than 13, less than 12, less than 11, less than 10, less than 9, less than 8, less than 7, less than 6, or less than 5 amino acid residues in length. Preferably, a peptide is about 5 to 20 amino acids in length, more preferably, a peptide is about 8 to 15 amino acid residues in length.

The TCRs of the present invention bind to a WT1 peptide when presented by an MHC. As used herein, the term WT1 peptide is understood to mean a peptide comprising an amino acid sequence derived from a WT1 protein.

For example, a WT1 peptide may comprise at least 5, at least 6, at least 7, at least 8, at least 9, at least 10, at least 11, at least 12, at least 13, at least 14, at least 15, at least 16, at least 17, at least 18, at least 19, at least 20, or at least 25 contiguous amino acid residues of a WT1 protein amino acid sequence.

The WT1 peptide may comprise or consist of the amino acid sequence of APVLDFAPPGA (SEQ ID NO: 117) or a variant thereof having up to three amino acid substitutions, additions or deletions. Examples of WT1 peptides comprising the amino acid sequence are AAQWAPVLDFAPPGA (SEQ ID NO: 115) and APVLDFAPPGASAYG (SEQ ID NO: 116).

The WT1 peptide may comprise or consist of an amino acid sequence selected from the group consisting of QCLSAFTVHFSGQFT (SEQ ID NO: 118), EDPMGQQGSLGEQQY (SEQ ID NO: 119), SQLECMTWNQMNLGA (SEQ ID NO: 120), and variants of SEQ ID NOs: 118-120 each having up to three amino acid substitutions, additions or deletions.

The WT1 peptide may comprise or consist of an amino acid sequence selected from the group consisting of EPASQHTLRSG (SEQ ID NO: 123), YESDNHTTPIL (SEQ ID NO: 126), and variants of SEQ ID NOs: 123 and 126 each having up to three amino acid substitutions, additions or deletions. Example WT1 peptides may have an amino acid sequence selected from the group consisting of TCVPEPASQHTLRSG (SEQ ID NO: 121), EPASQHTLRSGPGCL (SEQ ID NO: 122), HSTGYESDNHTTPIL (SEQ ID NO: 124) and YESDNHTTPILCGAQ (SEQ ID NO: 125).

The WT1 peptide may comprise or consist of the amino acid sequence of NHTTPILCGAQYRIH (SEQ ID NO: 127) or a variant thereof having up to three amino acid substitutions, additions or deletions.

The WT1 peptide may comprise or consist of the amino acid sequence of NQMNLGATLKG (SEQ ID NO: 250) or a variant thereof having up to three amino acid substitutions, additions or deletions. Example WT1 peptides may have an amino acid sequence selected from the group consisting of CMTWNQMNLGATLKG (SEQ ID NO: 248) and NQMNLGATLKGVAAG (SEQ ID NO: 249).

The WT1 peptide may comprise or consist of the amino acid sequence of DPGGIWAKLGAAEAS (SEQ ID NO: 251) or a variant thereof having up to three amino acid substitutions, additions or deletions.

The WT1 peptide may comprise or consist of an amino acid sequence selected from the group consisting of NHTTPILCGAQYRIH (SEQ ID NO: 252), KRHQRRHTGVKPFQC (SEQ ID NO: 253), PSCQKKFARSDELVR (SEQ ID NO: 254), and variants of SEQ ID NOs: 252, 253 and 254 each having up to three amino acid substitutions, additions or deletions.

In some embodiments, for WT1 peptides which bind to MHC molecules encoded by HLA-A*0201 allele it may be preferred that the amino acids at position 2 of the peptide (i.e. the second amino acid from the N-terminus) are leucine or methionine, although isoleucine, valine, alanine and threonine may also be preferable. It may also be preferred that the amino acid at position 9 or 10 is valine, leucine or isoleucine, although alanine, methionine and threonine may also be preferable. The preferred MHC binding motifs of other HLA alleles are disclosed in Celis et al (Molecular Immunology, Vol. 31, 8, December 1994, pages 1423 to 1430).

Various uses of the WT1 peptides described herein are contemplated by the present invention. For example, the WT1 peptides described herein may be administered to a subject, e.g. a human subject. Administration of the WT1 peptides of the present invention may elicit an immune response against cells expressing or overexpressing WT1 protein, i.e. the WT1 peptides are immunogenic WT1 peptides.

Thus in another aspect, the present invention provides an isolated immunogenic WT1 peptide comprising an amino acid sequence selected from the group consisting of EPASQHTLRSG (SEQ ID NO: 123), YESDNHTTPIL (SEQ ID NO: 126), NHTTPILCGAQYRIH (SEQ ID NO: 127), QCLSAFTVHFSGQFT (SEQ ID NO: 118), EDPMGQQGSLGEQQY (SEQ ID NO: 119), SQLECMTWNQMNLGA (SEQ ID NO: 120), APVLDFAPPGA (SEQ ID NO: 117), NQMNLGATLKG (SEQ ID NO: 250), DPGGIWAKLGAAEAS (SEQ ID NO: 251), NHTTPILCGAQYRIH (SEQ ID NO: 252), KRHQRRHTGVKPFQC (SEQ ID NO: 253), PSCQKKFARSDELVR (SEQ ID NO: 254), and variants thereof each having up to three amino acid substitutions, additions or deletions.

The WT1 peptides described herein, e.g. WT1 peptides comprising an amino acid sequence selected from the group consisting of EPASQHTLRSG (SEQ ID NO: 123) and YESDNHTTPIL (SEQ ID NO: 126), NHTTPILCGAQYRIH (SEQ ID NO: 127), QCLSAFTVHFSGQFT (SEQ ID NO: 118), EDPMGQQGSLGEQQY (SEQ ID NO: 119), SQLECMTWNQMNLGA (SEQ ID NO: 120), APVLDFAPPGA (SEQ ID NO: 117), NQMNLGATLKG (SEQ ID NO: 250), DPGGIWAKLGAAEAS (SEQ ID NO: 251), NHTTPILCGAQYRIH (SEQ ID NO: 252), KRHQRRHTGVKPFQC (SEQ ID NO: 253) PSCQKKFARSDELVR (SEQ ID NO: 254), and variants thereof each having up to three amino acid substitutions, additions or deletions, may be used to screen for and/or identify new TCR sequences which bind to WT1 cells. For example, T2 cells may be pulsed with a WT1 peptide mentioned in the present invention and incubated with a T-cell population isolated from a donor. In this approach, expression of cytokines, e.g. CD107a and IFNγ, may be indicative of T-cells which recognise WT1 peptides.

Accordingly, in one aspect, the present invention provides a T-cell receptor (TCR), which binds to a Wilms tumour 1 protein (WT1) peptide when presented by a major histocompatibility complex (MHC), wherein the WT1 peptide comprises an amino acid sequence selected from the group consisting of EPASQHTLRSG (SEQ ID NO: 123), YESDNHTTPIL (SEQ ID NO: 126), NHTTPILCGAQYRIH (SEQ ID NO: 127), QCLSAFTVHFSGQFT (SEQ ID NO: 118), EDPMGQQGSLGEQQY (SEQ ID NO: 119), SQLECMTWNQMNLGA (SEQ ID NO: 120), APVLDFAPPGA (SEQ ID NO: 117), NQMNLGATLKG (SEQ ID NO: 250), DPGGIWAKLGAAEAS (SEQ ID NO: 251), NHTTPILCGAQYRIH (SEQ ID NO: 252), KRHQRRHTGVKPFQC (SEQ ID NO: 253), PSCQKKFARSDELVR (SEQ ID NO: 254), and variants thereof each having up to three amino acid substitutions, additions or deletions.

TCR Sequences

We have determined the amino acid sequences for TCRs that bind to WT1 peptides described herein. In particular, we have determined the amino acid sequences of the TCR CDRs, which are important for WT1 peptide recognition and binding.

Thus, in one embodiment, the present invention provides a TCR comprising a CDR3α comprising the amino acid sequence of CGTAWINDYKLSF (SEQ ID NO: 3) or a variant thereof having up to three amino acid substitutions, additions or deletions, and a CDR3β comprising the amino acid sequence of CASRKTGGYSNQPQHF (SEQ ID NO: 8) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Thus, in one embodiment, the present invention provides, a TCR comprising a CDR3α comprising the amino acid sequence of CVVNLLSNQGGKLIF (SEQ ID NO: 36) or a variant thereof having up to three amino acid substitutions, additions or deletions, and a CDR3β comprising the amino acid sequence of CASSQDYLVSNEKLFF (SEQ ID NO: 41) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Thus, in one embodiment, the present invention provides, a TCR comprising a CDR3α comprising the amino acid sequence of CAANNARLMF (SEQ ID NO: 92) or a variant thereof having up to three amino acid substitutions, additions or deletions, and a CDR3β comprising the amino acid sequence of CASSDTRAREQFF (SEQ ID NO: 97) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Thus, in one embodiment, the present invention provides, a TCR comprising a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

In one embodiment, the present invention provides, a TCR comprising a CDR3α comprising the amino acid sequence of CAVEATDSWGKLQF (SEQ ID NO: 108) or a variant thereof having up to three amino acid substitutions, additions or deletions, and a CDR3β comprising the amino acid sequence of CSVGGSGSYNEQFF (SEQ ID NO: 169) or a variant thereof having up to three amino acid substitutions, additions or deletions, which binds to a WT1 peptide comprising the amino acid sequence of NQMNLGATLKG (SEQ ID NO: 250) or a variant thereof having up to three amino acid substitutions, additions or deletions when presented by an MHC.

In one embodiment, the present invention provides, a TCR comprising a CDR3α comprising the amino acid sequence of CAVRTSYDKVIF (SEQ ID NO: 113) or a variant thereof having up to three amino acid substitutions, additions or deletions, and a CDR3β comprising the amino acid sequence of CSVGGSGSYNEQFF (SEQ ID NO: 169) or a variant thereof having up to three amino acid substitutions, additions or deletions, which binds to a WT1 peptide comprising the amino acid sequence of NQMNLGATLKG (SEQ ID NO: 250) or a variant thereof having up to three amino acid substitutions, additions or deletions when presented by an MHC.

Thus, in one embodiment, the present invention provides, a TCR comprising a CDR3α comprising the amino acid sequence of CAASGGRDDKIIF (SEQ ID NO: 214) or a variant thereof having up to three amino acid substitutions, additions or deletions, and a CDR3β comprising the amino acid sequence of CASSYSRTESTDTQYF (SEQ ID NO: 219) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

The present invention also provides a TCR comprising:

a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions;

a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions;

a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions; or a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions; wherein the TCR binds to a WT1 peptide comprising or consisting of an amino acid sequence selected from the group consisting of QCLSAFTVHFSGQFT (SEQ ID NO: 118), EDPMGQQGSLGEQQY (SEQ ID NO: 119), and SQLECMTWNQMNLGA (SEQ ID NO: 120) or variants thereof each having up to three amino acid substitutions, additions or deletions when presented by an MHC.

Thus, in one embodiment, there is provided a TCR comprising a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions, which binds to a WT1 peptide comprising or consisting of the amino acid sequence of QCLSAFTVHFSGQFT (SEQ ID NO: 118) or a variant thereof having up to three amino acid substitutions, additions or deletions when presented by an MHC.

In one embodiment, there is provided a TCR comprising a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions, which binds to a WT1 peptide comprising or consisting of the amino acid sequence of EDPMGQQGSLGEQQY (SEQ ID NO: 119) or a variant thereof having up to three amino acid substitutions, additions or deletions when presented by an MHC.

In one embodiment, there is provided a TCR comprising a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions, which binds to a WT1 peptide comprising or consisting of the amino acid sequence of SQLECMTWNQMNLGA (SEQ ID NO: 120) or a variant thereof having up to three amino acid substitutions, additions or deletions when presented by an MHC.

In one embodiment, there is provided a TCR comprising a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions, which binds to a WT1 peptide comprising or consisting of the amino acid sequence of QCLSAFTVHFSGQFT (SEQ ID NO: 118) or a variant thereof having up to three amino acid substitutions, additions or deletions when presented by an MHC.

In one embodiment, there is provided a TCR comprising a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions, which binds to a WT1 peptide comprising or consisting of the of EDPMGQQGSLGEQQY (SEQ ID NO: 119) or a variant thereof having up to three amino acid substitutions, additions or deletions when presented by an MHC.

In one embodiment, there is provided a TCR comprising a CDR3α comprising the amino acid sequence of CAVRLSGSARQLTF (SEQ ID NO: 14) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions, which binds to a WT1 peptide comprising or consisting of the amino acid sequence of SQLECMTWNQMNLGA (SEQ ID NO: 120) or a variant thereof having up to three amino acid substitutions, additions or deletions when presented by an MHC.

In one embodiment, there is provided a TCR comprising a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions, which binds to a WT1 peptide comprising or consisting of the amino acid sequence of QCLSAFTVHFSGQFT (SEQ ID NO: 118) or a variant thereof having up to three amino acid substitutions, additions or deletions when presented by an MHC.

In one embodiment, there is provided a TCR comprising a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions, which binds to a WT1 peptide comprising or consisting of the amino acid sequence of EDPMGQQGSLGEQQY (SEQ ID NO: 119) or a variant thereof having up to three amino acid substitutions, additions or deletions when presented by an MHC.

In one embodiment, there is provided a TCR comprising a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLLGDEQYF (SEQ ID NO: 24) or a variant thereof having up to three amino acid substitutions, additions or deletions, which binds to a WT1 peptide comprising or consisting of the amino acid sequence of SQLECMTWNQMNLGA (SEQ ID NO: 120) or a variant thereof having up to three amino acid substitutions, additions or deletions when presented by an MHC.

In one embodiment, there is provided a TCR comprising a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions, which binds to a WT1 peptide comprising or consisting of the amino acid sequence of QCLSAFTVHFSGQFT (SEQ ID NO: 118) or a variant thereof having up to three amino acid substitutions, additions or deletions when presented by an MHC.

In one embodiment, there is provided a TCR comprising a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions, which binds to a WT1 peptide comprising or consisting of an amino acid sequence of EDPMGQQGSLGEQQY (SEQ ID NO: 119) or a variant thereof having up to three amino acid substitutions, additions or deletions when presented by an MHC.

In one embodiment, there is provided a TCR comprising a CDR3α comprising the amino acid sequence of CAYRSLKYGNKLVF (SEQ ID NO: 19) or a variant thereof having up to three amino acid substitutions, additions or deletions, and a CDR3β comprising the amino acid sequence of CASSLVALQGAGEQYF (SEQ ID NO: 30) or a variant thereof having up to three amino acid substitutions, additions or deletions, which binds to a WT1 peptide comprising or consisting of an amino acid sequence of SQLECMTWNQMNLGA (SEQ ID NO: 120) or a variant thereof having up to three amino acid substitutions, additions or deletions when presented by an MHC.

Further provided by the present invention is a TCR comprising a CDR3α comprising the amino acid sequence of CATDAYSGNTPLVF (SEQ ID NO: 47) or a variant thereof having up to three amino acid substitutions, additions or deletions, and a CDR3β comprising the amino acid sequence of CASRAAGLDTEAFF (SEQ ID NO: 57) or a variant thereof having up to three amino acid substitutions, additions or deletions, which binds to a WT1 peptide comprising comprising or consisting of an amino acid sequence of EPASQHTLRSG (SEQ ID NO: 123) or a variant thereof having up to three amino acid substitutions, additions or deletions when presented by an MHC.

Further provided by the present invention is a TCR comprising a CDR3α comprising the amino acid sequence of CAVRAEIYNQGGKLIF (SEQ ID NO: 52) or a variant thereof having up to three amino acid substitutions, additions or deletions, and a CDR3β comprising the amino acid sequence of CASTQTPYEQYF (SEQ ID NO: 63) or a variant thereof having up to three amino acid substitutions, additions or deletions, which binds to a WT1 peptide comprising comprising or consisting of an amino acid sequence of YESDNHTTPIL (SEQ ID NO: 126) or a variant thereof having up to three amino acid substitutions, additions or deletions when presented by an MHC.

Further provided by the present invention is a TCR comprising a CDR3α comprising the amino acid sequence of CAVRAEIYNQGGKLIF (SEQ ID NO: 52) or a variant thereof having up to three amino acid substitutions, additions or deletions, and a CDR3β comprising the amino acid sequence of CASSTVGGEDYGYTF (SEQ ID NO: 69) or a variant thereof having up to three amino acid substitutions, additions or deletions, which binds to a WT1 peptide comprising comprising or consisting of an amino acid sequence of YESDNHTTPIL (SEQ ID NO: 126) or a variant thereof having up to three amino acid substitutions, additions or deletions when presented by an MHC.

Further provided by the present invention is a TCR comprising a CDR3α comprising the amino acid sequence of CAASMAGAGSYQLTF (SEQ ID NO: 75) or a variant thereof having up to three amino acid substitutions, additions or deletions, and a CDR3β comprising the amino acid sequence of CAISVGQGALYEQYF (SEQ ID NO: 80) or a variant thereof having up to three amino acid substitutions, additions or deletions, which binds to a WT1 peptide comprising the amino acid sequence of NHTTPILCGAQYRIH (SEQ ID NO: 127) or a variant thereof having up to three amino acid substitutions, additions or deletions when presented by an MHC.

Further provided by the present invention is a TCR comprising a CDR3α comprising the amino acid sequence of CAASMAGAGSYQLTF (SEQ ID NO: 75) or a variant thereof having up to three amino acid substitutions, additions or deletions, and a CDR3β comprising the amino acid sequence of CASSVARDRRNYGYTF (SEQ ID NO: 86) or a variant thereof having up to three amino acid substitutions, additions or deletions, which binds to a WT1 peptide comprising the amino acid sequence of NHTTPILCGAQYRIH (SEQ ID NO: 127) or a variant thereof having up to three amino acid substitutions, additions or deletions when presented by an MHC.

Further provided by the present invention is a TCR comprising a CDR3α comprising the amino acid sequence of CAVTVGNKLVF (SEQ ID NO: 175) or a variant thereof having up to three amino acid substitutions, additions or deletions, and a CDR3β comprising the amino acid sequence of CASRGWREQFF (SEQ ID NO: 180) or a variant thereof having up to three amino acid substitutions, additions or deletions, which binds to a WT1 peptide comprising the amino acid sequence of DPGGIWAKLGAAEAS (SEQ ID NO: 251) or a variant thereof having up to three amino acid substitutions, additions or deletions when presented by an MHC.

Further provided by the present invention is a TCR comprising a CDR3α comprising the amino acid sequence of CAARSYNTDKLIF (SEQ ID NO: 186) or a variant thereof having up to three amino acid substitutions, additions or deletions, and a CDR3β comprising the amino acid sequence of CASSWGYQETQYF (SEQ ID NO: 196) or a variant thereof having up to three amino acid substitutions, additions or deletions, which binds to a WT1 peptide comprising the amino acid sequence of NHTTPILCGAQYRIH (SEQ ID NO: 252) or a variant thereof having up to three amino acid substitutions, additions or deletions when presented by an MHC.

Further provided by the present invention is a TCR comprising a CDR3α comprising the amino acid sequence of CAASYNNARLMF (SEQ ID NO: 191) or a variant thereof having up to three amino acid substitutions, additions or deletions, and a CDR3β comprising the amino acid sequence of CASSPTGGEYYGYTF (SEQ ID NO: 202) or a variant thereof having up to three amino acid substitutions, additions or deletions, which binds to a WT1 peptide comprising the amino acid sequence of KRHQRRHTGVKPFQC (SEQ ID NO: 253) or a variant thereof having up to three amino acid substitutions, additions or deletions when presented by an MHC.

Further provided by the present invention is a TCR comprising a CDR3α comprising the amino acid sequence of CAASYNNARLMF (SEQ ID NO: 191) or a variant thereof having up to three amino acid substitutions, additions or deletions, and a CDR3β comprising the amino acid sequence of CASSSYPLRTGRYNSYNSPLHF (SEQ ID NO: 208) or a variant thereof having up to three amino acid substitutions, additions or deletions, which binds to a WT1 peptide comprising the amino acid sequence of PSCQKKFARSDELVR (SEQ ID NO: 254) or a variant thereof having up to three amino acid substitutions, additions or deletions when presented by an MHC.

Further provided by the present invention is a TCR comprising a CDR3α comprising the amino acid sequence of CAANNARLMF (SEQ ID NO: 92) or a variant thereof having up to three amino acid substitutions, additions or deletions, and a CDR3β comprising the amino acid sequence of CASSPGQHGELFF (SEQ ID NO: 271) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Further provided by the present invention is a TCR comprising a CDR3α comprising the amino acid sequence of CAASATGNQFYF (SEQ ID NO: 266) or a variant thereof having up to three amino acid substitutions, additions or deletions, and a CDR3β comprising the amino acid sequence of CASSDTRAREQFF (SEQ ID NO: 97) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Further provided by the present invention is a TCR comprising a CDR3α comprising the amino acid sequence of CAASATGNQFYF (SEQ ID NO: 266) or a variant thereof having up to three amino acid substitutions, additions or deletions, and a CDR3β comprising the amino acid sequence of CASSPGQHGELFF (SEQ ID NO: 271) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Further provided by the present invention is a TCR comprising a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Further provided by the present invention is a TCR comprising comprises a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Further provided by the present invention is a TCR comprising a CDR3α comprising the amino acid sequence of CAVEATDSWGKLQF (SEQ ID NO: 108) or a variant thereof having up to three amino acid substitutions, additions or deletions, and a CDR3β comprising the amino acid sequence of CASSLGLSISQETQYF (SEQ ID NO: 288) or a variant thereof having up to three amino acid substitutions, additions or deletions, which binds to a WT1 peptide comprising the amino acid sequence of NQMNLGATLKG (SEQ ID NO: 250) or a variant thereof having up to three amino acid substitutions, additions or deletions when presented by an MHC.

Further provided by the present invention is a TCR comprising a CDR3α comprising the amino acid sequence of CAVRTSYDKVIF (SEQ ID NO: 113) or a variant thereof having up to three amino acid substitutions, additions or deletions, and a CDR3β comprising the amino acid sequence of CASSLGLSISQETQYF (SEQ ID NO: 288) or a variant thereof having up to three amino acid substitutions, additions or deletions, which binds to a WT1 peptide comprising the amino acid sequence of NQMNLGATLKG (SEQ ID NO: 250) or a variant thereof having up to three amino acid substitutions, additions or deletions when presented by an MHC.

Further provided by the present invention is a TCR comprising a CDR3α comprising the amino acid sequence of CAERLNTDKLIF (SEQ ID NO: 103) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Further provided by the present invention is a TCR comprising a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDSVSGNTIYF (SEQ ID NO: 163) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Further provided by the present invention is a TCR comprising a CDR3α comprising the amino acid sequence of CATDGDSSYKLIF (SEQ ID NO: 277) or a variant thereof having up to three amino acid substitutions, additions or deletions, and a CDR3β comprising the amino acid sequence of CSARDVLTGDYGYTF (SEQ ID NO: 282) or a variant thereof having up to three amino acid substitutions, additions or deletions, which binds to a WT1 peptide comprising the amino acid sequence of APVLDFAPPGA (SEQ ID NO: 117) or a variant thereof having up to three amino acid substitutions, additions or deletions when presented by an MHC.

Example TCR amino acid sequences of the present invention are provided in Table 1.

TABLE 1

| Donor: HD1 | | | |
|---|---|---|---|
| Chain | Region | Amino acid sequence | SEQ ID NO |
| Alpha (α) | CDR1α | KALYS | SEQ ID NO: 1 |
| | CDR2α | LLKGGEQ | SEQ ID NO: 2 |
| | CDR3α | CGTAWINDYKLSF | SEQ ID NO: 3 |
| | Variable | METLLKVLSGTLLWQLTWVRSQQPVQSPQAVILREGEDAVIN<br>CSSSKALYSVHWYRQKHGEAPVFLMILLKGGEQKGHEKISAS<br>FNEKKQQSSLYLTASQLSYSGTYFCGTAWINDYKLSFGAGTT<br>VTVRAN | SEQ ID NO: 4 |
| | Full- with<br>TRAC constant<br>domain | METLLKVLSGTLLWQLTWVRSQQPVQSPQAVILREGEDAVIN<br>CSSSKALYSVHWYRQKHGEAPVFLMILLKGGEQKGHEKISAS<br>FNEKKQQSSLYLTASQLSYSGTYFCGTAWINDYKLSFGAGTT<br>VTVRANIQNPDPAVYQLRDSKSSDKSVCLFTDFDSQTNVSQS<br>KDSDVYITDKTVLDMRSMDFKSNSAVAWSNKSDFACANAFNN | SEQ ID NO: 5 |

TABLE 1-continued

| | | | SIIPEDTFFPSPESSCDVKLVEKSFETDTNLNFQNLSVIGFR<br>ILLLKVAGFNLLMTLRLWSS | |
|---|---|---|---|---|
| Beta (β) | | CDR1β | SGHDY | SEQ ID NO: 6 |
| | | CDR2β | FNNNVP | SEQ ID NO: 7 |
| | | CDR3β | CASRKTGGYSNQPQHF | SEQ ID NO: 8 |
| | | Variable | MGSWTLCCVSLCILVAKHTDAGVIQSPRHEVTEMGQEVTLRC<br>KPISGHDYLFWYRQTMMRGLELLIYFNNNVPIDDSGMPEDRF<br>SAKMPNASFSTLKIQPSEPRDSAVYFCASRKTGGYSNQPQHF<br>GDGTRLSILE | SEQ ID NO: 9 |
| | | Full- with<br>TRBC1<br>constant<br>domain | MGSWTLCCVSLCILVAKHTDAGVIQSPRHEVTEMGQEVTLRC<br>KPISGHDYLFWYRQTMMRGLELLIYFNNNVPIDDSGMPEDRF<br>SAKMPNASFSTLKIQPSEPRDSAVYFCASRKTGGYSNQPQHF<br>GDGTRLSILEDLNKVFPPEVAVFEPSEAEISHTQKATLVCLA<br>TGFFPDHVELSWWVNGKEVHSGVSTDPQPLKEQPALNDSRYC<br>LSSRLRVSATFWQNPRNHFRCQVQFYGLSENDEWTQDRAKPV<br>TQIVSAEAWGRADCGFTSVSYQQGVLSATILYEILLGKATLY<br>AVLVSALVLMAMVKRKDF | SEQ ID NO: 10 |
| | | Full- with<br>TRBC2<br>constant<br>domain | MGSWTLCCVSLCILVAKHTDAGVIQSPRHEVTEMGQEVTLRC<br>KPISGHDYLFWYRQTMMRGLELLIYFNNNVPIDDSGMPEDRF<br>SAKMPNASFSTLKIQPSEPRDSAVYFCASRKTGGYSNQPQHF<br>GDGTRLSILEDLKNVFPPEVAVFEPSEAEISHTQKATLVCLA<br>TGFYPDHVELSWWVNGKEVHSGVSTDPQPLKEQPALNDSRYC<br>LSSRLRVSATFWQNPRNHFRCQVQFYGLSENDEWTQDRAKPV<br>TQIVSAEAWGRADCGFTSESYQQGVLSATILYEILLGKATLY<br>AVLVSALVLMAMVKRKDSRG | SEQ ID NO: 11 |

| Donor: HD2 | | | | |
|---|---|---|---|---|
| Clonotype | Chain | Region | Sequence | SEQ ID NO |
| HD2-1 | Alpha (α) | CDR1α | SSVPPY | SEQ ID NO: 12 |
| | | CDR2α | YTSAATLV | SEQ ID NO: 13 |
| | | CDR3α | CAVRLSGSARQLTF | SEQ ID NO: 14 |
| | | Variable domain | MLLLLVPVLEVIFTLGGTRAQSVTQLGSHVSV<br>SEGALVLLRCNYSSSVPPYLFWYVQYPNQGLQ<br>LLLKYTSAATLVKGINGFEAEFKKSETSFHLT<br>KPSAHMSDAAEYFCAVRLSGSARQLTFGSGTQ<br>LTVLPD | SEQ ID NO: 15 |
| | | Full- with TRAC<br>constant domain | MLLLLVPVLEVIFTLGGTRAQSVTQLGSHVSV<br>SEGALVLLRCNYSSSVPPYLFWYVQYPNQGLQ<br>LLLKYTSAATLVKGINGFEAEFKKSETSFHLT<br>KPSAHMSDAAEYFCAVRLSGSARQLTFGSGTQ<br>LTVLPDIQNPDPAVYQLRDSKSSDKSVCLFTD<br>FDSQTNVSQSKDSDVYITDKTVLDMRSMDFKS<br>NSAVAWSNKSDFACANAFNNSIIPEDTFFPSP<br>ESSCDVKLVEKSFETDTNLNFQNLSVIGFRIL<br>LLKVAGFNLLMTLRLWSS | SEQ ID NO: 16 |
| HD2-2 | Alpha (α) | CDR1α | TSESDYY | SEQ ID NO: 17 |
| | | CDR2α | QEAYKQQN | SEQ ID NO: 18 |
| | | CDR3α | CAYRSLKYGNKLVF | SEQ ID NO: 19 |
| | | Variable domain | MACPGFLWALVISTCLEFSMAQTVTQSQPEMS<br>VQEAETVTLSCTYDTSESDYYLFWYKQPPSRQ<br>MILVIRQEAYKQQNATENRFSVNFQKAAKSFS<br>LKISDSQLGDAAMYFCAYRSLKYGNKLVFGAG<br>TILRVKSY | SEQ ID NO: 20 |
| | | Full- with TRAC<br>constant domain | MACPGFLWALVISTCLEFSMAQTVTQSQPEMS<br>VQEAETVTLSCTYDTSESDYYLFWYKQPPSRQ<br>MILVIRQEAYKQQNATENRFSVNFQKAAKSFS<br>LKISDSQLGDAAMYFCAYRSLKYGNKLVFGAG<br>TILRVKSYIQNPDPAVYQLRDSKSSDKSVCLF<br>TDFDSQTNVSQSKDSDVYITDKTVLDMRSMDF<br>KSNSAVAWSNKSDFACANAFNNSIIPEDTFFP<br>SPESSCDVKLVEKSFETDTNLNFQNLSVIGFR<br>ILLLKVAGFNLLMTLRLWSS | SEQ ID NO: 21 |
| HD2-1β | Beta (β) | CDR1β | SGHAT | SEQ ID NO: 22 |
| | | CDR2β | FQNNGV | SEQ ID NO: 23 |
| | | CDR3β | CASSLLGDEQYF | SEQ ID NO: 24 |
| | | Variable domain | MGTRLLCWAALCLLGAELTEAGVAQSPRYKII<br>EKRQSVAFWCNPISGHATLYWYQQILGQGPKL<br>LIQFQNNGVVDDSQLPKDRFSAERLKGVDSTL<br>KIQPAKLEDSAVYLCASSLLGDEQYFGPGTRL<br>TVTE | SEQ ID NO: 25 |
| | | Full- with TRBC1<br>constant domain | MGTRLLCWAALCLLGAELTEAGVAQSPRYKII<br>EKRQSVAFWCNPISGHATLYWYQQILGQGPKL<br>LIQFQNNGVVDDSQLPKDRFSAERLKGVDSTL<br>KIQPAKLEDSAVYLCASSLLGDEQYFGPGTRL<br>TVTEDLNKVFPPEVAVFEPSEAEISHTQKATL | SEQ ID NO: 26 |

TABLE 1-continued

| | | | | |
|---|---|---|---|---|
| | | | VCLATGFFPDHVELSWWVNGKEVHSGVSTDPQ PLKEQPALNDSRYCLSSRLRVSATFWQNPRNH FRCQVQFYGLSENDEWTQDRAKPVTQIVSAEA WGRADCGFTSVSYQQGVLSATILYEILLGKAT LYAVLVSALVLMAMVKRKDF | |
| | | Full- with TRBC2 constant domain | MGTRLLCWAALCLLGAELTEAGVAQSPRYKII EKRQSVAFWCNPISGHATLYWYQQILGQGPKL LIQFQNNGVVDDSQLPKDRFSAERLKGVDSTL KIQPAKLEDSAVYLCASSLLGDEQYFGPGTRL TVTEDLKNVFPPEVAVFEPSEAEISHTQKATL VCLATGFYPDHVELSWWVNGKEVHSGVSTDPQ PLKEQPALNDSRYCLSSRLRVSATFWQNPRNH FRCQVQFYGLSENDEWTQDRAKPVTQIVSAEA WGRADCGFTSESYQQGVLSATILYEILLGKAT LYAVLVSALVLMAMVKRKDSRG | SEQ ID NO: 27 |
| HD2-2β | Beta (β) | CDR1β | SGHTA | SEQ ID NO: 28 |
| | | CDR2β | FQGNSA | SEQ ID NO: 29 |
| | | CDR3β | CASSLVALQGAGEQYF | SEQ ID NO: 30 |
| | | Variable domain | MGTRLLFWVAFCLLGADHTGAGVSQSPSNKVT EKGKDVELRCDPISGHTALYWYRQSLGQGLEF LIYFQGNSAPDKSGLPSDRFSAERTGGSVSTL TIQRTQQEDSAVYLCASSLVALQGAGEQYFGP GTRLTVTE | SEQ ID NO: 31 |
| | | Full- with TRBC1 constant domain | MGTRLLFWVAFCLLGADHTGAGVSQSPSNKVT EKGKDVELRCDPISGHTALYWYRQSLGQGLEF LIYFQGNSAPDKSGLPSDRFSAERTGGSVSTL TIQRTQQEDSAVYLCASSLVALQGAGEQYFGP GTRLTVTEDLNKVFPPEVAVFEPSEAEISHTQ KATLVCLATGFFPDHVELSWWVNGKEVHSGVS TDPQPLKEQPALNDSRYCLSSRLRVSATFWQN PRNHFRCQVQFYGLSENDEWTQDRAKPVTQIV SAEAWGRADCGFTSVSYQQGVLSATILYEILL GKATLYAVLVSALVLMAMVKRKDF | SEQ ID NO: 32 |
| | | Full- with TRBC2 constant domain | MGTRLLFWVAFCLLGADHTGAGVSQSPSNKVT EKGKDVELRCDPISGHTALYWYRQSLGQGLEF LIYFQGNSAPDKSGLPSDRFSAERTGGSVSTL TIQRTQQEDSAVYLCASSLVALQGAGEQYFGP GTRLTVTEDLKNVFPPEVAVFEPSEAEISHTQ KATLVCLATGFYPDHVELSWWVNGKEVHSGVS TDPQPLKEQPALNDSRYCLSSRLRVSATFWQN PRNHFRCQVQFYGLSENDEWTQDRAKPVTQIV SAEAWGRADCGFTSESYQQGVLSATILYEILL GKATLYAVLVSALVLMAMVKRKDSRG | SEQ ID NO: 33 |

| Donor: HD3 | | | | |
|---|---|---|---|---|
| Chain | Type | | Sequence | SEQ ID NO |
| Alpha (α) | CDR1α | | NSASQS | SEQ ID NO: 34 |
| | CDR2α | | VYSSGN | SEQ ID NO: 35 |
| | CDR3α | | CVVNLLSNQGGKLIF | SEQ ID NO: 36 |
| | Variable domain | | MISLRVLLVILWLQLSWVWSQRKEVEQDPGPFNVPEGATVAFNCTYS NSASQSFFWYRQDCREKEPKLLMSVYSSGNEDGRFTAQLNRASQYISL LIRDSKLSDSATYLCVVNLLSNQGGKLIFGQGTELSVKPN | SEQ ID NO: 37 |
| | Full- with TRAC constant domain | | MISLRVLLVILWLQLSWVWSQRKEVEQDPGPFNVPEGATVAFNCTYS NSASQSFFWYRQDCREKEPKLLMSVYSSGNEDGRFTAQLNRASQYISL LIRDSKLSDSATYLCVVNLLSNQGGKLIFGQGTELSVKPNIQNPDPA VYQLRDSKSSDKSVCLFTDFDSQTNVSQSKDSDVYITDKTVLDMRSM DFKSNSAVAWSNKSDFACANAFNNSIIPEDTFFPSPESSCDVKLVEK SFETDTNLNFQNLSVIGFRILLLKVAGFNLLMTLRLWSS | SEQ ID NO: 38 |
| Beta (β) | CDR1β | | LGHNA | SEQ ID NO: 39 |
| | CDR2β | | YSLEER | SEQ ID NO: 40 |
| | CDR3β | | CASSQDYLVSNEKLFF | SEQ ID NO: 41 |
| | Variable domain | | MGCRLLCCAVLCLLGAGELVPMETGVTQTPRHLVMGMTNKKSLKCEQ HLGHNAMYWYKQSAKKPLELMFVYSLEERVENNSVPSRFSPECPNSS HLFLHLHTLQPEDSALYLCASSQDYLVSNEKLFFGSGTQLSVLE | SEQ ID NO: 42 |
| | Full- with TRBC1 constant domain | | MGCRLLCCAVLCLLGAGELVPMETGVTQTPRHLVMGMTNKKSLKCEQ HLGHNAMYWYKQSAKKPLELMFVYSLEERVENNSVPSRFSPECPNSS HLFLHLHTLQPEDSALYLCASSQDYLVSNEKLFFGSGTQLSVLEDLN KVFPPEVAVFEPSEAEISHTQKATLVCLATGFFPDHVELSWWVNGKE VHSGVSTDPQPLKEQPALNDSRYCLSSRLRVSATFWQNPRNHFRCQV QFYGLSENDEWTQDRAKPVTQIVSAEAWGRADCGFTSVSYQQGVLSA TILYEILLGKATLYAVLVSALVLMAMVKRKDF | SEQ ID NO: 43 |
| | Full- with TRBC2 constant domain | | MGCRLLCCAVLCLLGAGELVPMETGVTQTPRHLVMGMTNKKSLKCEQ HLGHNAMYWYKQSAKKPLELMFVYSLEERVENNSVPSRFSPECPNSS HLFLHLHTLQPEDSALYLCASSQDYLVSNEKLFFGSGTQLSVLEDLK NVFPPEVAVFEPSEAEISHTQKATLVCLATGFYPDHVELSWWVNGKE VHSGVSTDPQPLKEQPALNDSRYCLSSRLRVSATFWQNPRNHFRCQV | SEQ ID NO: 44 |

TABLE 1-continued

QFYGLSENDEWTQDRAKPVTQIVSAEAWGRADCGFTSESYQQGVLSA
TILYEILLGKATLYAVLVSALVLMAMVKRKDSRG

Donor: HD4

| Clonotype | Chain | Region | Sequence | SEQ ID NO |
|---|---|---|---|---|
| HD4-1 | Alpha (α) | CDR1α | TSINN | SEQ ID NO: 45 |
| | | CDR2α | IRSNERE | SEQ ID NO: 46 |
| | | CDR3α | CATDAYSGNTPLVF | SEQ ID NO: 47 |
| | | Variable domain | METLLGVSLVILWLQLARVNSQQGEEDPQALS IQEGENATMNCSYKTSINNLQWYRQNSGRGLV HLILIRSNEREKHSGRLRVTLDTSKKSSSLLI TASRAADTASYFCATDAYSGNTPLVFGKGTRL SVIAN | SEQ ID NO: 48 |
| | | Full- with TRAC constant domain | METLLGVSLVILWLQLARVNSQQGEEDPQALS IQEGENATMNCSYKTSINNLQWYRQNSGRGLV HLILIRSNEREKHSGRLRVTLDTSKKSSSLLI TASRAADTASYFCATDAYSGNTPLVFGKGTRL SVIANIQNPDPAVYQLRDSKSSDKSVCLFTDF DSQTNVSQSKDSDVYITDKTVLDMRSMDFKSN SAVAWSNKSDFACANAFNNSIIPEDTFFPSPE SSCDVKLVEKSFETDTNLNFQNLSVIGFRILL LKVAGFNLLMTLRLWSS | SEQ ID NO: 49 |
| HD4-2 | Alpha (α) | CDR1α | DSAIYN | SEQ ID NO: 50 |
| | | CDR2α | IQSSQRE | SEQ ID NO: 51 |
| | | CDR3α | CAVRAEIYNQGGKLIF | SEQ ID NO: 52 |
| | | Variable domain | METLLGLLILWLQLQWVSSKQEVTQIPAALSV PEGENLVLNCSFTDSAIYNLQWFRQDPGKGLT SLLLIQSSQREQTSGRLNASLDKSSGRSTLYI AASQPGDSATYLCAVRAEIYNQGGKLIFGQGT ELSVKPN | SEQ ID NO: 53 |
| | | Full- with TRAC constant domain | METLLGLLILWLQLQWVSSKQEVTQIPAALSV PEGENLVLNCSFTDSAIYNLQWFRQDPGKGLT SLLLIQSSQREQTSGRLNASLDKSSGRSTLYI AASQPGDSATYLCAVRAEIYNQGGKLIFGQGT ELSVKPNIQNPDPAVYQLRDSKSSDKSVCLFT DFDSQTNVSQSKDSDVYITDKTVLDMRSMDFK SNSAVAWSNKSDFACANAFNNSIIPEDTFFPS PESSCDVKLVEKSFETDTNLNFQNLSVIGFRI LLLKVAGFNLLMTLRLWSS | SEQ ID NO: 54 |
| HD4-1 | Beta (β) | CDR1β | MNHNS | SEQ ID NO: 55 |
| | | CDR2β | SASEGT | SEQ ID NO: 56 |
| | | CDR3β | CASRAAGLDTEAFF | SEQ ID NO: 57 |
| | | Variable domain | MSIGLLCCVAFSLLWASPVNAGVTQTPKFQVL KTGQSMTLQCAQDMNHNSMYWYRQDPGMGLRL IYYSASEGTTDKGEVPNGYNVSRLNKREFSLR LESAAPSQTSVYFCASRAAGLDTEAFFGQGTR LTVVE | SEQ ID NO: 58 |
| | | Full- with TRBC1 constant domain | MSIGLLCCVAFSLLWASPVNAGVTQTPKFQVL KTGQSMTLQCAQDMNHNSMYWYRQDPGMGLRL IYYSASEGTTDKGEVPNGYNVSRLNKREFSLR LESAAPSQTSVYFCASRAAGLDTEAFFGQGTR LTVVEDLNKVFPPEVAVFEPSEAEISHTQKAT LVCLATGFFPDHVELSWWVNGKEVHSGVSTDP QPLKEQPALNDSRYCLSSRLRVSATFWQNPRN HFRCQVQFYGLSENDEWTQDRAKPVTQIVSAE AWGRADCGFTSVSYQQGVLSATILYEILLGKA TLYAVLVSALVLMAMVKRKDF | SEQ ID NO: 59 |
| | | Full- with TRBC2 constant domain | MSIGLLCCVAFSLLWASPVNAGVTQTPKFQVL KTGQSMTLQCAQDMNHNSMYWYRQDPGMGLRL IYYSASEGTTDKGEVPNGYNVSRLNKREFSLR LESAAPSQTSVYFCASRAAGLDTEAFFGQGTR LTVVEDLKNVFPPEVAVFEPSEAEISHTQKAT LVCLATGFYPDHVELSWWVNGKEVHSGVSTDP QPLKEQPALNDSRYCLSSRLRVSATFWQNPRN HFRCQVQFYGLSENDEWTQDRAKPVTQIVSAE AWGRADCGFTSESYQQGVLSATILYEILLGKA TLYAVLVSALVLMAMVKRKDSRG | SEQ ID NO: 60 |
| HD4-2 | Beta (β) | CDR1β | MNHNY | SEQ ID NO: 61 |
| | | CDR2β | SVGAGI | SEQ ID NO: 62 |
| | | CDR3β | CASTQTPYEQYF | SEQ ID NO: 63 |
| | | Variable domain | MSISLLCCAAFPLLWAGPVNAGVTQTPKFRIL KIGQSMTLQCTQDMNHNYMYWYRQDPGMGLKL IYYSVGAGITDKGEVPNGYNVSRSTTEDFPLR LELAAPSQTSVYFCASTQTPYEQYFGPGTRLT VTE | SEQ ID NO: 64 |

TABLE 1-continued

|  |  |  |  |  |
|---|---|---|---|---|
|  |  | Full- with TRBC1 constant domain | MSISLLCCAAFPLLWAGPVNAGVTQTPKFRIL KIGQSMTLQCTQDMNHNYMYWYRQDPGMGLKL IYYSVGAGITDKGEVPNGYNVSRSTTEDFPLR LELAAPSQTSVYFCASTQTPYEQYFGPGTRLT VTEDLNKVFPPEVAVFEPSEAEISHTQKATLV CLATGFFPDHVELSWWVNGKEVHSGVSTDPQP LKEQPALNDSRYCLSSRLRVSATFWQNPRNHF RCQVQFYGLSENDEWTQDRAKPVTQIVSAEAW GRADCGFTSVSYQQGVLSATILYEILLGKATL YAVLVSALVLMAMVKRKDF | SEQ ID NO: 65 |
|  |  | Full- with TRBC2 constant domain | MSISLLCCAAFPLLWAGPVNAGVTQTPKFRIL KIGQSMTLQCTQDMNHNYMYWYRQDPGMGLKL IYYSVGAGITDKGEVPNGYNVSRSTTEDFPLR LELAAPSQTSVYFCASTQTPYEQYFGPGTRLT VTEDLKNVFPPEVAVFEPSEAEISHTQKATLV CLATGFYPDHVELSWWVNGKEVHSGVSTDPQP LKEQPALNDSRYCLSSRLRVSATFWQNPRNHF RCQVQFYGLSENDEWTQDRAKPVTQIVSAEAW GRADCGFTSESYQQGVLSATILYEILLGKATL YAVLVSALVLMAMVKRKDSRG | SEQ ID NO: 66 |
| HD4-3 | Beta (β) | CDR1β | SGHNS | SEQ ID NO: 67 |
|  |  | CDR2β | FNNNVP | SEQ ID NO: 68 |
|  |  | CDR3β | CASSTVGGEDYGYTF | SEQ ID NO: 69 |
|  |  | Variable domain | MDSWTFCCVSLCILVAKHTDAGVIQSPRHEVT EMGQEVTLRCKPISGHNSLFWYRQTMMRGLEL LIYFNNNVPIDDSGMPEDRFSAKMPNASFSTL KIQPSEPRDSAVYFCASSTVGGEDYGYTFGSG TRLTVVE | SEQ ID NO: 70 |
|  |  | Full- with TRBC1 constant domain | MDSWTFCCVSLCILVAKHTDAGVIQSPRHEVT EMGQEVTLRCKPISGHNSLFWYRQTMMRGLEL LIYFNNNVPIDDSGMPEDRFSAKMPNASFSTL KIQPSEPRDSAVYFCASSTVGGEDYGYTFGSG TRLTVVEDLNKVFPPEVAVFEPSEAEISHTQK ATLVCLATGFFPDHVELSWWVNGKEVHSGVST DPQPLKEQPALNDSRYCLSSRLRVSATFWQNP RNHFRCQVQFYGLSENDEWTQDRAKPVTQIVS AEAWGRADCGFTSVSYQQGVLSATILYEILLG KATLYAVLVSALVLMAMVKRKDF | SEQ ID NO: 71 |
|  |  | Full- with TRBC2 constant domain | MDSWTFCCVSLCILVAKHTDAGVIQSPRHEVT EMGQEVTLRCKPISGHNSLFWYRQTMMRGLEL LIYFNNNVPIDDSGMPEDRFSAKMPNASFSTL KIQPSEPRDSAVYFCASSTVGGEDYGYTFGSG TRLTVVEDLKNVFPPEVAVFEPSEAEISHTQK ATLVCLATGFYPDHVELSWWVNGKEVHSGVST DPQPLKEQPALNDSRYCLSSRLRVSATFWQNP RNHFRCQVQFYGLSENDEWTQDRAKPVTQIVS AEAWGRADCGFTSESYQQGVLSATILYEILLG KATLYAVLVSALVLMAMVKRKDSRG | SEQ ID NO: 72 |

| Donor: HD5 | | | | |
|---|---|---|---|---|
| Clonotype | Chain | Region | Sequence | SEQ ID NO |
| HD5-1 | Alpha (α) | CDR1α | DSASNY | SEQ ID NO: 73 |
|  |  | CDR2α | IRSNVGE | SEQ ID NO: 74 |
|  |  | CDR3α | CAASMAGAGSYQLTF | SEQ ID NO: 75 |
|  |  | Variable domain | MTSIRAVFIFLWLQLDLVNGENVEQHPSTLSV QEGDSAVIKCTYSDSASNYFPWYKQELGKRPQ LIIDIRSNVGEKKDQRIAVTLNKTAKHFSLHI TETQPEDSAVYFCAASMAGAGSYQLTFGKGTK LSVIPN | SEQ ID NO: 76 |
|  |  | Full- with TRAC constant domain | MTSIRAVFIFLWLQLDLVNGENVEQHPSTLSV QEGDSAVIKCTYSDSASNYFPWYKQELGKRPQ LIIDIRSNVGEKKDQRIAVTLNKTAKHFSLHI TETQPEDSAVYFCAASMAGAGSYQLTFGKGTK LSVIPNIQNPDPAVYQLRDSKSSDKSVCLFTD FDSQTNVSQSKDSDVYITDKTVLDMRSMDFKS NSAVAWSNKSDFACANAFNNSIIPEDTFFPSP ESSCDVKLVEKSFETDTNLNFQNLSVIGFRIL LLKVAGFNLLMTLRLWSS | SEQ ID NO: 77 |
| HD5-1 | Beta (β) | CDR1β | ENHRY | SEQ ID NO: 78 |
|  |  | CDR2β | SYGVKD | SEQ ID NO: 79 |
|  |  | CDR3β | CAISVGQGALYEQYF | SEQ ID NO: 80 |
|  |  | Variable domain | MGTRLFFYVALCLLWTGHMDAGITQSPRHKVT ETGTPVTLRCHQTENHRYMYWYRQDPGHGLRL IHYSYGVKDTDKGEVSDGYSVSRSKTEDFLLT LESATSSQTSVYFCAISVGQGALYEQYFGPGT RLTVTE | SEQ ID NO: 81 |

TABLE 1-continued

| | | | | |
|---|---|---|---|---|
| | | Full-constant domain with TRBC1 | MGTRLFFYVALCLLWTGHMDAGITQSPRHKVT ETGTPVTLRCHQTENHRYMYWYRQDPGHGLRL IHYSYGVKDTDKGEVSDGYSVSRSKTEDFLLT LESATSSQTSVYFCAISVGQGALYEQYFGPGT RLTVTEDLNKVFPPEVAVFEPSEAEISHTQKA TLVCLATGFFPDHVELSWWVNGKEVHSGVSTD PQPLKEQPALNDSRYCLSSRLRVSATFWQNPR NHFRCQVQFYGLSENDEWTQDRAKPVTQIVSA EAWGRADCGFTSVSYQQGVLSATILYEILLGK ATLYAVLVSALVLMAMVKRKDF | SEQ ID NO: 82 |
| | | Full-constant domain with TRBC2 | MGTRLFFYVALCLLWTGHMDAGITQSPRHKVT ETGTPVTLRCHQTENHRYMYWYRQDPGHGLRL IHYSYGVKDTDKGEVSDGYSVSRSKTEDFLLT LESATSSQTSVYFCAISVGQGALYEQYFGPGT RLTVTEDLKNVFPPEVAVFEPSEAEISHTQKA TLVCLATGFYPDHVELSWWVNGKEVHSGVSTD PQPLKEQPALNDSRYCLSSRLRVSATFWQNPR NHFRCQVQFYGLSENDEWTQDRAKPVTQIVSA EAWGRADCGFTSESYQQGVLSATILYEILLGK ATLYAVLVSALVLMAMVKRKDSRG | SEQ ID NO: 83 |
| HD5-2 | Beta (β) | CDR1β | SGDLS | SEQ ID NO: 84 |
| | | CDR2β | YYNGEE | SEQ ID NO: 85 |
| | | CDR3β | CASSVARDRRNYGYTF | SEQ ID NO: 86 |
| | | Variable domain | MGFRLLCCVAFCLLGAGPVDSGVTQTPKHLIT ATGQRVTLRCSPRSGDLSVYWYQQSLDQGLQF LIQYYNGEERAKGNILERFSAQQFPDLHSELN LSSLELGDSALYFCASSVARDRRNYGYTFGSG TRLTVVE | SEQ ID NO: 87 |
| | | Full-constant domain with TRBC1 | MGFRLLCCVAFCLLGAGPVDSGVTQTPKHLIT ATGQRVTLRCSPRSGDLSVYWYQQSLDQGLQF LIQYYNGEERAKGNILERFSAQQFPDLHSELN LSSLELGDSALYFCASSVARDRRNYGYTFGSG TRLTVVEDLNKVFPPEVAVFEPSEAEISHTQK ATLVCLATGFFPDHVELSWWVNGKEVHSGVST DPQPLKEQPALNDSRYCLSSRLRVSATFWQNP RNHFRCQVQFYGLSENDEWTQDRAKPVTQIVS AEAWGRADCGFTSVSYQQGVLSATILYEILLG KATLYAVLVSALVLMAMVKRKDF | SEQ ID NO: 88 |
| | | Full-constant domain with TRBC2 | MGFRLLCCVAFCLLGAGPVDSGVTQTPKHLIT ATGQRVTLRCSPRSGDLSVYWYQQSLDQGLQF LIQYYNGEERAKGNILERFSAQQFPDLHSELN LSSLELGDSALYFCASSVARDRRNYGYTFGSG TRLTVVEDLNKVFPPEVAVFEPSEAEISHTQK ATLVCLATGFYPDHVELSWWVNGKEVHSGVST DPQPLKEQPALNDSRYCLSSRLRVSATFWQNP RNHFRCQVQFYGLSENDEWTQDRAKPVTQIVS AEAWGRADCGFTSESYQQGVLSATILYEILLG KATLYAVLVSALVLMAMVKRKDSRG | SEQ ID NO: 89 |

| Donor: HD6 | | | | |
|---|---|---|---|---|
| Clonotype | Chain | Region | Amino acid sequence | SEQ ID NO |
| HD6-1 | Alpha (α) | CDR1α | NSMFDY | SEQ ID NO: 90 |
| | | CDR2α | ISSIKDK | SEQ ID NO: 91 |
| | | CDR3α | CAANNARLMF | SEQ ID NO: 92 |
| | | Variable domain | MAMLLGASVLILWLQPDWVNSQQKNDDQQVKQ NSPSLSVQEGRISILNCDYTNSMFDYFLWYKK YPAEGPTFLISISSIKDKNEDGRFTVFLNKSA KHLSLHIVPSQPGDSAVYFCAANNARLMFGDG TQLVVKPN | SEQ ID NO: 93 |
| | | Full-constant domain with TRAC | MAMLLGASVLILWLQPDWVNSQQKNDDQQVKQ NSPSLSVQEGRISILNCDYTNSMFDYFLWYKK YPAEGPTFLISISSIKDKNEDGRFTVFLNKSA KHLSLHIVPSQPGDSAVYFCAANNARLMFGDG TQLVVKPNIQNPDPAVYQLRDSKSSDKSVCLF TDFDSQTNVSQSKDSDVYITDKTVLDMRSMDF KSNSAVAWSNKSDFACANAFNNSIIPEDTFFP SPESSCDVKLVEKSFETDTNLNFQNLSVIGFR ILLLKVAGFNLLMTLRLWSS | SEQ ID NO: 94 |
| HD6-2 | Alpha (α) | CDR1α | NSMFDY | SEQ ID NO: 264 |
| | | CDR2α | ISSIKDK | SEQ ID NO: 265 |
| | | CDR3α | CAASATGNQFYF | SEQ ID NO: 266 |
| | | Variable domain | MAMLLGASVLILWLQPDWVNSQQKNDDQQVKQ NSPSLSVQEGRISILNCDYTNSMFDYFLWYKK YPAEGPTFLISISSIKDKNEDGRFTVFLNKSA KHLSLHIVPSQPGDSAVYFCAASATGNQFYFG TGTSLTVIPN | SEQ ID NO: 267 |

TABLE 1-continued

| | | | | |
|---|---|---|---|---|
| | | Full-with TRAC constant domain | MAMLLGASVLILWLQPDWVNSQQKNDDQQVKQ NSPSLSVQEGRISILNCDYTNSMFDYFLWYKK YPAEGPTFLISISSIKDKNEDGRFTVFLNKSA KHLSLHIVPSQPGDSAVYFCAASATGNQFYFG TGTSLTVIPNIQNPDPAVYQLRDSKSSDKSVC LFTDFDSQTNVSQSKDSDVYITDKTVLDMRSM DFKSNSAVAWSNKSDFACANAFNNSIIPEDTF FPSPESSCDVKLVEKSFETDTNLNFQNLSVIG FRILLLKVAGFNLLMTLRLWSS | SEQ ID NO: 268 |
| HD6-1 | Beta (β) | CDR1β | SGHNS | SEQ ID NO: 95 |
| | | CDR2β | FNNNVP | SEQ ID NO: 96 |
| | | CDR3β | CASSDTAREQFF | SEQ ID NO: 97 |
| | | Variable domain | MDSWTFCCVSLCILVAKHTDAGVIQSPRHEVT EMGQEVTLRCKPISGHNSLFWYRQTMMRGLEL LIYFNNNVPIDDSGMPEDRFSAKMPNASFSTL KIQPSEPRDSAVYFCASSDTAREQFFGPGTR LTVLE | SEQ ID NO: 98 |
| | | Full-with TRBC1 constant domain | MDSWTFCCVSLCILVAKHTDAGVIQSPRHEVT EMGQEVTLRCKPISGHNSLFWYRQTMMRGLEL LIYFNNNVPIDDSGMPEDRFSAKMPNASFSTL KIQPSEPRDSAVYFCASSDTAREQFFGPGTR LTVLEDLNKVFPPEVAVFEPSEAEISHTQKAT LVCLATGFFPDHVELSWWVNGKEVHSGVSTDP QPLKEQPALNDSRYCLSSRLRVSATFWQNPRN HFRCQVQFYGLSENDEWTQDRAKPVTQIVSAE AWGRADCGFTSVSYQQGVLSATILYEILLGKA TLYAVLVSALVLMAMVKRKDF | SEQ ID NO: 99 |
| | | Full-with TRBC2 constant domain | MDSWTFCCVSLCILVAKHTDAGVIQSPRHEVT EMGQEVTLRCKPISGHNSLFWYRQTMMRGLEL LIYFNNNVPIDDSGMPEDRFSAKMPNASFSTL KIQPSEPRDSAVYFCASSDTAREQFFGPGTR LTVLEDLKNVFPPEVAVFEPSEAEISHTQKAT LVCLATGFYPDHVELSWWVNGKEVHSGVSTDP QPLKEQPALNDSRYCLSSRLRVSATFWQNPRN HFRCQVQFYGLSENDEWTQDRAKPVTQIVSAE AWGRADCGFTSESYQQGVLSATILYEILLGKA TLYAVLVSALVLMAMVKRKDSRG | SEQ ID NO: 100 |
| HD6-2 | Beta (β) | CDR1β | SGHRS | SEQ ID NO: 269 |
| | | CDR2β | YFSETQ | SEQ ID NO: 270 |
| | | CDR3β | CASSPGQHGELFF | SEQ ID NO: 271 |
| | | Variable domain | MGSRLLCWVLLCLLGAGPVKAGVTQTPRYLIK TRGQQVTLSCSPISGHRSVSWYQQTPGQGLQF LFEYFSETQRNKGNFPGRFSGRQFSNSRSEMN VSTLELGDSALYLCASSPGQHGELFFGEGSRL TVLE | SEQ ID NO: 272 |
| | | Full-with TRBC1 constant domain | MGSRLLCWVLLCLLGAGPVKAGVTQTPRYLIK TRGQQVTLSCSPISGHRSVSWYQQTPGQGLQF LFEYFSETQRNKGNFPGRFSGRQFSNSRSEMN VSTLELGDSALYLCASSPGQHGELFFGEGSRL TVLEDLNKVFPPEVAVFEPSEAEISHTQKATL VCLATGFFPDHVELSWWVNGKEVHSGVSTDPQ PLKEQPALNDSRYCLSSRLRVSATFWQNPRNH FRCQVQFYGLSENDEWTQDRAKPVTQIVSAEA WGRADCGFTSVSYQQGVLSATILYEILLGKAT LYAVLVSALVLMAMVKRKDF | SEQ ID NO: 273 |
| | | Full-with TRBC2 constant domain | MGSRLLCWVLLCLLGAGPVKAGVTQTPRYLIK TRGQQVTLSCSPISGHRSVSWYQQTPGQGLQF LFEYFSETQRNKGNFPGRFSGRQFSNSRSEMN VSTLELGDSALYLCASSPGQHGELFFGEGSRL TVLEDLKNVFPPEVAVFEPSEAEISHTQKATL VCLATGFYPDHVELSWWVNGKEVHSGVSTDPQ PLKEQPALNDSRYCLSSRLRVSATFWQNPRNH FRCQVQFYGLSENDEWTQDRAKPVTQIVSAEA WGRADCGFTSESYQQGVLSATILYEILLGKAT LYAVLVSALVLMAMVKRKDSRG | SEQ ID NO: 274 |

| Donor: HD7 | | | | |
|---|---|---|---|---|
| Clonotype | Chain | Region | Sequence | SEQ ID NO |
| HD7-1 | Alpha (α) | CDR1α | DSSSTY | SEQ ID NO: 101 |
| | | CDR2α | IFSNMDM | SEQ ID NO: 102 |
| | | CDR3α | CAERLNTDKLIF | SEQ ID NO: 103 |
| | | Variable domain | MKTFAGFSFLFLWLQLDCMSRGEDVEQSLFLS VREGDSSVINCTYTDSSSTYLYWYKQEPGAGL QLLTYIFSNMDMKQDQRLTVLLNKKDKHLSLR IADTQTGDSAIYFCAERLNTDKLIFGTGTRLQ VFPN | SEQ ID NO: 104 |

TABLE 1-continued

| | | | | |
|---|---|---|---|---|
| | | Full- with TRAC constant domain | MKTFAGFSFLFLWLQLDCMSRGEDVEQSLFLS VREGDSSVINCTYTDSSSTYLYWYKQEPGAGL QLLTYIFSNMDMKQDQRLTVLLNKKDKHLSLR IADTQTGDSAIYFCAERLNTDKLIFGTGTRLQ VFPNIQNPDPAVYQLRDSKSSDKSVCLFTDFD SQTNVSQSKDSDVYITDKTVLDMRSMDFKSNS AVAWSNKSDFACANAFNNSIIPEDTFFPSPES SCDVKLVEKSFETDTNLNFQNLSVIGFRILLL KVAGFNLLMTLRLWSS | SEQ ID NO: 105 |
| HD7-2 | Alpha (α) | CDR1α | DSVNN | SEQ ID NO: 106 |
| | | CDR2α | IPSGT | SEQ ID NO: 107 |
| | | CDR3α | CAVEATDSWGKLQF | SEQ ID NO: 108 |
| | | Variable domain | MKRILGALLGLLSAQVCCVRGIQVEQSPPDLI LQEGANSTLRCNFSDSVNNLQWFHQNPWGQLI NLFYIPSGTKQNGRLSATTVATERYSLLYISS SQTTDSGVYFCAVEATDSWGKLQFGAGTQVVV TPD | SEQ ID NO: 109 |
| | | Full- with TRAC constant domain | MKRILGALLGLLSAQVCCVRGIQVEQSPPDLI LQEGANSTLRCNFSDSVNNLQWFHQNPWGQLI NLFYIPSGTKQNGRLSATTVATERYSLLYISS SQTTDSGVYFCAVEATDSWGKLQFGAGTQVVV TPDIQNPDPAVYQLRDSKSSDKSVCLFTDFDS QTNVSQSKDSDVYITDKTVLDMRSMDFKSNSA VAWSNKSDFACANAFNNSIIPEDTFFPSPESS CDVKLVEKSFETDTNLNFQNLSVIGFRILLLK VAGFNLLMTLRLWSS | SEQ ID NO: 110 |
| HD7-3 | Alpha (α) | CDR1α | DSASNY | SEQ ID NO: 111 |
| | | CDR2α | IRSNVGE | SEQ ID NO: 112 |
| | | CDR3α | CAVRTSYDKVIF | SEQ ID NO: 113 |
| | | Variable domain | MTSIRAVFIFLWLQLDLVNGENVEQHPSTLSV QEGDSAVIKCTYSDSASNYFPWYKQELGKRPQ LIIDIRSNVGEKKDQRIAVTLNKTAKHFSLHI TETQPEDSAVYFCAVRTSYDKVIFGPGTSLSV IPN | SEQ ID NO: 114 |
| | | Full- with TRAC constant domain | MTSIRAVFIFLWLQLDLVNGENVEQHPSTLSV QEGDSAVIKCTYSDSASNYFPWYKQELGKRPQ LIIDIRSNVGEKKDQRIAVTLNKTAKHFSLHI TETQPEDSAVYFCAVRTSYDKVIFGPGTSLSV IPNIQNPDPAVYQLRDSKSSDKSVCLFTDFDS QTNVSQSKDSDVYITDKTVLDMRSMDFKSNSA VAWSNKSDFACANAFNNSIIPEDTFFPSPESS CDVKLVEKSFETDTNLNFQNLSVIGFRILLLK VAGFNLLMTLRLWSS | SEQ ID NO: 160 |
| HD7-4 | Alpha (α) | CDR1α | TSINN | SEQ ID NO: 275 |
| | | CDR2α | IRSNERE | SEQ ID NO: 276 |
| | | CDR3α | CATDGDSSYKLIF | SEQ ID NO: 277 |
| | | Variable domain | METLLGVSLVILWLQLARVNSQQGEEDPQALS IQEGENATMNCSYKTSINNLQWYRQNSGRGLV HLILIRSNEREKHSGRLRVTLDTSKKSSSLLI TASRAADTASYFCATDGDSSYKLIFGSGTRLL VRPD | SEQ ID NO: 278 |
| | | Full- with TRAC constant domain | METLLGVSLVILWLQLARVNSQQGEEDPQALS IQEGENATMNCSYKTSINNLQWYRQNSGRGLV HLILIRSNEREKHSGRLRVTLDTSKKSSSLLI TASRAADTASYFCATDGDSSYKLIFGSGTRLL VRPDIQNPDPAVYQLRDSKSSDKSVCLFTDFD SQTNVSQSKDSDVYITDKTVLDMRSMDFKSNS AVAWSNKSDFACANAFNNSIIPEDTFFPSPES SCDVKLVEKSFETDTNLNFQNLSVIGFRILLL KVAGFNLLMTLRLWSS | SEQ ID NO: 279 |
| HD7-1 | Beta (β) | CDR1β | DFQATT | SEQ ID NO: 161 |
| | | CDR2β | SNEGSKA | SEQ ID NO: 162 |
| | | CDR3β | CSARDSVSGNTIYF | SEQ ID NO: 163 |
| | | Variable domain | MLLLLLLLGPGISLLLPGSLAGSGLGAVVSQH PSWVICKSGTSVKIECRSLDFQATTMFWYRQF PKQSLMLMATSNEGSKATYEQGVEKDKFLINH ASLTLSTLTVTSAHPEDSSFYICSARDSVSGN TIYFGEGSWLTVVE | SEQ ID NO: 164 |
| | | Full- with TRBC1 constant domain | MLLLLLLLGPGISLLLPGSLAGSGLGAVVSQH PSWVICKSGTSVKIECRSLDFQATTMFWYRQF PKQSLMLMATSNEGSKATYEQGVEKDKFLINH ASLTLSTLTVTSAHPEDSSFYICSARDSVSGN TIYFGEGSWLTVVEDLNKVFPPEVAVFEPSEA EISHTQKATLVCLATGFFPDHVELSWWVNGKE VHSGVSTDPQPLKEQPALNDSRYCLSSRLRVS ATFWQNPRNHFRCQVQFYGLSENDEWTQDRAK | SEQ ID NO: 165 |

TABLE 1-continued

| | | | | |
|---|---|---|---|---|
| | | Full- with TRBC2 constant domain | PVTQIVSAEAWGRADCGFTSVSYQQGVLSATI LYEILLGKATLYAVLVSALVLMAMVKRKDF MLLLLLLLGPGISLLLPGSLAGSGLGAVVSQH PSWVICKSGTSVKIECRSLDFQATTMFWYRQF PKQSLMLMATSNEGSKATYEQGVEKDKFLINH ASLTLSTLTVTSAHPEDSSFYICSARDSVSGN TIYFGEGSWLTVVEDLKNVFPPEVAVFEPSEA EISHTQKATLVCLATGFYPDHVELSWWVNGKE VHSGVSTDPQPLKEQPALNDSRYCLSSRLRVS ATFWQNPRNHFRCQVQFYGLSENDEWTQDRAK PVTQIVSAEAWGRADCGFTSESYQQGVLSATI LYEILLGKATLYAVLVSALVLMAMVKRKDSRG | SEQ ID NO: 166 |
| HD7-2 | Beta (β) | CDR1β | SQVTM | SEQ ID NO: 167 |
| | | CDR2β | ANQGSEA | SEQ ID NO: 168 |
| | | CDR3β | CSVGGSGSYNEQFF | SEQ ID NO: 169 |
| | | Variable domain | MLSLLLLLLGLGSVFSAVISQKPSRDICQRGT SLTIQCQVDSQVTMMFWYRQQPGQSLTLTATA NQGSEATYESGFVIDKFPISRPNLTFSTLTVS NMSPEDSSIYLCSVGGSGSYNEQFFGPGTRLT VLE | SEQ ID NO: 170 |
| | | Full- with TRBC1 constant domain | MLSLLLLLLGLGSVFSAVISQKPSRDICQRGT SLTIQCQVDSQVTMMFWYRQQPGQSLTLTATA NQGSEATYESGFVIDKFPISRPNLTFSTLTVS NMSPEDSSIYLCSVGGSGSYNEQFFGPGTRLT VLEDLNKVFPPEVAVFEPSEAEISHTQKATLV CLATGFFPDHVELSWWVNGKEVHSGVSTDPQP LKEQPALNDSRYCLSSRLRVSATFWQNPRNHF RCQVQFYGLSENDEWTQDRAKPVTQIVSAEAW GRADCGFTSVSYQQGVLSATILYEILLGKATL YAVLVSALVLMAMVKRKDF | SEQ ID NO: 171 |
| | | Full- with TRBC2 constant domain | MLSLLLLLLGLGSVFSAVISQKPSRDICQRGT SLTIQCQVDSQVTMMFWYRQQPGQSLTLTATA NQGSEATYESGFVIDKFPISRPNLTFSTLTVS NMSPEDSSIYLCSVGGSGSYNEQFFGPGTRLT VLEDLNKVFPPEVAVFEPSEAEISHTQKATLV CLATGFYPDHVELSWWVNGKEVHSGVSTDPQP LKEQPALNDSRYCLSSRLRVSATFWQNPRNHF RCQVQFYGLSENDEWTQDRAKPVTQIVSAEAW GRADCGFTSESYQQGVLSATILYEILLGKATL YAVLVSALVLMAMVKRKDSRG | SEQ ID NO: 172 |
| HD7-3 | Beta (β) | CDR1β | DFQATT | SEQ ID NO: 280 |
| | | CDR2β | SNEGSKA | SEQ ID NO: 281 |
| | | CDR3β | CSARDVLTGDYGYTF | SEQ ID NO: 282 |
| | | Variable domain | MLLLLLLLGPGISLLLPGSLAGSGLGAVVSQH PSWVICKSGTSVKIECRSLDFQATTMFWYRQF PKQSLMLMATSNEGSKATYEQGVEKDKFLINH ASLTLSTLTVTSAHPEDSSFYICSARDVLTGD YGYTFGSGTRLTVV | SEQ ID NO: 283 |
| | | Full- with TRBC1 constant domain | MLLLLLLLGPGISLLLPGSLAGSGLGAVVSQH PSWVICKSGTSVKIECRSLDFQATTMFWYRQF PKQSLMLMATSNEGSKATYEQGVEKDKFLINH ASLTLSTLTVTSAHPEDSSFYICSARDVLTGD YGYTFGSGTRLTVVEDLNKVFPPEVAVFEPSE AEISHTQKATLVCLATGFFPDHVELSWWVNGK EVHSGVSTDPQPLKEQPALNDSRYCLSSRLRV SATFWQNPRNHFRCQVQFYGLSENDEWTQDRA KPVTQIVSAEAWGRADCGFTSVSYQQGVLSAT ILYEILLGKATLYAVLVSALVLMAMVKRKDF | SEQ ID NO: 284 |
| | | Full- with TRBC2 constant domain | MLLLLLLLGPGISLLLPGSLAGSGLGAVVSQH PSWVICKSGTSVKIECRSLDFQATTMFWYRQF PKQSLMLMATSNEGSKATYEQGVEKDKFLINH ASLTLSTLTVTSAHPEDSSFYICSARDVLTGD YGYTFGSGTRLTVVEDLKNVFPPEVAVFEPSE AEISHTQKATLVCLATGFYPDHVELSWWVNGK EVHSGVSTDPQPLKEQPALNDSRYCLSSRLRV SATFWQNPRNHFRCQVQFYGLSENDEWTQDRA KPVTQIVSAEAWGRADCGFTSESYQQGVLSAT ILYEILLGKATLYAVLVSALVLMAMVKRKDSR G | SEQ ID NO: 285 |
| HD7-4 | Beta (β) | CDR1β | SGHDY | SEQ ID NO: 286 |
| | | CDR2β | FNNNVP | SEQ ID NO: 287 |
| | | CDR3β | CASSLGLSISQETQYF | SEQ ID NO: 288 |
| | | Variable domain | MGSWTLCCVSLCILVAKHTDAGVIQSPRHEVT EMGQEVTLRCKPISGHDYLFWYRQTMMRGLEL LIYFNNNVPIDDSGMPEDRFSAKMPNASFSTL KIQPSEPRDSAVYFCASSLGLSISQETQYFGP GTRLLVLE | SEQ ID NO: 289 |

TABLE 1-continued

| | | | |
|---|---|---|---|
| | Full- with TRBC1 constant domain | MGSWTLCCVSLCILVAKHTDAGVIQSPRHEVT EMGQEVTLRCKPISGHDYLFWYRQTMMRGLEL LIYFNNNVPIDDSGMPEDRFSAKMPNASFSTL KIQPSEPRDSAVYFCASSLGLSISQETQYFGP GTRLLVLEDLNKVFPPEVAVFEPSEAEISHTQ KATLVCLATGFFPDHVELSWWVNGKEVHSGVS TDPQPLKEQPALNDSRYCLSSRLRVSATFWQN PRNHFRCQVQFYGLSENDEWTQDRAKPVTQIV SAEAWGRADCGFTSVSYQQGVLSATILYEILL GKATLYAVLVSALVLMAMVKRKDF | SEQ ID NO: 290 |
| | Full- with TRBC2 constant domain | MGSWTLCCVSLCILVAKHTDAGVIQSPRHEVT EMGQEVTLRCKPISGHDYLFWYRQTMMRGLEL LIYFNNNVPIDDSGMPEDRFSAKMPNASFSTL KIQPSEPRDSAVYFCASSLGLSISQETQYFGP GTRLLVLEDLKNVFPPEVAVFEPSEAEISHTQ KATLVCLATGFYPDHVELSWWVNGKEVHSGVS TDPQPLKEQPALNDSRYCLSSRLRVSATFWQN PRNHFRCQVQFYGLSENDEWTQDRAKPVTQIV SAEAWGRADCGFTSESYQQGVLSATILYEILL GKATLYAVLVSALVLMAMVKRKDSRG | SEQ ID NO: 291 |

Donor: HD8

| Chain | Region | Amino acid sequence | SEQ ID NO |
|---|---|---|---|
| Alpha (α) | CDR1α | VGISA | SEQ ID NO: 173 |
| | CDR2α | LSSGK | SEQ ID NO: 174 |
| | CDR3α | CAVTVGNKLVF | SEQ ID NO: 175 |
| | Variable domain | MVKIRQFLLAILWLQLSCVSAAKNEVEQSPQNLTAQEGEFIT INCSYSVGISALHWLQQHPGGGIVSLFMLSSGKKKHGRLIAT INIQEKHSSLHITASHPRDSAVYICAVTVGNKLVFGAGTILR VKSY | SEQ ID NO: 176 |
| | Full- with TRAC constant domain | MVKIRQFLLAILWLQLSCVSAAKNEVEQSPQNLTAQEGEFIT INCSYSVGISALHWLQQHPGGGIVSLFMLSSGKKKHGRLIAT INIQEKHSSLHITASHPRDSAVYICAVTVGNKLVFGAGTILR VKSYIQNPDPAVYQLRDSKSSDKSVCLFTDFDSQTNVSQSKD SDVYITDKTVLDMRSMDFKSNSAVAWSNKSDFACANAFNNSI IPEDTFFPSPESSCDVKLVEKSFETDTNLNFQNLSVIGFRIL LLKVAGFNLLMTLRLWSS | SEQ ID NO: 177 |
| Beta (β) | CDR1β | MNHNS | SEQ ID NO: 178 |
| | CDR2β | SASEGT | SEQ ID NO: 179 |
| | CDR3β | CASRGWREQFF | SEQ ID NO: 180 |
| | Variable domain | MSIGLLCCVAFSLLWASPVNAGVTQTPKFQVLKTGQSMTLQC AQDMNHNSMYWYRQDPGMGLRLIYYSASEGTTDKGEVPNGYN VSRLNKREFSLRLESAAPSQTSVYFCASRGWREQFFGPGTRL TVLE | SEQ ID NO: 181 |
| | Full- with TRBC1 constant domain | MSIGLLCCVAFSLLWASPVNAGVTQTPKFQVLKTGQSMTLQC AQDMNHNSMYWYRQDPGMGLRLIYYSASEGTTDKGEVPNGYN VSRLNKREFSLRLESAAPSQTSVYFCASRGWREQFFGPGTRL TVLEDLNKVFPPEVAVFEPSEAEISHTQKATLVCLATGFFPD HVELSWWVNGKEVHSGVSTDPQPLKEQPALNDSRYCLSSRLR VSATFWQNPRNHFRCQVQFYGLSENDEWTQDRAKPVTQIVSA EAWGRADCGFTSVSYQQGVLSATILYEILLGKATLYAVLVSA LVLMAMVKRKDF | SEQ ID NO: 182 |
| | Full- with TRBC2 constant domain | MSIGLLCCVAFSLLWASPVNAGVTQTPKFQVLKTGQSMTLQC AQDMNHNSMYWYRQDPGMGLRLIYYSASEGTTDKGEVPNGYN VSRLNKREFSLRLESAAPSQTSVYFCASRGWREQFFGPGTRL TVLEDLKNVFPPEVAVFEPSEAEISHTQKATLVCLATGFYPD HVELSWWVNGKEVHSGVSTDPQPLKEQPALNDSRYCLSSRLR VSATFWQNPRNHFRCQVQFYGLSENDEWTQDRAKPVTQIVSA EAWGRADCGFTSESYQQGVLSATILYEILLGKATLYAVLVSA LVLMAMVKRKDSRG | SEQ ID NO: 183 |

Donor: HD9

| Clonotype | Chain | Region | Sequence | SEQ ID NO |
|---|---|---|---|---|
| HD9-1 | Alpha (α) | CDR1α | VGISA | SEQ ID NO: 184 |
| | | CDR2α | LSSGK | SEQ ID NO: 185 |
| | | CDR3α | CAARSYNTDKLIF | SEQ ID NO: 186 |
| | | Variable domain | MVKIRQFLLAILWLQLSCVSAAKNEVEQSPQN LTAQEGEFITINCSYSVGISALHWLQQHPGGG IVSLFMLSSGKKKHGRLIATINIQEKHSSLHI TASHPRDSAVYICAARSYNTDKLIFGTGTRLQ VFPN | SEQ ID NO: 187 |
| | | Full- with TRAC constant domain | MVKIRQFLLAILWLQLSCVSAAKNEVEQSPQN LTAQEGEFITINCSYSVGISALHWLQQHPGGG IVSLFMLSSGKKKHGRLIATINIQEKHSSLHI TASHPRDSAVYICAARSYNTDKLIFGTGTRLQ | SEQ ID NO: 188 |

TABLE 1-continued

|  |  |  | VFPNIQNPDPAVYQLRDSKSSDKSVCLFTDFD SQTNVSQSKDSDVYITDKTVLDMRSMDFKSNS AVAWSNKSDFACANAFNNSIIPEDTFFPSPES SCDVKLVEKSFETDTNLNFQNLSVIGFRILLL KVAGFNLLMTLRLWSS |  |
| --- | --- | --- | --- | --- |
| HD9-2 | Alpha (α) | CDR1α | NSMFDY | SEQ ID NO: 189 |
|  |  | CDR2α | ISSIKDK | SEQ ID NO: 190 |
|  |  | CDR3α | CAASYNNARLMF | SEQ ID NO: 191 |
|  |  | Variable domain | MAMLLGASVLILWLQPDWVNSQQKNDDQQVKQ NSPSLSVQEGRISILNCDYTNSMFDYFLWYKK YPAEGPTFLISISSIKDKNEDGRFTVFLNKSA KHLSLHIVPSQPGDSAVYFCAASYNNARLMFG DGTQLVVKPN | SEQ ID NO: 192 |
|  |  | Full- with TRAC constant domain | MAMLLGASVLILWLQPDWVNSQQKNDDQQVKQ NSPSLSVQEGRISILNCDYTNSMFDYFLWYKK YPAEGPTFLISISSIKDKNEDGRFTVFLNKSA KHLSLHIVPSQPGDSAVYFCAASYNNARLMFG DGTQLVVKPNIQNPDPAVYQLRDSKSSDKSVC LFTDFDSQTNVSQSKDSDVYITDKTVLDMRSM DFKSNSAVAWSNKSDFACANAFNNSIIPEDTF FPSPESSCDVKLVEKSFETDTNLNFQNLSVIG FRILLLKVAGFNLLMTLRLWSS | SEQ ID NO: 193 |
| HD9-1 | Beta (β) | CDR1β | SGHTS | SEQ ID NO: 194 |
|  |  | CDR2β | YDEGEE | SEQ ID NO: 195 |
|  |  | CDR3β | CASSWGYQETQYF | SEQ ID NO: 196 |
|  |  | Variable domain | MGPRLLFWALLCLLGTGPVEAGVTQSPTHLIK TRGQQATLRCSPISGHTSVYWYQQALGLGLQF LLWYDEGEERNRGNFPPRFSGRQFPNYSSELN VNALELEDSALYLCASSWGYQETQYFGPGTRL LVLE | SEQ ID NO: 197 |
|  |  | Full- with TRBC1 constant domain | MGPRLLFWALLCLLGTGPVEAGVTQSPTHLIK TRGQQATLRCSPISGHTSVYWYQQALGLGLQF LLWYDEGEERNRGNFPPRFSGRQFPNYSSELN VNALELEDSALYLCASSWGYQETQYFGPGTRL LVLEDLNKVFPPEVAVFEPSEAEISHTQKATL VCLATGFFPDHVELSWWVNGKEVHSGVSTDPQ PLKEQPALNDSRYCLSSRLRVSATFWQNPRNH FRCQVQFYGLSENDEWTQDRAKPVTQIVSAEA WGRADCGFTSVSYQQGVLSATILYEILLGKAT LYAVLVSALVLMAMVKRKDF | SEQ ID NO: 198 |
|  |  | Full- with TRBC2 constant domain | MGPRLLFWALLCLLGTGPVEAGVTQSPTHLIK TRGQQATLRCSPISGHTSVYWYQQALGLGLQF LLWYDEGEERNRGNFPPRFSGRQFPNYSSELN VNALELEDSALYLCASSWGYQETQYFGPGTRL LVLEDLKNVFPPEVAVFEPSEAEISHTQKATL VCLATGFYPDHVELSWWVNGKEVHSGVSTDPQ PLKEQPALNDSRYCLSSRLRVSATFWQNPRNH FRCQVQFYGLSENDEWTQDRAKPVTQIVSAEA WGRADCGFTSESYQQGVLSATILYEILLGKAT LYAVLVSALVLMAMVKRKDSRG | SEQ ID NO: 199 |
| HD9-2 | Beta (β) | CDR1β | KGHSH | SEQ ID NO: 200 |
|  |  | CDR2β | LQKENI | SEQ ID NO: 201 |
|  |  | CDR3β | CASSPTGGEYYGYTF | SEQ ID NO: 202 |
|  |  | Variable domain | MDTRVLCCAVICLLGAGLSNAGVMQNPRHLVR RRGQEARLRCSPMKGHSHVYWYRQLPEEGLKF MVYLQKENIIDESGMPKERFSAEFPKEGPSIL RIQQVVRGDSAAYFCASSPTGGEYYGYTFGSG TRLTVVE | SEQ ID NO: 203 |
|  |  | Full- with TRBC1 constant domain | MDTRVLCCAVICLLGAGLSNAGVMQNPRHLVR RRGQEARLRCSPMKGHSHVYWYRQLPEEGLKF MVYLQKENIIDESGMPKERFSAEFPKEGPSIL RIQQVVRGDSAAYFCASSPTGGEYYGYTFGSG TRLTVVEDLNKVFPPEVAVFEPSEAEISHTQK ATLVCLATGFFPDHVELSWWVNGKEVHSGVST DPQPLKEQPALNDSRYCLSSRLRVSATFWQNP RNHFRCQVQFYGLSENDEWTQDRAKPVTQIVS AEAWGRADCGFTSVSYQQGVLSATILYEILLG KATLYAVLVSALVLMAMVKRKDF | SEQ ID NO: 204 |
|  |  | Full- with TRBC2 constant domain | MDTRVLCCAVICLLGAGLSNAGVMQNPRHLVR RRGQEARLRCSPMKGHSHVYWYRQLPEEGLKF MVYLQKENIIDESGMPKERFSAEFPKEGPSIL RIQQVVRGDSAAYFCASSPTGGEYYGYTFGSG TRLTVVEDLNKVFPPEVAVFEPSEAEISHTQK ATLVCLATGFYPDHVELSWWVNGKEVHSGVST DPQPLKEQPALNDSRYCLSSRLRVSATFWQNP RNHFRCQVQFYGLSENDEWTQDRAKPVTQIVS | SEQ ID NO: 205 |

TABLE 1-continued

|  |  |  | AEAWGRADCGFTSESYQQGVLSATILYEILLG<br>KATLYAVLVSALVLMAMVKRKDSRG |  |
| --- | --- | --- | --- | --- |
| HD9-3 | Beta (β) | CDR1β | MNHEY | SEQ ID NO: 206 |
|  |  | CDR2β | SVGAGI | SEQ ID NO: 207 |
|  |  | CDR3β | CASSSYPLRTGRYNSYNSPLHF | SEQ ID NO: 208 |
|  |  | Variable domain | MSIGLLCCAALSLLWAGPVNAGVTQTPKFQVL<br>KTGQSMTLQCAQDMNHEYMSWYRQDPGMGLRL<br>IHYSVGAGITDQGEVPNGYNVSRSTTEDFPLR<br>LLSAAPSQTSVYFCASSSYPLRTGRYNSYNSP<br>LHFGNGTRLTVTE | SEQ ID NO: 209 |
|  |  | Full- with TRBC1 constant domain | MSIGLLCCAALSLLWAGPVNAGVTQTPKFQVL<br>KTGQSMTLQCAQDMNHEYMSWYRQDPGMGLRL<br>IHYSVGAGITDQGEVPNGYNVSRSTTEDFPLR<br>LLSAAPSQTSVYFCASSSYPLRTGRYNSYNSP<br>LHFGNGTRLTVTEDLNKVFPPEVAVFEPSEAE<br>ISHTQKATLVCLATGFFPDHVELSWWVNGKEV<br>HSGVSTDPQPLKEQPALNDSRYCLSSRLRVSA<br>TFWQNPRNHFRCQVQFYGLSENDEWTQDRAKP<br>VTQIVSAEAWGRADCGFTSVSYQQGVLSATIL<br>YEILLGKATLYAVLVSALVLMAMVKRKDF | SEQ ID NO: 210 |
|  |  | Full- with TRBC2 constant domain | MSIGLLCCAALSLLWAGPVNAGVTQTPKFQVL<br>KTGQSMTLQCAQDMNHEYMSWYRQDPGMGLRL<br>IHYSVGAGITDQGEVPNGYNVSRSTTEDFPLR<br>LLSAAPSQTSVYFCASSSYPLRTGRYNSYNSP<br>LHFGNGTRLTVTEDLKNVFPPEVAVFEPSEAE<br>ISHTQKATLVCLATGFYPDHVELSWWVNGKEV<br>HSGVSTDPQPLKEQPALNDSRYCLSSRLRVSA<br>TFWQNPRNHFRCQVQFYGLSENDEWTQDRAKP<br>VTQIVSAEAWGRADCGFTSESYQQGVLSATIL<br>YEILLGKATLYAVLVSALVLMAMVKRKDSRG | SEQ ID NO: 211 |

| Donor: HD10 | | | |
| --- | --- | --- | --- |
| Chain | Region | Amino acid sequence | SEQ ID NO |
| Alpha (α) | CDR1α | NSMFDY | SEQ ID NO: 212 |
|  | CDR2α | ISSIKDK | SEQ ID NO: 213 |
|  | CDR3α | CAASGGRDDKIIF | SEQ ID NO: 214 |
|  | Variable domain | MAMLLGASVLILWLQPDWVNSQQKNDDQQVKQNSPSLSVQEG<br>RISILNCDYTNSMFDYFLWYKKYPAEGPTFLISISSIKDKNE<br>DGRFTVFLNKSAKHLSLHIVPSQPGDSAVYFCAASGGRDDKI<br>IFGKGTRLHILPN | SEQ ID NO: 215 |
|  | Full- with TRAC constant domain | MAMLLGASVLILWLQPDWVNSQQKNDDQQVKQNSPSLSVQEG<br>RISILNCDYTNSMFDYFLWYKKYPAEGPTFLISISSIKDKNE<br>DGRFTVFLNKSAKHLSLHIVPSQPGDSAVYFCAASGGRDDKI<br>IFGKGTRLHILPNIQNPDPAVYQLRDSKSSDKSVCLFTDFDS<br>QTNVSQSKDSDVYITDKTVLDMRSMDFKSNSAVAWSNKSDFA<br>CANAFNNSIIPEDTFFPSPESSCDVKLVEKSFETDTNLNFQN<br>LSVIGFRILLLKVAGFNLLMTLRLWSS | SEQ ID NO: 216 |
| Beta (β) | CDR1β | MNHEY | SEQ ID NO: 217 |
|  | CDR2β | SVGAGI | SEQ ID NO: 218 |
|  | CDR3β | CASSYSRTESTDTQYF | SEQ ID NO: 219 |
|  | Variable domain | MSIGLLCCAALSLLWAGPVNAGVTQTPKFQVLKTGQSMTLQC<br>AQDMNHEYMSWYRQDPGMGLRLIHYSVGAGITDQGEVPNGYN<br>VSRSTTEDFPLRLLSAAPSQTSVYFCASSYSRTESTDTQYFG<br>PGTRLTVLE | SEQ ID NO: 220 |
|  | Full- with TRBC1 constant domain | MSIGLLCCAALSLLWAGPVNAGVTQTPKFQVLKTGQSMTLQC<br>AQDMNHEYMSWYRQDPGMGLRLIHYSVGAGITDQGEVPNGYN<br>VSRSTTEDFPLRLLSAAPSQTSVYFCASSYSRTESTDTQYFG<br>PGTRLTVLEDLNKVFPPEVAVFEPSEAEISHTQKATLVCLAT<br>GFFPDHVELSWWVNGKEVHSGVSTDPQPLKEQPALNDSRYCL<br>SSRLRVSATFWQNPRNHFRCQVQFYGLSENDEWTQDRAKPVT<br>QIVSAEAWGRADCGFTSVSYQQGVLSATILYEILLGKATLYA<br>VLVSALVLMAMVKRKDF | SEQ ID NO: 221 |
|  | Full- with TRBC2 constant domain | MSIGLLCCAALSLLWAGPVNAGVTQTPKFQVLKTGQSMTLQC<br>AQDMNHEYMSWYRQDPGMGLRLIHYSVGAGITDQGEVPNGYN<br>VSRSTTEDFPLRLLSAAPSQTSVYFCASSYSRTESTDTQYFG<br>PGTRLTVLEDLKNVFPPEVAVFEPSEAEISHTQKATLVCLAT<br>GFYPDHVELSWWVNGKEVHSGVSTDPQPLKEQPALNDSRYCL<br>SSRLRVSATFWQNPRNHFRCQVQFYGLSENDEWTQDRAKPVT<br>QIVSAEAWGRADCGFTSESYQQGVLSATILYEILLGKATLYA<br>VLVSALVLMAMVKRKDSRG | SEQ ID NO: 222 |

Accordingly, the present invention provides isolated polypeptides comprising one or more amino acid sequences selected from the group consisting of SEQ ID NOs: 1-114 and 160-222, fragments, variants and homologues thereof.

In one aspect, the invention provides a TCR comprising a TCR alpha chain sequence selected from the group consisting of the HD1-HD10 alpha chain sequences of Table 1, and a TCR beta chain sequence independently selected from the group consisting of the HD1-HD10 beta chain sequences of Table 1.

Reduced Mispairing and Improved TCR Expression

The TCR of the invention may be expressed in a T-cell to alter the antigen specificity of the T-cell. TCR-transduced T-cells may express at least two TCR alpha and two TCR beta chains. While the endogenous TCR alpha/beta chains form a receptor that is self-tolerant, the introduced TCR alpha/beta chains form a receptor with defined specificity for the given target antigen.

However, TCR gene therapy requires sufficient expression of transferred TCRs. Trasferred TCR might be diluted by the presence of the endogeneous TCR, resulting in suboptimal expression of the tumor specific TCR. Furthermore, mispairing between endogenous and introduced chains may occur to form novel receptors, which might display unexpected specificities for self-antigens and cause autoimmune damage when transferred into patients.

Hence, several strategies have been explored to reduce the risk of mispairing between endogenous and introduced TCR chains. Mutations of the TCR alpha/beta interface is one strategy currently employed to reduce unwanted mispairing. For example, the introduction of a cysteine in the constant domains of the alpha and beta chain allows the formation of a disulfide bond and enhances the pairing of the introduced chains while reducing mispairing with wild type chains.

Accordingly, the TCRs of the present invention may comprise one or more mutations at the α chain/β chain interface, such that when the α chain and the β chain are expressed in a T-cell, the frequency of mispairing between said chains and endogenous TCR α and β chains is reduced. In one embodiment, the one or more mutations introduce a cysteine residue into the constant region domain of each of the α chain and the β chain, wherein the cysteine residues are capable of forming a disulphide bond between the α chain and the β chain.

Another strategy to reduce mispairing relies on the introduction of polynucleotide sequences encoding siRNA, added to the genes encoding for the tumor specific TCR α and or β chains, and designed to limit the expression of the endogenous TCR genes (Okamoto S. *Cancer research* 69, 9003-9011, 2009).

Accordingly, the vector or polynucleotide encoding the TCRs of the present invention may comprise one or more siRNA or other agents aimed at limiting or abrogating the expression of the endogenous TCR genes.

It is also possible to combine artificial nucleases, such as zinc finger nucleases (ZFN), transcription activator-like effector nucleases (TALEN) or CRISPR/Cas systems, designed to target the constant regions of the endogenous genes, e.g. TCR genes (TRAC and, or TRBC), to obtain the permanent disruption of the endogenous TCR alpha and/or beta chain genes, thus allowing full expression of the tumor specific TCR and thus reducing or abrogating the risk of TCR mispairing. This process, known as the TCR gene editing proved superior to TCR gene transfer in vitro and in vivo (Provasi E., Genovese P., *Nature Medicine* May; 18(5): 807-15; 2012).

Accordingly, the TCRs of the present invention may be used to edit T cell specificity by TCR disruption and genetic addition of the tumor specific TCR.

In addition, the genome editing technology allows targeted integration of a expression cassette, comprising a polynucleotide encoding a TCR of the present invention, and optionally one or more promoter regions and/or other expression control sequences, into an endogenous gene disrupted by the artificial nucleases (Lombardo A., *Nature biotechnology* 25, 1298-1306; 2007).

Accordingly, the TCRs of the present invention may be used to edit T-cell specificity by targeted integration of a polynucleotide encoding a TCR of the present invention at a genomic region. The integration may be targeted by an artificial nuclease.

Another strategy developed to increase expression of the transferred TCR and to reduce TCR mispairing consists in "murinization," which replaces the human TCR α and TCR β constant regions (e.g. the TRAC, TRBC1 and TRBC2 regions) by their murine counterparts. Murizination of TCR constant regions is described in, for example, Sommermeyer and Uckert J Immunol; 2010 (184:6223-6231). Accordingly, the TCRs of the present invention may be murinized.

Isolated Polynucleotide

The present invention relates to an isolated polynucleotide encoding a TCR receptor of the invention or a part thereof, such as the α chain and/or the β chain, a variable domain or a portion thereof.

The isolated polynucleotide may be double or single stranded, and may be RNA or DNA.

It will be understood by a skilled person that numerous different polynucleotides can encode the same polypeptide as a result of the degeneracy of the genetic code. In addition, it is to be understood that the skilled person may, using routine techniques, make nucleotide substitutions, additions or deletions that do not affect the polypeptide sequence encoded by the polynucleotides of the invention to reflect the codon usage of any particular host organism in which the polypeptides of the invention are to be expressed.

The polynucleotides described herein may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with Mrna or Cdna obtained from an animal or human cell, performing a polymerase chain reaction under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

Examples of nucleotide sequences encoding TCRs according to the present invention are provided in the Table 2.

TABLE 2

| DonorChain | Nucleotide sequence | SEQ ID NO |
|---|---|---|
| HD1 α (with TRAC) | ATGGAGACTCTCTCCTGAAAGTGCTTTCAGGCACCTTGTTGTGGcAGTTGACCTGGG<br>TGAGAAGCCAACAACCAGTGCAGAGTCCTCAAGCCGTGATCCTCCGAGAAGGGGA<br>AGATGCTGTCATCAACTGCAGTTCCTCCAAGGCTTTATATTCTGTACACTGGTAC<br>AGGCAGAAGCATGGTGAAGCACCCGTCTTCCTGATGATATTACTGAAGGGTGGAG<br>AACAGAAGGGTCATGAAAAAATATCTGCTTCATTTAATGAAAAAAAGCAGCAAAG<br>CTCCCTGTACCTTACGGCCTCCCAGCTCAGTTACTCAGGAACCTACTTCTGCGGC<br>ACAGTTGGATTAACGACTACAAGCTCAGCTTTGGAGCCGGAACCACAGTAACTG<br>TAAGAGCAAATATCCAGAACCCTGACCCTGCCGTGTACCAGCTGAGAGACTCTAA<br>ATCCAGTGACAAGTCTGTCTGCCTATTCACCGATTTTGATTCTCAAACAAATGTG<br>TCACAAAGTAAGGATTCTGATGTGTATATCACAGACAAAACTGTGCTAGACATGA<br>GGTCTATGGACTTCAAGAGCAACAGTGCTGTGGCCTGGAGCAACAAATCTGACTT<br>TGCATGTGCAAACGCCTTCAACAACAGCATTATTCCAGAAGACACCTTCTTCCCC<br>AGCCCAGAAAGTTCCTGTGATGTCAAGCTGGTCGAGAAAAGCTTTGAAACAGATA<br>CGAACCTAAACTTTCAAAACCTGTCAGTGATTGGGTTCCGAATCCTCCTCCTGAA<br>AGTGGCCGGGTTTAATCTGCTCATGACGCTGCGGCTGTGGTCCAGC | SEQ ID NO: 132 |
| β (with TRBC1) | ATGGGCTCCTGGACCCTCTGCTGTGTGTCCCTTTGCATCCTGGTAGCAAAGCACA<br>CAGATGCTGGAGTTATCCAGTCACCCCGGCACGAGGTGACAGAGATGGGACAAGA<br>AGTGACTCTGAGATGTAAACCAATTTCAGGACACGACTACCTTTTCTGGTACAGA<br>CAGACCATGATGCGGGGACTGGAGTTGCTCATTTACTTTAACAACAACGTTCCGA<br>TAGATGATTCAGGGATGCCCGAGGATCGATTCTCAGCTAAGATGCCTAATGCATC<br>ATTCTCCACTCTGAAGATCCAGCCCTCAGAACCCAGGGACTCAGCTGTGTACTTC<br>TGTGCCAGCAGAAAAACCGGGGGATATAGCAATCAGCCCCAGCATTTTGGTGATG<br>GGACTCGACTCTCCATCCTAGAGGACCTGAACAAGGTGTTCCCACCCGAGGTCGC<br>TGTGTTTGAGCCATCAGAAGCAGAGATCTCCCACACCCAAAAGGCCACACTGGTG<br>TGCCTGGCCACAGGCTTCTTCCCCGACCACGTGGAGCTGAGCTGGTGGGTGAATG<br>GGAAGGAGGTGCACAGTGGGGTCAGCACGGACCCGCAGCCCCTCAAGGAGCAGCC<br>CGCCCTCAATGACTCCAGATACTGCCTGAGCAGCCGCCTGAGGGTCTCGGCCACC<br>TTCTGGCAGAACCCCCGCAACCACTTCCGCTGTCAAGTCCAGTTCTACGGGCTCT<br>CGGAGAATGACGAGTGGACCCAGGATAGGGCCAAACCCGTCACCCAGATCGTCAG<br>CGCCGAGGCCTGGGGTAGAGCAGACTGTGGCTTTACCTCGGTGTCCTACCAGCAA<br>GGGGTCCTGTCTGCCACCATCCTCTATGAGATCCTGCTAGGGAAGGCCACCCTGT<br>ATGCTGTGCTGGTCAGCGCCCTTGTGTTGATGGCCATGGTCAAGAGAAAGGATTT<br>C | SEQ ID NO: 133 |
| β (with TRBC2) | ATGGGCTCCTGGACCCTCTGCTGTGTGTCCCTTTGCATCCTGGTAGCAAAGCACA<br>CAGATGCTGGAGTTATCCAGTCACCCCGGCACGAGGTGACAGAGATGGGACAAGA<br>AGTGACTCTGAGATGTAAACCAATTTCAGGACACGACTACCTTTCTGGTACAGA<br>CAGACCATGATGCGGGGACTGGAGTTGCTCATTTACTTTAACAACAACGTTCCGA<br>TAGATGATTCAGGGATGCCCGAGGATCGATTCTCAGCTAAGATGCCTAATGCATC<br>ATTCTCCACTCTGAAGATCCAGCCCTCAGAACCCAGGGACTCAGCTGTGTACTTC<br>TGTGCCAGCAGAAAAACCGGGGGATATAGCAATCAGCCCCAGCATTTTGGTGATG<br>GGACTGACTCTCCATCCTAGAGGACCTGAAAAACGTGTTCCCACCCGAGGTCGC<br>TGTGTTTGAGCCATCAGAAGCAGAGATCTCCCACACCCAAAAGGCCACACTGGTG<br>TGCCTGGCCACAGGCTTCTACCCCGACCACGTGGAGCTGAGCTGGTGGGTGAATG<br>GGAAGGAGGTGCACAGTGGGGTCAGCACAGACCCGCAGCCCCTCAAGGAGCAGCC<br>CGCCCTCAATGACTCCAGATACTGCCTGAGCAGCCGCCTGAGGGTCTCGGCCACC<br>TTCTGGCAGAACCCCCGCAACCACTTCCGCTGTCAAGTCCAGTTCTACGGGCTCT<br>CGGAGAATGACGAGTGGACCCAGGATAGGGCCAAACCTGTCACCCAGATCGTCAG<br>CGCCGAGGCCTGGGGTAGAGCAGACTGTGGCTTCACCTCCGAGTCTTACCAGCAA<br>GGGGTCCTGTCTGCCACCATCCTCTATGAGATCTTGCTAGGGAAGGCCACCTTGT<br>ATGCCGTGCTGGTCAGTGCCCTCGTGCTGATGGCCATGGTCAAGAGAAAGGATTC<br>CAGAGGC | SEQ ID NO: 134 |
| HD2-1α (with TRAC) | ATGCTCCTGCTGCTCGTCCCAGTGCTCGAGGTGATTTTTACCCTGGGAGGAACCA<br>GAGCCCAGTCGGTGACCCAGCTTGGCAGCCACGTCTCTGTCTCTGAAGGAGCCCT<br>GGTTCTGCTGAGGTGCAACTACTCATCGTCTGTTCCACCATATCTCTTCTGGTAT<br>GTGCAATACCCCAACCAAGGACTCCAGCTTCTCCTGAAGTACACATCAGCGGCCA<br>CCCTGGTTAAAGGCATCAACGGTTTTGAGGCTGAATTTAAGAAGAGTGAAACCTC<br>CTTCCACCTGACGAAACCCTCAGCCCATATGAGCGACGCGGCTGAGTACTTCTGT<br>GCTGTGAGATTATCTGGTTCTGCAAGGCAACTGACCTTTGGATCTGGGACACAAT<br>TGACTGTTTTACCTGATATCCAGAACCCTGACCCTGCCGTGTACCAGCTGAGAGA<br>CTCTAAATCCAGTGACAAGTCTGTCTGCCTATTCACCGATTTTGATTCTCAAACA<br>AATGTGTCACAAAGTAAGGATTCTGATGTGTATATCACAGACAAAACTGTGCTAG<br>ACATGAGGTCTATGGACTTCAAGAGCAACAGTGCTGTGGCCTGGAGCAACAAATC<br>TGACTTTGCATGTGCAAACGCCTTCAACAACAGCATTATTCCAGAAGACACCTTC<br>TTCCCCAGCCCAGAAAGTTCCTGTGATGTCAAGCTGGTCGAGAAAAGCTTTGAAA<br>CAGATACGAACCTAAACTTTCAAAACCTGTCAGTGATTGGGTTCCGAATCCTCCT<br>CCTGAAAGTGGCCGGGTTTAATCTGCTCATGACGCTGCGGCTGTGGTCCAGC | SEQ ID NO: 135 |
| β (with TRBC1) | ATGGGCACCAGGCTCCTCTGCTGGGCGGCCCTCTGTCTCCTGGGAGCAGAACTCA<br>CAGAAGCTGGAGTTGCCCAGTCTCCCAGATATAAGATTATAGAGAAAAGGCAGAG<br>TGTGGCTTTTTGGTGCAATCCTATATCTGGCCATGCTACCCTTTACTGGTACCAG<br>CAGATCCTGGGACAGGGCCCAAAGCTTCTGATTCAGTTTCAGAATAACGGTGTAG<br>TGGATGATTCACAGTTGCCTAAGGATCGATTTTCTGCAGAGAGGCTCAAAGGAGT<br>AGACTCCACTCTCAAGATCCAGCCTGCAAAGCTTGAGGACTCGGCCGTGTATCTC<br>TGTGCCAGCAGCTTACTGGGACGAGCAGTACTTCGGGCCGGGCACCAGGCTCA<br>CGGTCACAGAGGACCTGAACAAGGTGTTCCCACCCGAGGTCGCTGTGTTTGAGCC<br>ATCAGAAGCAGAGATCTCCCACACCCAAAAGGCCACACTGGTGTGCCTGGCCACA<br>GGCTTCTTCCCCGACCACGTGGAGCTGAGCTGGTGGGTGAATGGGAAGGAGGTGC<br>ACAGTGGGGTCAGCACGGACCCGCAGCCCCTCAAGGAGCAGCCCGCCCTCAATGA | SEQ ID NO: 136 |

TABLE 2 -continued

| DonorChain | Nucleotide sequence | SEQ ID NO |
|---|---|---|
|  | CTCCAGATACTGCCTGAGCAGCCGCCTGAGGGTCTCGGCCACCTTCTGGCAGAAC<br>CCCCGCAACCACTTCCGCTGTCAAGTCCAGTTCTACGGGCTCTCGGAGAATGACG<br>AGTGGACCCAGGATAGGGCCAAACCCGTCACCCAGATCGTCAGCGCCGAGGCCTG<br>GGGTAGAGCAGACTGTGGCTTTACCTCGGTGTCCTACCAGCAAGGGGTCCTGTCT<br>GCCACCATCCTCTATGAGATCCTGCTAGGGAAGGCCACCCTGTATGCTGTGCTGG<br>TCAGCGCCCTTGTGTTGATGGCCATGGTCAAGAGAAAGGATTTC |  |
| β (with TRBC2) | ATGGGCACCAGGCTCCTCTGCTGGGCGGCCCTCTGTCTCCTGGGAGCAGAACTCA<br>CAGAAGCTGGAGTTGCCCAGTCTCCCAGATATAAGATTATAGAGAAAAGGCAGAG<br>TGTGGCTTTTTGGTGCAATCCTATATCTGGCCATGCTACCCTTTACTGGTACCAG<br>CAGATCCTGGGACAGGGCCCAAAGCTTCTGATTCAGTTTCAGAATAACGGTGTAG<br>TGGATGATTCACAGTTGCCTAAGGATCGATTTTCTGCAGAGAGGCTCAAAGGAGT<br>AGACTCCACTCTCAAGATCCAGCCTGCAAAGCTTGAGGACTCGGCCGTGTATCTC<br>TGTGCCAGCAGCTTACTGGGAGACGAGCAGTACTTCGGGCCGGGCACCAGGCTCA<br>CGGTCACAGAGGACCTGAAAAACGTGTTCCCACCCGAGGTCGCTGTGTTTGAGCC<br>ATCAGAAGCAGAGATCTCCCACACCCAAAAGGCCACACTGGTGTGCCTGGCCACA<br>GGCTTCTACCCCGACCACGTGGAGCTGAGCTGGTGGGTGAATGGGAAGGAGGTGC<br>ACAGTGGGGTCAGCACAGACCCGCAGCCCCTCAAGGAGCAGCCCGCCCTCAATGA<br>CTCCAGATACTGCCTGAGCAGCCGCCTGAGGGTCTCGGCCACCTTCTGGCAGAAC<br>CCCCGCAACCACTTCCGCTGTCAAGTCCAGTTCTACGGGCTCTCGGAGAATGACG<br>AGTGGACCCAGGATAGGGCCAAACCTGTCACCCAGATCGTCAGCGCCGAGGCCTG<br>GGGTAGAGCAGACTGTGGCTTCACCTCCGAGTCTTACCAGCAAGGGGTCCTGTCT<br>GCCACCATCCTCTATGAGATCTTGCTAGGGAAGGCCACCTTGTATGCCGTGCTGG<br>TCAGTGCCCTCGTGCTGATGGCCATGGTCAAGAGAAAGGATTCCAGAGGC | SEQ ID NO: 137 |
| HD2-2α (with TRAC) | ATGGCATGCCCTGGCTTCCTGTGGGCACTTGTGATCTCCACCTGTCTTGAATTTA<br>GCATGGCTCAGACAGTCACTCAGTCTCAACCAGAGATGTCTGTGCAGGAGGCAGA<br>GACCGTGACCCTGAGCTGCACATATGACACCAGTGAGAGTGATTATTATTATTC<br>TGGTACAAGCAGCCTCCCAGCAGGCAGATGATTCTCGTTATTCGCCAAGAAGCTT<br>ATAAGCAACAGAATGCAACAGAGAATCGTTTCTCTGTGAACTTCCAGAAAGCAGC<br>CAAATCCTTCAGTCTCAAGATCTCAGACTCACAGCTGGGGATGCCGCGATGTAT<br>TTCTGTGCTTATAGGAGTCTAAAATATGGAAACAAACTGGTCTTTGGCAGGAA<br>CCATTCTGAGAGTCAAGTCCTATATCCAGAACCCTGACCCTGCCGTGTACCAGCT<br>GAGAGACTCTAAATCCAGTGACAAGTCTGTCTGCCTATTCACCGATTTTGATTCT<br>CAAACAAATGTGTCACAAAGTAAGGATTCTGATGTGTATATCACAGACAAAACTG<br>TGCTAGACATGAGGTCTATGGACTTCAAGAGCAACAGTGCTGTGGCCTGGAGCAA<br>CAAATCTGACTTTGCATGTGCAAACGCCTTCAACAACAGCATTATTCCAGAAGAC<br>ACCTTCTTCCCCAGCCCAGAAAGTTCCTGTGATGTCAAGCTGGTCGAGAAAAGCT<br>TTGAAACAGATACGAACCTAAACTTTCAAAACCTGTCAGTGATTGGGTTCCGAAT<br>CCTCCTCCTGAAAGTGGCCGGGTTTAATCTGCTCATGACGCTGCGGCTGTGGTCC<br>AGC | SEQ ID NO: 138 |
| β (with TRBC1) | ATGGGCACCAGGCTCCTCTTCTGGGTGGCCTTCTGTCTCCTGGGGGCAGATCACA<br>CAGGAGCTGGAGTCTCCCAGTCCCCAGTAACAAGGTCACAGAGAAGGGAAAGGA<br>TGTAGAGCTCAGGTGTGATCCAATTTCAGGTCATACTGCCCTTTACTGGTACCGA<br>CAGAGCCTGGGGCAGGGCCTGGAGTTTTTAATTTACTTCCAAGGCAACAGTGCAC<br>CAGACAAATCAGGGCTGCCCAGTGATCGCTTCTCTGCAGAGAGGACTGGGGGATC<br>CGTCTCCACTCTGACGATCCAGCGCACACAGCAGGAGGACTCGGCCGTGTATCTC<br>TGTGCCAGCAGCTTGGTAGCTTTACAGGGTGCGGGCGAGCAGTACTTCGGGCCGG<br>GCACCAGGCTCACGGTCACAGAGGACCTGAACAAGGTGTTCCCACCCGAGGTCGC<br>TGTGTTTGAGCCATCAGAAGCAGAGATCTCCCACACCCAAAAGGCCACACTGGTG<br>TGCCTGGCCACAGGCTTCTTCCCCGACCACGTGGAGCTGAGCTGGTGGGTGAATG<br>GGAAGGAGGTGCACAGTGGGGTCAGCACGGACCCGCAGCCCCTCAAGGAGCAGCC<br>CGCCCTCAATGACTCCAGATACTGCCTGAGCAGCCGCCTGAGGGTCTCGGCCACC<br>TTCTGGCAGAACCCCCGCAACCACTTCCGCTGTCAAGTCCAGTTCTACGGGCTCT<br>CGGAGAATGACGAGTGGACCCAGGATAGGGCCAAACCCGTCACCCAGATCGTCAG<br>CGCCGAGGCCTGGGGTAGAGCAGACTGTGGCTTTACCTCGGTGTCCTACCAGCAA<br>GGGGTCCTGTCTGCCACCATCCTCTATGAGATCCTGCTAGGGAAGGCCACCCTGT<br>ATGCTGTGCTGGTCAGCGCCCTTGTGTTGATGGCCATGGTCAAGAGAAAGGATTT<br>C | SEQ ID NO: 139 |
| β (with TRBC2) | ATGGGCACCAGGCTCCTCTTCTGGGTGGCCTTCTGTCTCCTGGGGGCAGATCACA<br>cAGGAGCTGGAGTCTCCCAGTCCCCAGTAACAAGGTCACAGAGAAGGGAAAGGA<br>TGTAGAGCTCAGGTGTGATCCAATTTCAGGTCATACTGCCCTTTACTGGTACCGA<br>CAGAGCCTGGGGCAGGGCCTGGAGTTTTTAATTTACTTCCAAGGCAACAGTGCAC<br>CAGACAAATCAGGGCTGCCCAGTGATCGCTTCTCTGCAGAGAGGACTGGGGGATC<br>CGTCTCCACTCTGACGATCCAGCGCACACAGCAGGAGGACTCGGCCGTGTATCTC<br>TGTGCCAGCAGCTTGGTAGCTTTACAGGGTGCGGGCGAGCAGTACTTCGGGCCGG<br>GCACCAGGCTCACGGTCACAGAGGACCTGAAAAACGTGTTCCCACCCGAGGTCGC<br>TGTGTTTGAGCCATCAGAAGCAGAGATCTCCCACACCCAAAAGGCCACACTGGTG<br>TGCCTGGCCACAGGCTTCTACCCCGACCACGTGGAGCTGAGCTGGTGGGTGAATG<br>GGAAGGAGGTGCACAGTGGGGTCAGCACAGACCCGCAGCCCCTCAAGGAGCAGCC<br>CGCCCTCAATGACTCCAGATACTGCCTGAGCAGCCGCCTGAGGGTCTCGGCCACC<br>TTCTGGCAGAACCCCCGCAACCACTTCCGCTGTCAAGTCCAGTTCTACGGGCTCT<br>CGGAGAATGACGAGTGGACCCAGGATAGGGCCAAACCTGTCACCCAGATCGTCAG<br>CGCCGAGGCCTGGGGTAGAGCAGACTGTGGCTTCACCTCCGAGTCTTACCAGCAA<br>GGGGTCCTGTCTGCCACCATCCTCTATGAGATCTTGCTAGGGAAGGCCACCTTGT<br>ATGCCGTGCTGGTCAGTGCCCTCGTGCTGATGGCCATGGTCAAGAGAAAGGATTC<br>CAGAGGC | SEQ ID NO: 140 |

TABLE 2 -continued

| DonorChain | Nucleotide sequence | SEQ ID NO |
| --- | --- | --- |
| HD3 α (with TRAC) | ATGATATCCTTGAGAGTTTTACTGGTGATCCTGTGGCTTCAGTTAAGCTGGGTTT GGAGCCAACGGAAGGAGGTGGAGCAGGATCCTGGACCCTTCAATGTTCCAGAGGG AGCCACTGTCGCTTTCAACTGTACTTACAGCAACAGTGCTTCTCAGTCTTTCTTC TGGTACAGACAGGATTGCAGGAAAGAACCTAAGTTGCTGATGTCCGTATACTCCA GTGGTAATGAAGATGGAAGGTTTACAGCACAGCTCAATAGAGCCAGCCAGTATAT TTCCCTGCTCATCAGAGACTCCAAGCTCAGTGATTCAGCCACCTACCTCTGTGTG GTGAACCTCCTGTCTAACCAGGGAGGAAAGCTTATCTTCGGACAGGGAACGGAGT TATCTGTGAAACCCAATATCCAGAACCCTGACCCTGCCGTGTACCAGCTGAGAGA CTCTAAATCCAGTGACAAGTCTGTCTGCCTATTCACCGATTTTGATTCTCAAACA AATGTGTCACAAAGTAAGGATTCTGATGTGTATATCACAGACAAAACTGTGCTAG ACATGAGGTCTATGGACTTCAAGAGCAACAGTGCTGTGGCCTGGAGCAACAAATC TGACTTTGCATGTGCAAACGCCTTCAACAACAGCATTATTCCAGAAGACACCTTC TTCCCCAGCCCAGAAGTTCCTGTGATGTCAAGCTGGTCGAGAAAAGCTTTGAAA CAGATACGAACCTAAACTTTCAAAACCTGTCAGTGATTGGGTTCCGAATCCTCCT CCTGAAAGTGGCCGGGTTTAATCTGCTCATGACGCTGCGGCTGTGGTCCAGC | SEQ ID NO: 141 |
| β (with TRBC1) | ATGGGCTGCAGGCTGCTCTGCTGTGCGGTTCTCTGTCTCCTGGGAGCGGGTGAGT TGGTCCCCATGGAAACGGGAGTTACGCAGACACCAAGACACCTGGTCATGGGAAT GACAAATAAGAAGTCTTTGAAATGTGAACAACATCTGGGTCATAACGCTATGTAT TGGTACAAGCAAAGTGCTAAGAAGCCACTGGAGCTCATGTTTGTCTACAGTCTTG AAGAACGGGTTGAAAACAACAGTGTGCCAAGTCGCTTCTCACCTGAATGCCCCAA CAGCTCTCACTTATTCCTTCACCTACACACCCTGCAGCCAGAAGACTCGGCCCTG TATCTCTGCGCCAGCAGCCAAGATTACTTGGTTTCTAATGAAAAACTGTTTTTTG GCAGTGGAACCCAGCTCTCTGTCTTGGAGGACCTGAACAAGGTGTTCCCACCCGA GGTCGCTGTGTTTGAGCCATCAGAAGCAGAGATCTCCCACACCCAAAAGGCCACA CTGGTGTGCCTGGCCACAGGCTTCTTCCCCGACCACGTGGAGCTGAGCTGGTGGG TGAATGGGAAGGAGGTGCACAGTGGGGTCAGCACGGACCCGCAGCCCCTCAAGGA GCAGCCCGCCCTCAATGACTCCAGATACTGCCTGAGCAGCCGCCTGAGGGTCTCG GCCACCTTCTGGCAGAACCCCCGCAACCACTTCCGCTGTCAAGTCCAGTTCTACG GGCTCTCGGAGAATGACGAGTGGACCCAGGATAGGGCCAAACCCGTCACCCAGAT CGTCAGCGCCGAGGCCTGGGGTAGAGCAGACTGTGGCTTTACCTCGGTGTCCTAC CAGCAAGGGGTCCTGTCTGCCACCATCCTCTATGAGATCCTGCTAGGGAAGGCCA CCCTGTATGCTGTGCTGGTCAGCGCCCTTGTGTTGATGGCCATGGTCAAGAGAAA GGATTTC | SEQ ID NO: 142 |
| β (with TRBC2) | ATGGGCTGCAGGCTGCTCTGCTGTGCGGTTCTCTGTCTCCTGGGAGCGGGTGAGT TGGTCCCCATGGAAACGGGAGTTACGCAGACACCAAGACACCTGGTCATGGGAAT GACAAATAAGAAGTCTTTGAAATGTGAACAACATCTGGGTCATAACGCTATGTAT TGGTACAAGCAAAGTGCTAAGAAGCCACTGGAGCTCATGTTTGTCTACAGTCTTG AAGAACGGGTTGAAAACAACAGTGTGCCAAGTCGCTTCTCACCTGAATGCCCCAA CAGCTCTCACTTATTCCTTCACCTACACACCCTGCAGCCAGAAGACTCGGCCCTG TATCTCTGCGCCAGCAGCCAAGATTACTTGGTTTCTAATGAAAAACTGTTTTTTG GCAGTGGAACCCAGCTCTCTGTCTTGGAGGACCTGAAAAACGTGTTCCCACCCGA GGTCGCTGTGTTTGAGCCATCAGAAGCAGAGATCTCCCACACCCAAAAGGCCACA CTGGTGTGCCTGGCCACAGGCTTCTACCCCGACCACGTGGAGCTGAGCTGGTGGG TGAATGGGAAGGAGGTGCACAGTGGGGTCAGCACAGACCCGCAGCCCCTCAAGGA GCAGCCCGCCCTCAATGACTCCAGATACTGCCTGAGCAGCCGCCTGAGGGTCTCG GCCACCTTCTGGCAGAACCCCCGCAACCACTTCCGCTGTCAAGTCCAGTTCTACG GGCTCTCGGAGAATGACGAGTGGACCCAGGATAGGGCCAAACCCGTCACCCAGAT CGTCAGCGCCGAGGCCTGGGGTAGAGCAGACTGTGGCTTCACCTCCGAGTCTTAC CAGCAAGGGGTCCTGTCTGCCACCATCCTCTATGAGATCTTGCTAGGGAAGGCCA CCTTGTATGCCGTGCTGGTCAGTGCCCTCGTGCTGATGGCCATGGTCAAGAGAAA GGATTCCAGAGGC | SEQ ID NO: 143 |
| HD4-1α1 (with TRAC) | ATGGAAACTCTCCTGGGAGTGTCTTTGGTGATTCTATGGCTTCAACTGGCTAGGG TGAACAGTCAACAGGGAGAAGAGGATCCTCAGGCCTTGAGCATCCAGGAGGGTGA AAATGCCACCATGAACTGCAGTTACAAAACTAGTATAAACAATTTACAGTGGTAT AGACAAAATTCAGGTAGAGGCCTTGTCCACCTAATTTTAATACGTTCAAATGAAA GAGAGAAACACAGTGGAAGATTAAGAGTCACGCTTGACACTTCCAAGAAAAGCAG TTCCTTGTTGATCACGGCTTCCCGGGCAGCAGACACTGCTTCTTACTTCTGTGCT ACGGACGCGTATTCAGGAAACACACCTCTTGTCTTTGGAAAGGGCACAAGACTTT CTGTGATTGCAAATATCCAGAACCCTGACCCTGCCGTGTACCAGCTGAGAGACTC TAAATCCAGTGACAAGTCTGTCTGCCTATTCACCGATTTTGATTCTCAAACAAAT GTGTCACAAAGTAAGGATTCTGATGTGTATATCACAGACAAAACTGTGCTAGACA TGAGGTCTATGGACTTCAAGAGCAACAGTGCTGTGGCCTGGAGCAACAAATCTGA CTTTGCATGTGCAAACGCCTTCAACAACAGCATTATTCCAGAAGACACCTTCTTC CCCAGCCCAGAAGTTCCTGTGATGTCAAGCTGGTCGAGAAAAGCTTTGAAACAG ATACGAACCTAAACTTTCAAAACCTGTCAGTGATTGGGTTCCGAATCCTCCTCCT GAAAGTGGCCGGGTTTAATCTGCTCATGACGCTGCGGCTGTGGTCCAGC | SEQ ID NO: 144 |
| β1 (with TRBC1) | ATGAGCATCCAGGCTCCTGTGCTGTGGCCTTTTCTCCTGTGGGCAAGTCCAG TGAATGCTGGTGTCACTCAGACCCCAAAATTCCAGGTCCTGAAGACAGGACAGAG CATGACACTGCAGTGTGCCCAGGATATGAACCATAACTCCATGTACTGGTATCGA CAAGACCCAGGCATGGGACTGAGGCTGATTTATTACTCAGCTTCTGAGGGTACCA CTGACAAAGGAGAAGTCCCCAATGGCTACAATGTCTCCAGATTAAACAAACGGGA GTTCTCGCTCAGGCTGGAGTCGGCTGCTCCCTCCCAGACATCTGTGTACTTCTGT GCCAGCAGGGCAGCAGGGTTGGACACTGAAGCTTTCTTTGGACAAGGCACCAGAC TCACAGTTGTAGAGGACCTGAACAAGGTGTTCCCACCCGAGGTCGCTGTGTTTGA GCCATCAGAAGCAGAGATCTCCCACACCCAAAAGGCCACACTGGTGTGCCTGGCC ACAGGCTTCTTCCCCGACCACGTGGAGCTGAGCTGGTGGGTGAATGGGAAGGAGG | SEQ ID NO: 145 |

TABLE 2 -continued

| DonorChain | Nucleotide sequence | SEQ ID NO |
|---|---|---|
| | TGCACAGTGGGGTCAGCACGGACCCGCAGCCCCTCAAGGAGCAGCCCGCCCTCAA<br>TGACTCCAGATACTGCCTGAGCAGCCGCCTGAGGGTCTCGGCCACCTTCTGGCAG<br>AACCCCCGCAACCACTTCCGCTGTCAAGTCCAGTTCTACGGGCTCTCGGAGAATG<br>ACGAGTGGACCCAGGATAGGGCCAAACCCGTCACCCAGATCGTCAGCGCCGAGGC<br>CTGGGGTAGAGCAGACTGTGGCTTTACCTCGGTGTCCTACCAGCAAGGGGTCCTG<br>TCTGCCACCATCCTCTATGAGATCCTGCTAGGGAAGGCCACCCTGTATGCTGTGC<br>TGGTCAGCGCCCTTGTGTTGATGGCCATGGTCAAGAGAAAGGATTTC | |
| β1 (with<br>TRBC2) | ATGAGCATCGGGCTCCTGTGCTGTGTGGCCTTTTCTCTCCTGTGGGCAAGTCCAG<br>TGAATGCTGGTGTCACTCAGACCCCAAAATTCCAGGTCCTGAAGACAGGACAGAG<br>CATGACACTGCAGTGTGCCCAGGATATGAACCATAACTCCATGTACTGGTATCGA<br>CAAGACCCAGGCATGGGACTGAGGCTGATTTATTACTCAGCTTCTGAGGGTACCA<br>CTGACAAAGGAGAAGTCCCCAATGGCTACAATGTCTCCAGATTAAACAAACGGGA<br>GTTCTCGCTCAGGCTGGAGTCGGCTGCTCCCTCCCAGACATCTGTGTACTTCTGT<br>GCCAGCAGGGCAGCAGGGTTGGACACTGAAGCTTTCTTTGGACAAGGCACCAGAC<br>TCACAGTTGTAGAGGACCTGAAAAACGTGTTCCCACCCGAGGTCGCTGTGTTTGA<br>GCCATCAGAAGCAGAGATCTCCCACACCCAAAAGGCCACACTGGTGTGCCTGGCC<br>ACAGGCTTCTACCCCGACCACGTGGAGCTGAGCTGGTGGGTGAATGGGAAGGAGG<br>TGCACAGTGGGGTCAGCACAGACCCGCAGCCCCTCAAGGAGCAGCCCGCCCTCAA<br>TGACTCCAGATACTGCCTGAGCAGCCGCCTGAGGGTCTCGGCCACCTTCTGGCAG<br>AACCCCCGCAACCACTTCCGCTGTCAAGTCCAGTTCTACGGGCTCTCGGAGAATG<br>ACGAGTGGACCCAGGATAGGGCCAAACCTGTCACCCAGATCGTCAGCGCCGAGGC<br>CTGGGGTAGAGCAGACTGTGGCTTCACCTCCGAGTCTTACCAGCAAGGGGTCCTG<br>TCTGCCACCATCCTCTATGAGATCTTGCTAGGGAAGGCCACCTTGTATGCCGTGC<br>TGGTCAGTGCCCTCGTGCTGATGGCCATGGTCAAGAGAAAGGATTCCAGAGGC | SEQ ID NO: 146 |
| HD4-2α2 (with<br>TRAC) | ATGGAGACCCTCTTGGGCCTGCTTATCCTTTGGCTGCAGCTGCAATGGGTGAGCA<br>GCAAACAGGAGGTGACGCAGATTCCTGCAGCTCTGAGTGTCCCAGAAGGAGAAAA<br>CTTGGTTCTCAACTGCAGTTTCACTGATAGCGCTATTTACAACCTCCAGTGGTTT<br>AGGCAGGACCCTGGGAAAGGTCTCACATCTCTGTTGCTTATTCAGTCAAGTCAGA<br>GAGAGCAAACAAGTGGAAGACTTAATGCCTCGCTGGATAAATCATCAGGACGTAG<br>TACTTTATACATTGCAGCTTCTCAGCCTGGTCACTCAGCCACCTACCTCTGTGCT<br>GTCCGGGCAGAGATTTATAACCAGGGAGGAAAGCTTATCTTCGGACAGGGAACGG<br>AGTTATCTGTGAAACCCAATATCCAGAACCCTGACCCTGCCGTGTACCAGCTGAG<br>AGACTCTAAATCCAGTGACAAGTCTGTCTGCCTATTCACCGATTTTGATTCTCAA<br>ACAAATGTGTCACAAAGTAAGGATTCTGATGTGTATATCACAGACAAAACTGTGC<br>TAGACATGAGGTCTATGGACTTCAAGAGCAACAGTGCTGTGGCCTGGAGCAACAA<br>ATCTGACTTTGCATGTGCAAACGCCTTCAACAACAGCATTATTCCAGAAGACACC<br>TTCTTCCCCAGCCCAGAAAGTTCCTGTGATGTCAAGCTGGTCGAGAAAAGCTTTG<br>AAACAGATACGAACCTAAACTTTCAAAACCTGTCAGTGATTGGGTTCCGAATCCT<br>CCTCCTGAAAGTGGCCGGGTTTAATCTGCTCATGACGCTGCGGCTGTGGTCCAGC | SEQ ID NO: 147 |
| β2 (with<br>TRBC1) | ATGAGCATCAGCCTCCTGTGCTGTGCAGCCTTTCCTCTCCTGTGGGCAGGTCCAG<br>TGAATGCTGGTGTCACTCAGACCCCAAAATTCCGCATCCTGAAGATAGGACAGAG<br>CATGACACTGCAGTGTACCCAGGATATGAACCATAACTACATGTACTGGTATCGA<br>CAAGACCCAGGCATGGGGCTGAAGCTGATTTATTATTCAGTTGGTGCTGGTATCA<br>CTGATAAAGGAGAAGTCCCCGAATGGCTACAATGTCTCCAGATCAACCACAGAGGA<br>TTTCCCGCTCAGGCTGGAGTTGGCTGCTCCCTCCCAGACATCTGTGTACTTCTGT<br>GCCAGTACCCAAACTCCCTACGAGCAGTACTTCGGGCCGGGCACCAGGCTCACGG<br>TCACAGAGGACCTGAACAAGGTGTTCCCACCCGAGGTCGCTGTGTTTGAGCCATC<br>AGAAGCAGAGATCTCCCACACCCAAAAGGCCACACTGGTGTGCCTGGCCACAGGC<br>TTCTTCCCCGACCACGTGGAGCTGAGCTGGTGGGTGAATGGGAAGGAGGTGCACA<br>GTGGGGTCAGCACGGACCCGCAGCCCCTCAAGGAGCAGCCCGCCCTCAATGACTC<br>CAGATACTGCCTGAGCAGCCGCCTGAGGGTCTCGGCCACCTTCTGGCAGAACCCC<br>CGCAACCACTTCCGCTGTCAAGTCCAGTTCTACGGGCTCTCGGAGAATGACGAGT<br>GGACCCAGGATAGGGCCAAACCCGTCACCCAGATCGTCAGCGCCGAGGCCTGGGG<br>TAGAGCAGACTGTGGCTTTACCTCGGTGTCCTACCAGCAAGGGGTCCTGTCTGCC<br>ACCATCCTCTATGAGATCCTGCTAGGGAAGGCCACCCTGTATGCTGTGCTGGTCA<br>GCGCCCTTGTGTTGATGGCCATGGTCAAGAGAAAGGATTTC | SEQ ID NO: 148 |
| β2 (with<br>TRBC2) | ATGAGCATCAGCCTCCTGTGCTGTGCAGCCTTTCCTCTCCTGTGGGCAGGTCCAG<br>TGAATGCTGGTGTCACTCAGACCCCAAAATTCCGCATCCTGAAGATAGGACAGAG<br>CATGACACTGCAGTGTACCCAGGATATGAACCATAACTACATGTACTGGTATCGA<br>CAAGACCCAGGCATGGGGCTGAAGCTGATTTATTATTCAGTTGGTGCTGGTATCA<br>CTGATAAAGGAGAAGTCCCCGAATGGCTACAATGTCTCCAGATCAACCACAGAGGA<br>TTTCCCGCTCAGGCTGGAGTTGGCTGCTCCCTCCCAGACATCTGTGTACTTCTGT<br>GCCAGTACCCAAACTCCCTACGAGCAGTACTTCGGGCCGGGCACCAGGCTCACGG<br>TCACAGAGGACCTGAAAAACGTGTTCCCACCCGAGGTCGCTGTGTTTGAGCCATC<br>AGAAGCAGAGATCTCCCACACCCAAAAGGCCACACTGGTGTGCCTGGCCACAGGC<br>TTCTACCCCGACCACGTGGAGCTGAGCTGGTGGGTGAATGGGAAGGAGGTGCACA<br>GTGGGGTCAGCACAGACCCGCAGCCCCTCAAGGAGCAGCCCGCCCTCAATGACTC<br>CAGATACTGCCTGAGCAGCCGCCTGAGGGTCTCGGCCACCTTCTGGCAGAACCCC<br>CGCAACCACTTCCGCTGTCAAGTCCAGTTCTACGGGCTCTCGGAGAATGACGAGT<br>GGACCCAGGATAGGGCCAAACCTGTCACCCAGATCGTCAGCGCCGAGGCCTGGGG<br>TAGAGCAGACTGTGGCTTCACCTCCGAGTCTTACCAGCAAGGGGTCCTGTCTGCC<br>ACCATCCTCTATGAGATCTTGCTAGGGAAGGCCACCTTGTATGCCGTGCTGGTCA<br>GTGCCCTCGTGCTGATGGCCATGGTCAAGAGAAAGGATTCCAGAGGC | SEQ ID NO: 149 |
| β3 (with<br>TRBC1) | ATGGACTCCTGGACCTTCTGCTGTGTGTCCCTTTGCATCCTGGTAGCGAAGCATA<br>CAGATGCTGGAGTTATCCAGTCACCCCGCCATGAGGTGACAGAGATGGGACAAGA<br>AGTGACTCTGAGATGTAAACCAATTTCAGGCCACAACTCCCTTTTCTGGTACAGA<br>CAGACCATGATGCGGGGACTGGAGTTGCTCATTTACTTTAACAACAACGTTCCGA | SEQ ID NO: 150 |

TABLE 2 -continued

| DonorChain | | Nucleotide sequence | SEQ ID NO |
|---|---|---|---|
| | | TAGATGATTCAGGGATGCCCGAGGATCGATTCTCAGCTAAGATGCCTAATGCATC<br>ATTCTCCACTCTGAAGATCCAGCCCTCAGAACCCAGGGACTCAGCTGTGTACTTC<br>TGTGCCAGCAGCACAGTGGGAGGGGAGGATTATGGCTACACCTTCGGTTCGGGGA<br>CCAGGTTAACCGTTGTAGAGGACCTGAACAAGGTGTTCCCACCCGAGGTCGCTGT<br>GTTTGAGCCATCAGAAGCAGAGATCTCCCACACCCAAAAGGCCACACTGGTGTGC<br>CTGGCCACAGGCTTCTTCCCCGACCACGTGGAGCTGAGCTGGTGGGTGAATGGGA<br>AGGAGGTGCACAGTGGGGTCAGCACGGACCCGCAGCCCCTCAAGGAGCAGCCCGC<br>CCTCAATGACTCCAGATACTGCCTGAGCAGCCGCCTGAGGGTCTCGGCCACCTTC<br>TGGCAGAACCCCGCAACCACTTCCGCTGTCAAGTCCAGTTCTACGGGCTCTCGG<br>AGAATGACGAGTGGACCCAGGATAGGGCCAAACCCGTCACCCAGATCGTCAGCGC<br>CGAGGCCTGGGGTAGAGCAGACTGTGGCTTTACCTCGGTGTCCTACCAGCAAGGG<br>GTCCTGTCTGCCACCATCCTCTATGAGATCCTGCTAGGGAAGGCCACCCTGTATG<br>CTGTGCTGGTCAGCGCCCTIGTGTTGATGGCCATGGTCAAGAGAAAGGATTTC | |
| | β3 (with<br>TRBC2) | ATGGACTCCTGGACCTTCTGCTGTGTGTCCCTTTGCATCCTGGTAGCGAAGCATA<br>CAGATGCTGGAGTTATCCAGTCACCCCGCCATGAGGTGACAGAGATGGACAAGA<br>AGTGACTCTGAGATGTAAACCAATTTCAGGCCACAACTCCCTTTTCTGGTACAGA<br>CAGACCATGATGCGGGGACTGGAGTTGCTCATTTACTTTAACAACAACGTTCCGA<br>TAGATGATTCAGGGATGCCCGAGGATCGATTCTCAGCTAAGATGCCTAATGCATC<br>ATTCTCCACTCTGAAGATCCAGCCCTCAGAACCCAGGGACTCAGCTGTGTACTTC<br>TGTGCCAGCAGCACAGTGGGAGGGGAGGATTATGGCTACACCTTCGGTTCGGGGA<br>CCAGGTTAACCGTTGTAGAGGACCTGAAAAACGTGTTCCCACCCGAGGTCGCTGT<br>GTTTGAGCCATCAGAAGCAGAGATCTCCCACACCCAAAAGGCCACACTGGTGTGC<br>CTGGCCACAGGCTTCTACCCCGACCACGTGGAGCTGAGCTGGTGGGTGAATGGGA<br>AGGAGGTGCACAGTGGGGTCAGCACAGACCCGCAGCCCCTCAAGGAGCAGCCCGC<br>CCTCAATGACTCCAGATACTGCCTGAGCAGCCGCCTGAGGGTCTCGGCCACCTTC<br>TGGCAGAACCCCGCAACCACTTCCGCTGTCAAGTCCAGTTCTACGGGCTCTCGG<br>AGAATGACGAGTGGACCCAGGATAGGGCCAAACCTGTCACCCAGATCGTCAGCGC<br>CGAGGCCTGGGGTAGAGCAGACTGTGGCTTCACCTCCGAGTCTTACCAGCAAGGG<br>GTCCTGTCTGCCACCATCCTCTATGAGATCTTGCTAGGGAAGGCCACCTTGTATG<br>CCGTGCTGGTCAGTGCCCTCGTGCTGATGGCCATGGTCAAGAGAAAGGATTCCAG<br>AGGC | SEQ ID NO: 151 |
| HD5 | α (with<br>TRAC) | ATGACATCCATTCGAGCTGTATTTATATTCCTGTGGCTGCAGCTGGACTTGGTGA<br>ATGGAGAGAATGTGGAGCAGCATCCTTCAACCCTGAGTGTCCAGGAGGGAGACAG<br>CGCTGTTATCAAGTGTACTTATTCAGACAGTGCCTCAAACTACTTCCCTTGGTAT<br>AAGCAAGAACTTGGAAAAAGACCTCAGCTTATTATAGACATTCGTTCAAATGTGG<br>GCGAAAAGAAAGACCAACGAATTGCTGTTACATTGAACAAGACAGCCAAACATTT<br>CTCCCTGCACATCACAGAGACCCAACCTGAAGACTCGGCTGTCTACTTCTGTGCA<br>GCAAGTATGGCTGGGGCTGGGAGTTACCAACTCACTTTCGGGAAGGGGACCAAAC<br>TCTCGGTCATACCAAATATCCAGAACCCTGACCCTGCCGTGTACCAGCTGAGAGA<br>CTCTAAATCCAGTGACAAGTCTGTCTGCCTATTCACCGATTTTGATTCTCAAACA<br>AATGTGTCACAAAGTAAGGATTCTGATGTGTATATCACAGACAAAACTGTGCTAG<br>ACATGAGGTCTATGGACTTCAAGAGCAACAGTGCTGTGGCCTGGAGCAACAAATC<br>TGACTTTGCATGTGCAAACGCCTTCAACAACAGCATTATTCCAGAAGACACCTTC<br>TTCCCCAGCCCAGAAAGTTCCTGTGATGTCAAGCTGGTCGAGAAAAGCTTTGAAA<br>CAGATACGAACCTAAACTTTCAAAACCTGTCAGTGATTGGGTTCCGAATCCTCCT<br>CCTGAAAGTGGCCGGGTTTAATCTGCTCATGACGCTGCGGCTGTGGTCCAGC | SEQ ID NO: 152 |
| | β1 (with<br>TRBC1) | ATGGGCACAAGGITGTTCTTCTATGTGGCCCTTTGTCTCCTGTGGACAGGACACA<br>TGGATGCTGGAATCACCCAGAGCCCAAGACACAAGGTCACAGAGACAGGAACACC<br>AGTGACTCTGAGATGTCACCAGACTGAGAACCACCGCTATATGTACTGGTATCGA<br>CAAGACCCGGGGCATGGGCTGAGGCTGATCCATTACTCATATGGTGTTAAAGATA<br>CTGACAAAGGAGAAGTCTCAGATGGCTATAGTGTCTCTAGATCAAAGACAGAGGA<br>TTTCCTCCTCACTCTGGAGTCCGCTACCAGCTCCCAGACATCTGTGTACTTCTGT<br>GCCATCTCGGTGGGACAGGGGGCCCTCTACGAGCAGTACTTCGGGCCGGGCACCA<br>GGCTCACGGTCACAGAGGACCTGAACAAGGTGTTCCCACCCGAGGTCGCTGTGTT<br>TGAGCCATCAGAAGCAGAGATCTCCCACACCCAAAAGGCCACACTGGTGTGCCTG<br>GCCACAGGCTTCTTCCCCGACCACGTGGAGCTGAGCTGGTGGGTGAATGGGAAGG<br>AGGTGCACAGTGGGGTCAGCACGGACCCGCAGCCCCTCAAGGAGCAGCCCGCCCT<br>CAATGACTCCAGATACTGCCTGAGCAGCCGCCTGAGGGTCTCGGCCACCTTCTGG<br>CAGAACCCCGCAACCACTTCCGCTGTCAAGTCCAGTTCTACGGGCTCTCGGAGA<br>ATGACGAGTGGACCCAGGATAGGGCCAAACCCGTCACCCAGATCGTCAGCGCCGA<br>GGCCTGGGGTAGAGCAGACTGTGGCTTTACCTCGGTGTCCTACCAGCAAGGGGTC<br>CTGTCTGCCACCATCCTCTATGAGATCCTGCTAGGGAAGGCCACCCTGTATGCTG<br>TGCTGGTCAGCGCCCTIGTGTTGATGGCCATGGTCAAGAGAAAGGATTTC | SEQ ID NO: 153 |
| | β1 (with<br>TRBC2) | ATGGGCACAAGGITGTTCTTCTATGTGGCCCTTTGTCTCCTGTGGACAGGACACA<br>TGGATGCTGGAATCACCCAGAGCCCAAGACACAAGGTCACAGAGACAGGAACACC<br>AGTGACTCTGAGATGTCACCAGACTGAGAACCACCGCTATATGTACTGGTATCGA<br>CAAGACCCGGGGCATGGGCTGAGGCTGATCCATTACTCATATGGTGTTAAAGATA<br>CTGACAAAGGAGAAGTCTCAGATGGCTATAGTGTCTCTAGATCAAAGACAGAGGA<br>TTTCCTCCTCACTCTGGAGTCCGCTACCAGCTCCCAGACATCTGTGTACTTCTGT<br>GCCATCTCGGTGGGACAGGGGGCCCTCTACGAGCAGTACTTCGGGCCGGGCACCA<br>GGCTCACGGTCACAGAGGACCTGAAAAACGTGTTCCCACCCGAGGTCGCTGTGTT<br>TGAGCCATCAGAAGCAGAGATCTCCCACACCCAAAAGGCCACACTGGTGTGCCTG<br>GCCACAGGCTTCTACCCCGACCACGTGGAGCTGAGCTGGTGGGTGAATGGGAAGG<br>AGGTGCACAGTGGGGTCAGCACAGACCCGCAGCCCCTCAAGGAGCAGCCCGCCCT<br>CAATGACTCCAGATACTGCCTGAGCAGCCGCCTGAGGGTCTCGGCCACCTTCTGG<br>CAGAACCCCGCAACCACTTCCGCTGTCAAGTCCAGTTCTACGGGCTCTCGGAGA<br>ATGACGAGTGGACCCAGGATAGGGCCAAACCTGTCACCCAGATCGTCAGCGCCGA | SEQ ID NO: 154 |

TABLE 2-continued

| DonorChain | | Nucleotide sequence | SEQ ID NO |
|---|---|---|---|
| | | GGCCTGGGGTAGAGCAGACTGTGGCTTCACCTCCGAGTCTTACCAGCAAGGGGTC CTGTCTGCCACCATCCTCTATGAGATCTTGCTAGGGAAGGCCACCTTGTATGCCG TGCTGGTCAGTGCCCTCGTGCTGATGGCCATGGTCAAGAGAAAGGATTCCAGAGG C | |
| | β2 (with TRBC1) | ATGGGCTTCAGGCTCCTCTGCTGTGTGGCCTTTTGTCTCCTGGGAGCAGGCCCAG TGGATTCTGGAGTCACACAAACCCCAAAGCACCTGATCACAGCAACTGGACAGCG AGTGACGCTGAGATGCTCCCCTAGGTCTGGAGACCTCTCTGTGTACTGGTACCAA CAGAGCCTGGACCAGGGCCTCCAGTTCCTCATTCAGTATTATAATGGAGAAGAGA GAGCAAAAGGAAACATTCTTGAACGATTCTCCGCACAACAGTTCCCTGACTTGCA CTCTGAACTAAACCTGAGCTCTCTGGAGCTGGGGGACTCAGCTTTGTATTTCTGT GCCAGCAGCGTAGCTCGGGACAGGCGGAACTATGGCTACACCTTCGGTTCGGGGA CCAGGTTAACCGTTGTAGAGGACCTGAACAAGGTGTTCCCACCCGAGGTCGCTGT GTTTGAGCCATCAGAAGCAGAGATCTCCCACACCCAAAAGGCCACACTGGTGTGC CTGGCCACAGGCTTCTTCCCCGACCACGTGGAGCTGAGCTGGTGGGTGAATGGGA AGGAGGTGCACAGTGGGGTCAGCACGGACCCGCAGCCCCTCAAGGAGCAGCCCGC CCTCAATGACTCCAGATACTGCCTGAGCAGCCGCCTGAGGGTCTCGGCCACCTTC TGGCAGAACCCCCGCAACCACTTCCGCTGTCAAGTCCAGTTCTACGGGCTCTCGG AGAATGACGAGTGGACCCAGGATAGGGCCAAACCCGTCACCCAGATCGTCAGCGC CGAGGCCTGGGGTAGAGCAGACTGTGGCTTTACCTCGGTGTCCTACCAGCAAGGG GTCCTGTCTGCCACCATCCTCTATGAGATCCTGCTAGGGAAGGCCACCCTGTATG CTGTGCTGGTCAGCGCCCTIGTGTTGATGGCCATGGTCAAGAGAAAGGATTTC | SEQ ID NO: 155 |
| | β2 (with TRBC2) | ATGGGCTTCAGGCTCCTCTGCTGTGTGGCCTTTTGTCTCCTGGGAGCAGGCCCAG TGGATTCTGGAGTCACACAAACCCCAAAGCACCTGATCACAGCAACTGGACAGCG AGTGACGCTGAGATGCTCCCCTAGGTCTGGAGACCTCTCTGTGTACTGGTACCAA CAGAGCCTGGACCAGGGCCTCCAGTTCCTCATTCAGTATTATAATGGAGAAGAGA GAGCAAAAGGAAACATTCTTGAACGATTCTCCGCACAACAGTTCCCTGACTTGCA CTCTGAACTAAACCTGAGCTCTCTGGAGCTGGGGGACTCAGCTTTGTATTTCTGT GCCAGCAGCGTAGCTCGGGACAGGCGGAACTATGGCTACACCTTCGGTTCGGGGA CCAGGTTAACCGTTGTAGAGGACCTGAAAAACGTGTTCCCACCCGAGGTCGCTGT GTTTGAGCCATCAGAAGCAGAGATCTCCCACACCCAAAAGGCCACACTGGTGTGC CTGGCCACAGGCTTCTACCCCGACCACGTGGAGCTGAGCTGGTGGGTGAATGGGA AGGAGGTGCACAGTGGGGTCAGCACAGACCCGCAGCCCCTCAAGGAGCAGCCCGC CCTCAATGACTCCAGATACTGCCTGAGCAGCCGCCTGAGGGTCTCGGCCACCTTC TGGCAGAACCCCCGCAACCACTTCCGCTGTCAAGTCCAGTTCTACGGGCTCTCGG AGAATGACGAGTGGACCCAGGATAGGGCCAAACCTGTCACCCAGATCGTCAGCGC CGAGGCCTGGGGTAGAGCAGACTGTGGCTTCACCTCCGAGTCTTACCAGCAAGGG GTCCTGTCTGCCACCATCCTCTATGAGATCTTGCTAGGGAAGGCCACCTTGTATG CCGTGCTGGTCAGTGCCCTCGTGCTGATGGCCATGGTCAAGAGAAAGGATTCCAG AGGC | SEQ ID NO: 156 |
| HD6 | α1 (with TRAC) | atggccatgctcctgggggcatcagtgctgattctgtggcttcagccagactggg taaacagtcaacagaagaatgatgaccagcaagttaagcaaaattcaccatccct gagcgtccaggaaggaagaatttctattctgaactgtgactatactaacagcatg tttgattatttcctatggtacaaaaaataccctgctgaaggtcctacattcctga tatctataagttccattaaggataaaaatgaagatggaagattcactgtcttctt aaacaaaagtgccaagcacctctctctgcacattgtgccctcccagcctggagac tctgcagtgtacttctgtgcagcaaacaatgccagactcatgtttggagatggaa ctcagctggtggtgaagccccaatatccagaaccctgaccctgccgtgtaccagt gagagactctaaatccagtgacaagtctgtctgcctattcaccgattttgattct caaacaaatgtgtcacaaagtaaggattctgatgtgtatatcacagacaaaactg tgctagacatgaggtctatggacttcaagagcaacagtgctgtggcctggagcaa caaatctgactttgcatgtgcaaacgccttcaacaacagcattattccagaagac accttcttccccagcccagaaagttcctgtgatgtcaagctggtcgagaaaagct ttgaaacagatacgaacctaaactttcaaaaacctgtcagtgattgggttccgaat cctcctcctgaaagtggccgggtttaatctgctcatgacgctgcggctgtggtcc agc | SEQ ID NO: 223 |
| | α2 (with TRAC) | ATGGCCATGCTCCTGGGGGCATCAGTGCTGATTCTGTGGCTTCAGCCAGACTGGG TAAACAGTCAACAGAAGAATGATGACCAGCAAGTTAAGCAAAATTCACCATCCCT GAGCGTCCAGGAAGGAAGAATTTCTATTCTGAACTGTGACTATACTAACAGCATG TTTGATTATTTCCTATGGTACAAAAAATACCCTGCTGAAGGTCCTACATTCCTGA TATCTATAAGTTCCATTAAGGATAAAAATGAAGATGGAAGATTCACTGTCTTCTT AAACAAAAGTGCCAAGCACCTCTCTCTGCACATTGTGCCCTCCCAGCCTGGAGAC TCTGCAGTGTACTTCTGTGCAGCAAGCGCTACCGGTAACCAGTTCTATTTTGGGA CAGGGACAAGTTTGACGGTCATTCCAAATATCCAGAACCCTGACCCTGCCGTGTA CCAGCTGAGAGACTCTAAATCCAGTGACAAGTCTGTCTGCCTATTCACCGATTTT GATTCTCAAACAAATGTGTCACAAAGTAAGGATTCTGATGTGTATATCACAGACA AAACTGTGCTAGACATGAGGTCTATGGACTTCAAGAGCAACAGTGCTGTGGCCTG GAGCAACAAATCTGACTTTGCATGTGCAAACGCCTTCAACAACAGCATTATTCCA GAAGACACCTTCTTCCCCAGCCCAGAAAGTTCCTGTGATGTCAAGCTGGTCGAGA AAAGCTTTGAAACAGATACGAACCTAAACTTTCAAAAACCTGTCAGTGATTGGGTT CCGAATCCTCCTCCTGAAAGTGGCCGGGTTTAATCTGCTCATGACGCTGCGGCTG TGGTCCAGCTGA | SEQ ID NO: 292 |
| | β1 (with TRBC1) | atggactcctggaccttctgctgtgtgtccctttgcatcctggtagcgaagcata cagatgctggagttatccagtcaccccgccatgaggtgacagagatgggacaaga agtgactctgagatgtaaaccaatttcaggccacaactcccttttctggtacaga cagaccatgatgcgggactggagttgctcatttactttaacaacaacgttccga tagatgattcagggatgcccgaggatcgattctcagctaagatgcctaatgcatc attctccactctgaagatccagcccctcagaacccaggggactcagctgtgtactc | SEQ ID NO: 224 |

TABLE 2 -continued

| DonorChain | | Nucleotide sequence | SEQ ID NO |
|---|---|---|---|
| | | tgtgccagcagtgataccagggcccgggagcagttcttcgggccagggacacggc<br>tcaccgtgctagaggacctgaacaaggtgttcccacccgaggtcgctgtgtttga<br>gccatcagaagcagagatctcccacacccaaaaggccacactggtgtgcctggcc<br>acaggcttcttccccgaccacgtggagctgagctggtgggtgaatgggaaggagg<br>tgcacagtggggtcagcacggaccgcagcccctcaaggagcagcccgccctcaa<br>tgactccagatactgcctgagcagccgcctgagggtctcggccaccttctggcag<br>aaccccgcaaccacttccgctgtcaagtccagttctacgggctctcggagaatg<br>acgagtggacccaggatagggccaaacccgtcacccagatcgtcagcgccgaggc<br>ctggggtagagcagactgtggctttacctcggtgtcctaccagcaaggggtcctg<br>tctgccaccatcctctatgagatcctgctagggaaggccaccctgtatgctgtgc<br>tggtcagcgcccttgtgttgatggccatggtcaagagaaaggatttc | |
| | β1 (with<br>TRBC2) | atggactcctggaccttctgctgtgtgtcccctttgcatcctggtagcgaagcata<br>cagatgctggagttatccagtcaccccgccatgaggtgacagagatgggacaaga<br>agtgactctgagatgtaaaccaatttcaggccacaactcccttttctggtacaga<br>cagaccatgatgcggggactggagttgctcatttactttaacaacaacgttccga<br>tagatgattcagggatgcccgaggatcgattctcagctaagatgcctaatgcatc<br>attctccactctgaagatccagccctcagaacccagggactcagctgtgtacttc<br>tgtgccagcagtgataccagggcccgggagcagttcttcgggccagggacacggc<br>tcaccgtgctagaggacctgaaaaacgtgttcccacccgaggtcgctgtgtttga<br>gccatcagaagcagagatctcccacacccaaaaggccacactggtgtgcctggcc<br>acaggcttctaccccgaccacgtggagctgagctggtgggtgaatgggaaggagg<br>tgcacagtggggtcagcacagaccgcagcccctcaaggagcagcccgccctcaa<br>tgactccagatactgcctgagcagccgcctgagggtctcggccaccttctggcag<br>aaccccgcaaccacttccgctgtcaagtccagttctacgggctctcggagaatg<br>acgagtggacccaggatagggccaaacccgtcacccagatcgtcagcgccgaggc<br>ctggggtagagcagactgtggcttcacctccgagtcttaccagcaaggggtcctg<br>tctgccaccatcctctatgagatcttgctagggaaggccaccttgtatgctgtgc<br>tggtcagtgccctcgtgctgatggccatggtcaagagaaaggattccagaggc | SEQ ID NO: 225 |
| | β2 (with<br>TRBC1) | ATGGGCTCCAGGCTGCTCTGTTGGGTGCTGCTTTGTCTCCTGGGAGCAGGCCCAG<br>TAAAGGCTGGAGTCACTCAAACTCCAAGATATCTGATCAAAACGAGAGGACAGCA<br>AGTGACACTGAGCTGCTCCCCTATCTCTGGGCATAGGAGTGTATCCTGGTACCAA<br>CAGACCCCAGGACAGGGCCTTCAGTTCCTCTTTGAATACTTCAGTGAGACACAGA<br>GAAACAAAGGAAACTTCCTGGTCGATTCTCAGGGCGCCAGTTCTCTAACTCTCG<br>CTCTGAGATGAATGTGAGCACCTTGGAGCTGGGGGACTCGGCCCTTTATCTTTGC<br>GCCAGCAGCCCTGGACAGCACGGGGAGCTGTTTTTTGGAGAAGGCTCTAGGCTGA<br>CCGTACTGGAGGACCTGAACAAGGTGTTCCCACCCGAGGTCGCTGTGTTTGAGCC<br>ATCAGAAGCAGAGATCTCCCACACCCAAAAGGCCACACTGGTGTGCCTGGCCACA<br>GGCTTCTTCCCCGACCACGTGGAGCTGAGCTGGTGGGTGAATGGGAAGGAGGTGC<br>ACAGTGGGGTCAGCACGGACCGCAGCCCCTCAAGGAGCAGCCCGCCCTCAATGA<br>CTCCAGATACTGCCTGAGCAGCCGCCTGAGGGTCTCGGCCACCTTCTGGCAGAAC<br>CCCCGCAACCACTTCCGCTGTCAAGTCCAGTTCTACGGGCTCTCGGAGAATGACG<br>AGTGGACCCAGGATAGGGCCAAACCCGTCACCCAGATCGTCAGCGCCGAGGCCTG<br>GGGTAGAGCAGACTGTGGCTTTACCTCGGTGTCCTACCAGCAAGGGGTCCTGTCT<br>GCCACCATCCTCTATGAGATCCTGCTAGGGAAGGCCACCCTGTATGCTGTGCTGG<br>TCAGCGCCCTTGTGTTGATGGCCATGGTCAAGAGAAAGGATTTC | SEQ ID NO: 293 |
| | β2 (with<br>TRBC2) | ATGGGCTCCAGGCTGCTCTGTTGGGTGCTGCTTTGTCTCCTGGGAGCAGGCCCAG<br>TAAAGGCTGGAGTCACTCAAACTCCAAGATATCTGATCAAAACGAGAGGACAGCA<br>AGTGACACTGAGCTGCTCCCCTATCTCTGGGCATAGGAGTGTATCCTGGTACCAA<br>CAGACCCCAGGACAGGGCCTTCAGTTCCTCTTTGAATACTTCAGTGAGACACAGA<br>GAAACAAAGGAAACTTCCTGGTCGATTCTCAGGGCGCCAGTTCTCTAACTCTCG<br>CTCTGAGATGAATGTGAGCACCTTGGAGCTGGGGGACTCGGCCCTTTATCTTTGC<br>GCCAGCAGCCCTGGACAGCACGGGGAGCTGTTTTTTGGAGAAGGCTCTAGGCTGA<br>CCGTACTGGAGGACCTGAAAAACGTGTTCCCACCCGAGGTCGCTGTGTTTGAGCC<br>ATCAGAAGCAGAGATCTCCCACACCCAAAAGGCCACACTGGTGTGCCTGGCCACA<br>GGCTTCTACCCCGACCACGTGGAGCTGAGCTGGTGGGTGAATGGGAAGGAGGTGC<br>ACAGTGGGGTCAGCACAGACCGCAGCCCCTCAAGGAGCAGCCCGCCCTCAATGA<br>CTCCAGATACTGCCTGAGCAGCCGCCTGAGGGTCTCGGCCACCTTCTGGCAGAAC<br>CCCCGCAACCACTTCCGCTGTCAAGTCCAGTTCTACGGGCTCTCGGAGAATGACG<br>AGTGGACCCAGGATAGGGCCAAACCCGTCACCCAGATCGTCAGCGCCGAGGCCTG<br>GGGTAGAGCAGACTGTGGCTTCACCTCCGAGTCTTACCAGCAAGGGGTCCTGTCT<br>GCCACCATCCTCTATGAGATCTTGCTAGGGAAGGCCACCTTGTATGCTGTGCTGG<br>TCAGTGCCCTCGTGCTGATGGCCATGGTCAAGAGAAAGGATTCCAGAGGC | SEQ ID NO: 294 |
| HD7 | α1 (with<br>TRAC) | atgaagacatttgctggattttcgttcctgttttttgtggctgcagctggactgta<br>tgagtagaggagaggatgtggagcagagtctttcctgagtgtccgagagggaga<br>cagctccgttataaactgcacttacacagacagtcctccacctacttatactgg<br>tataagcaagaacctggagcaggtctccagttgctgacgtatatttttttcaaata<br>tggacatgaaacaagaccaaagactcactgttctattgaataaaaaggataaaca<br>tctgtctctgcgcattgcagacacccagactggggactcagctatctacttctgt<br>gcagagaggcttaacaccgacaagctcatctttgggactgggaccagattacaag<br>tcttttccaaatatccagaaccctgaccctgccgtgtaccagctgagagactctaa<br>atccagtgacaagtctgtctgcctattcaccgattttgattctcaaacaaatgtg<br>tcacaaagtaaggattctgatgtgtatatcacagacaaaactgtctagacatga<br>ggtctatggacttcaagagcaacagtgctgtggcctggagcaacaaatctgactt<br>tgcatgtgcaaacgccttcaacaacagcattattccagaagacaccttcttcccc<br>agcccagaaagttcctgtgatgtcaagctggtcgagaaaagctttgaaacagata<br>cgaacctaaactttcaaaacctgtcagtgattgggttccgaatcctcctcctgaa<br>agtggccgggtttaatctgctcatgacgctgcggctgtggtccagc | SEQ ID NO: 226 |

TABLE 2 -continued

| DonorChain | Nucleotide sequence | SEQ ID NO |
|---|---|---|
| α2 (with TRAC) | atgaagaggatatattgggagctctgctggggctcttgagtgcccaggtttgctgtg<br>tgagaggaataacaagtggagcagagtcctccagacctgattctccaggagggagc<br>caattccacgctgcggtgcaattttttctgactctgtgaacaatttgcagtggttt<br>catcaaaaccccttgggggacagctcatcaacctgttttacattccctcagggacaa<br>aacagaatggaagattaagcgccacgactgtcgctacggaacgctacagcttatt<br>gtacatttcctcttcccagaccacagactcaggcgtttatttctgtgctgtggag<br>gcaactgacagctgggggaaattgcagtttggagcagggacccaggttgtggtca<br>ccccagatatccagaaccctgaccctgccgtgtaccagctgagagactctaaatc<br>cagtgacaagtctgtctgcctattcaccgattttgattctcaaacaaatgtgtca<br>caaagtaaggattctgatgtgtatatcacagacaaaactgtgctagacatgaggt<br>ctatggacttcaagagcaacagtgctgtggcctggagcaacaaatctgactttgc<br>atgtgcaaacgccttcaacaacagcattattccagaagacaccttcttccccagc<br>ccagaaaagttcctgtgatgtcaagctggtcgagaaaagctttgaaacagatacga<br>acctaaactttcaaaacctgtcagtgattgggttccgaatcctcctcctgaaagt<br>ggccgggtttaatctgctcatgacgctgcggctgtggtccagc | SEQ ID NO: 227 |
| α3 (with TRAC) | atgacatccattcgagctgtatttatattcctgtggctgcagctggacttggtga<br>atggagagaatgtggagcagcatccttcaaccctgagtgtccaggagggagacag<br>cgctgttatcaagtgtacttattcagacagtgcctcaaactacttcccttggtat<br>aagcaagaacttggaaaaagaccctcagcttattatagacattcgttcaaatgtgg<br>gcgaaaagaaagaccaacgaattgctgttacattgaacaagacagccaaacattt<br>ctccctgcacatcacagagacccaacctgaagactcggctgtctacttctgtgca<br>gtacgaacctcctacgacaaggtgatatttgggcagggacaagcttatcagtca<br>ttccaaatatccagaaccctgaccctgccgtgtaccagctgagagactctaaatc<br>cagtgacaagtctgtctgcctattcaccgattttgattctcaaacaaatgtgtca<br>caaagtaaggattctgatgtgtatatcacagacaaaactgtgctagacatgaggt<br>ctatggacttcaagagcaacagtgctgtggcctggagcaacaaatctgactttgc<br>atgtgcaaacgccttcaacaacagcattattccagaagacaccttcttccccagc<br>ccagaaaagttcctgtgatgtcaagctggtcgagaaaagctttgaaacagatacga<br>acctaaactttcaaaacctgtcagtgattgggttccgaatcctcctcctgaaagt<br>ggccgggtttaatctgctcatgacgctgcggctgtggtccagc | SEQ ID NO: 228 |
| α-4 (with TRAC) | ATGGAAACTCTCCTGGGAGTGTCTTTGGTGATTCTATGGCTTCAACTGGCTAGGG<br>TGAACAGTCAACAGGGAGAAGAGGATCCTCAGGCCTTGAGCATCCAGGAGGGTGA<br>AAATGCCACCATGAACTGCAGTTACAAAACTAGTATAAACAATTTACAGTGGTAT<br>AGACAAAATTCAGGTAGAGGCCTTGTCCACCTAATTTTAATACGTTCAAATGAAA<br>GAGAGAAACACAGTGGAAGATTAAGAGTCACGCTTGACACTTCCAAGAAAAGCAG<br>TTCCTTGTTGATCACGGCTTCCCGGGCAGCAGACACTGCTTCTTACTTCTGTGCT<br>ACGGACGGGGATAGCAGCTATAAATTGATCTTCGGGAGTGGGACCAGACTGCTGG<br>TCAGGCCTGATATCCAGAACCCTGACCCTGCCGTGTACCAGCTGAGAGACTCTAA<br>ATCCAGTGACAAGTCTGTCTGCCTATTCACCGATTTTGATTCTCAAACAAATGTG<br>TCACAAAGTAAGGATTCTGATGTGTATATCACAGACAAAACTGTGCTAGACATGA<br>GGTCTATGGACTTCAAGAGCAACAGTGCTGTGGCCTGGAGCAACAAATCTGACTT<br>TGCATGTGCAAACGCCTTCAACAACAGCATTATTCCAGAAGACACCTTCTTCCCC<br>AGCCCAGAAAGTTCCTGTGATGTCAAGCTGGTCGAGAAAAGCTTTGAAACAGATA<br>CGAACCTAAACTTTCAAAACCTGTCAGTGATTGGGTTCCGAATCCTCCTCCTGAA<br>AGTGGCCGGGITTAATCTGCTCATGACGCTGCGGCTGTGGTCCAGC | SEQ ID NO: 295 |
| β1 (with TRBC1) | atgctgctgcttctgctgcttctggggccaggtataagcctccttctacctggga<br>gcttggcaggctccgggcttggtgctgtcgtctctcaacatccgagctgggttat<br>ctgtaagagtggaacctctgtgaagatcgagtgccgttccctggactttcaggcc<br>acaactatgttttggtatcgtcagttcccgaaacagagtctcatgctgatggcaa<br>cttccaatgagggctccaaggccacatacgagcaaggcgtcgagaaggacaagtt<br>tctcatcaaccatgcaagcctgaccttgtccactctgacagtgaccagtgcccat<br>cctgaagacagcagcttctacatctgcagtgctagggacagtgtgtctggaaaca<br>ccatatattttggagagggaagttggctcactgttgtagaggacctgaacaaggt<br>gttcccacccgaggtcgctgtgtttgagccatcagaagcagagatctcccacacc<br>caaaaggccacactggtgtgcctggccacaggcttcttccccgaccacgtggagc<br>tgagctggtgggtgaatgggaaggaggtgcacagtggggtcagcacggaccccgca<br>gccccctcaaggagcagcccgccctcaatgactccagatactgcctgagcagccgc<br>ctgagggtctcggccacctctggcagaaccccgcaaccacttccgctgtcaag<br>tccagttctacgggctctcggagaatgacgagtggacccaggatagggccaaacc<br>cgtcacccagatcgtcagcgccgaggcctgggtagagcagactgtggctttacc<br>tcggtgtcctaccagcaagggtcctgtctgccaccatcctctatgatcctgc<br>tagggaaggccaccctgtatgctgctggtcagcgcccttgtgttgatggccat<br>ggtcaagagaaaggatttc | SEQ ID NO: 229 |
| β1 (with TRBC2) | atgctgctgcttctgctgcttctggggccaggtataagcctccttctacctggga<br>gcttggcaggctccgggcttggtgctgtcgtctctcaacatccgagctgggttat<br>ctgtaagagtggaacctctgtgaagatcgagtgccgttccctggactttcaggcc<br>acaactatgttttggtatcgtcagttcccgaaacagagtctcatgctgatggcaa<br>cttccaatgagggctccaaggccacatacgagcaaggcgtcgagaaggacaagtt<br>tctcatcaaccatgcaagcctgaccttgtccactctgacagtgaccagtgcccat<br>cctgaagacagcagcttctacatctgcagtgctagggacagtgtgtctggaaaca<br>ccatatattttggagagggaagttggctcactgttgtagaggacctgaaaaacgt<br>gttcccacccgaggtcgctgtgtttgagccatcagaagcagagatctcccacacc<br>caaaaggccacactggtgtgcctggccacaggcttctaccccgacgtggagc<br>tgagctggtgggtgaatgggaaggaggtgcacagtggggtcagcacagaccccgca<br>gccccctcaaggagcagcccgccctcaatgactccagatactgcctgagcagccgc<br>ctgagggtctcggccacctctggcagaaccccgcaaccacttccgctgtcaag<br>tccagttctacgggctctcggagaatgacgagtggacccaggatagggccaaacc<br>tgtcacccagatcgtcagcgccgaggcctgggtagagcagactgtggcttcacc | SEQ ID NO: 230 |

TABLE 2 -continued

| DonorChain | Nucleotide sequence | SEQ ID NO |
|---|---|---|
| | tccgagtcttaccagcaaggggtcctgtctgccaccatcctctatgagatcttgc<br>tagggaaggccaccttgtatgccgtgctggtcagtgccctcgtgctgatggccat<br>ggtcaagagaaaggattccagaggc | |
| β2 (with TRBC1) | atgctgagtcttctgctcccttctcctgggactaggctctgtgttcagtgctgtca<br>tctctcaaaagccaagcagggatatctgtcaacgtggaacctccctgacgatcca<br>gtgtcaagtcgatagccaagtcaccatgatgttctggtaccgtcagcaacctgga<br>cagagcctgacactgatcgcaactgcaaatcagggctctgaggccacatatgaga<br>gtggatttgtcattgacaagtttcccatcagccgcccaaacctaacattctcaac<br>tctgactgtgagcaacatgagccctgaagacagcagcatatatctgcagcgtt<br>gggggtagcgggagttacaatgagcagttcttcgggccagggacacggctcaccg<br>tgctagaggacctgaacaaggtgttcccacccgaggtcgctgtgtttgagccatc<br>agaagcagagatctcccacacccaaaaggccacactggtgtgcctggccacaggc<br>ttcttccccgaccacgtggagctgagctggtgggtgaatgggaaggaggtgcaca<br>gtggggtcagcacggacccgcagccctcaaggagcagcccgccctcaatgactc<br>cagatactgcctgagcagccgcctgagggtctcggccaccttctggcagaacccc<br>cgcaaccacttccgctgtcaagtccagttctacgggctctcggagaatgacgagt<br>ggacccaggatagggccaaaccgtcacccagatcgtcagcgccgaggcctgggg<br>tagagcagactgtggctttacctcggtgtcctaccagcaaggggtcctgtctgcc<br>accatcctctatgagatcctgctagggaaggccaccctgtatgctgtgctggtca<br>gcgcccttgtgttgatggccatggtcaagagaaaggatttc | SEQ ID NO: 231 |
| β2 (with TRBC2) | atgctgagtcttctgctcccttctcctgggactaggctctgtgttcagtgctgtca<br>tctctcaaaagccaagcagggatatctgtcaacgtggaacctccctgacgatcca<br>gtgtcaagtcgatagccaagtcaccatgatgttctggtaccgtcagcaacctgga<br>cagagcctgacactgatcgcaactgcaaatcagggctctgaggccacatatgaga<br>gtggatttgtcattgacaagtttcccatcagccgcccaaacctaacattctcaac<br>tctgactgtgagcaacatgagccctgaagacagcagcatatatctgcagcgtt<br>gggggtagcgggagttacaatgagcagttcttcgggccagggacacggctcaccg<br>tgctagaggacctgaaaaacgtgttcccacccgaggtcgctgtgtttgagccatc<br>agaagcagagatctcccacacccaaaaggccacactggtgtgcctggccacaggc<br>ttctaccccgaccacgtggagctgagctggtgggtgaatgggaaggaggtgcaca<br>gtggggtcagcacagacccgcagccctcaaggagcagcccgccctcaatgactc<br>cagatactgcctgagcagccgcctgagggtctcggccaccttctggcagaacccc<br>cgcaaccacttccgctgtcaagtccagttctacgggctctcggagaatgacgagt<br>ggacccaggatagggccaaaccgtcacccagatcgtcagcgccgaggcctgggg<br>tagagcagactgtggcttcacctccgagtcttaccagcaaggggtcctgtctgcc<br>accatcctctatgagatcttgctagggaaggccaccctgtatgccgtgctggtca<br>gtgccctcgtgctgatggccatggtcaagagaaaggattccagaggc | SEQ ID NO: 232 |
| β-3 (with TRBC1) | ATGCTGCTGCTTCTGCTGCTTCTGGGGCCAGGTATAAGCCTCCTTCTACCTGGGA<br>GCTTGGCAGGCTCCGGGCTTGGTGCTGTCGTCTCTCAACATCCGAGCTGGGTTAT<br>CTGTAAGAGTGGAACCTCTGTGAAGATCGAGTGCCGTTCCCTGGACTTTCAGGCC<br>ACAACTATGTTTTGGTATCGTCAGTTCCCGAAACAGAGTCTCATGCTGATGGCAA<br>CTTCCAATGAGGGCTCCAAGGCCACATACGAGCAAGGCGTCGAGAAGGACAAGTT<br>TCTCATCAACCATGCAAGCCTGACCTTGTCCACTCTGACAGTGACCAGTGCCCAT<br>CCTGAAGACAGCAGCTTCTACATCTGCAGTGCTAGAGACGTACTGACAGGGGACT<br>ATGGCTACACCTTCGGTTCGGGGACCAGGTTAACCGTTGTAGAGGACCTGAACAA<br>GGTGTTCCCACCCGAGGTCGCTGTGTTTGAGCCATCAGAAGCAGAGATCTCCCAC<br>ACCCAAAAGGCCACACTGGTGTGCCTGGCCACAGGCTTCTTCCCCGACCACGTGG<br>AGCTGAGCTGGTGGGTGAATGGGAAGGAGGTGCACAGTGGGGTCAGCACGGACCC<br>GCAGCCCCTCAAGGAGCAGCCCGCCCTCAATGACTCCAGATACTGCCTGAGCAGC<br>CGCCTGAGGGTCTCGGCCACCTTCTGGCAGAACCCCGCAACCACTTCCGCTGTC<br>AAGTCCAGTTCTACGGGCTCTCGGAGAATGACGAGTGGACCCAGGATAGGGCCAA<br>ACCCGTCACCCAGATCGTCAGCGCCGAGGCCTGGGGTAGAGCAGACTGTGGCTTT<br>ACCTCGGTGTCCTACCAGCAAGGGGTCCTGTCTGCCACCATCCTCTATGAGATCC<br>TGCTAGGGAAGGCCACCCTGTATGCTGTGCTGGTCAGCGCCCTIGTGTTGATGGC<br>CATGGTCAAGAGAAAGGATTTC | SEQ ID NO: 296 |
| β-3 (with TRBC2) | ATGCTGCTGCTTCTGCTGCTTCTGGGGCCAGGTATAAGCCTCCTTCTACCTGGGA<br>GCTTGGCAGGCTCCGGGCTTGGTGCTGTCGTCTCTCAACATCCGAGCTGGGTTAT<br>CTGTAAGAGTGGAACCTCTGTGAAGATCGAGTGCCGTTCCCTGGACTTTCAGGCC<br>ACAACTATGTTTTGGTATCGTCAGTTCCCGAAACAGAGTCTCATGCTGATGGCAA<br>CTTCCAATGAGGGCTCCAAGGCCACATACGAGCAAGGCGTCGAGAAGGACAAGTT<br>TCTCATCAACCATGCAAGCCTGACCTTGTCCACTCTGACAGTGACCAGTGCCCAT<br>CCTGAAGACAGCAGCTTCTACATCTGCAGTGCTAGAGACGTACTGACAGGGGACT<br>ATGGCTACACCTTCGGTTCGGGGACCAGGTTAACCGTTGTAGAGGACCTGAAAAA<br>CGTGTTCCCACCCGAGGTCGCTGTGTTTGAGCCATCAGAAGCAGAGATCTCCCAC<br>ACCCAAAAGGCCACACTGGTGTGCCTGGCCACAGGCTTCTACCCCGACCACGTGG<br>AGCTGAGCTGGTGGGTGAATGGGAAGGAGGTGCACAGTGGGGTCAGCACAGACCC<br>GCAGCCCCTCAAGGAGCAGCCCGCCCTCAATGACTCCAGATACTGCCTGAGCAGC<br>CGCCTGAGGGTCTCGGCCACCTTCTGGCAGAACCCCGCAACCACTTCCGCTGTC<br>AAGTCCAGTTCTACGGGCTCTCGGAGAATGACGAGTGGACCCAGGATAGGGCCAA<br>ACCTGTCACCCAGATCGTCAGCGCCGAGGCCTGGGGTAGAGCAGACTGTGGCTTC<br>ACCTCCGAGTCTTACCAGCAAGGGGTCCTGTCTGCCACCATCCTCTATGAGATCT<br>TGCTAGGGAAGGCCACCTTGTATGCCGTGCTGGTCAGCGCCCTCGTGCTGATGGC<br>CATGGTCAAGAGAAAGGATTCCAGAGGC | SEQ ID NO: 297 |
| β-4 (with TRBC1) | ATGGGCTCCTGGACCCTCTGCTGTGTGTCCCTTTGCATCCTGGTAGCAAAGCACA<br>CAGATGCTGGAGTTATCCAGTCACCCCGGCACGAGGTGACAGAGATGGGACAAGA<br>AGTGACTCTGAGATGTAAACCAATTTCAGGACACGACTACCTTTTCTGGTACAGA<br>CAGACCATGATGCGGGGACTGGAGTTGCTCATTTACTTTAACAACAACGTTCCGA<br>TAGATGATTCAGGGATGCCCGAGGATCGATTCTCAGCTAAGATGCCTAATGCATC | SEQ ID NO: 298 |

TABLE 2 -continued

| DonorChain | | Nucleotide sequence | SEQ ID NO |
|---|---|---|---|
| | | ATTCTCCACTCTGAAGATCCAGCCCTCAGAACCCAGGGACTCAGCTGTGTACTTC TGTGCCAGCAGTTTAGGACTGAGCATTTCCCAAGAGACCCAGTACTTCGGGCCAG GCACGCGGCTCCTGGTGCTCGAGGACCTGAACAAGGTGTTCCCACCCGAGGTCGC TGTGTTTGAGCCATCAGAAGCAGAGATCTCCCACACCCAAAAGGCCACACTGGTG TGCCTGGCCACAGGCTTCTTCCCCGACCACGTGGAGCTGAGCTGGTGGGTGAATG GGAAGGAGGTGCACAGTGGGGTCAGCACGGACCCGCAGCCCCTCAAGGAGCAGCC CGCCCTCAATGACTCCAGATACTGCCTGAGCAGCCGCCTGAGGGTCTCGGCCACC TTCTGGCAGAACCCCGCAACCACTTCCGCTGTCAAGTCCAGTTCTACGGGCTCT CGGAGAATGACGAGTGGACCCAGGATAGGGCCAAACCCGTCACCCAGATCGTCAG CGCCGAGGCCTGGGGTAGAGCAGACTGTGGCTTTACCTCGGTGTCCTACCAGCAA GGGGTCCTGTCTGCCACCATCCTCTATGAGATCCTGCTAGGGAAGGCCACCCTGT ATGCCTGTGCTGGTCAGCGCCCTTGTGTTGATGGCCATGGTCAAGAGAAAGGATTT C | |
| | β-4 (with TRBC2) | ATGGGCTCCTGGACCCTCTGCTGTGTGTCCCTTTGCATCCTGGTAGCAAAGCACA CAGATGCTGGAGTTATCCAGTCACCCCGGCACGAGGTGACAGAGATGGACAAGA AGTGACTCTGAGATGTAAACCAATTTCAGGACACGACTACCTTTTCTGGTACAGA CAGACCATGATGCGGGGACTGGAGTTGCTCATTTACTTTAACAACAACGTTCCGA TAGATGATTCAGGGATGCCCGAGGATCGATTCTCAGCTAAGATGCCTAATGCATC ATTCTCCACTCTGAAGATCCAGCCCTCAGAACCCAGGGACTCAGCTGTGTACTTC TGTGCCAGCAGTTTAGGACTGAGCATTTCCCAAGAGACCCAGTACTTCGGGCCAG GCACGCGGCTCCTGGTGCTCGAGGACCTGAAAAACGTGTTCCCACCCGAGGTCGC TGTGTTTGAGCCATCAGAAGCAGAGATCTCCCACACCCAAAAGGCCACACTGGTG TGCCTGGCCACAGGCTTCTACCCCGACCACGTGGAGCTGAGCTGGTGGGTGAATG GGAAGGAGGTGCACAGTGGGGTCAGCACAGACCCGCAGCCCCTCAAGGAGCAGCC CGCCCTCAATGACTCCAGATACTGCCTGAGCAGCCGCCTGAGGGTCTCGGCCACC TTCTGGCAGAACCCCCGCAACCACTTCCGCTGTCAAGTCCAGTTCTACGGGCTCT CGGAGAATGACGAGTGGACCCAGGATAGGGCCAAACCTGTCACCCAGATCGTCAG CGCCGAGGCCTGGGGTAGAGCAGACTGTGGCTTCACCTCCGAGTCTTACCAGCAA GGGGTCCTGTCTGCCACCATCCTCTATGAGATCTTGCTAGGGAAGGCCACCTTGT ATGCCGTGCTGGTCAGTGCCCTCGTGCTGATGGCCATGGTCAAGAGAAAGGATTC CAGAGGC | SEQ ID NO: 299 |
| HD8 | α (with TRAC) | atggtgaagatccggcaattttttgttggctattttgtggcttcagctaagctgtg taagtgccgccaaaaatgaagtggagcagagtcctcagaacctgactgcccagga aggagaatttatcacaatcaactgcagttactcggtaggaataagtgccttacac tggctgcaacagcatccaggaggaggcattgtttccttgtttatgctgagctcag ggaagaagaagcatggaagattaattgccacaataaaacatacaggaaaagcacag ctccctgcacatcacagcctcccatcccagagactctgccgtctacatctgtgct gtcacagtcggaaacaaactggtctttggcgcaggaaccattctgagagtcaagt cctatatccagaaccctgaccctgccgtgtaccagctgagagactctaaatccag tgacaagtctgtctgcctattcaccgatttgattctcaaacaaatgtgtcacaa agtaaggattctgatgtgtatatcacagacaaaactgtgctagacatgaggtcta tggacttcaagagcaacagtgctgtggcctggagcaacaaatctgactttgcatg tgcaaacgccttcaacaacagcattattccagaagacaccttcttccccagccca gaaagttcctgtgatgtcaagctggtcgagaaaagctttgaaacagatacgaacc taaactttcaaaacctgtcagtgattgggttccgaatcctcctcctgaaagtggc cgggtttaatctgctcatgacgctgcggctgtggtccagc | SEQ ID NO: 233 |
| | β (with TRBC1) | atgagcatccggctcctgtgctgtgtggccttttctctcctgtgggcaagtccag tgaatgctggtgtcactcagacccccaaaattccaggtcctgaagacaggacagag catgacactgcagtgtgcccaggatatgaaccataactccatgtactggtatcga caagacccaggcatgggactgaggctgatttattactcagcttctgagggtacca ctgacaaaggagaagtccccaatggctacaatgtctccagattaaacaaacggga gttctcgctcaggctggagtcggctgctccctcccagacatctgtgtacttctgt gccagcagggggtggcgtgagcagttcttcgggcagggacacggctcaccgtgc tagaggacctgaacaaggtgttcccacccgaggtcgctgtgtttgagccatcaga agcagagatctcccacacccaaaaggccacactggtgtgcctggccacaggcttc ttccccgaccacgtggagctgagctggtgggtgaatgggaaggaggtgcacagtg gggtcagcacggacccgcagcccctcaaggagcagcccgccctcaatgactccag atactgcctgagcagccgcctgagggtctcggccaccttctggcagaacccccgc aaccacttccgctgtcaagtccagttctacgggctctcggagaatgacgagtgga cccaggatagggccaaacccgtcacccagatcgtcagcgccgaggcctggggtag agcagactgtggctttacctcggtgtcctaccagcaaggggtcctgtctgccacc atcctctatgagatcctgctagggaaggccaccctgtatgctgtgctggtcagcg cccttgtgttgatggccatggtcaagagaaaggatttc | SEQ ID NO: 234 |
| | β (with TRBC2) | atgagcatccggctcctgtgctgtgtggccttttctctcctgtgggcaagtccag tgaatgctggtgtcactcagacccccaaaattccaggtcctgaagacaggacagag catgacactgcagtgtgcccaggatatgaaccataactccatgtactggtatcga caagacccaggcatgggactgaggctgatttattactcagcttctgagggtacca ctgacaaaggagaagtccccaatggctacaatgtctccagattaaacaaacggga gttctcgctcaggctggagtcggctgctccctcccagacatctgtgtacttctgt gccagcagggggtggcgtgagcagttcttcgggcagggacacggctcaccgtgc tagaggacctgaaaaacgtgttcccacccgaggtcgctgtgtttgagccatcaga agcagagatctcccacacccaaaaggccacactggtgtgcctggccacaggcttc taccccgaccacgtggagctgagctggtgggtgaatgggaaggaggtgcacagtg gggtcagcacggacccgcagcccctcaaggagcagcccgccctcaatgactccag atactgcctgagcagccgcctgagggtctcggccaccttctggcagaacccccgc aaccacttccgctgtcaagtccagttctacgggctctcggagaatgacgagtgga cccaggatagggccaaacctgtcacccagatcgtcagcgccgaggcctggggtag | SEQ ID NO: 235 |

TABLE 2 -continued

| DonorChain | | Nucleotide sequence | SEQ ID NO |
|---|---|---|---|
| | | agcagactgtggcttcacctccgagtcttaccagcaaggggtcctgtctgccacc atcctctatgagatcttgctagggaaggccaccttgtatgccgtgctggtcagtg ccctcgtgctgatggccatggtcaagagaaaggattccgagggc | |
| HD9 | α1 (with TRAC) | atggtgaagatccggcaattttttgttggctattttgtggcttcagctaagctgtg taagtgccgccaaaaatgaagtggagcagagtcctcagaacctgactgcccagga aggagaaatttatcacaatcaactgcagttactcggtaggaataagtgccttacac tggctgcaacagcatccaggaggaggcattgtttccttgtttatgctgagctcag ggaagaagaagcatgcaagattaattgccacaataaacatacaggaaaagcacag ctccctgcacatcacagcctccccatcccagagactctgccgtctacatctgtgct gcccgatcttataacaccgacaagctcatctttgggactgggaccagattacaag tcttccaaatatccagaaccctgaccctgccgtgtaccagctgagagactctaa atccagtgacaagtctgtctgcctattcaccgattttgattctcaaacaaatgtg tcacaaagtaaggattctgatgtgtatatcacagacaaaactgtgctagacatga ggtctatggacttcaagagcaacagtgctgtggcctggagcaacaaatctgactt tgcatgtgcaaacgccttcaacaacagcattattccagaagacaccttcttcccc agcccagaaagttcctgtgatgtcaagctggtcgagaaaagctttgaaacagata cgaacctaaactttcaaaacctgtcagtgattgggttccgaatcctcctcctgaa agtggccgggttttaatctgctcatgacgctgcggctgtggtccagc | SEQ ID NO: 236 |
| | α2 (with TRAC) | atggccatgctcctgggggcatcagtgctgattctgtggcttcagcagactggg taaacagtcaacagaagaatgatgaccagcaagttaagcaaaattcaccatccct gagcgtccaggaaggaagaatttctattctgaactgtgactatactaacagcatg tttattatttcctatggtacaaaaaataccctgctgaaggtcctacattcctga tatctataagttccattaaggataaaaatgaagatggaagattcactgtcttctt aaacaaaagtgccaagcacctctctctgcacattgtgccctcccagcctggagac tctgcagtgtacttctgtgcagcaagttacaacaatgccagactcatgtttggag atggaactcagctggtggtgaagcccaatatccagaaccctgaccctgccgtgta ccagctgagagactctaaatccagtgacaagtctgtctgcctattcaccgattttg gattctcaaacaaatgtgtcacaaagtaaggattctgatgtgtatatcacagaca aaactgtgctagacatgaggtctatggacttcaagagcaacagtgctgtggcctg gagcaacaaatctgactttgcatgtgcaaacgccttcaacaacagcattattcca gaagacaccttcttccccagcccagaaagttcctgtgatgtcaagctggtcgaga aaagctttgaaacagatacgaacctaaactttcaaaacctgtcagtgattgggtt ccgaatcctcctcctgaaagtggccgggtttaatctgctcatgacgctgcggctg tggtccagc | SEQ ID NO: 237 |
| | α3 (with TRAC) | atggccatgctcctgggggcatcagtgctgattctgtggcttcagcagactggg taaacagtcaacagaagaatgatgaccagcaagttaagcaaaattcaccatccct gagcgtccaggaaggaagaatttctattctgaactgtgactatactaacagcatg tttgattatttcctatggtacaaaaaataccctgctgaaggtcctacattcctga tatctataagttccattaaggataaaaatgaagatggaagattcactgtcttctt aaacaaaagtgccaagcacctctctctgcacattgtgccctcccagcctggagac tctgcagtgtacttctgtgcagcaagttacaacaatgccagactcatgtttggag atggaactcagctggtggtgaagcccaatatccagaaccctgaccctgccgtgta ccagctgagagactctaaatccagtgacaagtctgtctgcctattcaccgattttg gattctcaaacaaatgtgtcacaaagtaaggattctgatgtgtatatcacagaca aaactgtgctagacatgaggtctatggacttcaagagcaacagtgctgtggcctg gagcaacaaatctgactttgcatgtgcaaacgccttcaacaacagcattattcca gaagacaccttcttccccagcccagaaagttcctgtgatgtcaagctggtcgaga aaagctttgaaacagatacgaacctaaactttcaaaacctgtcagtgattgggtt ccgaatcctcctcctgaaagtggccgggtttaatctgctcatgacgctgcggctg tggtccagc | SEQ ID NO: 238 |
| | β1 (with TRBC1) | atgggaccccaggctcctcttctgggcactgctttgtctcctcggaacaggcccag tggaggctggagtcacacaaagtcccacacacctgatcaaaacgagaggacagca agcgactctgagatgctctcctatctctgggcacaccagtgtgtactggtaccaa caggccctgggtctgggcctccagttcctcctttggtatgacgagggtgaagaga gaaacagaggaaacttccctcctagattttcaggtcgccagttccctaattatag ctctgagctgaatgtgaacgccttggagctggaggactcggccctgtatctctgt gccagcagctgggggtaccaagagacccagtacttcgggccaggcacgcggctcc tggtgctcgaggacctgaacaaggtgttccacccgaggtcgctgtgttgagcc atcagaagcagagatctcccacaccccaaaaggccacactggtgtgcctggcaca ggcttcttccccgaccacgtggagctgagctggtgggtgaatgggaaggaggtgc acagtgggggtcagcacggaccccgcagcccctcaaggagcagcccgccctcaatga ctccagatactgcctgagcagccgcctgagggtctcggccaccttctggcagaac ccccgcaaccacttccgctgtcaagtccagttctacgggctctcggagaatgacg agtggaccccaggatagggccaaacccgtcacccagatcgtcagcgccgaggcctg gggtagagcagactgtggcttacctcggtgtcctaccagcaaggggtcctgtct gccaccatcctctatgagatcctgctagggaaggccacccctgtatgctgtgctgg tcagcgcccttgtgttgatggccatggtcaagagaaaggattc | SEQ ID NO: 239 |
| | β1 (with TRBC2) | atgggaccccaggctcctcttctgggcactgctttgtctcctcggaacaggcccag tggaggctggagtcacacaaagtcccacacacctgatcaaaacgagaggacagca agcgactctgagatgctctcctatctctgggcacaccagtgtgtactggtaccaa caggccctgggtctgggcctccagttcctcctttggtatgacgagggtgaagaga gaaacagaggaaacttccctcctagattttcaggtcgccagttccctaattatag ctctgagctgaatgtgaacgccttggagctggaggactcggccctgtatctctgt gccagcagctgggggtaccaagagacccagtacttcgggccaggcacgcggctcc tggtgctcgaggacctgaaaaacgtgttccacccgaggtcgctgtgttgagcc atcagaagcagagatctcccacaccccaaaaggccacactggtgtgcctggcaca ggcttctaccccgaccacgtggagctgagctggtgggtgaatgggaaggaggtgc | SEQ ID NO: 240 |

TABLE 2 -continued

| DonorChain | Nucleotide sequence | SEQ ID NO |
|---|---|---|
| | acagtggggtcagcacagacccgcagcccctcaaggagcagcccgccctcaatga<br>ctccagatactgcctgagcagccgcctgagggtctcggccaccttctggcagaac<br>ccccgcaaccacttccgctgtcaagtccagttctacgggctctcggagaatgacg<br>agtggacccaggatagggccaaacctgtcacccagatcgtcagcgccgaggcctg<br>gggtagagcagactgtggcttcacctccgagtcttaccagcaaggggtcctgtct<br>gccaccatcctctatgagatcttgctagggaaggccaccttgtatgccgtgctgg<br>tcagtgccctcgtgctgatggccatggtcaagagaaaggattccagaggc | |
| β2 (with TRBC1) | atggacaccagagtactctgctgtgcggtcatctgtcttctgggggcaggtctct<br>caaatgccggcgtcatgcagaacccaagacacctggtcaggaggaggggacagga<br>ggcaagactgagatgcagcccaatgaaaggacacagtcatgtttactggtatcgg<br>cagctcccagaggaaggtctgaaattcatggtttatctccagaaagaaaatatca<br>tagatgagtcaggaatgccaaaggaacgattttctgctgaatttcccaaagaggg<br>ccccagcatcctgaggatccagcaggtagtgcgaggagattcggcagcttatttc<br>tgtgccagctcaccgacaggtggcgagtactatggctacaccttcggttcgggga<br>ccaggttaaccgttgtagaggacctgaacaaggtgttcccaccgaggtcgctgt<br>gtttgagccatcagaagcagagatctcccacacccaaaaggccacactggtgtgc<br>ctggccacaggcttcttccccgaccacgtggagctgagctggtgggtgaatggga<br>aggaggtgcacagtgggtcagcacagacccgcagcccctcaaggagcagcccgc<br>cctcaatgactccagatactgcctgagcagccgcctgagggtctcggccaccttc<br>tggcagaaccccgcaaccacttccgctgtcaagtccagttctacgggctctcgg<br>agaatgacgagtggacccaggatagggccaaacccgtcacccagatcgtcagcgc<br>cgaggcctggggtagagcagactgtggctttacctcggtgtcctaccagcaaggg<br>gtcctgtctgccaccatcctctatgagatcttgctagggaaggccacccttgtatg<br>ctgtgctggtcagcgcccttgtgttgatggccatggtcaagagaaaggatttc | SEQ ID NO: 241 |
| β2 (with TRBC2) | atggacaccagagtactctgctgtgcggtcatctgtcttctgggggcaggtctct<br>caaatgccggcgtcatgcagaacccaagacacctggtcaggaggaggggacagga<br>ggcaagactgagatgcagcccaatgaaaggacacagtcatgtttactggtatcgg<br>cagctcccagaggaaggtctgaaattcatggtttatctccagaaagaaaatatca<br>tagatgagtcaggaatgccaaaggaacgattttctgctgaatttcccaaagaggg<br>ccccagcatcctgaggatccagcaggtagtgcgaggagattcggcagcttatttc<br>tgtgccagctcaccgacaggtggcgagtactatggctacaccttcggttcgggga<br>ccaggttaaccgttgtagaggacctgaaaaacgtgttcccaccgaggtcgctgt<br>gtttgagccatcagaagcagagatctcccacacccaaaaggccacactggtgtgc<br>ctggccacaggcttctaccccgaccacgtggagctgagctggtgggtgaatggga<br>aggaggtgcacagtgggtcagcacagacccgcagcccctcaaggagcagcccgc<br>cctcaatgactccagatactgcctgagcagccgcctgagggtctcggccaccttc<br>tggcagaaccccgcaaccacttccgctgtcaagtccagttctacgggctctcgg<br>agaatgacgagtggacccaggatagggccaaacctgtcacccagatcgtcagcgc<br>cgaggcctggggtagagcagactgtggcttcacctccgagtcttaccagcaaggg<br>gtcctgtctgccaccatcctctatgagatcttgctagggaaggccaccttgtatg<br>ccgtgctggtcagtgcccctcgtgctgatggccatggtcaagagaaaggattccag<br>aggc | SEQ ID NO: 242 |
| β3 (with TRBC1) | atgagcatcggcctcctgtgctgtgcagccttgtctctcctgtgggcaggtccag<br>tgaatgctggtgtcactcagaccccaaaattccaggtcctgaagacaggacagag<br>catgacactgcagtgtgcccaggatatgaaccatgaatacatgtcctggtatcga<br>caagacccaggcatgggctgaggctgattcattactcagttggtgctggtatca<br>ctgaccaaggagaagtccccaatggctacaatgtctccagatcaaccacagagga<br>tttcccgctcaggctgctgtcggctgctccctcccagacatctgtgtacttctgt<br>gccagcagttcataccccttcggacagggcgatacaactcctataattcaccc<br>tccactttgggaacgggaccaggctcactgtgacagaggacctgaacaaggtgtt<br>cccacccgaggtcgctgtgtttgagccatcagaagcagagatctcccacacccaa<br>aaggccacactggtgtgcctggccacaggcttcttccccgaccacgtggagctga<br>gctggtgggtgaatgggaaggaggtgcacagtgggtcagcacggacccgcagcc<br>cctcaaggagcagcccgccctcaatgactccagatactgcctgagcagccgcctg<br>agggtctcggccaccttctggcagaaccccgcaaccacttccgctgtcaagtcc<br>agttctacgggctctcggagaatgacgagtggacccaggatagggccaaacccgt<br>cacccagatcgtcagcgccgaggcctggggtagagcagactgtggctttacctcg<br>gtgtcctaccagcaaggggtcctgtctgccaccatcctctatgagatcctgctag<br>ggaaggccacccttgtatgctgtgctggtcagcgcccttgtgttgatggccatggt<br>caagagaaaggatttctga | SEQ ID NO: 243 |
| β3 (with TRBC2) | atgagcatcggcctcctgtgctgtgcagccttgtctctcctgtgggcaggtccag<br>tgaatgctggtgtcactcagaccccaaaattccaggtcctgaagacaggacagag<br>catgacactgcagtgtgcccaggatatgaaccatgaatacatgtcctggtatcga<br>caagacccaggcatgggctgaggctgattcattactcagttggtgctggtatca<br>ctgaccaaggagaagtccccaatggctacaatgtctccagatcaaccacagagga<br>tttcccgctcaggctgctgtcggctgctccctcccagacatctgtgtacttctgt<br>gccagcagttcataccccttcggacagggcgatacaactcctataattcaccc<br>tccactttgggaacgggaccaggctcactgtgacagaggacctgaaaaacgtgtt<br>cccacccgaggtcgctgtgtttgagccatcagaagcagagatctcccacacccaa<br>aaggccacactggtgtgcctggccacaggcttctaccccgaccacgtggagctga<br>gctggtgggtgaatgggaaggaggtgcacagtgggtcagcacagacccgcagcc<br>cctcaaggagcagcccgccctcaatgactccagatactgcctgagcagccgcctg<br>agggtctcggccaccttctggcagaaccccgcaaccacttccgctgtcaagtcc<br>agttctacgggctctcggagaatgacgagtggacccaggatagggccaaacctgt<br>cacccagatcgtcagcgccgaggcctggggtagagcagactgtggcttcacctcc<br>gagtcttaccagcaaggggtcctgtctgccaccatcctctatgagatcttgctag<br>ggaaggccaccttgtatgccgtgctggtcagtgccctcgtgctgatggccatggt<br>caagagaaaggattccagaggc | SEQ ID NO: 244 |

TABLE 2 -continued

| DonorChain | Nucleotide sequence | SEQ ID NO |
|---|---|---|
| HD10 α (with TRAC) | atggccatgctcctgggggcatcagtgctgattctgtggcttcagccagactggg taaacagtcaacagaagaatgatgaccagcaagttaagcaaaattcaccatccct gagcgtccaggaaggaagaatttctattctgaactgtgactatactaacagcatg tttgattatttcctatggtacaaaaaatacctgctgaaggtcctacattcctga tatctataagttccattaaggataaaaatgaagatggaagattcactgtcttctt aaacaaaagtgccaagcacctctctctgcacattgtgccctcccagcctggagac tctgcagtgtacttctgtgcagcaagcggaggaagagatgacaagatcatctttg gaaaagggacacgacttcatattctcccaatatccagaaccctgaccctgccgt gtaccagctgagagactctaaatccagtgacaagtctgtctgcctattcaccgat tttgattctcaaacaaatgtgtcacaaagtaaggattctgatgtgtatatcacag acaaaactgtgctagacatgaggtctatggacttcaagagcaacagtgctgtggc ctggagcaacaaatctgactttgcatgtgcaaacgccttcaacaacagcattatt ccagaagacaccttcttccccagcccagaaagttcctgtgatgtcaagctggtcg agaaaagctttgaaacagatacgaacctaaactttcaaaacctgtcagtgattgg gttccgaatcctcctcctgaaagtggccgggtttaatctgctcatgacgctgcgg ctgtggtccagc | SEQ ID NO: 245 |
| β (with TRBC1) | atgagcatcggcctcctgtgctgtgcagccttgtctctcctgtgggcaggtccag tgaatgctggtgtcactcagacccccaaaattccaggtcctgaagacaggacagag catgacactgcagtgtgcccaggatatgaaccatgaatacatgtcctggtatcga caagacccaggcatggggctgaggctgattcattactcagttggtgctggtatca ctgaccaaggagaagtccccaatggctacaatgtctccagatcaaccacagagga tttcccgctcaggctgctgtcggctgctccctcccagacatctgtgtacttctgt gccagcagctactcccggacagagagcacagatacgcagtattttggcccaggca cccggctgacagtgctcgaggacctgaacaaggtgttccacccgaggtcgctgt gtttgagccatcagaagcagagatctcccacacccaaaaggccacactggtgtgc ctggccacaggcttcttccccgaccacgtggagctgagctggtgggtgaatggga aggaggtgcacagtggggtcagcacggacccgcagcccctcaaggagcagcccgc cctcaatgactccagatactgcctgagcagccgcctgagggtctcggccaccttc tggcagaaccccgcaaccacttccgctgtcaagtccagttctacgggctctcgg agaatgacgagtggacccaggatagggccaaaccgtcacccagatcgtcagcgc cgaggcctggggtagagcagactgtggcttacctccggtgtcctaccagcaaggg gtcctgtctgccaccatcctctatgagatcctgctagggaaggccaccctgtatg ctgtgctggtcagcgcccttgtgttgatggccatggtcaagagaaaggatttc | SEQ ID NO: 246 |
| β (with TRBC2) | atgagcatcggcctcctgtgctgtgcagccttgtctctcctgtgggcaggtccag tgaatgctggtgtcactcagacccccaaaattccaggtcctgaagacaggacagag catgacactgcagtgtgcccaggatatgaaccatgaatacatgtcctggtatcga caagacccaggcatggggctgaggctgattcattactcagttggtgctggtatca ctgaccaaggagaagtccccaatggctacaatgtctccagatcaaccacagagga tttcccgctcaggctgctgtcggctgctccctcccagacatctgtgtacttctgt gccagcagctactcccggacagagagcacagatacgcagtattttggcccaggca cccggctgacagtgctcgaggacctgaaaaacgtgttccacccgaggtcgctgt gtttgagccatcagaagcagagatctcccacacccaaaaggccacactggtgtgc ctggccacaggcttctaccccgaccacgtggagctgagctggtgggtgaatggga aggaggtgcacagtggggtcagcacagacccgcagcccctcaaggagcagcccgc cctcaatgactccagatactgcctgagcagccgcctgagggtctcggccaccttc tggcagaaccccgcaaccacttccgctgtcaagtccagttctacgggctctcgg agaatgacgagtggacccaggatagggccaaacctgtcacccagatcgtcagcgc cgaggcctggggtagagcagactgtggcttcacctccgagtcttaccagcaaggg gtcctgtctgccaccatcctctatgagatcttgctagggaaggccaccttgtatg ccgtgctggtcagtgccctcgtgctgatggccatggtcaagagaaaggattccag aggc | SEQ ID NO: 247 |

Accordingly, the present invention provides an isolated polynucleotide comprising one or more nucleotide sequences selected from the group consisting of SEQ ID NOs: 132-156, 223-247 and 292-299, or variants thereof having at least 40%, at least 50%, at least 60%, at least 70%, at least 75%, at least 80%, at least 85%, at least 90%, at least 95%, at least 96%, at least 97%, at least 98%, or at least 99% sequence identity thereto.

The present invention also provides a TCR comprising an α chain encoded by a nucleotide sequence selected from the group consisting of SEQ ID NOs: 132, 135, 138, 141, 144, 147, 152, 223, 226, 227, 228, 233, 236, 237, 238, 245, 292, 295, and variants thereof having at least 40%, at least 50%, at least 60%, at least 70%, at least 75%, at least 80%, at least 85%, at least 90%, at least 95%, at least 96%, at least 97%, at least 98%, or at least 99% sequence identity thereto.

The present invention also provides a TCR comprising a β chain encoded by a nucleotide sequence selected from the group consisting of SEQ ID Nos: 133, 134, 136, 137, 139, 140, 142, 143, 145, 146, 148, 149, 150, 151, 153, 154, 155, 156, 224, 225, 229, 230, 231, 232, 234, 235, 239, 240, 241, 242, 243, 244, 246, 247, 293, 294, 296-299, and variants thereof having at least 40%, at least 50%, at least 60%, at least 70%, at least 75%, at least 80%, at least 85%, at least 90%, at least 95%, at least 96%, at least 97%, at least 98%, or at least 99% sequence identity thereto.

Further provided by the present invention are isolated polynucleotide sequences derived from the sequences present in Table 2. For example, the present invention provides an isolated polynucleotide encoding a variable region of a TCR according to the present invention, wherein the isolated polynucleotide comprises a stretch of nucleotides of any one of SEQ ID Nos: 132-156, 223-247 and 292-299.

The variant sequences may have additions, deletions or substitutions, of one or more bases. If the variation involves addition(s) or deletion(s) they may either occur in threes or be balanced (i.e. an addition for each deletion) so that the variation does not cause a frame-shift for translation of the remainder of the sequence.

Some or all of the variations may be "silent" in the sense that they do not affect the sequence of the encoded protein due to the degeneracy of the genetic code.

Some or all of the variations may produce conservative amino acid substitutions, additions or deletions as explained above. The variation may be concentrated in one or more regions, such as the regions encoding the constant regions, the linker, or the framework regions of the α or β chains, or they may be spread throughout the molecule.

The variant sequence should retain the capacity to encode all or part of a TCR amino acid sequence which binds to a WT1 peptide.

Codon Optimisation

The polynucleotides used in the present invention may be codon-optimised. Codon optimisation has previously been described in WO 1999/41397 and WO 2001/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved.

Codon usage tables are known in the art for mammalian cells, as well as for a variety of other organisms.

Codon optimisation may also involve the removal of mRNA instability motifs and cryptic splice sites.

Vector

The present invention provides a vector comprising a polynucleotide described herein.

A vector is a tool that allows or facilitates the transfer of an entity from one environment to another. In accordance with the present invention, and by way of example, some vectors used in recombinant nucleic acid techniques allow entities, such as a segment of nucleic acid (e.g. a heterologous DNA segment, such as a heterologous Cdna segment), to be transferred into a target cell. The vector may serve the purpose of maintaining the heterologous nucleic acid (DNA or RNA) within the cell, facilitating the replication of the vector comprising a segment of nucleic acid, or facilitating the expression of the protein encoded by a segment of nucleic acid. Vectors may be non-viral or viral. Examples of vectors used in recombinant nucleic acid techniques include, but are not limited to, plasmids, chromosomes, artificial chromosomes and viruses. The vector may be single stranded or double stranded. It may be linear and optionally the vector comprises one or more homology arms. The vector may also be, for example, a naked nucleic acid (e.g. DNA). In its simplest form, the vector may itself be a nucleotide of interest.

The vectors used in the invention may be, for example, plasmid or virus vectors and may include a promoter for the expression of a polynucleotide and optionally a regulator of the promoter.

Vectors comprising polynucleotides used in the invention may be introduced into cells using a variety of techniques known in the art, such as transformation, transfection and transduction. Several techniques are known in the art, for example transduction with recombinant viral vectors, such as retroviral, lentiviral, adenoviral, adeno-associated viral, baculoviral and herpes simplex viral vectors, Sleeping Beauty vectors; direct injection of nucleic acids and biolistic transformation.

Non-viral delivery systems include but are not limited to DNA transfection methods. Here, transfection includes a process using a non-viral vector to deliver a gene to a target cell. Typical transfection methods include electroporation, DNA biolistics, lipid-mediated transfection, compacted DNA-mediated transfection, liposomes, immunoliposomes, lipofectin, cationic agent-mediated transfection, cationic facial amphiphiles (CFAs) (Nature Biotechnology 1996 14; 556) and combinations thereof.

The term "transfection" is to be understood as encompassing the delivery of polynucleotides to cells by both viral and non-viral delivery.

In addition, the invention may employ gene targeting protocols, for example the delivery of DNA-modifying agents.

The term "vector" includes an expression vector i.e. a construct capable of in vivo or in vitrolex vivo expression. Expression may be controlled by a vector sequence, or, for example in the case of insertion at a target site, expression may be controlled by a target sequence. A vector may be integrated or tethered to the cell's DNA.

Viral delivery systems include but are not limited to adenovirus vector, an adeno-associated viral (AAV) vector, a herpes viral vector, a retroviral vector, a lentiviral vector, and a baculoviral vector.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses also belong to the retrovirus family, but they can infect both dividing and non-dividing cells (Lewis et al (1992) EMBO J. 3053-3058).

The vector may be capable of transferring a nucleotide sequence encoding a WT1-specific TCR described herein to a cell, such as a T-cell, such that the cell expresses the WT1-specific TCR. Preferably the vector will be capable of sustained high-level expression in T-cells, so that the introduced TCR may compete successfully with the endogenous TCR for a limited pool of CD3 molecules.

Increasing the supply of CD3 molecules may increase TCR expression, for example, in a cell that has been modified to express the TCRs of the present invention. Accordingly, the vector of the present invention may further comprise one or more genes encoding CD3-gamma, CD3-delta, CD3-epsilon and/or CD3-zeta. In one embodiment, the vector of the present invention comprises a gene encoding CD3-zeta. The vector may comprise a gene encoding CD8. The vector may encode a selectable marker or a suicide gene, to increase the safety profile of the genetically engineered cell, e.g. a cell of the present invention, or a cell that has been modified to express the TCRs of the present invention (Bonini, Science 1997, Ciceri, Bonini Lancet Oncol. 2009, Oliveira et al., STM 2015). The genes comprised in the vector of the present invention may be linked by self-cleaving sequences, such as the 2A self-cleaving sequence.

Alternatively one or more separate vectors encoding a CD3 gene may be provided for co-transfer to a cell simultaneously, sequentially or separately with one or more vectors of the present invention, e.g. one or more vectors encoding TCRs of the present invention.

Cell

The present invention relates to a cell comprising a polynucleotide or a vector according to the present invention.

The cell may be a T-cell, a lymphocyte, or a stem cell. The T-cell, the lymphocyte, or the stem cell may be selected from the group consisting of CD4 cells, CD8 cells, naive T-cells, memory stem T-cells, central memory T-cells, double negative T-cells, effector memory T-cells, effector T-cells, Th0 cells, Tc0 cells, Th1 cells, Tc1 cells, Th2 cells, Tc2 cells, Th17 cells, Th22 cells, gamma/delta T-cells, natural killer (NK) cells, natural killer T (NKT) cells, hematopoietic stem cells and pluripotent stem cells.

The type of cell may be selected in order to provide desirable and advantageous in vivo persistence and to provide desirable and advantageous functions and characteristics to the cells of present invention.

The cell may have been isolated from a subject.

The cell of the present invention may be provided for use in adoptive cell transfer. As used herein the term "adoptive cell transfer" refers to the administration of a cell population to a patient. Typically, the cells are T-cells isolated from a subject and then genetically modified and cultured in vitro in order to express a TCR of the present invention before being administered to the patient.

Adoptive cell transfer may be allogenic or autologous.

By "autologous cell transfer" it is to be understood that the starting population of cells (which are then transduced according to a method of the invention, or are transduced with a vector according to the present invention) is obtained from the same subject as that to which the transduced T-cell population is administered. Autologous transfer is advantageous as it avoids problems associated with immunological incompatibility and are available to subjects irrespective of the availability of a genetically matched donor.

By "allogeneic cell transfer" is to be understood that the starting population of cells (which are then transduced according to a method of the invention, or are transduced with a vector according to the present invention) is obtained from a different subject as that to which the transduced cell population is administered. Preferably, the donor will be genetically matched to the subject to which the cells are administered to minimise the risk of immunological incompatibility. Alternatively, the donor may be mismatched and unrelated to the patient.

Suitable doses of transduced cell populations are such as to be therapeutically and/or prophylactically effective. The dose to be administered may depend on the subject and condition to be treated, and may be readily determined by a skilled person.

The cell may be derived from a T-cell isolated from a subject. The T-cell may be part of a mixed cell population isolated from the subject, such as a population of peripheral blood lymphocytes (PBL). T-cells within the PBL population may be activated by methods known in the art, such as using anti-CD3 and/or anti-CD28 antibodies or cell sized beads conjugated with anti-CD3 and/or anti-CD28 antibodies.

The T-cell may be a $CD4^+$ helper T cell or a $CD8^+$ cytotoxic T cell. The cell may be in a mixed population of $CD4^+$ helper T cell/$CD8^+$ cytotoxic T-cells. Polyclonal activation, for example using anti-CD3 antibodies optionally in combination with anti-CD28 antibodies will trigger the proliferation of $CD4^+$ and $CD8^+$ T-cells.

The cell may be isolated from the subject to which the genetically modified cell is to be adoptively transferred. In this respect, the cell may be made by isolating a T-cell from a subject, optionally activating the T-cell, transferring the TCR gene to the cell ex vivo. Subsequent immunotherapy of the subject may then be carried out by adoptive transfer of the TCR-transduced cells. As used herein this process refers to autologous T-cell transfer—i.e. the TCR-transduced cells are administered to the same subject from which the T-cells were originally derived.

Alternatively the T-cell may be isolated from a different subject, such that it is allogeneic. The T-cell may be isolated from a donor subject. For example, if the subject is undergoing allogeneic haematopoietic stem cell transplantation (Allo-HSCT) or solid organ transplantation or cell transplantation or stem cell therapy, the cell may be derived from the donor, from which the organs, tissues or cells are derived. The donor and the subject undergoing treatment may be siblings.

Alternatively the cell may be, or may be derived from, a stem cell, such as a haemopoietic stem cell (HSC). Gene transfer into HSCs does not lead to TCR expression at the cell surface as stem cells do not express CD3 molecules. However, when stem cells differentiate into lymphoid precursors that migrate to the thymus, the initiation of CD3 expression leads to the surface expression of the introduced TCR in thymocytes.

An advantage of this approach is that the mature T-cells, once produced, express only the introduced TCR and little or no endogenous TCR chains, because the expression of the introduced TCR chains suppresses rearrangement of endogenous TCR gene segments to form functional TCR alpha and beta genes. A further benefit is that the gene-modified stem cells are a continuous source of mature T-cells with the desired antigen specificity. The cell may therefore be a gene-modified stem cell, preferably a gene-modified hematopoeitic stem cell, which, upon differentiation, produces a T-cell expressing a TCR of the invention.

Other approaches known in the art may be used to reduce, limit, prevent, silence, or abrogate experession of endogenous genes in the cells of the present invention or cells prepared by the methods of the present invention.

As used herein the term "disrupting" refers to reducing, limiting, preventing, silencing, or abrogating expression of a gene. The person skilled in the art is able to use any method known in the art to disrupt an endogenous gene, e.g., any suitable method for genome editing, gene silencing, gene knock-down or gene knock-out.

For example, an endogenous gene may be disrupted with an artificial nuclease. An artificial nuclease is, e.g., an artificial restriction enzyme engineered to selectively target a specific polynucleotide sequence (e.g. encoding a gene of interest) and induce a double strand break in said polynucleotide sequence. Typically, the double strand break (DSB) will be repaired by error-prone non-homologous end joining (NHEJ) thereby resulting in the formation of a non-functional polynucleotide sequence, which may be unable to express an endogenous gene.

In some embodiments, the artificial nuclease is selected from the group consisting of zinc finger nucleases (ZFN), transcription activator-like effector nucleases (TALEN) and CRISPR/Cas (e.g. CRISPR/Cas9).

The methods of preparing a cell (e.g. a T-cell) of the present invention may comprise the step of targeted integration of a expression cassette into an endogenous gene (e.g. an endogenous TCR α chain gene and/or an endogenous TCR β chain gene). As used herein the term expression cassette refers to a polynucleotide sequence (e.g. a DNA polynucleotide sequence) comprising one or more polynucleotide sequences encoding one or more genes of interest such that said genes of interest are capable of expression. Endogenous sequences may facilitate expression from the expression cassete, and/or transcription control seuqences within the expression cassette may facilitate expression. For example, the expression cassette may comprise a polynucleotide sequence of the present invention, or a polynucleotide sequence encoding a TCR of the present invention, operably linked to an expression control sequence, e.g. a promoter or an enhancer sequence. The one or more genes of interest may be located between one or more sets of restriction sites. Suitably, the restriction sites may facilitate the integration of the expression cassette into, e.g., a vector, a plasmid, or genomic DNA (e.g. host cell genomic DNA).

For example, an expression cassette of the present invention may be transferred from a first polynucleotide sequence, e.g. on a vector, to another by 'cutting', e.g. excising, the expression cassette using one or more suitable restriction enzymes and 'pasting', e.g. integrating, the expression cassette into a second polynucleotide sequence.

The expression cassette may comprise a polynucleotide of the present invention. The expression cassette may comprise a polynucleotide encoding one or more TCRs of the present invention. The expression cassette may further comprise an antibiotic resistance gene or other selectable marker gene that allows cells that have successfully integrated the expression cassette into their DNA to be identified. The polynucleotide sequences comprised in the expression cassette may be operably linked to expression control sequences, e.g. a suitable promoter or enhancer sequence. The person skilled in the art will be able to select suitable expression control sequences.

The present invention also contemplates a cell expressing a TCR of the present invention, which has been engineered to disrupt one or more endogenous MHC genes. Disruption of an endogenous MHC gene can reduce or prevent expression of MHC on the engineered cell surface. Accordingly, such an engineered cell with reduced or no MHC expression will have limited or no capacity to present antigens on its cell surface. Such a cell is particulary advantageous for adoptive cell transfer since the cell will be non-alloreactive, e.g., the cell will not present antigens which could be recognized by the immune system of a subject receiving the adoptively transferred cell. As a result, the transferred cell will not be recognized as 'non-self' and an adverse immune reaction to the cell can be avoided. Such a cell is termed a 'universal cell' since it is suitable for adoptive transfer to a variety of different hosts regardless of HLA type.

Accordingly, the present invention provides a method of preparing a non-alloreactive universal T-cell, which expresses a TCR of the present invention. Further provided by the present invention is a non-alloreactive universal T-cell, which expresses a TCR of the present invention.

The present invention further contemplates cells which have been engineered to disrupt one more endogenous genes to modify the cell to enhance advantageous properties, characteristics or functions of the cell and/or reduce undesirable properties, characteristics or functions. For example, by disrupting an endogenous cell the persistence, expansion, activity, resistance to exhaustion/senescence/inhibitory signals, homing capacity, or other cell functions may be modified. As used in this context, the term 'modify' refers to a change in one or more characteristics relative to an equivalent unmodified cell, e.g. a cell in which an endogenous gene has not been disrupted. For example, the change may be an increase, an enhancement or an introduction of a characteristic or function of the cell relative to an equivalent unmodified cell. Alternatively, the change may be a decrease, suppression or abrogation of a characteristic or function of the cell relative to an equivalent unmodified cell.

The polynucleotides and vectors of the present invention may be transferred into specific T-cell subsets, including CD4 and or CD8, naive, memory stem T cells, central memory, effector memory or effector cells, or in other cellular subsets such as to promote different in vivo length of persistence and function in the cells of the present invention.

The polynucleotides and vectors of the present invention may also be transferred into T-cell subsets such as naïve, memory stem T cells, central memory cells, effector memory cells, effectors.

The polynucleotides and vectors of the present invention may also be transferred into T-cell subsets with different polarizations, such as Th0/Tc0, Th1/Tc1, Th2/Tc2, Th17, Th22 or others, depending on the cytokine background most appropriate to target a particular tumor type.

Furthermore, the polynucleotides and vectors of the present invention encoding the antigen-specific regions of the TCRs of the present invention may be transferred in other cellular subsets, including gamma/delta T-cells, NK cells, NKT cells, hematopoietic stem cells or other cells, in order to obtain the therapeutic effect.

Further provided by the present invention is a method of preparing a cell, which comprises the step of transducing a cell in vitro or ex vivo with a vector of the present invention. Various methods for transduction of a cell with a vector are known in the art (see e.g. Sambrook et al).

The present invention also provides a method of producing a T-cell expressing a TCR of the invention by inducing the differentiation of a stem cell which comprises a polynucleotide or a vector of the present invention.

A population of cells may be purified selectively for cells that exhibit a specific phenotype or characteristic, and from other cells which do not exhibit that phenotype or characteristic, or exhibit it to a lesser degree. For example, a population of cells that expresses a specific marker (e.g. CD3, CD4, CD8, CD25, CD127, CD152, CXCR3, or CCR4) may be purified from a starting population of cells. Alternatively, or in addition, a population of cells that does not express another marker may be purified.

By "enriching" a population of cells for a certain type of cells it is to be understood that the concentration of that type of cells is increased within the population. The concentration of other types of cells may be concomitantly reduced.

Purification or enrichment may result in the population of cells being substantially pure of other types of cell.

Purifying or enriching for a population of cells expressing a specific marker (e.g. CD3, CD4, CD8, CD25, CD127, CD152, CXCR3, or CCR4) may be achieved by using an agent that binds to that marker, preferably substantially specifically to that marker. An agent that binds to a cellular marker may be an antibody, for example antibody which binds to CD3, CD4, CD8, CD25, CD127, CD152, CXCR3, or CCR4.

The term "antibody" refers to complete antibodies or antibody fragments capable of binding to a selected target, and including Fv, ScFv, F(ab') and F(ab')$_2$, monoclonal and polyclonal antibodies, engineered antibodies including chimeric, CDR-grafted and humanised antibodies, and artificially selected antibodies produced using phage display or alternative techniques.

In addition, alternatives to classical antibodies may also be used in the invention, for example "avibodies", "avimers", "anticalins", "nanobodies" and "DARPins".

The agents that bind to specific markers may be labelled so as to be identifiable using any of a number of techniques known in the art. The agent may be inherently labelled, or may be modified by conjugating a label thereto. By "conjugating" it is to be understood that the agent and label are operably linked. This means that the agent and label are linked together in a manner which enables both to carry out their function (e.g. binding to a marker, allowing fluorescent identification, or allowing separation when placed in a magnetic field) substantially unhindered. Suitable methods of conjugation are well known in the art and would be readily identifiable by the skilled person.

A label may allow, for example, the labelled agent and any cell to which it is bound to be purified from its environment (e.g. the agent may be labelled with a magnetic bead or an affinity tag, such as avidin), detected or both. Detectable markers suitable for use as a label include fluorophores (e.g. green, cherry, cyan and orange fluorescent proteins) and peptide tags (e.g. His tags, Myc tags, FLAG tags and HA tags).

A number of techniques for separating a population of cells expressing a specific marker are known in the art. These include magnetic bead-based separation technologies (e.g. closed-circuit magnetic bead-based separation), flow cytometry, fluorescence-activated cell sorting (FACS), affinity tag purification (e.g. using affinity columns or beads, such as biotin columns to separate avidin-labelled agents) and microscopy-based techniques.

It may also be possible to perform the separation using a combination of different techniques, such as a magnetic bead-based separation step followed by sorting of the resulting population of cells for one or more additional (positive or negative) markers by flow cytometry.

Clinical grade separation may be performed, for example, using the CliniMACS® system (Miltenyi). This is an example of a closed-circuit magnetic bead-based separation technology.

It is also envisaged that dye exclusion properties (e.g. side population or rhodamine labelling) or enzymatic activity (e.g. ALDH activity) may be used to enrich for HSCs.

Chimeric Molecules

In another aspect, the present invention provides a chimeric molecule comprising a TCR of the present invention, a TCR encoded by a polynucleotide of the present invention, or a portion thereof, conjugated to a non-cellular substrate. The conjugation may be covalent or non-covalent.

The non-cellular substrate may be a nanoparticle, an exosome, or any non-cellular substrate known in the art.

The chimeric molecule of the present invention may be soluble.

In another aspect the present invention provides a chimeric molecule comprising a TCR of the present invention, a TCR encoded by a polynucleotide of the present invention, or a portion thereof, conjugated to a toxin or an antibody.

The toxin or antibody may be cytotoxic. The toxin may be a cytotoxic molecule or compound, e.g. a radioactive molecule or compound. The TCR portion of the chimeric molecule may confer the ability to recognize cells expressing WT1 protein or peptides. Thus, the chimeric molecule may specifically recognize and/or bind to WT1-expressing tumor cells. Accordingly, the chimeric molecules of the present invention may provide WT1-targeted delivery of cytotoxic toxins, antibodies and/or compounds.

WT1-Related Diseases

WT1 is widely expressed on a variety of hematological and solid tumors, while showing limited expression on various healthy tissues (e.g. gonads, uterus, kidney, mesothelium, progenitor cells in different tissues). The present inventors have identified and determined the amino acid sequences of TCRs that recognise WT1 peptides. Furthermore, they have demonstrated that T-cells expressing TCRs according to the present invention target and kill cells which present WT1 peptide or overexpress WT1 protein.

Accordingly, the present invention provides a method for treating and/or preventing a disease associated with expression of WT1, which comprises the step of administering a TCR, an isolated polynucleotide, a vector, or a cell of the present invention to a subject in need thereof. The present invention also provides a method for treating and/or preventing a disease associated with expression of WT1, comprises the step of administering a cell prepared by the method of the present invention to a subject in need thereof.

Further provided by the present invention is a TCR of the present invention, an isolated polynucleotide of the present invention, a vector of the present invention, a cell according of the present invention, or a cell prepared by the method of the present invention for use in treating and/or preventing a disease associated with expression of WT1.

The term 'preventing' is intended to refer to averting, delaying, impeding or hindering the contraction of the disease. The treatment may, for example, prevent or reduce the likelihood of developing or contracting a disease associated with expression of WT1.

'Treating' as used herein refers to caring for a diseased subject, in order to ameliorate, cure or reduce the symptoms of the disease, or in order to reduce, halt or delay the progression of the disease.

The subject may be a human subject. The human subject may be a child. For example, the child may be less than 10 years in age, less than 9 years in age, less than 8 years in age, less than 7 years in age, less than 6 years in age, less than 5 years in age, less than 4 years in age, less than 3 years in age, or less than 2 years in age. The human subject may be an infant.

The subject may have been previously determined to be in need of a TCR, an isolated polynucleotide, a vector, or a cell of the present invention, or a cell prepared by the method of the present invention on the basis of expression of WT1. For example, the subject may have a cell population that exhibits increased expression of WT1 relative to a healthy control cell population. A variety of techniques known in the art may be used to determine WT1 expression—e.g. quantitative RT-PCR can be used to determine the amount of WT1 RNA transcript, which is indicative of WT1 protein expression. The person skilled in the art will also appreciate that WT1 protein expression may be determined by performing western blots using commercially available antibodies specific for WT1.

The subject may also have been previously identified as having an alteration (e.g. mutation or deletion) in a WT1 gene. Such an alteration may be hereditary. Thus, the disease associated with expression of WT1 may be a hereditary disease. Examples of hereditary disases associated with expression of WT1 include but are not limited to WAGR (Wilms tumor-Aniridia-Genitourinary malformation-Retardation) syndrome, Denys-Drash syndrome (DDS), Frasier syndrome (FS), genitourinary anomalies (abnormalities of the reproductive and urinary systems) syndrome.

Subjects with hereditary disases associated with expression of WT1 may be at higher risk of developing a proliferative disorder (e.g. a cancer).

The disease associated with expression of WT1 may be a proliferative disorder.

The proliferative disorder may be a hematological malignancy or a solid tumor. The hematological malignancy may be selected from the group consisting of acute myeloid leukemia (AML), chronic myeloid leukemia (CML), lymphoblastic leukemia, myelodisplastic syndromes, lymphoma, multiple myeloma, non Hodgkin lymphoma, and Hodgkin lymphoma.

The solid tumor may be selected from the group consisting of lung cancer, breast cancer, oesophageal cancer, gastric cancer, colon cancer, cholangiocarcinoma, pancreatic cancer, ovarian cancer, head and neck cancers, synovial sarcoma, angiosarcoma, osteosarcoma, thyroid cancer, endometrial cancer, neuroblastoma, rabdomyosarcoma, liver cancer, melanoma, prostate cancer, renal cancer, soft tissue sarcoma, urothelial cancer, biliary cancer, glioblastoma, mesothelioma, cervical cancer, and colorectal cancer.

The disease associated with expression of WT1 may be selected from a group consisting of acute myeloid leukemia (AML), chronic myeloid leukemia (CML), lymphoblastic leukemia, myelodisplastic syndromes, lymphoma, multiple myeloma, non Hodgkin lymphoma, and Hodgkin lymphoma, lung cancer, breast cancer, oesophageal cancer, gastric cancer, colon cancer, cholangiocarcinoma, pancreatic cancer, ovarian cancer, head and neck cancers, synovial sarcoma, angiosarcoma, osteosarcoma, thyroid cancer, endometrial cancer, neuroblastoma, rabdomyosarcoma, liver cancer, melanoma, prostate cancer, renal cancer, soft tissue sarcoma, urothelial cancer, biliary cancer, glioblastoma, mesothelioma, cervical cancer, and colorectal cancer.

Pharmaceutical Composition

The TCRs of the present invention, the polynucleotides of the present invention, the vectors of the present invention, the cells of the present invention, the cells prepared by the methods of the present invention, the chimeric molecules of the present invention, and the mixed cell population of the present invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy products is preferably performed in compliance with FACT-JACIE International Standards for cellular therapy.

Method of Treatment

In another aspect, the present invention provides a method for treating and/or preventing a disease associated with expression of WT1, which comprises the step of administering a TCR of the present invention, an isolated polynucleotide of the present invention, a vector of the present invention, a cell of the present invention, a cell prepared by a method of the present invention, a chimeric molecule of the present invention, or a mixed cell population of the present invention to a subject in need thereof.

The subject may be a human subject. The subject may be a non-human animal subject.

The subject may have a disease associated with expression of WT1. The subject may be at risk of developing a dieases associated with expression of WT1. The subject may have been previously determined to be at risk of developing a disease associated with expression of WT1. The subject may have an increased risk of developing a disease associated with WT1.

The increased risk may have been determined by genetic screening and/or by reviewing the subject's family history. The subject may express genetic markers indicative of increased risk of developing a disease associated with expression of WT1.

Suitably, a person skilled in the art will be aware of genetic risk factors (e.g. genetic markers) associated with increased risk of developing a disease associated with WT1. The skilled person may be able to use any suitable method or technique known in the art to determine whether the subject has an increased risk of developing a disease associated with expression of WT1.

The subject may have previously received treatment for a disease associated with expression of WT1. The subject may be in remission. The subject may be resistant to chemotherapy. The subject may be resistant to an anti-WT1 therapy.

In one embodiment, the method for treating and/or preventing a disease associated with expression of WT1 comprises the step of administering a chemotherapy to the subject. The chemotherapy may be administered to the subject simultaneously, sequentially or separately with the TCR of the present invention, the isolated polynucleotide of the present invention, the vector of the present invention, the cell according of the present invention, the cell prepared by the method of the present invention, or the chimeric molecule of the present invention.

In another aspect, the present invention provides a method of treating and/or preventing a disease associated with expression of WT1, which comprises the step of administering a mixed cell population, wherein the mixed cell population comprises a plurality of cell populations each expressing a different TCR of the present invention.

In another aspect, the present invention provides a mixed cell population comprising a plurality of cell populations each expressing a different TCR of the present invention.

In another aspect, the present invention provides a method for preparing a mixed cell population comprising a plurality of cell populations each expressing a different TCR of the present invention, wherein the method comprises the step of transducing a cell in vitro or ex vivo with a vector of the present invention.

In another aspect, the present invention provides a mixed cell population for use in treating and/or preventing a disease associated with expression of WT1, wherein the mixed cell population comprises a plurality of cell populations each expressing a different TCR of the present invention.

For example, the mixed cell population may comprise a first cell population expressing a first TCR of the present invention and a second cell population expressing a second TCR of the present invention. For example, the mixed cell population may comprise a first cell population expressing a first TCR of the present invention, a second cell population expressing a second TCR of the present invention, and a third cell population expressing a third TCR of the present invention, and so on.

Each cell population of the mixed cell population may, for example, express a single TCR of the present invention only. The endogenous TCR genes of the cell populations in the mixed cell population may be disrupted or deleted. Expression of endogenous TCR genes of the cells in the mixed cell population may be disrupted, e.g. by gene editing with an artificial nuclease.

In another aspect, the present invention provides use of TCR of the present invention, an isolated polynucleotide of the present invention, a vector of the present invention, a cell of the present invention, a cell prepared by a method of the present invention, a chimeric molecule of the present invention, or a mixed cell population of the present invention, for the manufacture of a medicament for the treatment of a disease associated with expression of WT1.

Both human and veterinary treatments are within the scope of the present invention.

The practice of the present invention will employ, unless otherwise indicated, conventional techniques of cell biology, molecular biology, histology, immunology, oncology, which are within the capabilities of a person of ordinary skill in the art. Such techniques are explained in the literature.

See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

Various preferred features and embodiments of the present invention will now be described by way of non-limiting examples.

EXAMPLES

Example 1

Generation of Functional WT1-Specific Cytotoxic T-Lymphocytes (CTLs) from Healthy Donors (HDs)

In order to identify novel TCRs specific for WT1 epitopes restricted to different HLA alleles, we stimulated peripheral blood mononuclear cells (PBMCs) from ten different HDs with a pool of pentadecapeptides (15mer) with an 11 amino acid overlap spanning the complete sequence of the WT1 protein (see materials and methods). This peptide design ensures the optimal stimulation of both $CD4^+$ and $CD8^+$ T-cells.

After 26-30 hours of stimulation, we enriched T-cells expressing CD137. CD137 is molecule upregulated upon T cell receptor engagement and has been previously shown to be a reliable marker for the rapid identification, isolation and expansion in vitro of antigen-specific memory and naive $CD4^+$ and $CD8^+$ T-cells. The CD137-negative fraction was further depleted of the CD3 fraction, then irradiated at 30 Gy and used as antigen presenting cells (APCs) for the $CD137^+$ fraction. Sorted $CD137^+$ cells were expanded in vitro for ~9 days and restimulated with autologous APCs represented by CD3-depleted cells or by immortalized autologous B cells loaded with the peptide pool every 7-14 days. This procedure led to the enrichment of the WT1-specific T lymphocytes as shown by the cytofluorimetric results presented in FIGS. 1A-1J. Functional characterization of T cells was performed at different time points. More in detail, T cells were co-cultured with autologous APCs loaded with the peptide pool and, after 6 hours of co-culture, expression of CD107a and IFNγ in the T-cell population was identified by intracellular staining. The expression of CD107a after antigen encounter indicates antigen-induced degranulation and lytic potential.

As a negative control, cells were stimulated with an unrelated peptide pool. Control stimulation resulted in minimal secretion of IFNγ and CD107a by T-cells derived from each healthy donor.

Example 2

Mapping of WT1 Epitopes Eliciting a T Cell Response

Figure 1A:
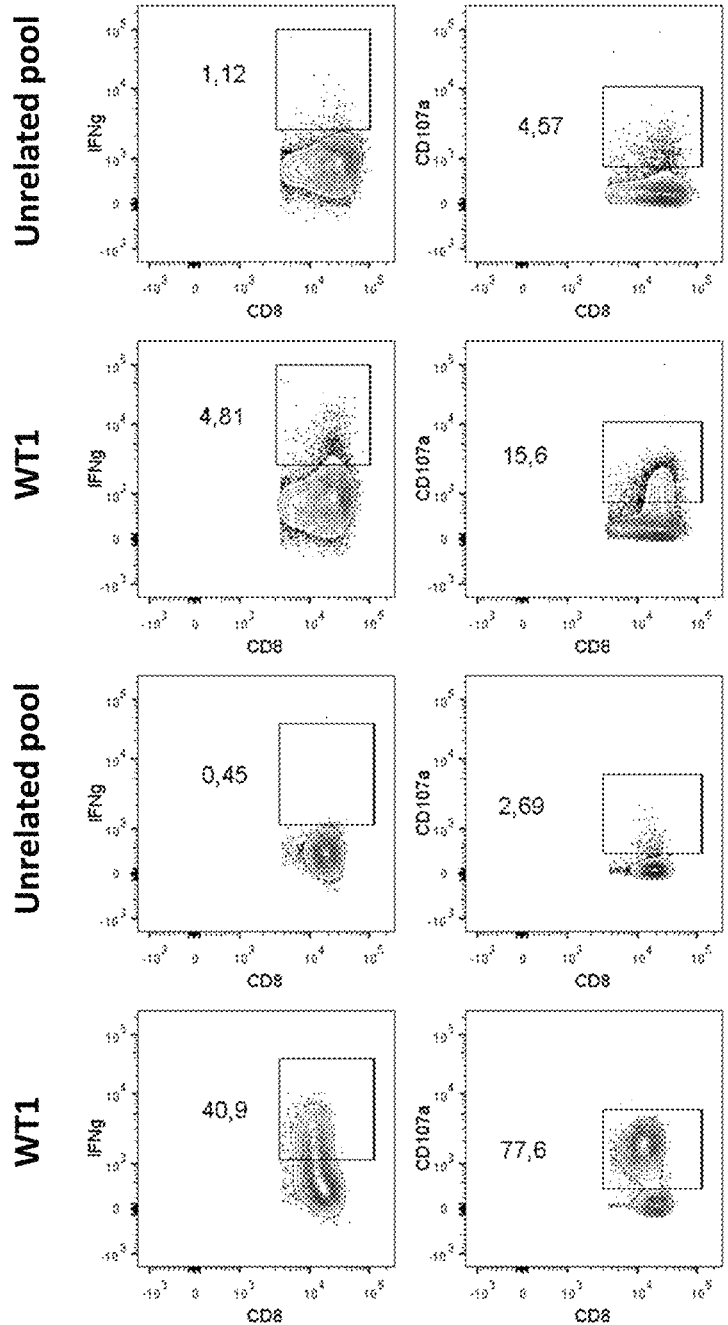
FIGS. 1A-1J. Plots showing the results of in vitro expansion of functional WT-1 specific T-cells from peripheral blood of ten healthy donors Peripheral blood mononuclear cells of ten healthy donors (HD) were stimulated with pooled, overlapping WT1 15-mer peptides for 26-30 hours, enriched for CD137+ cells, and expanded for 9-19 days. Expanded T-cells were re-stimulated for 6 hours with autologous antigen presenting cells (APCs) loaded with an unrelated peptide pool or WT1 peptide pool. Additionally, negative (T-cells unstimulated) and positive (T-cells cultured in the presence of PMA and Ionomycin) controls were included in the experimental setting (not shown). Dot plots indicate the results of the intracellular staining for IFNγ production and CD107a exposure on cell surface. After several re-stimulations with autologous APCs loaded with WT1 peptide pool, T-cells specificity was tested by intracellular staining as previously described. Results showed an enrichment of WT1-specific T-cells in the CD8 T cell compartment for HD1 (FIG. 1A), HD3 (FIG. 1C), HD4 (FIG. 1D), HD5 (FIG. 1E), HD6 (FIG. 1F), HD7 (FIG. 1G), and HD10 (FIG. 1J) and in the CD4 T cell compartment for HD2 (FIG. 1B), HD8 (FIG. 1H) and HD9 (FIG. 1I). WT1, Wilms Tumor 1; PMA, Phorbol 12-myristate 13-acetate; IFNγ, interferon-γ; S, stimulation.
Figure 1B:
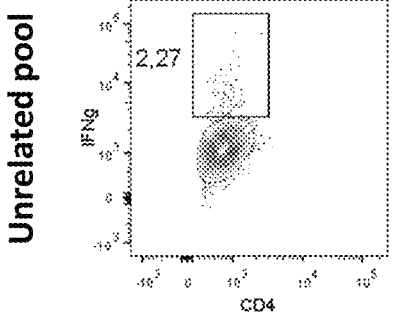
Figure 1B:
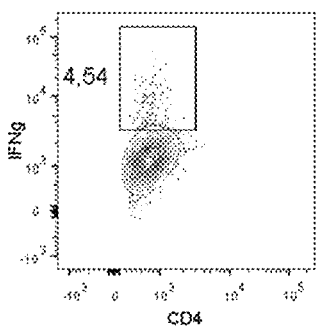
Figure 1B:
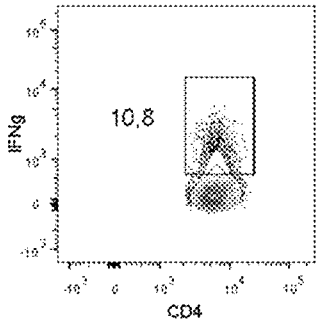
Figure 1B:
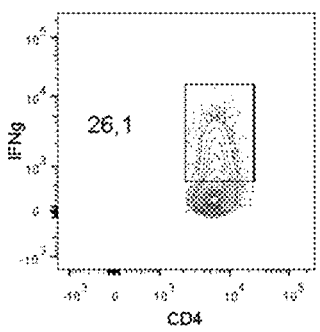
Figure 1C:
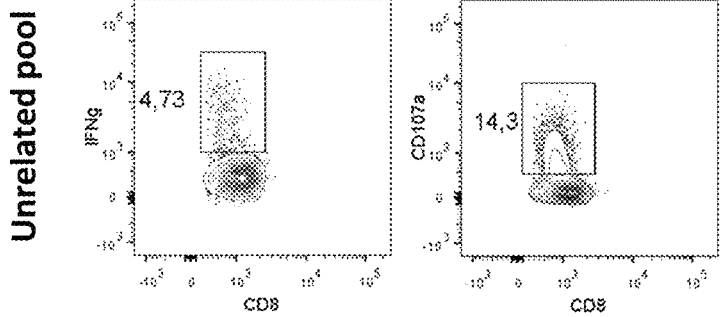
Figure 1C:
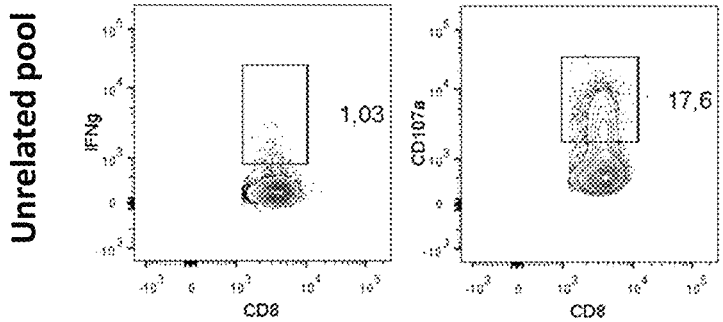
Figure 1C:
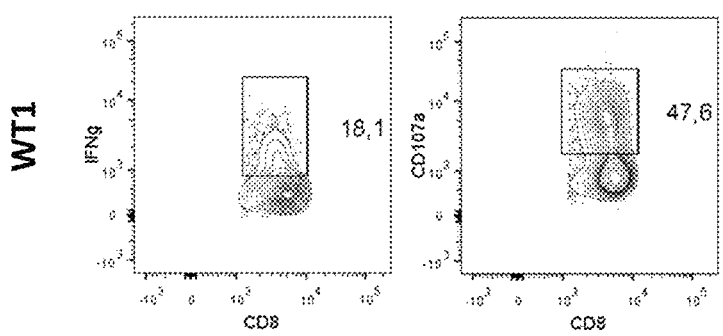
Figure 1D:
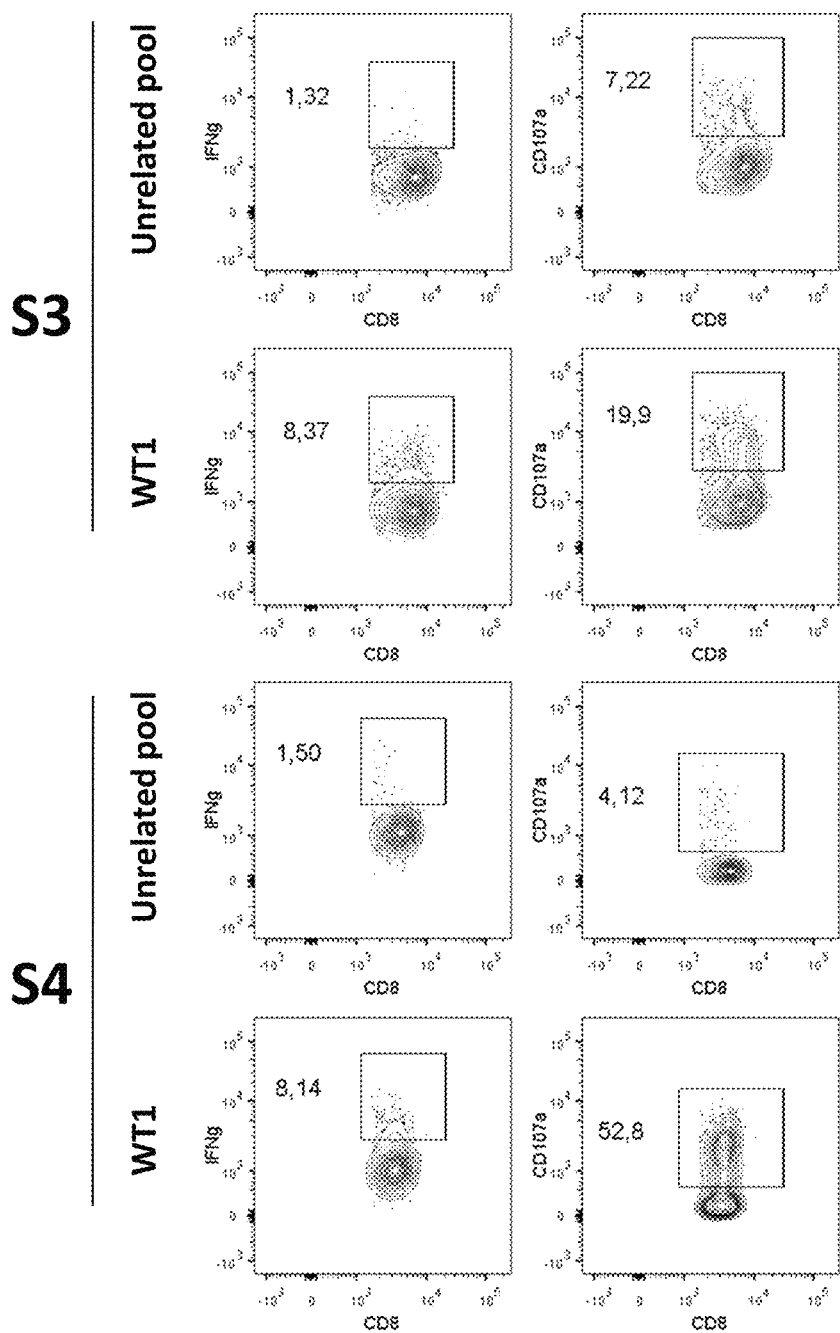
Figure 1E:
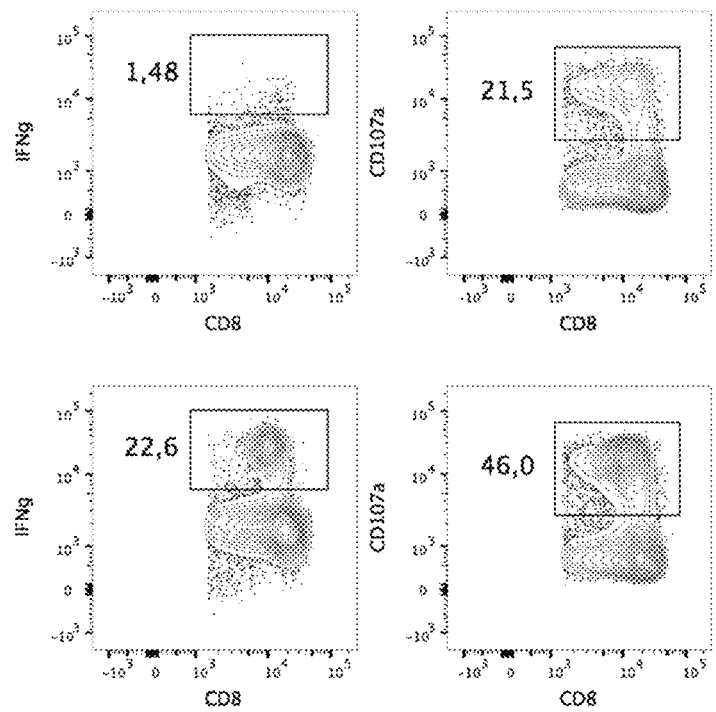
Figure 1F:
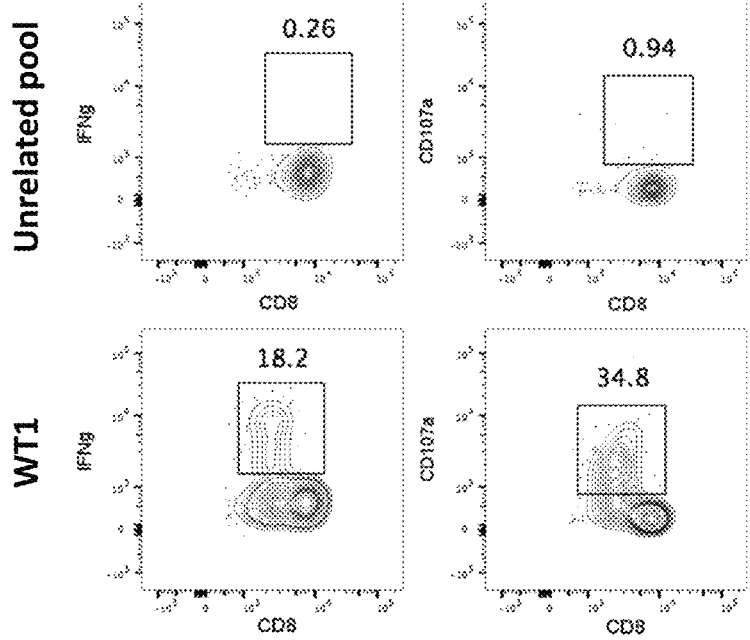
Figure 1F:
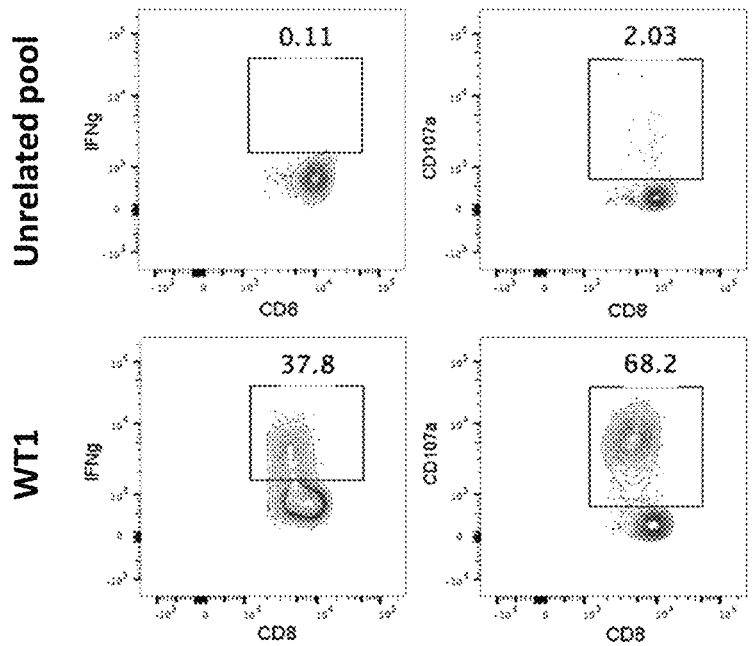
Figure 1G:
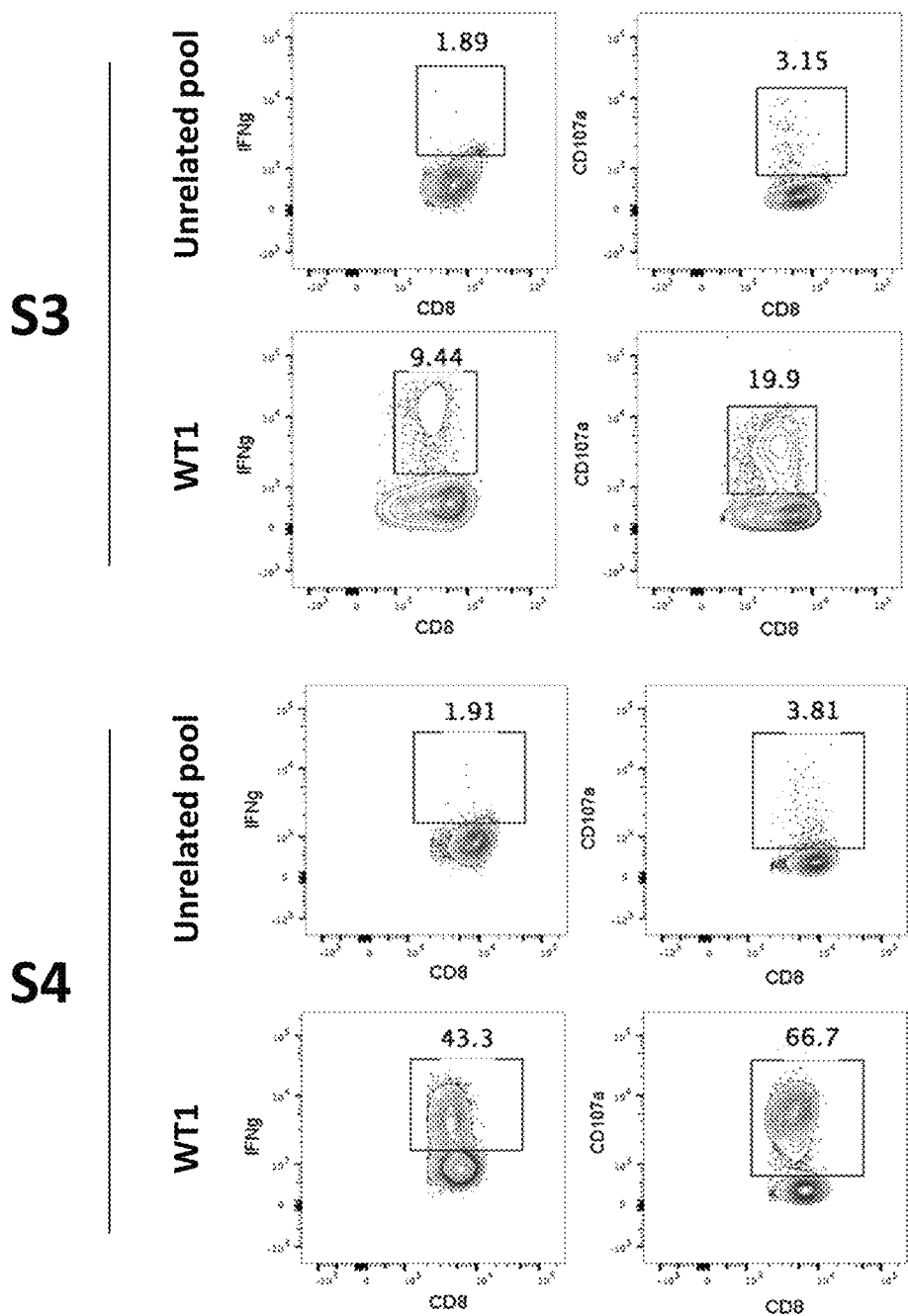
Figure 1H:
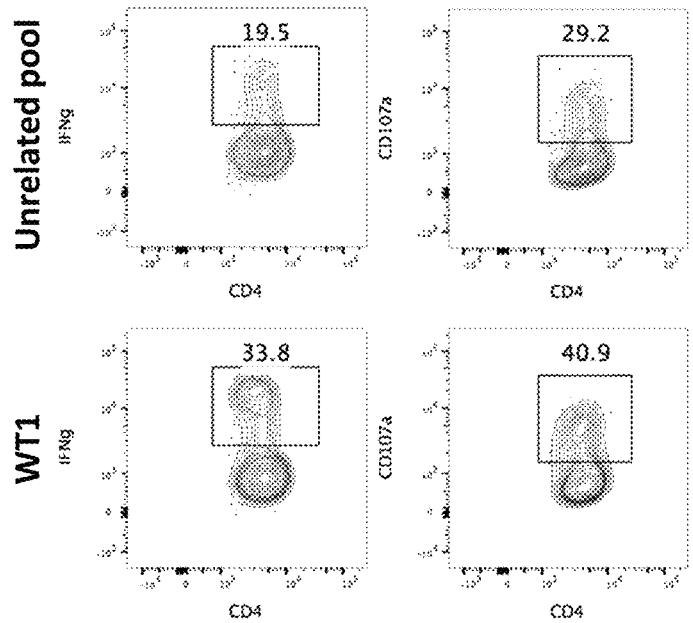
Figure 1H:
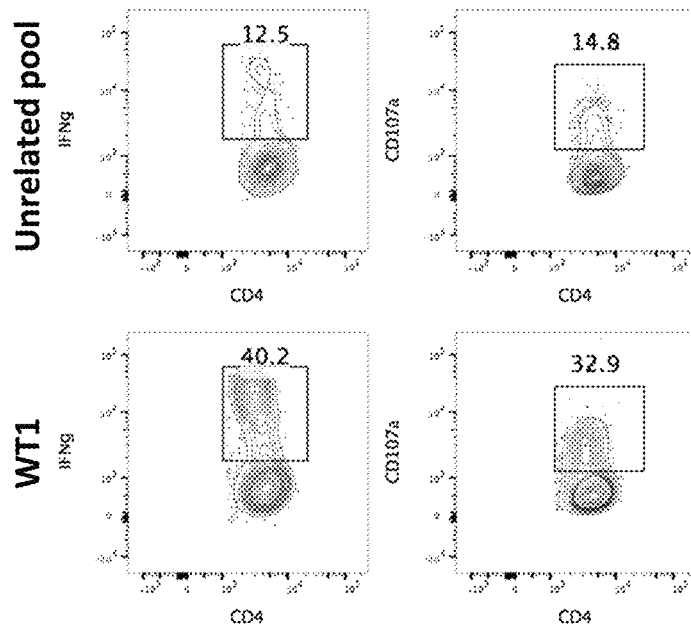
Figure 1I:
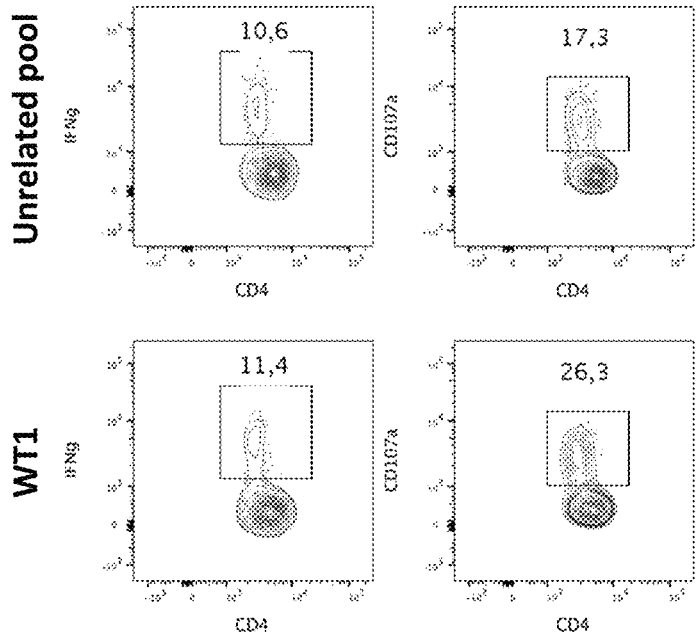
Figure 1I:
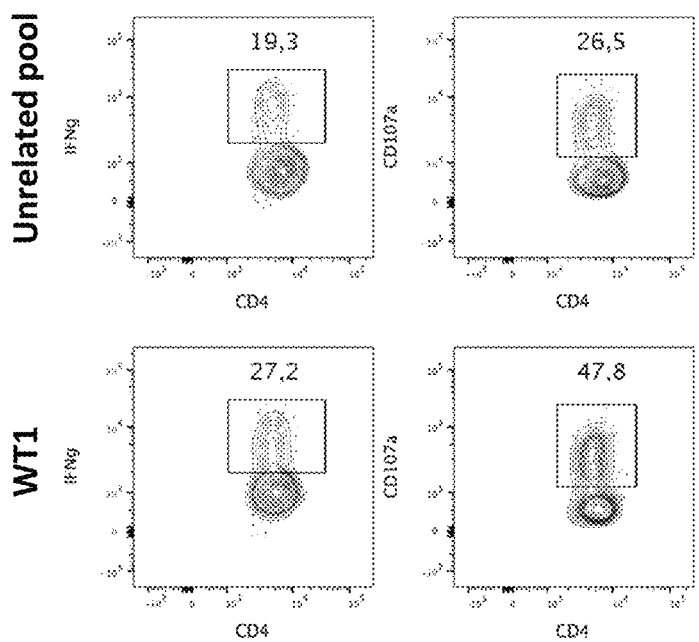
Figure 1J:
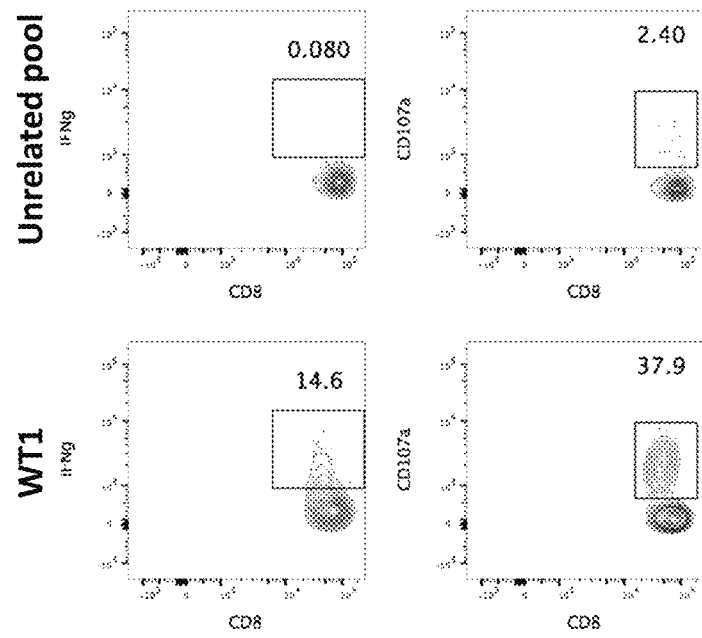
Figure 1J:
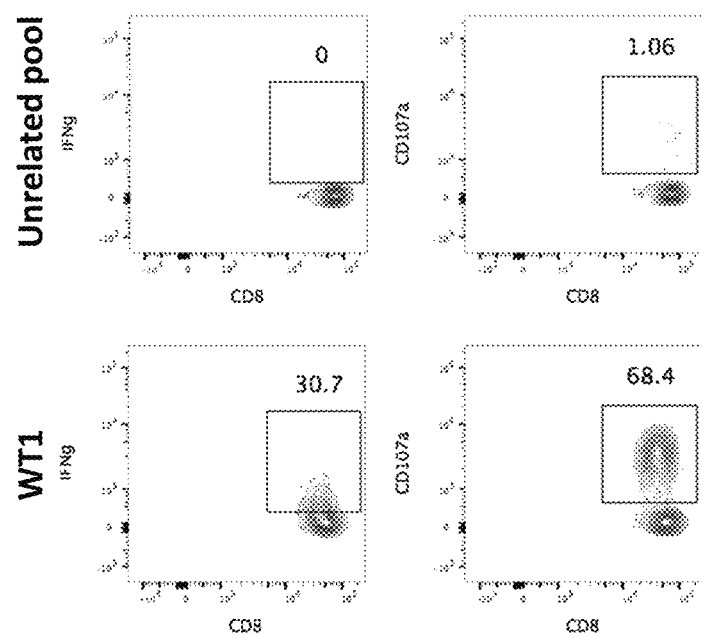
Figure 2A:
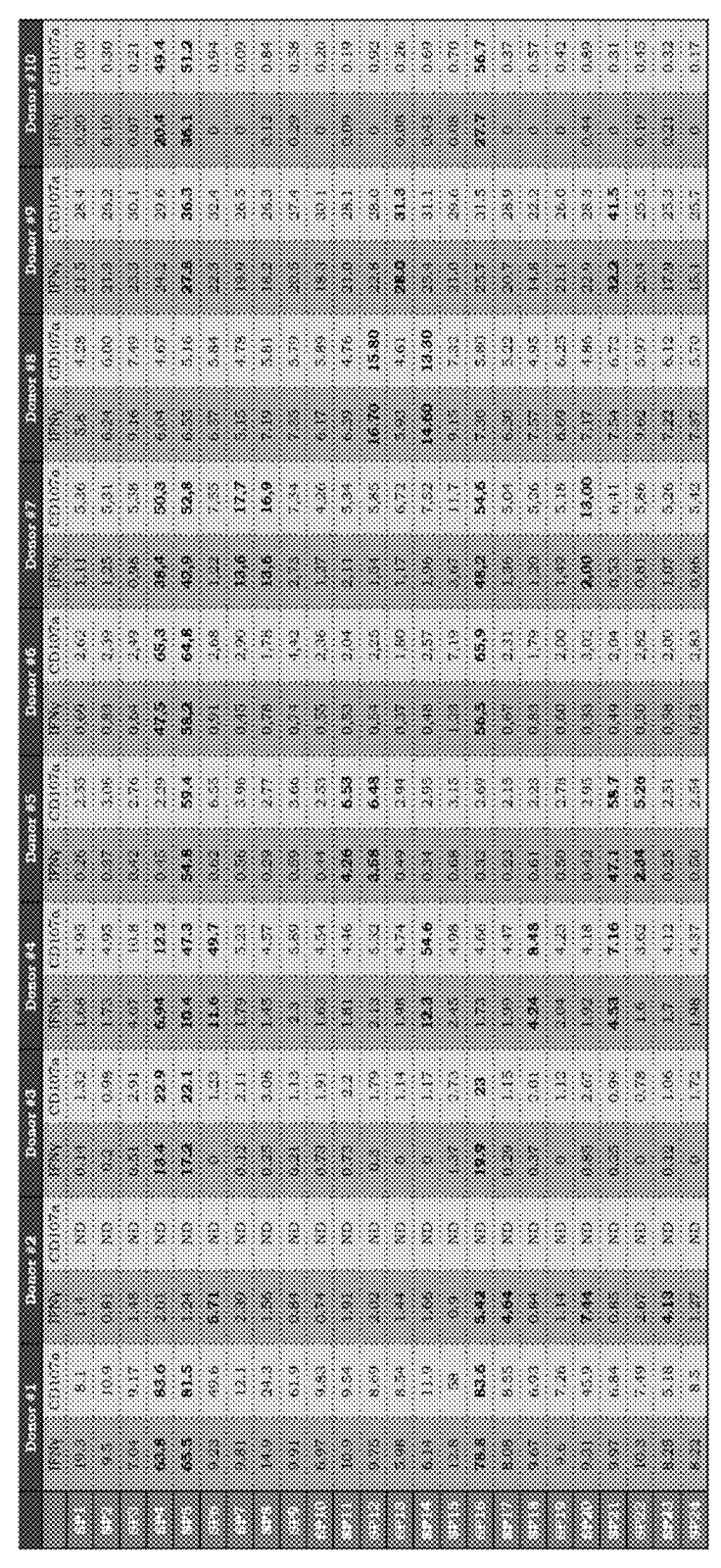
Figure 2B:
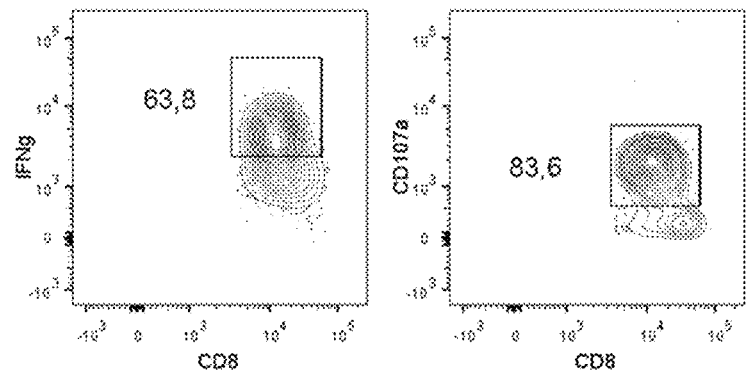
Figure 2B:
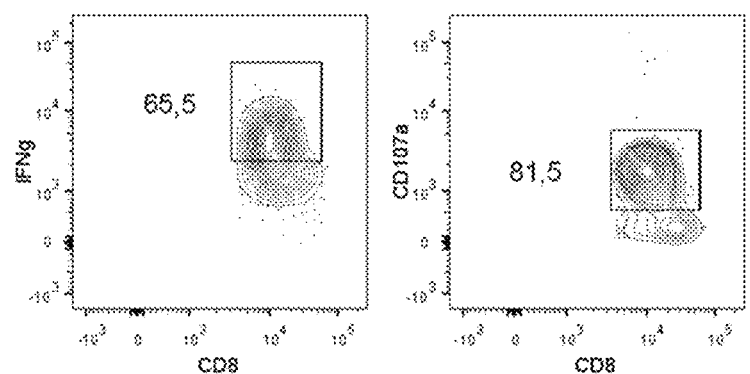
Figure 2B:
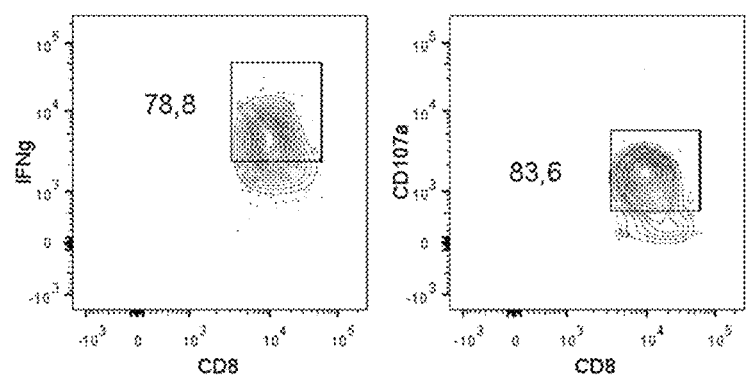

To identify the WT1 epitope recognized by T-cells, IFNγ secretion was quantified after 6 hours of in vitro co-culture of the WT1-stimulated/enriched T-cells with autologous APCs loaded with peptide subpools each containing up to 12 peptides according to a mapping grid. The mapping grid consists of 24 subpools with each peptide being uniquely contained within two intersecting subpools (Doubrovina, E. et al. Blood 120, 1633-1646 (2012)). Results are summarized in FIG. 2a.

Figure 2C:
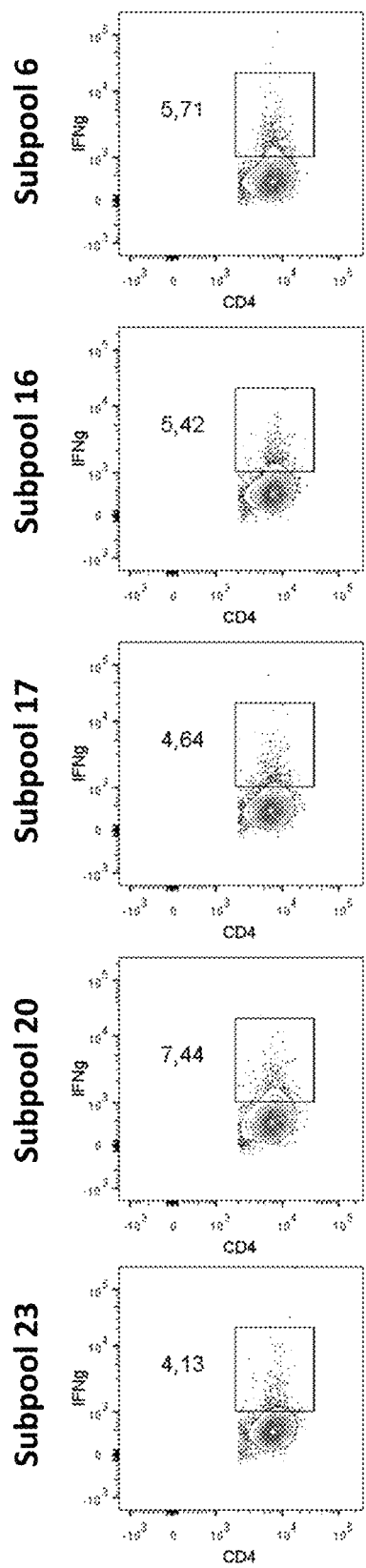
Figure 2D:
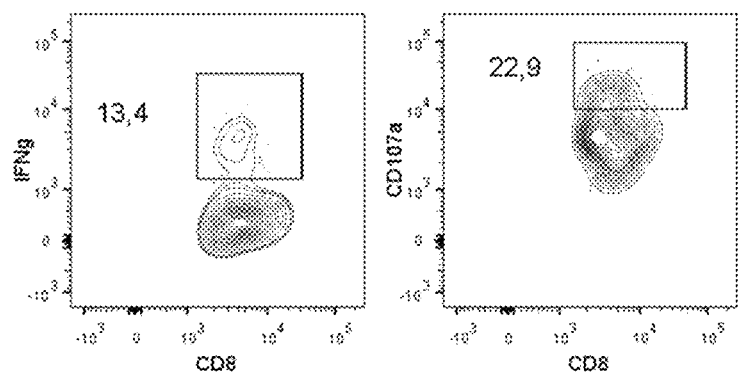
Figure 2D:
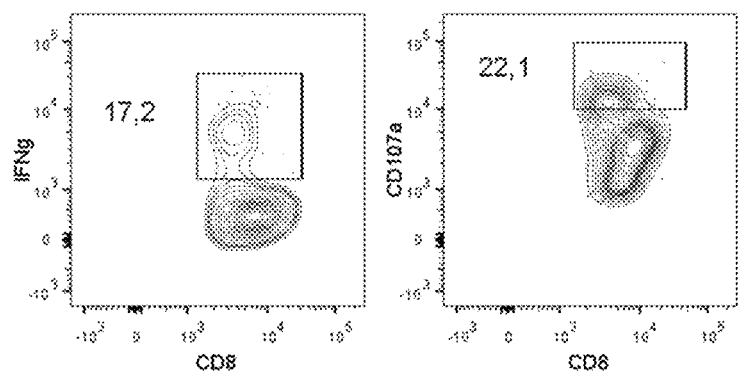
Figure 2D:
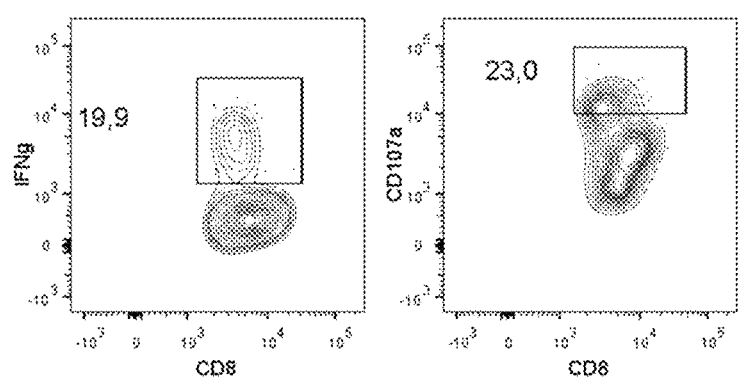
Figure 2E:
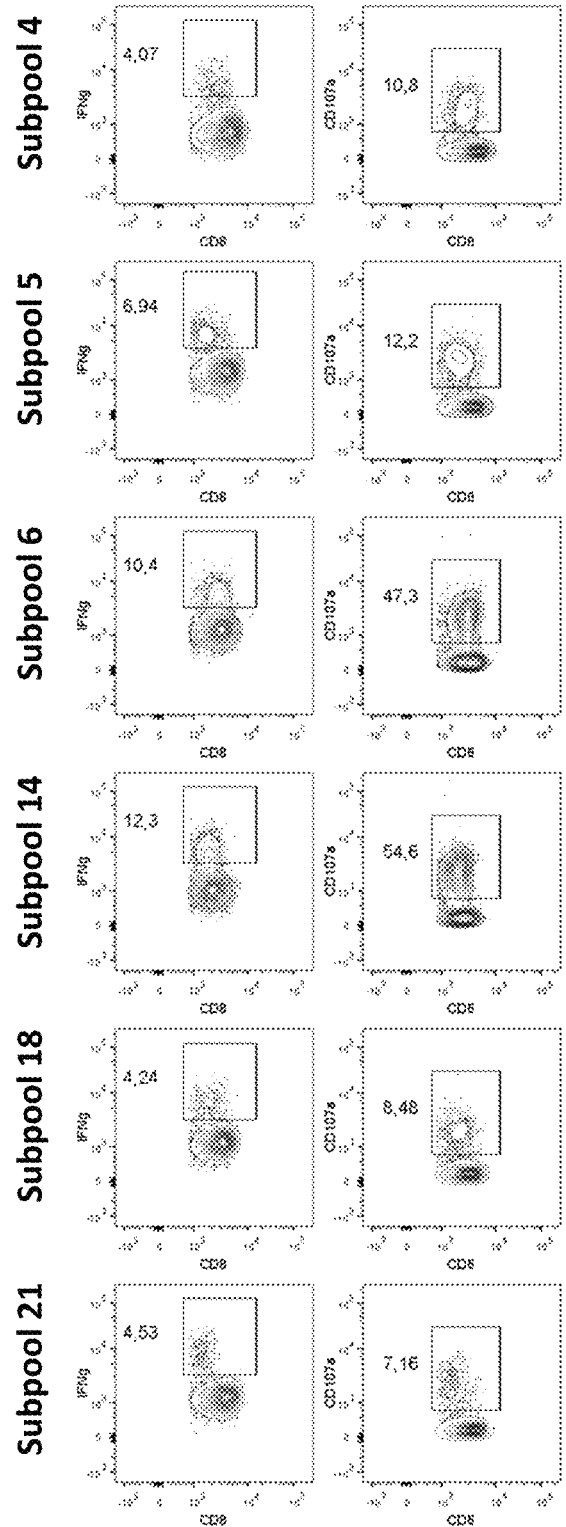
Figure 2F:
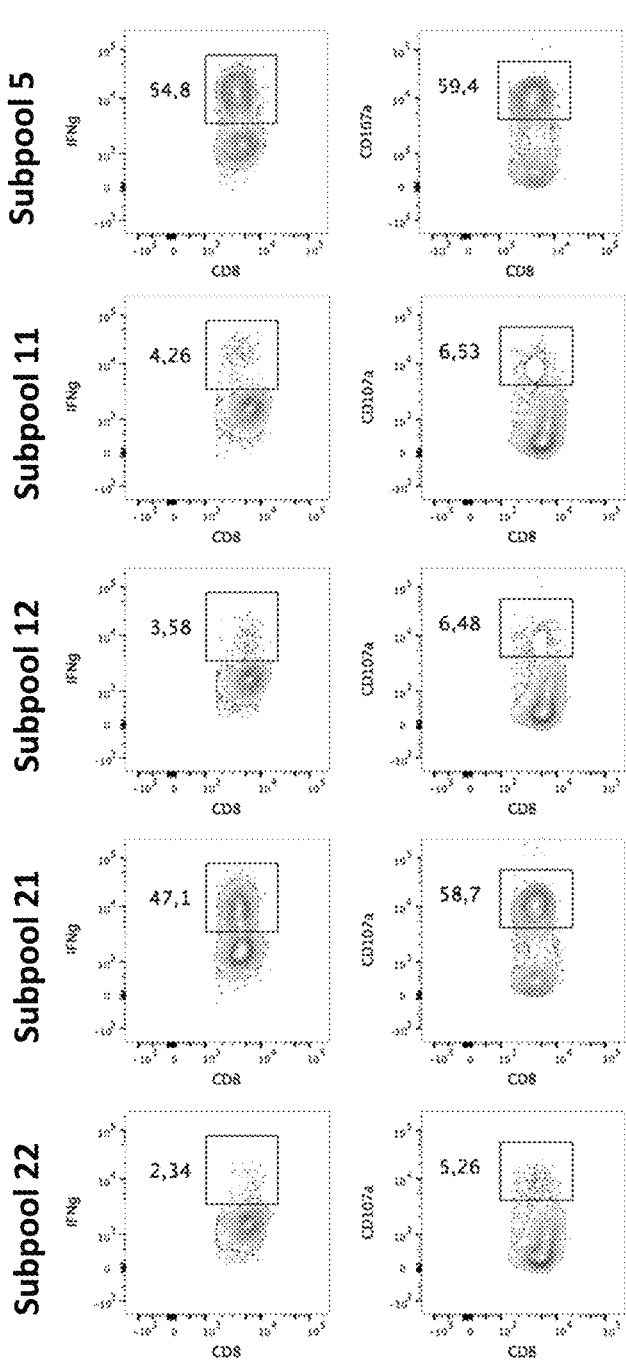
Figure 2G:
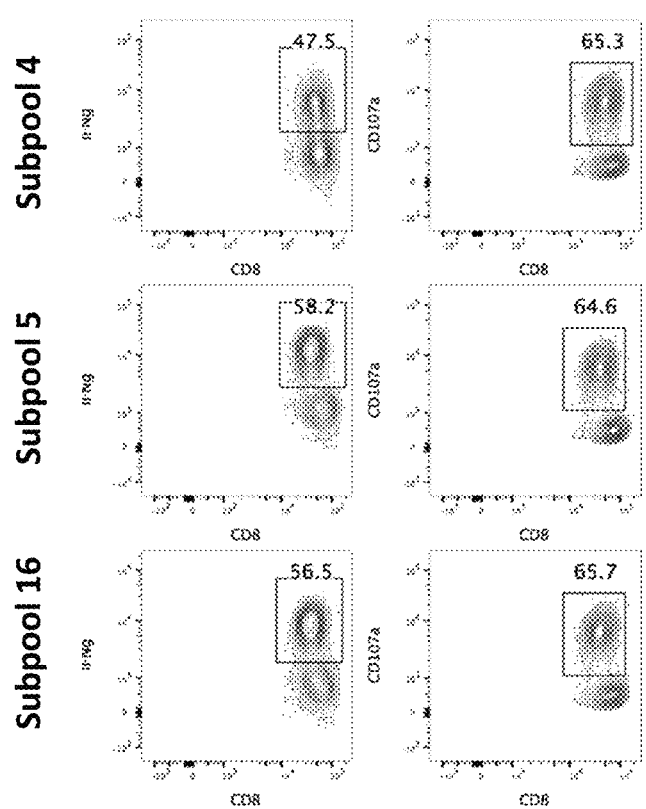
Figure 2H:
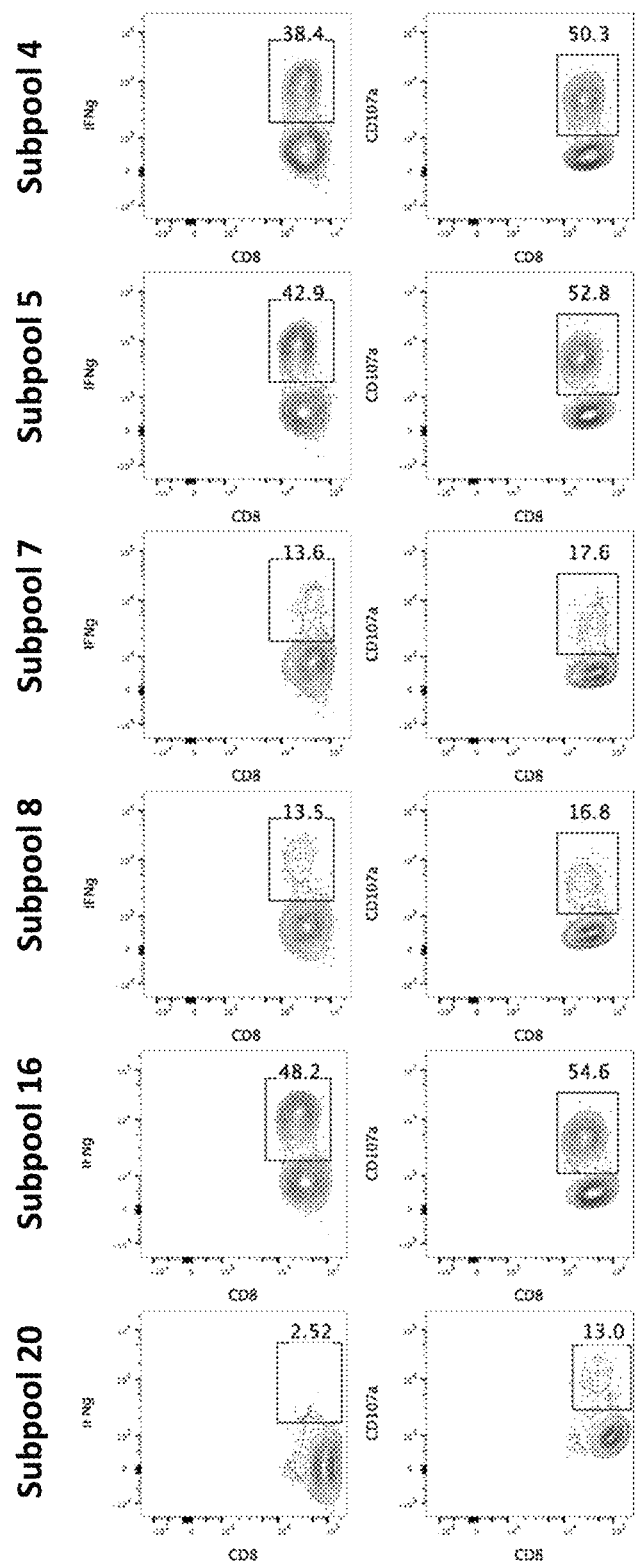
Figure 2I:
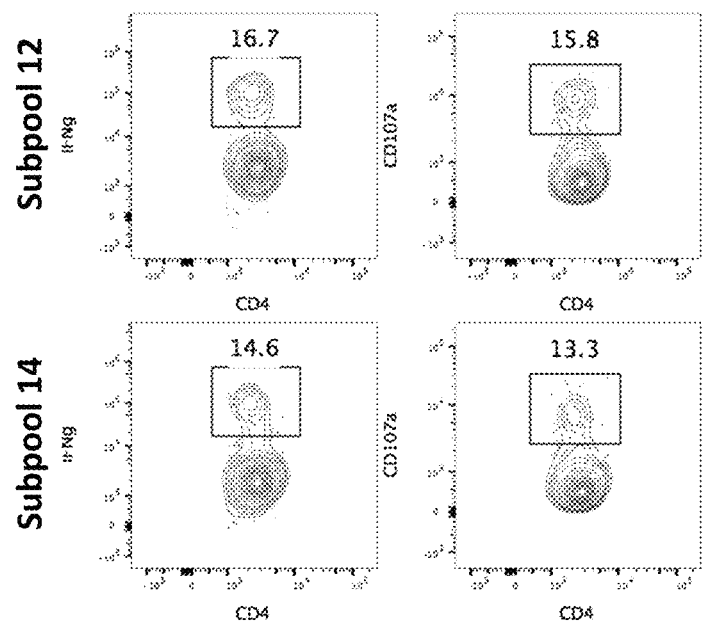
Figure 2J:
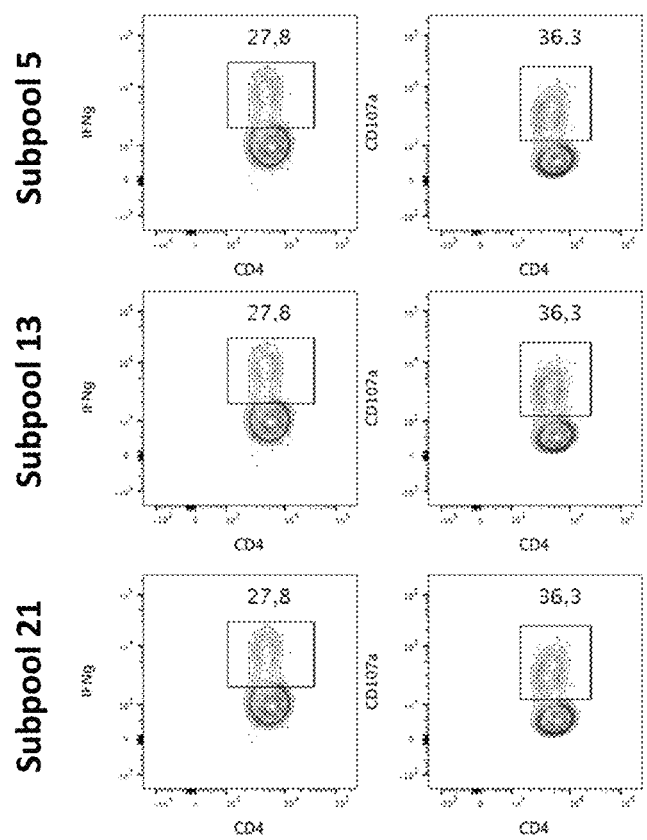
Figure 2K:
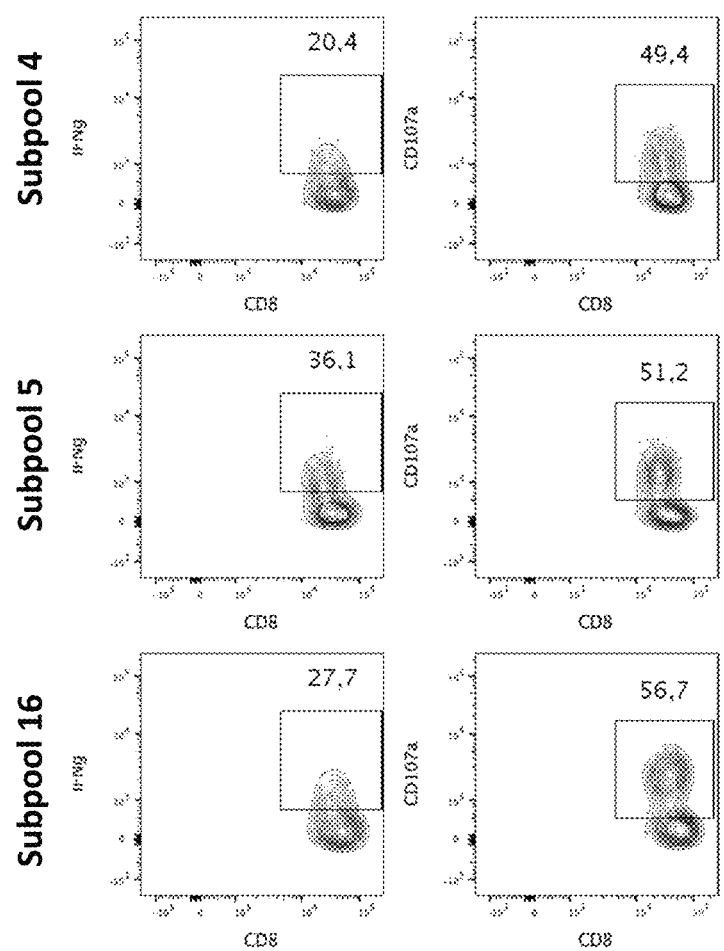

FACS analysis showed substantial expression of IFNγ and CD107a by the HD1-, HD3-, HD6-, HD7-, HD10-derived T-cells after stimulation with subpools 4, 5 and 16 (FIGS. 2b, 2d, 2g, 2h, 2k). Substantial expression of IFNγ was observed for HD2-derived T-cells stimulated by subpools 6, 16, 17, and 20 (FIG. 2c), whereas subpools 4, 5, 6 14, 18, 21 stimulated expression of IFNγ and CD107a by HD4-derived T-cells (FIG. 2e) and subpools 5, 11, 12, 21, 22 stimulated expression of IFNγ in HD5 (FIG. 2f). For HD7, we additionally observed an increased expression of IFNγ and CD107a, even though at a lower level compared to the one observed with subpools 4, 5 and 16, after stimulation with subpools 7, 8, 20 (FIG. 2h). Furthermore, we observed an increased expression of IFNγ and CD107a after stimulation of HD8-derived T cells cells with subpools 12 and 14 (FIG. 2i) and of HD9-derived T cells with subpools 5,13, 21 (FIG. 2j).

Afterwards, the HD-derived T-cells were stimulated for 6 hours with APCs pulsed with the single pentadecapeptides shared by the subpools eliciting the highest immune response and with at least one unrelated 15mer. FACS analysis indicated an increased expression of CD107a and/or IFNγ for peptides 40 and 41 in HD1 T-cells (FIG. 3a), peptides 54, 77, 90 for HD2 T-cells (FIG. 3b), peptide VLDFAPPGA (SEQ ID NO: 157; which is a nonamer of the peptide represented by SEQ ID NO: 117) for HD3 T-cells (FIG. 3c), peptides 17, 18, 99, 100 for HD4 (FIG. 3d, e), peptide 101 for HD5 (FIG. 3f), peptide VLDFAPPGA (SEQ ID NO: 157; which is a nonamer of the peptide represented by SEQ ID NO: 117) for HD6 T-cells (FIG. 3g), peptides 101, 125 and 137 for HD9 T-cells (FIG. 3h), peptide VLDFAPPGA (SEQ ID NO: 157; which is a nonamer of the peptide represented by SEQ ID NO: 117) for HD10 T-cells (FIG. 3i). In this way, the dominant immunogenic sequences were identified. No relevant immune responses (i.e. increased expression of CD107a and/or IFNγ) were observed after co-culture with unrelated control peptides. For HD7 and HD8, due to the reduced cell fitness, it was not possible to perform culture experiments to identify the immunogenic peptides. Still, we could predict the recognized peptide by the deconvolution of the mapping grid. We identified the overlapping sequence of peptides 41 and 42 (originated from SP4, 5, 16) and the overlapping sequence of peptides 91 and 92 (originated from SP7, 8, 20) for HD7 and peptide 24 for HD8.

To determine the HLA-restriction of the WT1 immunogenic peptide recognized by T-cells expanded from HD4, HD5 and HD10, the T-cells from these were co-cultured for 6 hours with a panel of different target EBV-BLCL cells each expressing a different HLA-A or HLA-B allele that had been pulsed with a relevant peptide (peptide 17 for HD4; peptide 101 for HD5; peptide VLDFAPPGA (SEQ ID NO: 157) for HD10) or an unrelated control peptide. Results of this experiment showed that peptide 17 is presented by the HLA-B*3502 allele and is recognized by T-cells derived from HD4 (FIG. 3j), peptide 101 is presented by the HLA-B*3501 and is recognized by T-cells derived from HD5 (FIG. 3k); peptide VLDFAPPGA (SEQ ID NO: 157) is presented by the HLA-A*0201 and is recognized by T-cells derived from HD10 (FIG. 3l).

Sequences of the WT1 peptides recognized by WT1-specific T-cells expanded from HD1-HD10 are shown in Table 3 below.

TABLE 3

| Binding TCR donor | Peptide | Sequence | SEQ ID NO |
|---|---|---|---|
| HD1/HD3/ HD6/ HD7/HD10 | 40 | AAQWAPVLDFAPPGAS | SEQ ID NO: 115 |
| | 41 | APVLDFAPPGASAYG | SEQ ID NO: 116 |
| | Overlapping sequence ("11 mer" in FIG. 3c) | APVLDFAPPGA | SEQ ID NO: 117 |
| HD2 | 54 | QCLSAFTVHFSGQFTS | SEQ ID NO: 118 |
| | 77 | EDPMGQQGSLGEQQYS | SEQ ID NO: 119 |
| | 90 | SQLECMTWNQMNLGAS | SEQ ID NO: 120 |
| HD4 | 17 | TCVPEPASQHTLRSGS | SEQ ID NO: 121 |
| | 18 | EPASQHTLRSGPGCLS | SEQ ID NO: 122 |
| | Overlapping sequence | EPASQHTLRSG | SEQ ID NO: 123 |
| | 99 | HSTGYESDNHTTPILS | SEQ ID NO: 124 |
| | 100 | YESDNHTTPILCGAQS | SEQ ID NO: 125 |
| | Overlapping sequence | YESDNHTTPIL | SEQ ID NO: 126 |
| HD5 | 101 | NHTTPILCGAQYRIHS | SEQ ID NO: 127 |
| HD7 | 91 | CMTWNQMNLGATLKGS | SEQ ID NO: 248 |
| | 92 | NQMNLGATLKGVAAGS | SEQ ID NO: 249 |
| | Overlapping sequence | NQMNLGATLKG | SEQ ID NO: 250 |
| HD8 | 24 | DPGGIWAKLGAAEASS | SEQ ID NO: 251 |
| HD9 | 101 | NHTTPILCGAQYRIHS | SEQ ID NO: 252 |
| | 125 | KRHQRRHTGVKPFQCS | SEQ ID NO: 253 |
| | 137 | PSCQKKFARSDELVRS | SEQ ID NO: 254 |

Example 3

WT1-Specific T-Cells Selectively Eliminate WT1 Expressing Cells

To determine the HLA restriction of the WT1 specific T-cells and their ability to eliminate WT1-expressing cells, T cells were co-cultured with different target cells.

HD1-Derived T-Cells

Being aware that HD1 harbors the HLA-A*0201 allele, we co-cultured enriched WT1-specific T-cells with different target cells: T2 cells pulsed with the overlapping peptide pool comprising peptides 40 and 41 (see Table 3); T2 cells pulsed with the MelanA/MART1 pool as a negative control (T2 MelanA/MART1 pool); or K562 cells genetically modified in order to express both the HLA-A*0201 allele and to overexpress the WT1 protein (K562 HLA-A*0201 WT1).

After 6 hours of co-culture, expression of CD107a was established by FACS. Results for HD1 indicate the expression of CD107a in >60% of CD8$^+$ T-cells following co-culture with T2 cells pulsed with the WT1 pool (FIG. 4a). Similarly, co-culture of WT1 specific T-cells with genetically modified K562 cells (expressing HLA-A*0201 allele and the WT1 protein) resulted in CD107a expression by >60% of CD8$^+$ T-cells (FIG. 4a).

In contrast, CD107a expression by CD8$^+$ T-cells co-cultured with T2 cells pulsed with the negative control MelanA/MART1 pool was minimal (FIG. 4a).

These results demonstrate that isolated HD1-derived T-cells specifically recognize WT1 peptide comprising the sequence APVLDFAPPGA (SEQ ID NO: 117) when presented by MHC molecules encoded by the HLA-A*0201 allele. Moreover, the results show that HD1-derived T-cells are able to specifically target cells overexpressing the WT1 protein. Accordingly, these experimental data demonstrate that TCRs expressed by HD1-derived T-cells specifically bind to the peptides comprising the APVLDFAPPGA (SEQ ID NO: 117) amino acid sequence and that such TCRs are HLA-A*0201 restricted.

HD3-Derived T-Cells

Being aware that HD3 harbors the HLA-A*0201 allele, we co-cultured enriched WT1-specific T-cells with different target cells: T2 cells pulsed with subpool 16 which was previously determined to contain the immunogenic peptide eliciting immune response (T2-5P16); T2 cells pulsed with the MelanA/MART1 pool as a negative control (T2-Melan A); wild type K562 cells (K562) as negative control; or K562 cells genetically modified to express both the HLA-A*0201 allele and to overexpress the WT1 protein (K562 A2+WT1+).

After 4 days of co-culture, the ability of the HD3 derived T-cells to kill target cells was expressed as elimination index-calculated as the total number of target cells still present after co-culture with the WT1-specific T-cells divided by the total number of target cells alone.

The results demonstrate the ability of WT1-specific T-cells to eliminate target cells expressing the identified specific WT1 epitope (FIG. 4b). In particular, the HD3-derived T-cells eliminated about 95% of the T2 cells pulsed with WT1 peptides comprising APVLDFAPPGA (SEQ ID NO: 117) amino acid sequence (subpool 16; SP16). Furthermore, the HD3-derived T-cells eliminated about 78% of the K562 cells expressing MHC molecules encoded by the HLA-A*0201 allele and overexpressing WT1 protein. In contrast, none of the negative control MelanA/MART1 pool-pulsed T2 cells were eliminated by the HD3-derived T-cells. Similarly, there was minimal elimination of control wild-type K562 cells (FIG. 4b).

These results demonstrate that isolated HD3-derived T-cells specifically recognize WT1 peptide comprising the amino acid sequence APVLDFAPPGA (SEQ ID NO: 117). Moreover, the results show that HD3-derived T-cells are able to specifically target and kill cells overexpressing the WT1 protein via peptide presentation by HLA-A*0201 encoded MHC. Accordingly, these experimental data demonstrate WT1 peptide specificity for TCRs expressed by HD3-derived T-cells and that HD3-derived TCRs are HLA-A*0201 restricted.

HD4-Derived T-Cells

The ability of HD4-derived T-cells to eliminate target cells was assessed by co-culturing the T-cells with primary leukemic blasts (CD33$^+$ cells) isolated from an acute myeloid leukemia (AML) patient who was selected on the basis of high expression of the WT1 antigen and HLA typing (HLA-B*3502). As a negative control, HD4-derived T-cells were co-cultured with leukemic blasts from an AML patient who did not express the HLA-B*3502 allele.

After three days of co-culture at an effector to target ratio of 10 to 1, FACS analysis showed the nearly complete clearance of the leukemic blasts (CD33$^+$) harvested from the AML patient expressing the HLA-B*3502 allele following the co-culture with HD4 WT1-specific T-cells (CD3$^+$ cells) (FIG. 4c, upper panel). Indeed, only 0.54% of the remaining total cell population was positive for CD33 expression.

In contrast, no clearance of CD33$^+$ cells was seen following co-culture of WT1-specific T-cells with the unrelated control AML blasts (FIG. 4c, lower panel). Indeed, in the control sample 7.9% of the total cell population was positive for CD33 expression following co-culture with the HD4-derived WT1-specific T-cells.

Importantly, these results demonstrate the ability of the WT1-specific T-cells derived from HD4 to specifically target and kill leukemic blasts (AML cancer cells) overexpressing WT1 and MHC encoded by the HLA-B*3502. Thus, TCRs derived from HD4 are able to specifically target and kill cancer cells in HLA-B*3502 restricted manner.

Example 4

Immunoprofiling of VR Sequences for WT1 Specific T-Cells

To better identify the TCRs involved in antigenic recognition by the WT1 specific T-cells from HD1-6 and 10 (for HD7, HD8 and HD9, it was not possible to perform the Vβ Immunoprofiling analysis due to a reduced cell fitness), we first performed a multi-parametric FACS analysis to quantitatively determine the TCR Vβ repertoire. Thus, in order to determine the clonality of the expanded WT1-specific T-cells, we used the 10 Test Beta Mark TCR V beta repertoire kit according to manufacturer's recommendations. This kit allows the detection of the expression of 24 different V beta genes in eight individual tubes. In particular, coverage of 75% of the complete repertoire of V beta is guaranteed by using this approach. Results of FACS staining indicated the great prevalence of a specific Vβ for HD1, HD2, HD3, HD5—see FIG. 5. For HD4, HD6 and HD10, an exhaustive determination of the predominant Vβ was not possible, likely due to the intrinsic limitation of the kit which includes antibodies covering 75% of the existing Vβ proteins.

Example 5

High Throughput Sequencing of TCR α and β Chains Isolated from WT1-Specific T Cells WT1-specific T-cells were collected at different time points over the co-culture time frame and their RNA was extracted by using the Arcturus Pico Pure RNA extraction kit. CDR3 sequences of the WT1-specific T-cells were amplified by using a modified RACE approach in which a magnetic capture was included after the cDNA synthesis in order to increase the specificity of the reaction and eliminate unwanted templates (Ruggiero et al. Nat. Commun. 6, 8081 (2015)). Samples were sequenced using an Illumina MiSeq sequencer and the CDR3 clonotypes were identified using the MiXTCR software (Bolotin, D A et al. Nature Methods 12, 380-381 (2015)) Additionally, CDR1, CDR2 and CDR3 were further determined using the IMGT V-quest tool (Brochet, X. et al., Nucl. Acids Res. 36, W503-508 (2008). PMID: 18503082; Giudicelli, V., Brochet, X., Lefranc, M.-P., Cold Spring Harb Protoc. 2011 Jun. 1; 2011(6). pii: pdb.prot5633. doi: 10.1101/pdb.prot5633. PMID: 21632778 Abstract also in IMGT booklet with generous provision from Cold Spring Harbor (CSH) Protocol).

Sequencing results demonstrated the increasing predominance of a specific CDR3 clonotype in the WT1-specific T cell population over time for both TCR chains in HD1-10. Predominant α and β chain genotypes, and CDR3 sequences are provided in FIGS. 6A-6J.

In addition, the full length α and β chain amino acid sequences for TCRs derived from HD1-10 were determined—see Table 1. The corresponding nucleotide sequences were also determined—see Table 2.

Example 6

Functional Validation of the Newly Identified TCRs

TCRs α and β sequences isolated from HD1 and HD3 and recognizing the WT1 VLDFAPPGA (SEQ ID NO: 157) peptide when presented by the HLA-A*0201 allele were cloned into a lentiviral vector under the control of a bidirectional promoter to promote robust and coordinate expression of both TCR chains in transduced lymphocytes. T cells from a healthy individual were transduced with the viral vector encoding either the HD1 TCR or the HD3 TCR. As control, we also transduced cells with the WT1 126-134 TCR. Transduced T cells were functionally validated by co-culture with different target cells represented by the T2 cells pulsed with one of the 2 recognized peptides (VLD-FAPPGA (SEQ ID NO: 157) for HD1 and HD3 TCR; RMFPNAPYL (SEQ ID NO: 255) for WT1 126-134 TCR) (FIG. 7a), K562 cells either wild type or engineered in order to express the HLA-A*0201 allele (FIG. 7b), primary AML blasts derived from 3 AML patients and selected according to the expression of the HLA-A*0201 allele and the WT1 expression (FIG. 7c). Upon 3 days of co-culture we observed the ability of each transduced T cell population in specifically recognizing the target peptide when presented by the HLA-A*0201 allele (FIG. 7a) and the greater potential of HD1 T cells in mediating a near complete elimination of the engineered K562 cells. The higher potency of HD1 TCR in recognizing the target antigen was further confirmed by the results of the co-culture with pAML blasts. Here, we observed a greater elimination of both pAML blasts harbouring the HLA-A*0201 allele upon co-culture with HD1

TR T cells compared to the conditions in which HD3 TR and WT1 126-134 TR T lymphocytes were used as effector cells.

Materials and Methods

The WT1 protein sequence previously published by Gessler et al. (Gessler, M. et al. (1990) Nature 343: 774-778) was used to design the peptides used for the stimulation and isolation of WT1-specific T cells. This sequence contains 575 amino acids and includes the first 126 amino acids in the N-terminus missing in the (exon 5+, KTS+) isoform of WT1. We designed 141 pentadecapeptides spanning the whole sequence of the WT1 protein, each overlapping the next one by 11 amino acids.

Peptides were synthesized by PRIMM to specifications of validated sequence, 70% purity, sterility and absence of endotoxin. These peptides were mixed in equal amounts in the WT1 pool at a concentration of 1 µg/ml per peptide. Additionally, 24 subpools were generated, each containing up to 12 peptides (4.17 pg/ml/per peptide) according to a specific mapping matrix in order to have each peptide included in only two overlapping subpools as shown in Table 4 (see mapping grid strategy in Doubrovina, E. et al. Blood 120, 1633-1646 (2012)).

TABLE 4

|      | SP1 | SP2 | SP3 | SP4 | SP5 | SP6 | SP7 | SP8 | SP9 | SP10 | SP11 | SP12 |
|------|-----|-----|-----|-----|-----|-----|-----|-----|-----|------|------|------|
| SP13 | 1   | 2   | 3   | 4   | 5   | 6   | 7   | 8   | 9   | 10   | 11   | 12   |
| SP14 | 13  | 14  | 15  | 16  | 17  | 18  | 19  | 20  | 21  | 22   | 23   | 24   |
| SP15 | 25  | 26  | 27  | 28  | 29  | 30  | 31  | 32  | 33  | 34   | 35   | 36   |
| SP16 | 37  | 38  | 39  | 40  | 41  | 42  | 43  | 44  | 45  | 46   | 47   | 48   |
| SP17 | 49  | 50  | 51  | 52  | 53  | 54  | 55  | 56  | 57  | 58   | 59   | 60   |
| SP18 | 61  | 62  | 63  | 64  | 65  | 66  | 67  | 68  | 69  | 70   | 71   | 72   |
| SP19 | 73  | 74  | 75  | 76  | 77  | 78  | 79  | 80  | 81  | 82   | 83   | 84   |
| SP20 | 85  | 86  | 87  | 88  | 89  | 90  | 91  | 92  | 93  | 94   | 95   | 96   |
| SP21 | 97  | 98  | 99  | 100 | 101 | 102 | 103 | 104 | 105 | 106  | 107  | 108  |
| SP22 | 109 | 110 | 111 | 112 | 113 | 114 | 115 | 116 | 117 | 118  | 119  | 120  |
| SP23 | 121 | 122 | 123 | 124 | 125 | 126 | 127 | 128 | 129 | 130  | 131  | 132  |
| SP24 | 133 | 134 | 135 | 136 | 137 | 138 | 139 | 140 | 141 |      |      |      |

Isolation of Peripheral Blood Mononuclear Cells

Peripheral blood was obtained from ten healthy donors at San Raffaele Hospital upon informed consent. Peripheral blood mononuclear cells were isolated using Ficoll-Hypaque density gradient centrifugation.

Immortalized B Cells

Autologous B cells were isolated from PBMCs of healthy donors using the CD19 Microbeads (Miltenyi Biotech). Cells were transduced with a lentiviral vector harbouring the BCL-6/BCL-XL transgene (Kwakkenbos, M. J. et al. Nat. Med. 16, 123 (2009)) and the H/F pseudotype (Levy, C. et al. Molecular Therapy20 9, 1699-1712, (2012)) and cultured in IMDM supplemented with 10% fetal bovine serum (FBS), penicillin-streptomycin, and 10 ng/ml of IL21 (Miltenyi Biotech). B-cells were re-stimulated every 5 days by co-culture with irradiated (50 Gy) mouse L-cell fibroblasts expressing CD40L (3T3-CD40L) at a B-cell:3T3-CD40L ratio of 10:1.

Cell Lines

We cultured the T2 and K562 cell lines in RPMI 1640 (GIBCO-BRL) supplemented with penicillin, streptomycin, glutamine and 10% FBS (BioWhittaker).

Leukemic Cells

Primary AML cells were obtained from San Raffaele Hospital (OSR) Leukemia biobank and selected according to the expression of WT1 by quantitative PCR and to the HLA typing. All EBV-BLCLs and primary leukemia cells were typed for HLA-A, HLA-B, HLA-C, HLA-DR and HLA-DQ alleles at high resolution at the HLA laboratory of the OSR.

Flow Cytometry

We used FITC-, PE-, PerCP-, APC-, PE-Cychrome 7-, APC Cychrome 7-, Pacific Blue and Brillant Violet—conjugated antibodies directed to human CD3, CD4, CD8, CD107a, IFNγ, TNFα, CD33, CD117, CD34, CD14, Vβ21.3, Vβ8, Vβ7.2 and HLA-A2. APC fluorescently-labelled WT1 VLDFAPPGA (SEQ ID NO: 157) and PE fluorescently-labelled WT1 RMFPNAPYL (SEQ ID NO: 255) dextramers were used following the manufacturer's instructions. Cells were incubated with antibodies for 15 minutes at 4° C. and washed with phosphate-buffered saline containing 1% FBS. Samples were run through a fluorescence-activated cell sorter (FACS) Canto II flow cytometer (BD Biosciences), and data were analyzed by Flow Jo software (Tree star Inc). For intracellular evaluation of cytokine secretion and expression of degranulation markers, the Fix/Perm buffer set (Biolegend) was used according to manufacturer instructions.

Stimulation, Isolation and Expansion of WT1-Specific T-Cells

Freshly isolated PBMCs were resuspended in X-VIVO supplemented with 5% human AB serum, 2 mM glutamine and 1 µg/ml CD28 monoclonal antibody, seeded at a density of $10^7$ cells/ml and stimulated with the WT1 overlapping peptide pool, each peptide present at a concentration of 1 µg/ml.

Antigen-specific T-cells were isolated after 26-30 hours by CD137 expression. More specifically, cells were stained with the PE-conjugated CD137 antibody and sorted using anti-PE microbeads (Miltenyi Biotech). The CD137⁻ fraction was depleted of the CD3 cells using CD3-Microbeads (Miltenyi Biotech), irradiated 30 Gy and used as peptide-loaded APCs in a co-culture with the CD137⁺ fraction at a ratio of 100:1 when possible or at least 20:1 and a final density of $5 \times 10^6$ cells/ml. X-VIVO supplemented with 5% human AB serum, 5 ng/ml IL7, 5 ng/ml IL15 and 10 ng/ml IL21 was used as the medium. Media, including cytokines, was replaced every 2-3 days.

Re-Stimulation of Expanded Antigen-Specific T-Cells

Cells were re-stimulated every 7-14 days with WT1-pulsed autologous APCs (PBMC CD3-depleted cells; immortalized B cells). In the initial re-stimulations, cells were washed 2 days before and plated in cytokine-free medium. APCs were irradiated with 30 Gy, pulsed with the peptide pool overnight and co-cultured with effector cells in X-VIVO supplemented with 5% human AB serum, 1 µg/ml CD28 monoclonal antibody and IL7 (5 ng/ml), IL15 (5 ng/ml), IL21 (10 ng/ml).

Assessment of T Cell Response

The percentage of T-cells responding to the WT1 peptide pool was measured by performing a 6 hours co-culture of the effector cells with autologous APCs (ratio of at least 1:1) pulsed with the desired antigen (WT1 peptide pool, WT1 subpools, WT1 individual peptides, unrelated peptide pool as control). Co-cultures were seeded in X-VIVO supplemented with 5% human AB serum and supplemented with the CD28 monoclonal antibody (1 µg/ml), Golgi Stop (BD) and CD107a-FITC antibody for assessment of degranulation. Cells were then fixed, permeabilized and stained intracellularly to determine the percentage of CD3$^+$CD8$^+$ or CD3$^+$CD4$^+$ cells expressing IFNγ and CD107a.

Mapping of Immunogenic Peptides

T-cells stimulated with the WT1 pool were seeded in different wells and co-cultured with autologous APCs loaded with one of each of the WT1 subpools at a ratio of at least 1:1. T-cell responses to each subpool were measured as previously described by FACS analysis. Deconvolution of the mapping grid was essential to determine which shared peptides were eliciting a T cell response. Once determined the immunogenic peptides, T-cells were further stimulated with APCs loaded with the individual peptides to confirm their immunogenicity.

Evaluation of T Cell Ability to Recognize WT1-Expressing Cells

WT1-specificity and HLA-restricted ability of T-cells to recognize target cells was measured with different experimental procedures. For T-cells derived from HD1, secretion of CD107a was determined by FACS analysis after 6 hours co-culture with target cells; for T cells derived from HD3, elimination index was calculated as the total number of target cells still present after 4 days co-culture with the WT1-specific T-cells divided by the total number of target cells alone; for T-cells derived from HD4, the percentage of CD33$^+$ target cells (AML primary cells harbouring the HLA alleles of interest and as control, of AML primary cells not harbouring the specific HLA allele) still present after 3 days co-culture with CD3$^+$ WT1-specific T cells was assessed by cytofluorimetric analysis.

Assessment of T Cell Clonality

In order to determine the clonality of the expanded WT1-specific T cells, the IO Test Beta Mark TCR V beta repertoire kit was used according to manufacturer's recommendations.

TCR Repertoire Sequencing

WT1-specific T cells were collected at different time points over the co-culture time frame and RNA was extracted by using the Arcturus Pico Pure RNA extraction kit. Complementarity determining region (CDR) 3 sequences of the WT1-specific T cells were amplified by using a modified RACE approach (Ruggiero, E. et al. Nat. Commun. 6,8081 (2015)). Samples were sequenced by using an IlluminaMiSeq sequencer and CDR3 clonotypes identified using the MiXCR software (Bolotin, D A et al. Nature Methods 12, 380-381 (2015)).

Lentiviral Vectors

TCR α and β chain genes isolated from HD1 and HD3 were codon-optimized, cysteine-modified and cloned in a lentiviral vector (LV) under a bidirectional promoter. The amino acid (aa) and nucleotide (nt) sequences were:

| | | SEQ ID NO: |
|---|---|---|
| HD1 α chain- seq nt | ATGGAAACCCTGCTGAAGGTGCTGAGCGGCACACTGCTGTGGCAGC TGACATGGGTCCGATCTCAGCAGCCTGTGCAGTCTCCTCAGGCCGT GATTCTGAGAGAAGGCGAGGACGCCGTGATCAACTGCAGCAGCTCT AAGGCCCTGTACAGCGTGCACTGGTACAGACAGAAGCACGGCGAGG CCCCTGTGTTCCTGATGATCCTGCTGAAAGGCGGCGAGCAGAAGGG CCACGAGAAGATCAGCGCCAGCTTCAACGAGAAGAAGCAGCAGTCC AGCCTGTACCTGACAGCCAGCCAGCTGAGCTACAGCGGCACCTACT TTTGTGGCACCGCCTGGATCAACGACTACAAGCTGTCTTTCGGAGCC GGCACCACAGTGACAGTGCGGGCCAATATTCAGAACCCCGATCCTG CCGTGTACCAGCTGAGAGACAGCAAGAGCAGCGACAAGAGCGTGTG CCTGTTCACCGACTTCGACAGCCAGACCAACGTGTCCCAGAGCAAG GACAGCGACGTGTACATCACCGATAAGTGCGTGCTGGACATGCGGA GCATGGACTTCAAGAGCAACAGCGCCGTGGCCTGGTCCAACAAGAG CGATTTCGCCTGCGCCAACGCCTTCAACAACAGCATTATCCCCGAGG ACACATTCTTCCCAAGTCCTGAGAGCAGCTGCGACGTGAAGCTGGT GGAAAAGAGCTTCGAGACAGACACCAACCTGAACTTCCAGAACCTGA GCGTGATCGGCTTCAGAATCCTGCTGCTCAAGGTGGCCGGCTTCAA CCTGCTGATGACCCTGAGACTGTGGTCCAGC | 256 |
| HD1 α chain- seq aa | METLLKVLSGTLLWQLTWVRSQQPVQSPQAVILREGEDAVINCSSSKAL YSVHWYRQKHGEAPVFLMILLKGGEQKGHEKISASFNEKKQQSSLYLTA SQLSYSGTYFCGTAWINDYKLSFGAGTTVTVRANIQNPDPAVYQLRDSK SSDKSVCLFTDFDSQTNVSQSKDSDVYITDKCVLDMRSMDFKSNSAVA WSNKSDFACANAFNNSIIPEDTFFPSPESSCDVKLVEKSFETDTNLNFQ NLSVIGFRILLLKVAGFNLLMTLRLWSS | 257 |
| HD1 β chain- seq nt | ATGGGATCTTGGACACTGTGTTGCGTGTCCCTGTGCATCCTGGTGGC CAAGCACACAGATGCCGGCGTGATCCAGTCTCCTAGACACGAAGTG ACCGAGATGGGCCAAGAAGTGACCCTGCGCTGCAAGCCTATCAGCG GCCACGATTACCTGTTCTGGTACAGACAGACCATGATGAGAGGCCTG GAACTGCTGATCTACTTCAACAACAACGTGCCCATCGACGACAGCGG CATGCCCGAGGATAGATTCAGCGCCAAGATGCCCAACGCCAGCTTC AGCACCCTGAAGATCCAGCCTAGCGAGCCCAGAGATAGCGCCGTGT ACTTCTGCGCCAGCAGAAAGACAGGCGGCTACAGCAATCAGCCCCA GCACTTTGGAGATGGCACCCGGCTGAGCATCCTGGAAGATCTGAAG AACGTGTTCCCACCTGAGGTGGCCGTGTTCGAGCCTTCTGAGGCCG AGATCAGCCACACACAGAAAGCCACACTCGTGTGTCTGGCCACCGG CTTCTATCCCGATCACGTGGAACTGTCTTGGTGGGTCAACGGCAAAG AGGTGCACAGCGGCGTCTGTACCGATCCTCAGCCTCTGAAAGAGCA GCCCGCTCTGAACGACAGCAGATACTGCCTGAGCAGCAGACTGAGA | 258 |

| | | SEQ ID NO: |
|---|---|---|
| | GTGTCCGCCACCTTCTGGCAGAACCCCAGAAACCACTTCAGATGCCA<br>GGTGCAGTTCTACGGCCTGAGCGAGAACGATGAGTGGACCCAGGAT<br>AGAGCCAAGCCTGTGACACAGATCGTGTCTGCCGAAGCCTGGGGCA<br>GAGCCGATTGTGGCTTTACCAGCGAGAGCTACCAGCAGGGCGTGCT<br>GTCTGCCACAATCCTGTACGAGATCCTGCTGGGCAAAGCCACTCTGT<br>ACGCCGTGCTGGTGTCTGCCCTGGTGCTGATGGCCATGGTCAAGCG<br>GAAGGATAGCAGGGGC | |
| HD1<br>β chain-<br>seq aa | MGSWTLCCVSLCILVAKHTDAGVIQSPRHEVTEMGQEVTLRCKPISGHD<br>YLFWYRQTMMRGLELLIYFNNNVPIDDSGMPEDRFSAKMPNASFSTLKI<br>QPSEPRDSAVYFCASRKTGGYSNQPQHFGDGTRLSILEDLKNVFPPEV<br>AVFEPSEAEISHTQKATLVCLATGFYPDHVELSWWVNGKEVHSGVCTD<br>PQPLKEQPALNDSRYCLSSRLRVSATFWQNPRNHFRCQVQFYGLSEN<br>DEWTQDRAKPVTQIVSAEAWG RADCGFTSESYQQGVLSATILYEILLGK<br>ATLYAVLVSALVLMAMVKRKDSRG | 259 |
| HD3<br>α chain-<br>seq nt | ATGATCAGCCTGAGAGTGCTGCTGGTCATCCTGTGGCTGCAGCTGT<br>CTTGGGTCTGGTCCCAGCGGAAAGAGGTGGAACAGGACCCCGGAC<br>CTTTCAATGTGCCTGAAGGCGCCACCGTGGCCTTCAACTGCACCTAC<br>AGCAATAGCGCCAGCCAGAGCTTCTTCTGGTACAGACAGGACTGCC<br>GGAAAGAACCCAAGCTGCTGATGAGCGTGTACAGCAGCGGCAACGA<br>GGACGGCAGATTCACAGCCCAGCTGAACAGAGCCAGCCAGTACATC<br>AGCCTGCTGATCCGGGATAGCAAGCTGAGCGATAGCGCCACCTACC<br>TGTGCGTGGTCAACCTGCTGTCTAATCAAGGCGGCAAGCTGATCTTC<br>GGCCAGGGCACAGAGCTGAGCGTGAAGCCCAACATTCAGAACCCCG<br>ATCCTGCCGTGTACCAGCTGAGAGACAGCAAGAGCAGCGACAAGAG<br>CGTGTGCCTGTTCACCGACTTCGACAGCCAGACCAACGTGTCCCAG<br>AGCAAGGACAGCGACGTGTACATCACCGATAAGTGCGTGCTGGACA<br>TGCGGAGCATGGACTTCAAGAGCAACAGCGCCGTGGCCTGGTCCAA<br>CAAGAGCGATTTCGCCTGCGCCAACGCCTTCAACAACAGCATTATCC<br>CCGAGGACACATTCTTCCCAAGTCCTGAGAGCAGCTGCGACGTGAA<br>GCTGGTGGAAAAGAGCTTCGAGACAGACACCAACCTGAACTTCCAG<br>AACCTGTCCGTGATCGGCTTCCGGATCCTGCTGCTGAAAGTGGCCG<br>GCTTCAACCTCCTGATGACCCTGAGACTGTGGTCCAGC | 260 |
| HD3<br>α chain-<br>seq aa | MISLRVLLVILWLQLSWVWSQRKEVEQDPGPFNVPEGATVAFNCTYSN<br>SASQSFFWYRQDCRKEPKLLMSVYSSGNEDGRFTAQLNRASQYISLLIR<br>DSKLSDSATYLCVVNLLSNQGGKLIFGQGTELSVKPNIQNPDPAVYQLR<br>DSKSSDKSVCLFTDFDSQTNVSQSKDSDVYITDKCVLDMRSMDFKSNS<br>AVAWSNKSDFACANAFNNSIIPEDTFFPSPESSCDVKLVEKSFETDTNLN<br>FQNLSVIGFRILLLKVAGFNLLMTLRLWSS | 261 |
| HD3<br>β chain-<br>seq nt | ATGGGATGTAGACTTCTGTGTTGCGCCGTGCTGTGTCTGCTTGGAGC<br>TGGCGAACTGGTGCCTATGGAAACCGGCGTGACCCAGACACCTAGA<br>CACCTGGTCATGGGCATGACAAACAAGAAAAGCCTGAAGTGCGAGC<br>AGCACCTGGGCCACAATGCCATGTACTGGTACAAGCAGAGCGCCAA<br>GAAACCCCTGGAACTGATGTTCGTGTACAGCCTGGAAGAGAGGGTC<br>GAGAACAACAGCGTGCCCAGCAGATTCAGCCCTGAGTGCCCTAATA<br>GCAGCCACCTGTTTCTGCATCTGCACACCCTGCAGCCTGAGGACTCT<br>GCCCTGTATCTGTGTGCCAGCAGCCAGGACTACCTGGTGTCCAACG<br>AGAAGCTGTTCTTCGGCAGCGGCACAGCTGAGCGTGCTGGAAGA<br>TCTGAAGAACGTGTTCCCACCTGAGGTGGCCGTGTTCGAGCCTTCTG<br>AGGCCGAGATCAGCCACACACAGAAAGCCACACTCGTGTGTCTGGC<br>CACCGGCTTCTATCCCGATCACGTGGAACTGTCTTGGTGGGTCAACG<br>GCAAAGAGGTGCACAGCGGCGTCTGTACCGATCCTCAGCCTCTGAA<br>AGAGCAGCCCGCTCTGAACGACAGCAGATACTGCCTGAGCAGCAGA<br>CTGAGAGTGTCCGCCACCTTCTGGCAGAACCCCAGAAACCACTTCA<br>GATGCCAGGTGCAGTTCTACGGCCTGAGCGAGAACGATGAGTGGAC<br>CCAGGATAGAGCCAAGCCTGTGACACAGATCGTGTCTGCCGAAGCC<br>TGGGGCAGAGCCGATTGTGGCTTTACCAGCGAGAGCTACCAGCAGG<br>GCGTGCTGTCTGCCACAATCCTGTACGAGATCCTGCTGGGAAAAGC<br>CACTCTGTACGCTGTGCTGGTGTCCGCTCTGGTGCTGATGGCCATG<br>GTCAAGCGGAAGGATAGCAGGGGC | 262 |
| HD3<br>β chain-<br>seq aa | MGCRLLCCAVLCLLGAGELVPMETGVTQTPRHLVMGMTNKKSLKCEQH<br>LGHNAMYWYKQSAKKPLELMFVYSLEERVENNSVPSRFSPECPNSSHL<br>FLHLHTLQPEDSALYLCASSQDYLVSNEKLFFGSGTQLSVLEDLKNVFPP<br>EVAVFEPSEAEISHTQKATLVCLATGFYPDHVELSWWVNGKEVHSGVC<br>TDPQPLKEQPALNDSRYCLSSRLRVSATFWQNPRNHFRCQVQFYGLSE<br>NDEWTQDRAKPVTQIVSAEAWGRADCGFTSESYQQGVLSATILYEILLG<br>KATLYAVLVSALVLMAMVKRKDSRG | 263 |

LVs were packaged by an integrase-competent third-generation construct and pseudotyped by the vescicular stomatitis virus (VSV) envelope. As control, we included the LV encoding for a WT1 126-134 TCR recognizing the RMFPNAPYL (SEQ ID NO: 255) peptide.

Vector Transductions

For transduction with WT1-TCR lentiviral vector, T lymphocytes isolated from a healthy individual were activated and sorted using magnetic beads conjugated to antibodies to CD3 and CD28 (ClinExVivo CD3/CD28; Invitrogen), following the manufacturer instructions, and cultured in Iscove's Modified Dulbecco's Media (IMDM) (GIBCO-BRL) supplemented with penicillin, streptomycin, 10% FBS and 5 ng ml$^{-1}$ of each IL-7 and IL-15 (PeproTech). For transduction, T lymphocytes were plated at $2.5 \times 10^6$ cells ml$^{-1}$ and infected with the LV for 24 h. Afterwards, T cells were cultured at $10^6$ cells ml$^{-1}$ and expanded. Transduction efficiency was determined by measuring the percentage of the CD3 T cells expressing the specific dextramers. Cells were sorted using APC or PE-fluorescently-labelled HLA-A*0201 dextramer specific for the VLDFAPPGA (SEQ ID NO: 157) or RMFPNAPYL (SEQ ID NO: 255) peptide (Immudex) using anti-APC or anti-PE microbeads (Miltenyi Biotec) following the manufacturer instructions.

Functional Assays

The ability of HD1, HD3 and WT1 126-134 TCR-transferred T-cells to recognize WT1-expressing target cells was measured upon co-culture with (a) T2 cells either pulsed with the WT1 126-134 peptide or with the VLDFAPPGA (SEQ ID NO: 157) peptide (effector:target ratio=1:1); (b) K562 cells either wild type (K562) or genetically modified in order to express the HLA-A*0201 allele (effector:target ratio=1:1); (c) 3 different primary AML blasts selected according to the expression of the HLA-A*0201 allele and of the WT1 antigen (effector:target ratio=5:1). For the co-culture with T2 and K562 cell lines, we included untransduced T cells as control. After 3 days of culture, the percentage of target cells was assessed by cytofluorimetric analysis. The elimination index was calculated as follows: 1-(total number of target cells still present after 3 days co-culture with the WT1-specific T-cells/total number of target cells alone).

All publications mentioned in the above specification are herein incorporated by reference. Various modifications and variations of the described present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in cell biology, immunology, immunotherapy, molecular biology, oncology, or related fields are intended to be within the scope of the following claims.

The invention claimed is:

1. A T-cell receptor (TCR), which binds to a Wilms tumour 1 protein (WT1) peptide when presented by a major histocompatibility complex (MHC), wherein the TCR comprises the following CDR sequences:

```
                                    (SEQ ID NO: 1)
(i) CDR1α-KALYS, (SEQ ID NO: 2)
CDR2α-LLKGGEQ, (SEQ ID NO: 3)
CDR3α-CGTAWINDYKLSF, (SEQ ID NO: 6)
CDR1β-SGHDY, (SEQ ID NO: 7)
CDR2β-FNNNVP,
and (SEQ ID NO: 8)
CDR3β-CASRKTGGYSNQPQHF,
```

2. A TCR according to claim 1 comprising an α chain variable domain comprising the amino acid sequence of SEQ ID NO: 4 or a variant thereof having at least 75% sequence identity thereto; and a β chain variable domain comprising the amino acid sequence of SEQ ID NO: 9 or a variant thereof having at least 75% sequence identity thereto.

3. A TCR according to claim 1 comprising an α chain comprising the amino acid sequence of SEQ ID NO: 5 or a variant thereof having at least 75% sequence identity thereto; and a β chain comprising an amino acid sequence selected from the group consisting of SEQ ID NO: 10, SEQ ID NO: 11 and variants of SEQ ID NOs: 10 and 11 having at least 75% sequence identity thereto.

4. A TCR according to claim 1 which binds to an MHC I and/or MHC II peptide complex.

5. A TCR according to claim 1, which is restricted to a human leukocyte antigen (HLA) allele.

6. A TCR according to claim 1 which is restricted to HLA-A*0201.

7. A TCR according to claim 1 comprising one or more mutations at the α chain/β chain interface, such that when the α chain and the β chain are expressed in a T-cell, the frequency of mispairing between said chains and endogenous TCR α and β chains is reduced.

8. A TCR according to claim 7, wherein the one or more mutations introduce a cysteine residue into the constant region domain of each of the α chain and the β chain, wherein the cysteine residues are capable of forming a disulphide bond between the α chain and the β chain.

9. A TCR according to claim 1, which comprises a murinized constant region.

10. A TCR according to claim 1, wherein the TCR is a soluble TCR.

11. An isolated polynucleotide comprising a nucleotide sequence encoding an α chain of a T-cell receptor (TCR), and/or a nucleotide sequence encoding a β chain of a TCR, wherein the TCR binds to a Wilms tumour 1 protein (WT1) peptide when presented by a major histocompatibility complex (MHC), and wherein the TCR comprises the following CDR sequences:

```
                                    (SEQ ID NO: 1)
CDR1α  -  KALYS, (SEQ ID NO: 2)
CDR2α  -  LLKGGEQ, (SEQ ID NO: 3)
CDR3α  -  CGTAWINDYKLSF, (SEQ ID NO: 6)
CDR1β  -  SGHDY, (SEQ ID NO: 7)
CDR2β  -  FNNNVP, and (SEQ ID NO: 8)
CDR3β  -  CASRKTGGYSNQPQHF
```

12. An isolated polynucleotide according to claim 11, wherein the polynucleotide comprises a nucleotide sequence encoding the α chain linked to the β chain.

13. An isolated polynucleotide according to claim 11, which further encodes one or more short interfering RNA (siRNA) or other agents capable of reducing or preventing expression of one or more endogenous TCR gene.

14. A vector comprising a polynucleotide according to claim 11.

15. A vector according to claim 14 comprising a polynucleotide which encodes one or more CD3 chains, CD8, a suicide gene, and/or a selectable marker.

16. A cell comprising a TCR according to claim 1, or one or more polynucleotides encoding the α chain and the β chain thereof.

17. A cell according to claim 16, wherein the cell is a T-cell, a lymphocyte, or a stem cell.

18. A cell according to claim 17, wherein the cell is a T-cell which has been isolated from a subject.

19. A cell according to claim 16, wherein an endogenous gene encoding a TCR α chain and/or an endogenous gene encoding a TCR β chain is disrupted.

20. A method of preparing a cell, which comprises the step of introducing a vector according to claim 14 into a cell in vitro, ex vivo or in vivo.

21. A method of preparing a cell according to claim 20, which comprises the step of T-cell editing, which comprises disrupting an endogenous gene encoding a TCR α chain and/or an endogenous gene encoding a TCR β chain with an artificial nuclease.

22. A method of preparing a cell, which comprises the step of integrating an expression cassette into an endogenous gene encoding the TCR α chain and/or an endogenous gene encoding the TCR β chain of the cell, wherein the endogenous gene is disrupted by an artificial nuclease, and wherein the expression cassette comprises one or more polynucleotide sequence(s) comprising a nucleotide sequence encoding the TCR of claim 1.

23. A method of preparing a cell according to claim 20, which comprises the step of disrupting one or more endogenous genes encoding an MHC.

24. A method of preparing a cell according to claim 20, which comprises the step of disrupting one or more endogenous genes to modify the persistence, expansion, activity, resistance to exhaustion/senescence/inhibitory signals, homing capacity, or other T-cell functions.

25. A chimeric molecule comprising a TCR of claim 1, conjugated to a non-cellular substrate, a toxin and/or an antibody.

26. A method for treating a disease associated with expression of WT1, which comprises the step of administering a TCR according to claim 1, or at least one polynucleotide encoding said TCR, or a cell comprising said TCR, to a subject in need thereof, wherein the disease associated with expression of WT1 is a hematological malignancy or a solid tumor.

27. A method of adoptive cell transfer comprising administering a cell according to claim 16 to a subject in need thereof.

28. The method of claim 26, wherein the hematological malignancy is acute myeloid leukemia.

29. The method of claim 26, wherein the proliferative disorder is a solid tumor.

30. The TCR of claim 2 comprising an α chain variable domain comprising the amino acid sequence of SEQ ID NO: 4, and a β chain variable domain comprising the amino acid sequence of SEQ ID NO: 9.

31. The TCR of claim 3 comprising an α chain comprising the amino acid sequence of SEQ ID NO: 5 and a β chain comprising an amino acid sequence of SEQ ID NO: 10.

32. The TCR of claim 3 comprising an α chain comprising the amino acid sequence of SEQ ID NO: 5 and a β chain comprising an amino acid sequence of SEQ ID NO: 11.

33. A polypeptide encoded by a polynucleotide comprising a nucleotide sequence encoding an α chain of a T-cell receptor (TCR), and/or a nucleotide sequence encoding a β chain of a TCR, wherein the TCR binds to a Wilms tumour 1 protein (WT1) peptide when presented by a major histocompatibility complex (MHC), and wherein the TCR comprises the following CDR sequences:

```
                                         (SEQ ID NO: 1)
         CDR1α - KALYS, (SEQ ID NO: 2)
         CDR2α - LLKGGEQ, (SEQ ID NO: 3)
         CDR3α - CGTAWINDYKLSF, (SEQ ID NO: 6)
         CDR1β - SGHDY, (SEQ ID NO: 7)
         CDR2β - FNNNVP, and (SEQ ID NO: 8)
         CDR3β - CASRKTGGYSNQPQHF
```

34. The isolated polynucleotide according to claim 12, wherein a linker is present in between the α chain and β chain.

35. The isolated polynucleotide according to claim 34, wherein the linker is a 2A self-cleaving peptide.

36. The isolated polynucleotide according to claim 12, wherein the nucleotide sequence encoding the β chain is 5' of the nucleotide sequence encoding the α chain.

37. The isolated polynucleotide according to claim 12, wherein the nucleotide sequence encoding the α chain is 5' of the nucleotide sequence encoding the β chain.

38. The vector according to claim 14, wherein the vector is an AAV.

39. The cell according to claim 19, wherein the endogenous gene encoding the TCR α chain is disrupted by insertion of an expression cassette comprising a polynucleotide sequence encoding the TCR.

40. The cell according to claim 39, wherein the polynucleotide sequence encoding the TCR is operably linked to an expression control sequence.

41. The cell according to claim 40, wherein the expression control sequence is a promoter.

\* \* \* \* \*